US010738339B2

(12) United States Patent
Chin et al.

(10) Patent No.: US 10,738,339 B2
(45) Date of Patent: Aug. 11, 2020

(54) USE OF ERF1 MUTANTS IN UNNATURAL AMINO ACID INCORPORATION

(71) Applicant: United Kingdom Research and Innovation, Swindon (GB)

(72) Inventors: Jason W Chin, Cambridge (GB); Wolfgang H Schmied, Cambridge (GB); Simon J Elsasser, Cambridge (GB); Eugene Y Kym, Cambridge (GB)

(73) Assignee: United Kingdom Research and Innovation, Swindon (GB)

( * ) Notice: Subject to any disclaimer, the term of this patent is extended or adjusted under 35 U.S.C. 154(b) by 160 days.

(21) Appl. No.: 15/521,103

(22) PCT Filed: Oct. 21, 2015

(86) PCT No.: PCT/GB2015/053141
§ 371 (c)(1),
(2) Date: Apr. 21, 2017

(87) PCT Pub. No.: WO2016/066995
PCT Pub. Date: May 6, 2016

(65) Prior Publication Data
US 2017/0356023 A1 Dec. 14, 2017

(30) Foreign Application Priority Data
Oct. 27, 2014 (GB) .................................. 1419109.2

(51) Int. Cl.
C12P 21/02 (2006.01)
C12N 15/67 (2006.01)
C07K 14/47 (2006.01)
C12N 9/00 (2006.01)

(52) U.S. Cl.
CPC .............. *C12P 21/02* (2013.01); *C07K 14/47* (2013.01); *C07K 14/4702* (2013.01); *C12N 9/93* (2013.01); *C12N 15/67* (2013.01); *C12Y 601/01026* (2013.01)

(58) Field of Classification Search
None
See application file for complete search history.

(56) References Cited

U.S. PATENT DOCUMENTS

2012/0077186 A1 3/2012 Skach et al.

FOREIGN PATENT DOCUMENTS

WO 2006110182 10/2006

OTHER PUBLICATIONS

Sergey Lekomtsev (Different modes of stop codon restriction by the Stylonychia and Paramecium eRF1 translation termination factoe. PNAS vol. 104, No. 26 pp. 10824-10829. (Year: 2007).*
Ilegems, Erwin, et al. "Downregulation of eRF1 by RNA interference increases mis-acylated tRNA suppression efficiency in human cells" Protein Engineering, Design & Selection, vol. 17, No. 12, pp. 821-827, 2004.
Kolosov, Petr, et al. "Invariant amino acids essential for decoding function of polypeptide release factor eRF1" Nucleic Acids Research, 2005, vol. 33, No. 19; pp. 6418-6425.
Bulygin, Konstantin N., et al. "Three distinct peptides from the N domain of translation termination factor eRF1 surround stop codon in the ribosome" RNA (2010), 16:1902-1914.
Seit-Nebi, Alim, et al. "Conversion of omnipotent translation termination factor eRF1 into ciliate-like UGA-only unipotent eRF1" European Molecular Biology Organization, vol. 3, No. 9; pp. 881-886, 2002.
Kryuchkova, Polina "Two-step model of stop codon recognition by eukaryotic release factor eRF1" Nucleic Acids Research, 2013, vol. 41, No. 8, pp. 4573-4586.
Lekomtsev, Sergey, et al. "Different modes of stop codon restriction by the Stylonychia and Paramecium eRF1 translation termination factors" PNAS, 2007, vol. 104, No. 26; pp. 10824-10829.
Schmied, Wolfgang, H., et al. "Efficient Multisite Unnatural Amino Acid Incorporation in Mammalian Cells via Optimized Pyrrolysyl tRNA Synthetase/tRNA Expression and Engineered eRF1" J. Am. Chem. Soc., 2014, 136, 15577-15583.
Chin, Jason W. "Expanding and Reprogramming the Genetic Code of Cells and Animals" Annu. Rev., Biochem., 2014, 83: 379-408.
Elliott, Thomas S., et al. "Proteome labeling and protein identification in specific tissues and at specific developmental stages in an animal" Nature Biotechnology, vol. 32, No. 5, May 2014.
Ramon, Moreno "Notification of Transmittal of the International Preliminary Report on Patentability—Application No. PCT/GB2015/053141" dated Feb. 3, 2017; European Patent Office; pp. 1-19.
Seroz, Thierry "International Search Report and Written Opinion—application No. PCT/GB2015/053141" dated Feb. 2, 2016; European Patent Office; pp. 1-15.

* cited by examiner

*Primary Examiner* — Kagnew H Gebreyesus
(74) *Attorney, Agent, or Firm* — Cooley LLP

(57) ABSTRACT

The invention relates to a method for incorporating an unnatural amino acid into a protein of interest in a eukaryotic cell, said method comprising the steps of: i) providing a eukaryotic cell expressing an orthogonal tRNA synthetase-tRNA pair, a nucleic acid sequence of interest encoding said protein of interest, and a mutant eRF1, said mutant eRF1 having amino acid sequence having at least 60% sequence identity to the human wild type eRF1 sequence of SEQ ID NO: 4, said nucleic acid sequence of interest comprising a codon recognised by the tRNA at the position for incorporation of an unnatural amino acid; ii) incubating the eukaryotic cell in the presence of an unnatural amino acid to be incorporated into a protein encoded by the nucleic acid sequence of interest, wherein said unnatural amino acid is a substrate for the orthogonal tRNA synthetase; and iii) incubating the eukaryotic cell to allow incorporation of said unnatural amino acid into the protein of interest via the orthogonal tRNA synthetase-t RNA pair. The invention also relates to uses, host cells, combinations and kits.

17 Claims, 22 Drawing Sheets

Specification includes a Sequence Listing.

FIG. 1A
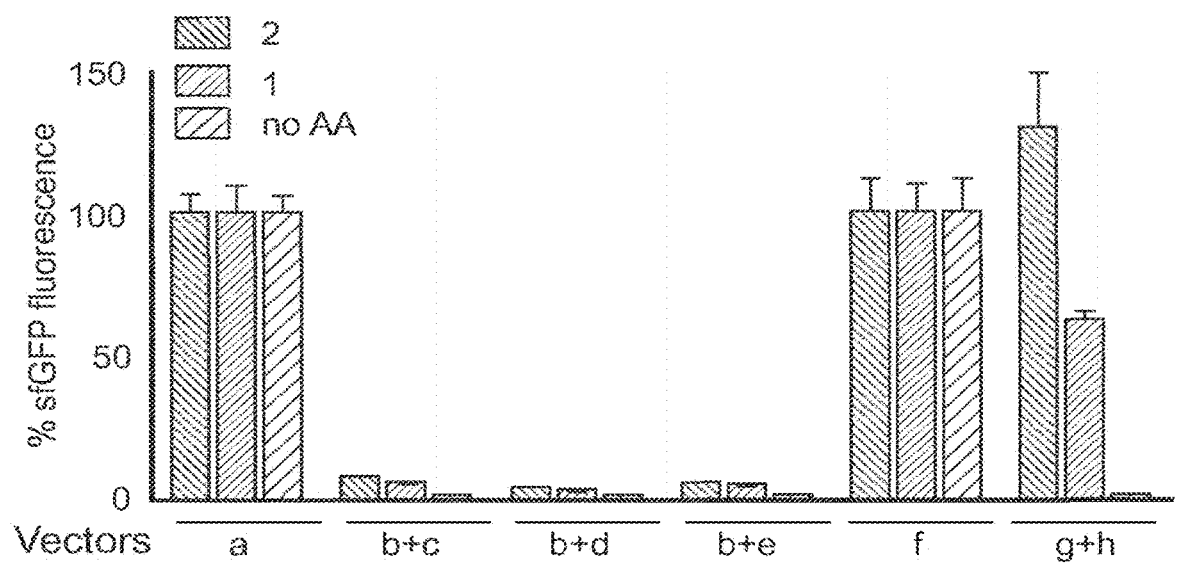
FIG. 1B
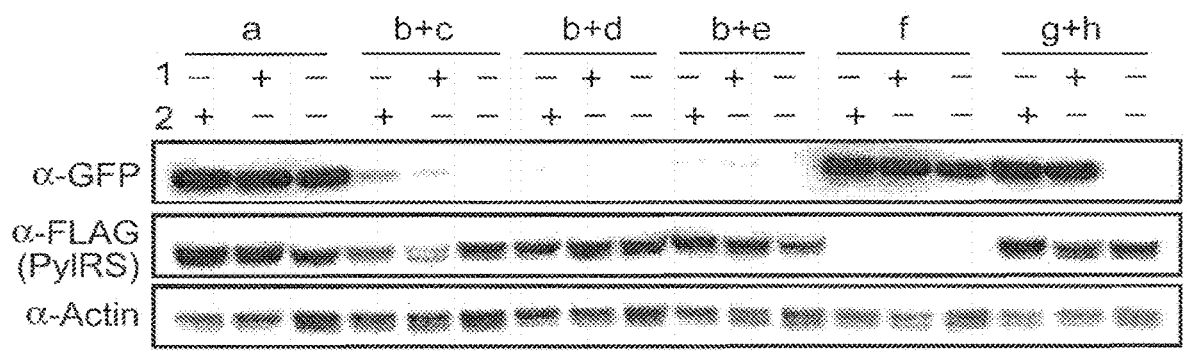
FIG. 1C

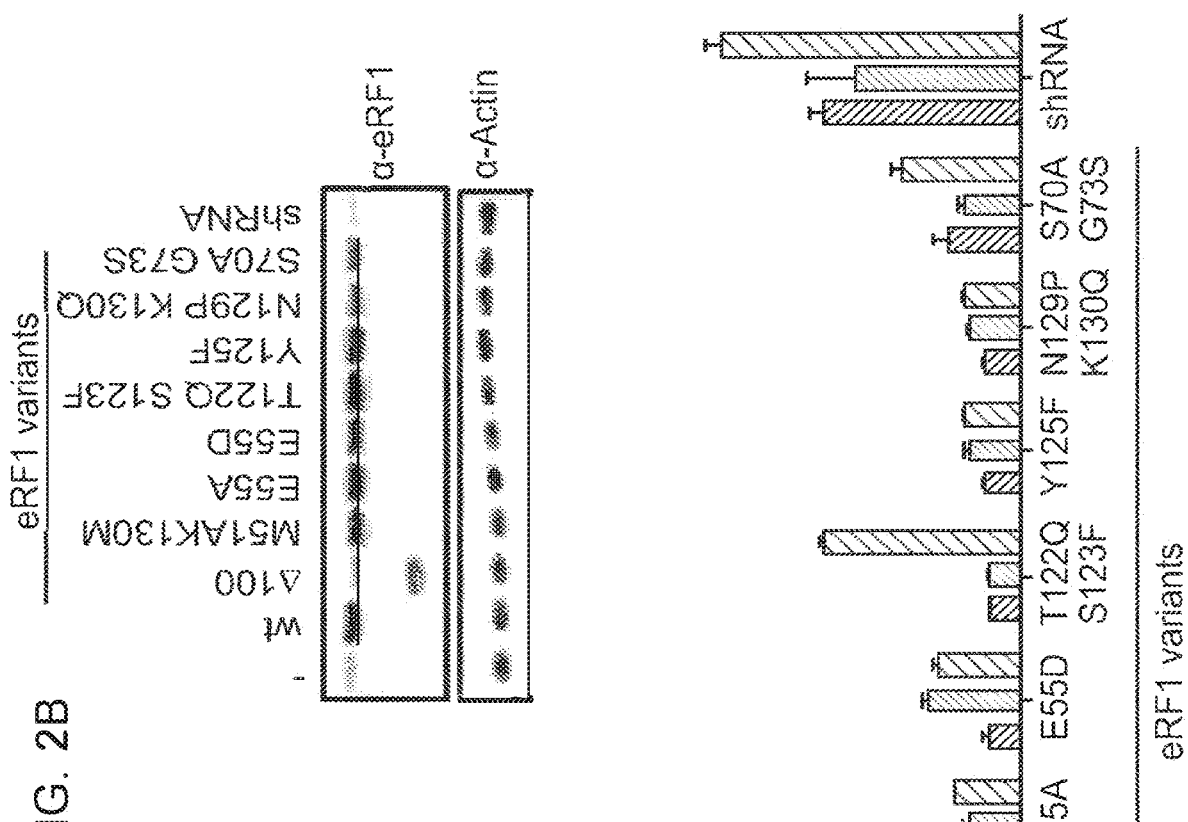
FIG. 2A
FIG. 2B
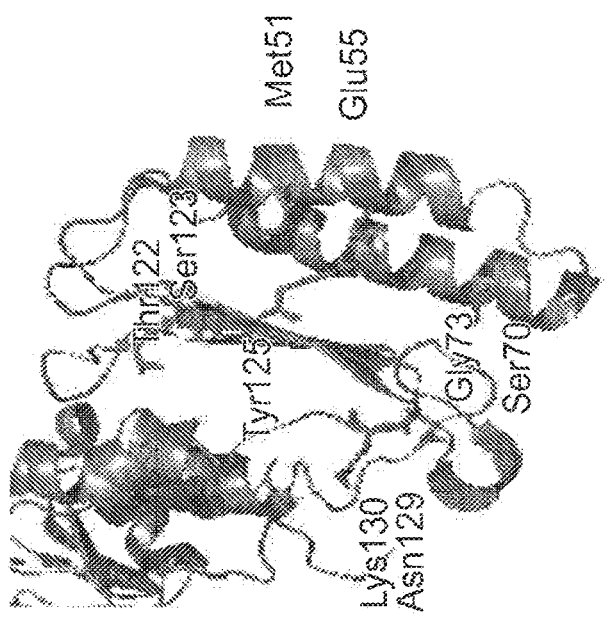
FIG. 2C

PylT U25C   PylT U25C Opt

FIG. 17

```
              1         10         20         30         40         50         60        69
              |         |          |          |          |          |          |         |
1.MmPylt      GGAAACCTGATCATGTAGATCGAATGGACTCTAAATCCGTTCAGCCGGGTTAGATCCCGGGGTTCCG
2.MmPylt U25C GGAAACCTGATCATGTAGATCGAACGGACTCTAAATCCGTTCAGCCGGGTTAGATCCCGGGGTTCCG
2.MmPylt U25C Opt GGAAACCTGATCATGTAGATCGAACGGACTCTAAATCCGTTCAGTGGGGTTAGATCCCCACCTTCCG
```

USE OF ERF1 MUTANTS IN UNNATURAL AMINO ACID INCORPORATION

CROSS-REFERENCE TO RELATED APPLICATIONS

This application is a national stage under 35 U.S.C. 371 of International Application PCT/GB2015/053141, filed on Oct. 21, 2015 (currently published). International Application PCT/GB2015/053141 cites the priority of Great Britain Patent Application No. 1419109.2, filed Oct. 27, 2014 (expired).

FIELD OF THE INVENTION

The present invention is in the general field of protein expression, in particular the incorporation of an unnatural amino acid(s) into a protein of interest.

BACKGROUND TO THE INVENTION

Genetic code expansion has allowed the site-specific incorporation of more than a hundred unnatural amino acids into proteins. However, the utility of these approaches may be limited by the efficiency with which unnatural amino acids are incorporated into proteins. The efficient, co-translational, site-specific incorporation of unnatural amino acids into proteins will enable emerging approaches for creating site-specifically modified recombinant proteins (1, 2), as well as strategies to precisely control and image protein function in vivo (3, 4), and many other approaches in which designer unnatural amino acids are used to control or report on protein function.

Orthogonal tRNA synthetase/tRNA pairs direct the incorporation of unnatural amino acids, most commonly in response to the amber stop codon (UAG). The efficiency of unnatural amino acid incorporation is defined both by i) the intrinsic efficiency with which the orthogonal synthetase/tRNA pair enables translational elongation in response to a UAG codon in the A site of the ribosome, and ii) the efficiency with which release factors compete with the aminoacylated orthogonal $tRNA_{CUA}$ to terminate protein synthesis. The pyrrolyl-tRNA synthetase (PylRS)/$tRNA_{CUA}$ pair is arguably the most useful pair to be developed for genetic code expansion because i) it is orthogonal in a range of hosts including E. coli, yeast, mammalian cells, C. degans and D. melanogaster, ii) PylRS does not recognize the common 20 amino acids, iii) PylRS does not recognize the anticodon of its cognate $tRNA_{CUA}$, iv) the active site of PylRS accommodates a range of unnatural amino acids bearing useful functional groups without the need for directed evolution, v) the active site of PylRS can be evolved to recognize structurally diverse unnatural amino acids bearing a range of useful functional groups in E. coli and vi) the synthetase variants discovered in E. coli may be used in diverse eukaryotic hosts, where directed evolution of synthetases is challenging to implement (5).

Unnatural amino acid incorporation is currently less efficient in eukaryotic cells than in E. coli. The efficient, site-specific introduction of unnatural amino acids into proteins in eukaryotic cells is an outstanding challenge in realizing the potential of genetic code expansion approaches. Addressing this challenge will allow the synthesis of modified recombinant proteins in eukaryotic cells and augment emerging strategies that introduce new chemical functionalities into proteins to control and image their function with high spatial and temporal precision in eukaryotic cells.

The present invention seeks to address this need.

SUMMARY OF THE INVENTION

The present inventors have developed an expression system based on orthogonal synthetase/tRNA pairs for efficiently incorporating one or more unnatural amino acids into a protein of interest expressed in a eukaryotic cell—such as a mammalian cell or an insect cell. Advantageously, the expression system described herein increases the efficiency of unnatural amino acid incorporation in such cells.

In addition, the present inventors have engineered eRF1—that normally terminates translation on all three stop codons in mammalian cells—to provide a substantial increase in unnatural amino acid incorporation in response to the TAG codon without increasing read-through of other stop codons. The data presented herein provide the first demonstration that—despite native eRF1 recognizing all three stop codons—it is possible to engineer eRF1 to selectively enhance the efficiency of unnatural amino acid incorporation in eukaryotic cells in response to the amber stop codon, without increasing read through of opal or ochre stop codons.

Release factors exist in prokaryotic systems—such as E. coli expression systems. Temperature sensitive release factors—such as tsRF1 have been studied for the transient increase of amber suppression in prokaryotic expression systems. The interaction of bacterial RF1 with rRNA has been pinpointed to the 530 loop of rRNA in prokaryotic systems. For example, WO 2008/065398 makes mention of this interaction at page 4, lines 31 to 35. However, there is no crossover from the E. coli system to eukaryotic systems which are the subject of the invention. There is no direct analogy between the prokaryotic and eukaryotic proteins apart from their names.

It is not possible to transfer mutants from the very different bacterial proteins to eukaryotic proteins which are the subject of the present invention. In the prokaryotic system, different RF proteins carry out different biological functions compared to eukaryotic systems there is a "split function" arrangement having a very different biology. By contrast, in eukaryotic systems a single eRF1 protein provides multiple termination functions. Therefore, the mammalian eRF1 protein can be considered to be technically very different from the release factor proteins in prokaryotic systems. Thus, strategies developed in E. coli to enhance unnatural amino acid incorporation in response to the amber codon through selective disruption of RF1 function (12-16) cannot be extended to the eukaryotic system. Certain eRF1 mutants are known in the art. These mutants have been described purely in the course attempting to study eRF1 function. The disclosures focus on academic studies of eRF1 biology. In contrast, the present inventors teach for the first time the use of certain eRF7 mutants in incorporation of unnatural amino acids into proteins. Indeed, there are no known reports of engineering the eukaryotic translational machinery to enhance the efficiency with which unnatural amino acids are site-specifically incorporated into proteins in eukaryotic cells using orthogonal tRNA synthetase/tRNA pairs. The inventors are the first to realise the utility of the eRF1 mutants in the context of amber codon expression systems.

It is therefore an advantage of the present invention that the inventors teach for the first time enhanced suppression of amber codons by use of eRF1 mutants. It is therefore an advantage of the present invention that the inventors teach for the first time use of eRF1 mutants in enhanced suppression of amber codons.

Advantageously, by combining the improved expression system with the engineered eRF1, the yield of protein bearing a single unnatural amino acid is increased 17- to 20-fold. Proteins can be produced containing unnatural amino acids with comparable yields to proteins produced from a gene that does not contain a stop codon. Moreover the improved system increases the yield of protein, incorporating an unnatural amino acid at multiple sites (for example, 3 or more sites) from unmeasurably low levels up to 43% of a no amber stop control. This approach may enable the efficient production of site-specifically modified therapeutic proteins, and the quantitative replacement of targeted cellular proteins with versions bearing unnatural amino acids that allow imaging or synthetic regulation of protein function.

Advantageously, the present disclosure may enable the efficient production of site-specifically modified therapeutic proteins in eukaryotic cells, as well as the quantitative replacement of targeted cellular proteins with versions bearing unnatural amino acids that allow imaging or synthetic regulation of protein function.

Thus in one aspect the invention provides a method for incorporating an unnatural amino acid into a protein of interest in a eukaryotic cell, said method comprising the steps of:

i) providing a eukaryotic cell expressing an orthogonal tRNA synthetase-tRNA pair, a nucleic acid sequence of interest encoding said protein of interest, and a mutant eRF1, said mutant eRF1 having amino acid sequence having at least 67% sequence identity to the human wild type eRF1 sequence of SEQ ID NO: 4, said nucleic acid sequence of interest comprising a codon recognised by the tRNA at the position for incorporation of an unnatural amino acid;

ii) incubating the eukaryotic cell in the presence of an unnatural amino acid to be incorporated into a protein encoded by the nucleic acid sequence of interest, wherein said unnatural amino acid is a substrate for the orthogonal tRNA synthetase; and iii) incubating the eukaryotic cell to allow incorporation of said unnatural amino acid into the protein of interest via the orthogonal tRNA synthetase-tRNA pair.

In one aspect, the invention relates to use of a mutant eRF1, said mutant eRF1 having amino acid sequence having at least 60%, more suitably 67%, sequence identity to the human wild type eRF1 sequence of SEQ ID NO: 4, for incorporating an unnatural amino acid into a protein of interest in a eukaryotic cell.

In one aspect, the invention relates to a mutant eRF1 polypeptide, said mutant eRF1 having amino acid sequence having at least 60%, more suitably 67%, sequence identity to the human wild type eRF1 sequence of SEQ ID NO: 4, or a nucleic acid encoding same, for use in aiding incorporation of an unnatural amino acid into a polypeptide of interest by translation of nucleic acid encoding said polypeptide of interest, said nucleic acid comprising an orthogonal codon directing incorporation of said unnatural amino acid into said polypeptide of interest.

In one aspect, the invention relates to a eukaryotic host cell comprising the mutant eRF1 polypeptide or nucleic acid as described above.

In one aspect, the invention relates to a eukaryotic host cell comprising
(i) an orthogonal tRNA synthetase-tRNA pair, and
(ii) a mutant eRF1, said mutant eRF1 having amino acid sequence having at least 60%, more suitably 67%, sequence identity to the human wild type eRF1 sequence of SEQ ID NO: 4, and optionally
(iii) a nucleic acid sequence of interest encoding a protein of interest, said nucleic acid sequence of interest comprising a codon recognised by the tRNA at a position for incorporation of an unnatural amino acid.

In one aspect, the invention relates to a combination or kit comprising nucleic acid(s) encoding:
(i) CO an orthogonal tRNA synthetase tRNA pair, and
(ii) a mutant eRF1, said mutant eRF1 having amino acid sequence having at least 60%, more suitably 67%, sequence identity to the human wild type eRF1 sequence of SEQ ID NO: 4, and optionally
(iii) a nucleic acid sequence of interest encoding a protein of interest, said nucleic acid sequence of interest comprising a codon recognised by the tRNA at a position for incorporation of an unnatural amino acid.

In one aspect, the invention relates to a eukaryotic host cell as described above or a combination or kit as described above, further comprising an unnatural amino acid such as BocK or CypK or BCNK; more suitably BocK or CypK.

Suitably said mutant eRF1 provides increased efficiency of unnatural amino acid incorporation relative to a wild type eRF1 control.

Suitably said mutant eRF1 comprises a mutation or combination of mutations relative to SEQ ID NO: 4 selected from the group consisting of
(i) E55
(ii) N129, K130
(iii) T122, S123
(iv) Y125
(v) T58, S60, S64, L125, N129
(vi) S123, L124, Y125
(vii) S123, L124, Y125
(viii) S123, L124, Y125
(ix) M51K130
(x) S123, L124, Y125
(xi) S123, L124, Y125
(xii) S123, L124, Y125
(xiii) S123, L124, Y125

Suitably said mutant eRF1 comprises a mutation or combination of mutations relative to SEQ ID NO: 4 selected from the group consisting of
(i) E55D
(ii) N129P, K130Q
(iii) T122Q, S123F
(iv) E55A
(v) Y125F
(vi) T58K, S60T, S64D, L125F, N129S
(vii) S123A, L124I, Y125L
(viii) S123R, L124W, Y125R
(ix) S123H, L124A, Y125G
(x) M51A, K130M
(xi) S123A, L124L, Y125V
(xii) S123L, L124C, Y125S
(xiii) S123L, L124S, Y125S
(xiv) S123V, L124T, Y125P Suitably said eukaryotic cell is a mammalian or insect cell.

Suitably said codon is a stop codon. More suitably said stop codon is UAG.

Suitably the orthogonal tRNA synthetase-tRNA pair comprises a pyrrolysyl-tRNA synthetase (PylRS)/PylT tRNA$_{CUA}$ pair.

Suitably the tRNA is:
(i) a U25C variant of PylT, or
(ii) an Opt variant of PylT, or
(iii) a U25C-Opt variant of PylT.

Further Aspects and Embodiments of the Invention

In a first aspect, there is provided a nucleic acid construct for expressing a tRNA synthetase and tRNA pair in a eukaryotic cell such as a mammalian cell or an insect cell comprising: (i) a nucleic acid sequence encoding the tRNA synthetase operably linked to a first promoter capable of expressing the tRNA synthetase; and (ii) a nucleic acid sequence encoding the tRNA operably linked to a second promoter capable of expressing the tRNA, wherein the first and second promoters are in opposite directions to each other, or wherein the tRNA is present in multiple copies on the nucleic acid construct. An exemplary nucleotide sequence encoding this construct is set forth in SEQ ID NO:1.

Suitably, the nucleic acid construct can further comprise a nucleic acid sequence encoding a nucleic acid sequence of interest operably linked to a further promoter capable of expressing the nucleic acid sequence of interest in a eukaryotic cell.

Suitably, the promoter that is capable of expressing the nucleic acid sequence of interest is oriented in the same direction as the first promoter according to the first aspect recited above.

Suitably, the promoter that is capable of expressing the nucleic acid sequence of interest is the same as the first promoter or different to the first promoter. In one embodiment, this promoter is or is derived from an EF-1 promoter as described herein or is or is derived from a CMV promoter.

Suitably, the nucleic acid construct further comprises a nucleic acid sequence encoding a mutant eRF1 as described herein. In one embodiment, the eRF1 mutant is expressed from a CMV promoter downstream 3') of the first Pol II open reading frame expressing the tRNA synthetase.

Suitably, the nucleic acid sequence encoding the mutant eRF1 and the nucleic acid sequence encoding the tRNA synthetase are linked via a self-cleaving peptide in the same open reading frame. Suitably, the nucleic acid sequence encoding the tRNA synthetase and the nucleic acid sequence encoding mutant eRF1 are linked via a self-cleaving peptide in the same open reading frame. An exemplary T2A self-cleaving peptide is described in *PLoS ONE* 6(4) (2011).

In a second aspect, there is provided a nucleic acid construct for expressing a tRNA and a nucleic acid sequence of interest in a eukaryotic cell—such as a mammalian cell or an insect cell, said nucleic acid sequence of interest comprising a codon recognised by the tRNA at the position for incorporation of an unnatural amino acid comprising: (i) a nucleic acid sequence comprising the nucleic acid sequence of interest operably linked to a first promoter capable of expressing the nucleic acid sequence of interest in a eukaryotic cell; and (ii) a nucleic acid sequence encoding the tRNA operably linked to a second promoter capable of expressing the tRNA, wherein the first and second promoters are in opposite directions to each other, or wherein the tRNA is present in multiple copies on the nucleic acid construct. An exemplary nucleotide sequence encoding this construct is set forth in SEQ ID NO:2.

Suitably, the construct comprises a nucleic acid sequence encoding a mutant eRF1, suitably a mutant mammalian eRF1, suitably a mutant *home sapiens* eRF1, suitably, wherein the mutant eRF1 is selected from the group consisting of E55D, E55A, N129P/K130Q and Y125F or a combination of two or more thereof.

Suitably, the first and second promoters are in opposite directions to each other and the tRNA is present in multiple copies on the nucleic acid construct.

Suitably, the nucleic acid construct comprises the tRNA linked directly to the promoter. According to this embodiment, the tRNA is linked directly to the promoter without any intermediate sequences located between the tRNA and the promoter.

Suitably, the nucleic acid construct comprises the tRNA linked directly to the promoter. According to this embodiment, the tRNA is linked directly to the promoter with no intermediate sequence(s) located between the tRNA and the promoter. The 3' end of the tRNA can be linked indirectly to a terminator sequence. By way of example, a terminator sequence (for example, TTTTT) can be connected to the tRNA via a linker, said linker optionally comprising the sequence GACAAGTGCGG.

Suitably, each copy of the nucleic acid sequence encoding the tRNA is under the control of a separate (its own) promoter.

Suitably, the promoter arrangement comprises an elongation factor promoter oriented in a first direction and a Pol III promoter oriented in a second direction.

Suitably, the first promoter is or is derived from an EF-1 promoter.

Suitably, the second promoter is or is derived from a U6 promoter.

Suitably, the tRNA is present in 4, 5, 6, 7 or 8 or more copies on the nucleic acid construct(s).

Suitably, the tRNA is a wild-type or a variant tRNA, suitably a U25C variant of PylT.

Suitably, the nucleic acid sequence of interest comprises at least 1, 2, 3 or 4 or more stop codons, suitably, at least 1, 2 or 3 codons.

Suitably, the nucleic acid sequence of interest encodes an antibody or an antibody fragment.

Suitably, said tRNA synthetase is orthogonal to the endogenous tRNAs in the eukaryotic cell and/or said tRNA is orthogonal to the endogenous tRNA synthetases in the eukaryotic cell and/or said tRNA synthetase is orthogonal to the endogenous tRNAs in the eukaryotic cell and said tRNA is orthogonal to the endogenous tRNA synthetases. In a further aspect, there is provided a combination of nucleic acid constructs comprising the nucleic acid construct according to the first aspect and the nucleic acid construct according to the second aspect.

In a further aspect, there is provided a combination of nucleic acid constructs comprising the nucleic acid construct according to the first aspect of the invention and the nucleic acid construct according to the second aspect of the invention.

Suitably, the nucleic acid sequence encoding the mutant eRF1 is on a further separate construct.

In a further aspect, there is provided a vector comprising the nucleic acid construct according to the first aspect of the present invention or the nucleic acid construct according to the second aspect of the present invention.

In a further aspect, there is provided a combination of vectors comprising a vector comprising the nucleic acid construct according to the first aspect of the present invention and the nucleic acid construct according to the second aspect of the present invention.

Suitably, the nucleic acid sequence encoding the mutant eRF1 is on a further separate vector.

In a further aspect, there is provided a cell comprising the nucleic acid construct according to the first aspect of the present invention or the nucleic acid construct according to the second aspect of the present invention, the combination of nucleic acid constructs, the vector or the combination of vectors.

Suitably, the cell further comprises a nucleic acid construct encoding a mutant eRF1, suitably a mutant *Homo sapiens* eRF1. Suitably, the nucleic acid sequence encoding the mutant eRF1 is on a separate construct or vector.

Suitably, the mutant eRF1 is selected from the group consisting of E55D, E55A, N129P/K130Q and Y125F or a combination of two or more thereof, suitably, where in the mutations are made in the *Homo sapiens* eRF1 gene sequence as described in GenBank Accession Number AF095901.1. In one embodiment, the mutations are made in a codon optimised *Homo sapiens* eRF1 gene sequence. An example of a codon optimised *Homo sapiens* eRF1 gene sequence is set forth in SEQ ID NO:3

Suitably, the cell is a mammalian cell or an insect cell.

Suitably, the cell is transiently or stably transfected with the nucleic acid.

In a further aspect, there is provided a kit for incorporating an unnatural amino acid into a protein in a eukaryotic cell—such as a mammalian cell or an insect cell comprising: (i) the nucleic acid construct according to the first or second aspect of the present invention; or (ii) the combination of nucleic acid constructs; or (iii) the vector; or (iv) the combination of vectors; or (v) the eukaryotic cell; and (vi) optionally, an unnatural amino acid.

Suitably, the kit further comprises a nucleic acid construct or a vector encoding a mutant eRF1, or a cell comprising same.

In a further aspect, there is provided a method for incorporating an unnatural amino acid into a protein of interest in a eukaryotic cell—such as a mammalian cell or an insect cell comprising the steps of: i) providing the cell, wherein said cell comprises the combination of nucleic acid constructs or the combination of vectors as described herein; ii) incubating the cell in the presence of the unnatural amino acid to be incorporated into a protein of interest encoded by the nucleic acid sequence of interest, wherein said unnatural amino acid is a substrate for the tRNA synthetase; and iii) incubating the cell to allow incorporation of said unnatural amino acid into the protein of interest via the orthogonal tRNA-tRNA synthetase pair.

Suitably, at least 1, 2, 3, 4, or 5 unnatural amino acids are incorporated into the protein of interest.

In a further aspect, there is provided a method of preparing an antibody-drug conjugate comprising the steps of: i) providing a eukaryotic cell—such as a mammalian cell or an insect cell, wherein the nucleic acid sequence of interest encodes an antibody or an antibody fragment, and wherein said cell comprises the combination of nucleic acid constructs or the combination of vectors described herein, and ii) incubating the cell in the presence of the unnatural amino acid to be incorporated into the antibody or antibody fragment, wherein said unnatural amino acid is a substrate for the tRNA synthetase; iii) obtaining an antibody or antibody fragment in which an unnatural amino acid has been incorporated therein; and vi) conjugating the antibody or antibody fragment with a drug moiety via the unnatural amino acid.

In a further aspect, there is provided the use of: (i) the nucleic acid construct according to the first or second aspects of the present invention; and/or (ii) the combination of nucleic acid constructs; and/or (iii) the vector; and/or (iv) the combination of vectors; and/or (v) the eukaryotic cell—such as a mammalian cell or an insect cell, for incorporating an unnatural amino acid into a protein of interest in a eukaryotic cell.

In a further aspect, there is provided a method for incorporating an unnatural amino acid into a protein of interest in a eukaryotic cell—such as a mammalian cell or an insect cell comprising the steps of: i) providing a eukaryotic cell expressing a tRNA synthetase and tRNA pair, a nucleic acid sequence of interest and a mutant eRF1; ii) incubating the cell in the presence of an unnatural amino acid to be incorporated into a protein encoded by the nucleic acid sequence of interest, wherein said unnatural amino acid is a substrate for the tRNA synthetase; and iii) incubating the cell to allow incorporation of said unnatural amino acid into the protein of interest via the orthogonal tRNA-tRNA synthetase pair.

In a further aspect, there is provided the use of a mutant eRF1 for incorporating an unnatural amino acid into a protein of interest in a eukaryotic cell—such as a mammalian cell or an insect cell.

In a further aspect, there is provided a method of identifying a mutant of eRF1 that increases the incorporation of an unnatural amino acid in a protein of interest, comprising the steps of: (i) providing a cell that is capable in incorporating an unnatural amino into a protein of interest, suitably, wherein said cell comprises the combination of nucleic acid constructs or the combination of vectors described herein; (ii) incubating the cell in the presence of the unnatural amino acid to be incorporated into the protein of interest and in the presence and absence of the mutant of eRF1, wherein said unnatural amino acid is a substrate for the tRNA synthetase; and (iii) determining the level of unnatural amino acid incorporation into the protein of interest in the presence and absence of the mutant of eRF1, wherein an increase in the level of unnatural amino acid incorporation into the protein of interest in the presence the mutant of eRF1 is indicative that said mutant of eRF1 increases the incorporation of an unnatural amino acid in the protein of interest.

In a further aspect, there is provided a construct, vector, cell, kit, method or use substantially as described herein with reference to the accompanying description and drawings.

DESCRIPTION OF THE DRAWINGS

Embodiments of the present invention will now be described further, with reference to the accompanying drawings, in which:

FIGS. 1A-1C illustrates optimizing PylRS/tRNA$_{CUA}$ expression vectors for the incorporation of unnatural amino acids in response to the TAG codon in mammalian cells. (FIG. 1A) Quantification of incorporation of 1 (2 mM) and 2 (0.5 mM) into sfGFP measured in a fluorescence assay. The indicated constructs were expressed transiently in HEK293T cells and sfGFP quantified in lysates by fluorescence at 520 nm, following excitation at 485 nm. A no amino acid control is included for each vector combination. The data are plotted as a percentage of the fluorescence exhibited by an equivalent sfGFP control plasmid with a leucine codon in place of a stop codon (construct a in FIG. 22A). Data represent the mean±SE of triplicates). (FIG. 1B) sfGFP yields in lysate visualized by western blot. Equal amounts of cell lysate from cells transfected with the indicated vectors and grown in the presence of the indicated amino acid, or no amino acid, were immunoblotted with α-GFP, α-actin and α-FLAG antibodies. (FIG. 1C) Northern blot analysis of relative PylT/PylT* expression from constructs b+c, b+d, b+e, g+h, in the absence of amino acid. See FIG. 8 for loading control.

FIGS. 2A-2E illustrates the effect of mutations in eRF1 on stop codon read-through, and incorporation of 1 (2 mM) using the PylRS/tRNA$_{CUA}$ pair. (FIG. 2A) eRF1 positions mutated in this study. Structure of the N-terminal domain from eRF1 (PDB ID:3E1Y)[29], the residues mutated in this study are in red. (FIG. 2B) Human eRF1 variants are expressed following transient transfection of HEK 293T cells with peRF1 (X), where X designates the mutations introduced, and CMV-PylRS/CMV-DLR(TAG). The negative control (−) detects endogenous eRF1, shRNA is a knockdown of endogenous eRF1. (FIG. 2C) Read-through of all three stop codons is determined by the expression of a Ronilla-TAG-firefly luciferase reporter and eRF1 variants in HEK293T cells in the absence of a suppressor tRNA. CMV-PylRS/CMV-DLR(TAG) (or the corresponding TAA, TGA or serine codon variant) were transiently transfected into cells and expression levels determined after 20 hours. TAG, TAA, or TGA readthrough was normalized against data from the serine codon (TCC) containing construct. Data represents the mean±SE of quadruplet measurements. The negative control (−) detects endogenous eRF1, shRNA is a knockdown of endogenous eRF1. Wt is human eRF1 recoiled with *D. melanogaster* codon useage. Data for the Δ100 mutant are off scale, the values are: 1.6% (TAA), 2% (TAG) and 15% (TGA). (FIG. 2D) Transient transfection of HEK 293T cells with peRF1 (X), where X designates the mutations introduced, plasmid C expressing PylT from a U6 promoter (FIG. 22A) and CMV-PylRS/CMV-Renilla-TAG-firefly, a version of plasmid a (FIG. 22A) in which sfGFP is replaced by Renilla-TAG-firefly. The negative control (−) detects endogenous eRF1, shRNA is a knockdown of endogenous eRF1. Equal amounts of cell lysate were immunoblotted with α-eRF1 and α-actin antibodies. (FIG. 2E) eRF1 (X) variants increase unnatural amino acid incorporation in response to an amber stop codon using the Pyrolysyl tRNA/synthetase pair. HEK293T cells were transfected as described for panel d, and grown in the presence of 1 mM amino acid 1, and measurements made after 20 h. % readthrough was measured relative to a Renilla-TCC-firefly reporter bearing a serine codon in place of the amber stop codon.

(FIG. 3A) Plasmids g, h (or i, FIG. 22A) and eRF1 E55D were transiently transfected into HEK293T cells, and grown in the presence or absence of 2 mM amino acid 1 for 48 hours. Full-length sfGFP was quantified in cell lysate at 520 nm, following excitation at 485 nm. Data represents the mean±SE of four independent measurements. (FIG. 3B) Western blots from lysates. (FIG. 3C) As in panel a, but using 0.5 mM amino acid 2. (FIG. 3D) Western blots from lysates.

(FIG. 4B) Electrospray ionization mass spectrometry confirms the quantitative incorporation of unnatural amino acids 1 and 2, at one or three sites in sfGFP (see also FIGS. 11A-11B).

FIG. 5A Plasmids g and h or i according to FIG. 1A were transiently transfected into T-Rex293 cells containing genomic integrated eRF1 E55D with *D. melanogaster* codon usage. Cells were grown in the presence or absence of 0.5 mM amino acid 2 for 48 hours. Expression of eRF1 E55D was induced by the addition of 1 µg/ml tetracycline sixteen hours prior to transfection. Certified tetracycline-free growth media was used throughout all experiments. Full-length sfGFP was quantified in cell lysate at 520 nm, following excitation at 485 nm. Data represents the mean±SE of 4 independent measurements.

FIG. 5B Western blots from lysates, as shown in FIG. 5A. Equal amounts of cell lysates were loaded. Stable lines constitutively expressing shRNAs against endogenous eRF1 were created by transforming T-Rex293 Flp-in lines with inserted eRF1 wt or E55D with lentiviral shRNA(eRF1) constructs (Santa Cruz, as in FIGS. 3A-3D), and puromycin selection against naïve cells. eRF1 wt and E55D were refractory to shRNA(eRF1) due to a lack of sequences complementary to the shRNA after *D. melanogaster* codon optimization.

FIG. 5C sfGFP(TAG) was expressed following transient transfection of constructs g and h (FIGS. 1A-1C) for 48 hours in the presence or absence of 2, and with the addition of 1 µg/ml tetracycline in the growth media, to induce expression of the release factor variant. Full-length sfGFP was quantified in cell lysate at 520 nm, following excitation at 485 nm. Data represents the mean±SE of four independent measurements FIG. 5D. As FIG. 5C, but expressing sfGFP(TAG)$_3$.

FIG. 6A. Human eRF1 variants (recoded with *D. melanogaster* codon usage) are expressed following transient transfection of Dmel cells with peRF1 (X), where X designates the mutations introduced, and UAS-PylRS/UAS-GFP-(TAG)-mCherry/(U6-PylT)$_4$. The no stop control serves as a size marker for full length protein, the negative control (−) establishes baseline suppression efficiency in the presence of endogenous eRF1 and the negative control without 2 indicates the level of readthrough in the absence of 1. Cells were transfected and grown for 48 hours. Readthrough is quantified from blots immunostained against GFP under non-saturated exposure conditions, by calculating the ratio of the intensity of the band representing full length product over truncated product. Each bar represents the mean±SE of three independent transfection and quantification experiments.

FIG. 6B. Expression levels of proteins in lysates visualized by western blot. Equal amounts of cell lysate from cells transfected with the indicated vectors and grown in the presence of 1 mM amino acid 1, or no amino acid, were immunostained with α-GFP, α-eRF1 and α-HA antibodies, as described for FIG. 6A. The α-GFP blot shown was exposed for thirty seconds to show distinct bands for the full length product in print. The corresponding exposures of the blot used for the quantification was exposed for five seconds and displays no saturation, as well as the additional replicates.

FIG. 6C. Constructs used for transient transfections.

FIG. 17 shows sequences of PylT U25C and PylT U25C Opt variants

FIG. 22A shows schematics of vectors used. PylT is the gene encoding Pyl tRNA$_{CUA}$ and PylT* encodes the U25C varient. U6 indicates the U6 promoter, CMV is the CMV promoter, CMV enh is the 5'enhancer fragment of CMA promoter, EF$_1$ prom is the EF-1αpromoter. Red bars indicate location of ambver stop codons. FIG. 22B shows chemical structure of 1 (N$^ε$-[(tert-butoxy)carbonyl]-1-lysine) and 2 (N$^ε$- [((2-methylcyclo-prop-2-en-1 yl)methoxy)carbonyl]-1-lysine).

DETAILED DESCRIPTION

Constructs and Vectors

Figure 2E:
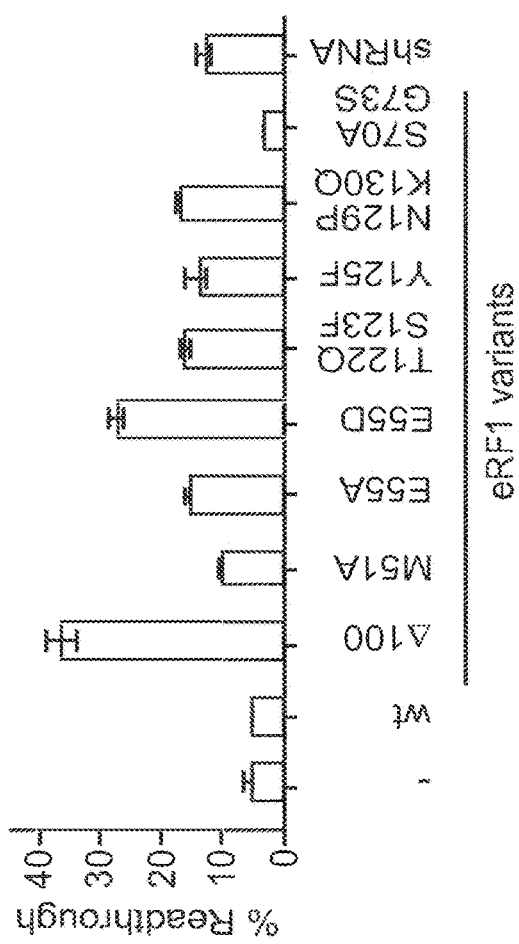

As used herein, the term "construct" or "vector" refers generally to a nucleic acid capable of transporting a nucleic acid sequence of interest to which it has been linked.

One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (for example, bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

Nucleic acid sequences of interest can be incorporated into a construct or a vector such as an expression vector. The vector may be used to replicate the nucleic acid in a compatible host cell. The vector may be recovered from the host cell.

The vector may be an expression vector that is used to express the nucleic acid sequence of interest in a compatible host cell—such as a eukaryotic cell—such as a mammalian cell or an insect cell. Suitably, the nucleic acid sequence of interest is operably linked to a control sequence—such as a promoter or an enhancer—that is capable of providing for the expression of the nucleic acid sequence of interest in the host cell. The term "operably linked" means that the components described are in a relationship permitting them to function in their intended manner. A regulatory sequence "operably linked" to a nucleic acid sequence of interest is ligated in such a way that expression of the nucleic acid sequence of interest is achieved under conditions compatible with the control sequences.

Vectors may be transformed or transfected into a suitable host cell to provide for the expression of a protein. This process may comprise culturing a host cell transformed with an expression vector under conditions to provide for expression by the vector of a nucleic acid sequence of interest encoding the protein, and optionally recovering the expressed protein.

The vectors may be for example, plasmid or virus vectors provided with an origin of replication, optionally a promoter for the expression of the nucleic acid sequence of interest and optionally a regulator of the promoter. The vectors may contain one or more selectable marker genes, for example an ampicillin resistance gene in the case of a bacterial plasmid.

In one aspect, there is provided a nucleic acid construct for expressing a tRNA synthetase and tRNA pair in a eukaryotic cell comprising: (i) a nucleic acid sequence encoding the tRNA synthetase operably linked to a first promoter capable of expressing the tRNA synthetase; and (ii) a nucleic acid sequence encoding the tRNA operably linked to a second promoter capable of expressing the tRNA, wherein the first and second promoters are in opposite directions to each other, or wherein the tRNA is present in multiple copies on the nucleic acid construct.

In another aspect, there is provided a nucleic acid construct for expressing a tRNA and a nucleic acid sequence of interest in a eukaryotic cell, said nucleic acid sequence of interest comprising a codon recognised by the tRNA at the position for incorporation of an unnatural amino acid comprising: (i) a nucleic acid sequence comprising the nucleic acid sequence of interest operably linked to a first promoter capable of expressing the nucleic acid sequence of interest in the cell; and (ii) a nucleic acid sequence encoding the tRNA operably linked to a second promoter capable of expressing the tRNA, wherein the first and second promoters are in opposite directions to each other, or wherein the tRNA is present in multiple copies on the nucleic acid construct.

In another aspect, there is also provided a combination of nucleic acid constructs comprising each of the nucleic acid constructs described above.

In another aspect, there is also provided a vector comprising or separately comprising each the nucleic acid constructs described above.

In another aspect, there is also provided a combination of vectors comprising a vector separately comprising each of the nucleic acid constructs described above.

In certain embodiments, the first and second promoters in the nucleic acid constructs are separate promoters that are placed in opposite directions. According to this embodiment, the first and second promoters can be said to be bidirectional promoters in which each of the promoters are coded on opposite strands with their 5' ends oriented toward one another. Each of the nucleic acids operably linked to the promoters will have a corresponding orientation. Thus, for example, the promoter and the tRNA sequence to be expressed can be encoded on the reverse strand. The promoter and the tRNA synthetase gene to be expressed can be encoded on the forward strand. By way of further example, the U6 promoter and the tRNA sequence to be expressed can be encoded on the reverse strand. By way of further example, the EF-1a promoter and the tRNA synthetase gene to be expressed can be encoded on the forward strand.

In addition to the first and second promoters, one or more further promoters may also be included, which may be the same promoter as the first and/or second promoters or may be different to the first and/or second promoters. The further promoter(s) can be oriented in the same direction as the first or second promoter. Suitably, the further promoter(s) is oriented in the same direction as the first promoter.

Suitably, the construct described herein further comprise a nucleic acid sequence encoding a mutant eRF7 as described herein. The promoter expressing the mutant eRF1 can be oriented in the same direction as the first or second promoter. Suitably, the promoter is oriented in the same direction as the first promoter.

Suitably, the nucleic acid sequence encoding the mutant eRF1 and the nucleic acid sequence encoding the tRNA synthetase are linked via a self-cleaving peptide in the same open reading frame. Suitably, the nucleic acid sequence encoding the tRNA synthetase and the nucleic acid sequence encoding mutant eRF1 are linked via a self-cleaving peptide in the same open reading frame. An exemplary T2A self-cleaving peptide is described in *PLoS ONE* 6(4) (2011).

Suitably, the constructs provide a multi-copy tRNA arrangement. Suitably at least 2, 3, 4, 5, 6, 7, 8, 9, 10, 11 or 12 copies of the tRNA gene are provided in the constructs described herein. Suitably at least 4 copies of the tRNA gene are provided in a construct. Suitably at least 8 copies of the tRNA gene are provided in a construct. The multiple copies of the tRNA gene may be provided on the same or a different construct.

In one embodiment, at least 4 copies of the tRNA gene are provided on a first construct and at least 4 copies of the tRNA gene are provided on a second construct.

In one embodiment, multiple copies of the tRNA gene are under the control of a single promoter. In another embodiment, multiple copies of the tRNA gene are under the control of multiple different promoters. In another embodiment, each copy of the tRNA gene is under the control of a separate promoter, which may be the same promoter or two or more different promoters. In another embodiment, each copy of the tRNA gene is under the control of multiple promoters, which may be the same promoter or two or more different promoters. Suitably, each tRNA gene is under the control of a separate promoter, which is the same promoter for each tRNA gene. Suitably, the promoter or promoters controlling each of the tRNA gene(s) provided is the same. In this context by "same" is meant the same in terms of its sequence rather than implying a single promoter sequence controlling multiple tRNA sequences. Clearly, there may be multiple copies of the same promoter as described herein.

In one embodiment, a multi-copy tRNA arrangement is provided in which at least 4 copies of the tRNA are provided, with each copy operably linked to a promoter.

In another embodiment, a multi-copy tRNA arrangement is provided in which at least 4 copies of the tRNA are provided, with each copy operably linked to a promoter, each promoter being the same promoter—such as a RNA pol III promoter, for example a U6 promoter.

In one embodiment, the 5' end of the tRNA is directly defined by the transcription start site of the promoter that is used to express the tRNA.

It should be noted that the nucleotide constructs provided herein have broad application and may be used in opal and/or ochre suppression as well as in amber suppression. When applying the nucleic acid constructs of the invention to amber/opal/ochre suppression, the skilled operator will choose the appropriate tRNAs and/or tRNA synthetases accordingly together with the appropriate amber/opal/ochre codon.

Combinations of Constructs and Vectors

Combinations of the constructs and vectors described herein are contemplated for use in incorporating one or more unnatural amino acids into a cell.

By way of example, a combination of constructs comprising: (1) the nucleic acid construct comprising: (i) a nucleic acid sequence encoding the tRNA synthetase operably linked to a first promoter capable of expressing the tRNA synthetase; and (ii) a nucleic acid sequence encoding the tRNA operably linked to a second promoter capable of expressing the tRNA, wherein the first and second promoters are in opposite directions to each other, or wherein the tRNA is present in multiple copies on the nucleic acid construct; and (2) the nucleic acid construct comprising: (i) a nucleic acid sequence comprising the nucleic acid sequence of interest operably linked to a first promoter capable of expressing the nucleic acid sequence of interest in a eukaryotic cell; and (ii) a nucleic acid sequence encoding the tRNA operably linked to a second promoter capable of expressing the tRNA, wherein the first and second promoters are in opposite directions to each other, or wherein the tRNA is present in multiple copies on the nucleic acid construct.

In one embodiment, the nucleic sequence of interest from construct (1) noted above further comprises a nucleic acid sequence encoding a nucleic acid sequence of interest operably linked to a further promoter capable of expressing the nucleic acid sequence of interest in a eukaryotic cell. According to this embodiment, construct (1) does not necessarily have to be used together with construct (2) because the nucleic acid sequence of interest and the tRNA from construct (2) is incorporated into construct (1). According to this embodiment, it may be desirable to include one or more further copies of tRNA on another vector. This other vector may exclusively comprise the tRNA(s) under the control of one or more promoters. Optionally other elements may be incorporated into this other vector as desired.

The combination of constructs comprising: (1) and (2) as noted above can be used together with a further construct encoding a mutant eRF1 as described herein.

Alternatively, the nucleic acid sequence encoding the mutant eRF1 can be incorporated into the constructs (1) and/or (2). Suitably, the nucleic acid sequence encoding the mutant eRIF1 is incorporated into construct (1). According to this embodiment, there is disclosed a nucleic acid construct comprising: (i) a nucleic acid sequence encoding the tRNA synthetase operably linked to a first promoter capable of expressing the tRNA synthetase; and (ii) a nucleic acid sequence encoding the tRNA operably linked to a second promoter capable of expressing the tRNA wherein the first and second promoters are in opposite directions to each other, or wherein the tRNA is present in multiple copies on the nucleic acid construct; optionally (iii) a nucleic acid sequence encoding a nucleic acid sequence of interest operably linked to a further promoter capable of expressing the nucleic acid sequence of interest in a eukaryotic cell; and optionally (iv) a nucleic acid sequence of interest encoding a mutant eRF1 as described herein Vectors and cells comprising these various combinations of constructs is also disclosed.

tRNA Synthetase

The tRNA synthetase (suitably, aminoacyl-tRNA synthetase) used herein may be varied. Although specific tRNA synthetase sequences may have been used in the examples, the invention is not intended to be confined only to those examples. In principle any tRNA synthetase which provides a tRNA charging (aminoacylation) function can be employed. For example the tRNA synthetase may be from any suitable species such as from archea, for example from *Methanosarcina*—such as *Methanosarcina barkeri* MS; *Methanosarcina barkeri* str. Fusaro; *Methanosarcina mazei* G01; *Methanosarcina acetivorans* C2A; *Methanosarcina thermophila*; or *Methanococcoides*—such as *Methanococcoides burtonii*. Alternatively the tRNA synthetase may be from bacteria, for example from *Desulfitobacterium*—such as *Desulfitobacterium hafniense* DCB-2; *Desulfitobacterium hafniense* Y51; *Desulfitobacterium hafniense* PCP1; or *Desulfotomaculam acetoxidans* DSM 771.

In one embodiment, the tRNA synthetase is pyrrolysyl tRNA synthetase (PylRS), which is a protein having pyrrolysl tRNA synthetase biological activity. The PylRS is capable of acylating a tRNA with an unnatural amino acid.

The PylRS may be a wild-type or a genetically engineered PylRS. Genetically engineered PylRS has been described, for example, by Neumann et al. (*Nat Chem Biol* 4:232, 2008) and by Yanagisawa et al. (*Chem Biol* 2008, 1.5:118), and in EP2192185A1. Suitably, a genetically engineered tRNA synthetase gene is selected that increases the incorporation efficiency of unnatural amino acid(s).

According to one embodiment, the PylRS is from *Methanosarcina barkeri* (MbPylRS), optionally comprising or consisting of the codon optimised sequence set forth below:

```
ATGGACTACAAGGACGACGACGACAAGGACAAGAAACCCCTGGACGTGCT
GATCAGCGCCACCGGCCTGTGGATGAGCCGGACCGGCACCCTGCACAAGA
TCAAGCACCACGAGGTGTCAAGAAGCAAAATCTACATCGAGATGGCCTGC
GGCGACCACCTGGTGGTGAACAACAGCAGAAGCTGCCGGACCGCCAGAGC
CTTCCGGCACCACAAGTACAGAAAGACCTGCAAGCGGTGCCGGGTGTCCG
ACGAGGACATCAACAACTTTCTGACCAGAAGCACCGAGAGCAAGAACAGC
GTGAAAGTGCGGGTGGTGTCCGCCCCCAAAGTGAAGAAAGCCATGCCCAA
GAGCGTGTCCAGAGCCCCCAAGCCCTGGAAAACAGCGTGTCCGCCAAGG
CCAGCACCAACACCAGCCGCAGCATGCCCAGCCCCGCCAAGAGCACCCCC
AACAGCTCCGTGCCCGCCTCTGCTCCTGCTCCCAGCCTGACACGGTCCCA
GCTGGACAGAGTGGAGGCCCTGCTGTCCCCCGAGGACAAGATCAGCCTGA
ACATGGCCAAGCCTTTCCGGGAGCTGGAACCCGAGCTGGTGACCCGGCGG
AAGAACGACTTCCAGCGGCTGTACACCAACGACCGGGAGGACTACCTGGG
CAAGCTGGAACGGGACATCACCAAGTTCTTCGTGGACCGGGGCTTCCTGG
AAATCAAGAGCCCCATCCTGATCCCCGCCGAGTACGTGGAGCGGATGGGC
ATCAACAACGACACCGAGCTGTCCAAGCAGATTTTCCGGGTGGACAAGAA
CCTGTGCCTGCGGCCTATGCTGGCCCCCACCCTGTACAACTACCTGCGGA
AACTGGACAGAATCCTGCCTGGCCCCATCAAGATTTTCGAAGTGGGACCC
TGCTACCGGAAAGAGAGCGACGGCAAAGAGCACCTGGAAGAGTTTACAAT
GGTGAATTTTTGCCAGATGGGCAGCGGCTGCACCCGGGAGAACCTGGAAG
CCCTGATCAAAGAGTTCCTGGATTACCTGGAAATCGACTTCGAGATCGTG
GGCGACAGCTGCATGGTGTACGGCGACACCCTGGACATCATGCACGGCGA
CCTGGAACTGAGCAGCGCCGTGGTGGGACCCGTGTCCCTGGACCGGGAGT
GGGGCATCGACAAGCCCTGGATCGGAGCCGGCTTCGGCCTGGAACGGCTG
CTGAAAGTGATGCACGGCTTCAAGAACATCAAGCGGGCCAGCAGAAGCGA
GAGCTACTACAACGGCATCAGCACCAACCTGTGATGATAA
```

According to a particular embodiment, the PYlRS is from *Methanosarcina mazei* (MmPylRS), optionally comprising or consisting of the codon optimised sequence set forth below:

```
ATGGACTACAAGGACGACGAGGACAAGGGACAAGAAGCCCCTGAACACCC
TGATCAGCGCCACAGGACTGTGGATGTCCAGAACCGGCACCATCCACAAG
ATCAAGCACCACGAGGTGTCCCGGTCCAAAATCTACATCGAGATGGCCTG
CGGCGATCACCTGGTCGTCAACAACAGCAGAAGCAGCCGGACAGCCAGAG
CCCTGCGGCACCACAAGTACAGAAAGACCTGCAAGCGGTGCAGAGTGTCC
GACGAGGACCTGAACAAGTTCCTGACCAAGGCCAACGAGGACCAGACCAG
CGTGAAAGTGAAGCTGGTGTCCGCCCCCACCCGGACCAAGAAAGCCATGC
CCAAGAGCGTGGCCAGAGCCCCCAAGCCCCTGGAAAACACCGAAGCCGCT
CAGGCCCAGCCCAGCGGCAGCAAGTTCAGCCCCGCCATCCCCGTGTCTAC
CCAGGAAAGCGTGAGCGTCCCCGCCAGCGTGTCCACCAGCATCTCTAGCA
TCTCAACCGGGGCCACAGCTTCTGCCCTCGTCAAGCGCAACACCAACCCC
ATCACCACCATGTCTGCCCCTGTGCAGGCCTCTGCCCCAGCCCTGACCAA
GTCCCAGACCGACCGGCTGGAAGTGCTCCTGAACCCCAAGGACGAGATCA
GCCTGAACAGCGGCAAGCCTTCCGGGAGCTGGAAAGCGAGCTGCTGAGC
CGGCGGAAGAAGGACCTCCAGCAAATCTACGCCGAGGAACGGGAGAACTA
CCTGGGCAAGCTGGAAAGAGAGATCACCCGGTTCTTCGTGGACCGGGGCT
TCCTGGAAATCAAGAGCCCCATCCTGATCCCCCTGGAGTACATCGAGCGG
```

-continued

```
ATGGGCATCGACAACGACACCGAGCTGAGCAAGCAGATTTTCCGGGTGGA

CAAGAACTTCTGCCTGCGGCCCATGCTGGCCCCCAACCTGTACAACTACC

TGCGGAAACTGGATCGCGCTCTGCCCGACCCCATCAAGATTTTCGAGATC

GGCCCCTGCTACCGGAAAGAGAGCGACGGCAAAGAGCACCTGGAAGAGTT

TACAATGCTGAACTTTTGCCAGATGGGCAGCGGCTGCACCAGAGAGAACC

TGGAATCCATCATCACCGACTTTCTGAACCACCTGGGGATCGACTTCAAG

ATCGTGGGCGACAGCTGCATGGTGTACGGCGACACCCTGGACGTGATGCA

CGGCGACCTGGAACTGTCTAGCGCCGTCGTGGGACCCATCCCTCTGGACC

GGGAGTGGGGCATCGATAAGCCCTGGATCGGAGCCGGCTTCGGCCTGGAA

CGGCTGCTGAAAGTCAAGCACGACTTTAAGAACATCAAGCGGGCTGCCAG

AAGCGAGAGCTACTACAACGGCATCAGCACCAACCTGTGATGATAA
```

Suitably the nucleotide sequence encoding the tRNA synthetase is codon optimised.

tRNA

The tRNA used herein may be varied. Although specific tRNAs may have been used in the examples, the invention is not intended to be confined only to those examples. In principle, any tRNA can be used provided that it is compatible with the selected tRNA synthetase.

The tRNA may be from any suitable species such as from archea, for example from *Methanosarcina*—such as *Methanosarcina barkeri* MS; *Methanosarcina barkeri* str. Fusaro; *Methanosarcina mazei* G01; *Methanosarcina acetivorans* C2A; *Methanosarcina thermophila*; or *Methanococcoides*—such as *Methanococcoides burtonii*. Alternatively the tRNA may be from bacteria, for example from *Desulfitobacterium*—such as *Desulfitobacterium hafniense* DCB-2; *Desulfitobacterium hafniense* Y51; *Desulfitobacterium hafniense* PCP1; or *Desulfotomaculum acetoxidans* DSM 771.

The tRNA gene can be a wild-type tRNA gene or it may be a mutated tRNA gene. Suitably, a mutated tRNA gene is selected that increases the incorporation efficiency of unnatural amino acid(s). In one embodiment, the mutated tRNA gene, for example, the mutated tRNA$_{CUA}$ gene, is a U25C variant of PylT as described in *Biochemistry* (2013) 52, 10.

In one embodiment, the mutated tRNA gene, for example, the mutated tRNA$_{CUA}$ gene, is an Opt variant of PylT as described in Fan et al 2015 (Nucleic Acids Research doi: 10.1093/nar/gkv800).

In one embodiment, the mutated tRNA gene, for example, the mutated tRNA$_{CUA}$ gene, has both the U25C and the Opt variants of PylT, i.e. in this embodiment the tRNA, such as the PylT tRNA$_{CUA}$ gene, comprises both the U25C and the Opt mutations.

In one embodiment, the sequence encoding the tRNA is the pyrrolysine tRNA (PylT) gene from *Methanosarcina mazei* pyrrolysine which encodes tRNA$^{Pyl}$, more suitably tRNA$^{Pyl}_{CUA}$. This incorporates unnatural amino acids by amber suppression i.e. by recognition of the amber codon.

An example of a nucleic acid sequence encoding PylT from *Methanosarcina mazei* is:

```
GGAAACCTGATCATGTAGATCGAATGGACTCTAAATCCGTTCAGCCGGGT

TAGATTCCCGG
```

In another embodiment, the PylT from *Methanosarcina mazei* is expressed from a U6 promoter with a linker followed by a terminator at the 3' end of the PylT. An exemplary sequence is (U6 promoter in lowercase and bold; PlyT underlined; linker in capitals and bold; terminator in uppercase and underlined):

tgggcaggaagagggcctatttcccatgattccttcatatttgcatata cgatacaaggctgttagagagataattagaattaatttgactgtaaaca caaagatattagtacaaaatacgtgacgtagaaagtaataatttcttgg gtagtttgcagtttaaaattatgttttaaaatggactatcatatgctt accgtaacttgaaagtatttcgatttcttggctttatatatcttgtgga aaggacgaaacaccgg<u>aaacctgatcatgtagatcgaatggactctaaa</u>

<u>tccgttcagccgggttagattcccggggtttccg</u>GACAAGTGCGGTTTT

T tRNA Synthetase/tRNA Pair

Suitably, the tRNA-tRNA synthetase pair is one that does not recognise any of the 20 naturally occurring amino acids.

It will be appreciated that corresponding or cognate tRNA or tRNA synthetases may be combined from different species—such as different species of *Methanococcus* bacterium. For example, it may be possible to use a pyrrolysine tRNA from *Methanosarcina mazei* together with a pyrrolysyl tRNA synthetase from *Methanosarcina barkeri*. The functionality of such pairings is easily tested using methods that are known in the art, for example, by combining together the different components in a host cell and analysing for an intact protein of interest being produced.

In one embodiment, the tRNA-tRNA synthetase pair is the pyrrolysyl-tRNA synthetase (PylRS)/tRNA$_{CUA}$ pair, suitably from *Methanococcus*.

In one embodiment, the tRNA synthetase is or is derived from the PylRS from *Methanosarcina barkeri* (MbPylRS) and the tRNA is or is derived from the pyrrolysine tRNA (PylT) from *Methanosarcina mazei* pyrrolysine.

In one embodiment, the tRNA synthetase is or is derived from the PylRS from *Methanosarcina barkeri* (MbPylRS) and the tRNA is or is derived from the pyrrolysine tRNA (PylT) from *Methanosarcina mazei* pyrrolysine.

Suitably, said tRNA synthetase is orthogonal to the endogenous tRNAs in the eukaryotic cell and/or said tRNA is orthogonal to the endogenous tRNA synthetase in the eukaryotic cell and/or said tRNA synthetase is orthogonal to the endogenous tRNAs in the eukaryotic cell and said tRNA is orthogonal to the endogenous tRNA synthetases.

Control Sequence

Control sequences operably linked to nucleic acid sequences include promoters, enhancers and other expression regulation signals. These control sequences may be selected to be compatible with the host cell for which the construct or vector is designed to be used in. The term promoter is well-known in the art and encompasses nucleic acid regions ranging in size and complexity from minimal promoters to promoters including upstream elements and enhancers.

Suitably, one of the promoter sequences is a RNA Poi III promoter—such as a U6 promoter. Suitably, the RNA Pol III promoter is operably linked to a tRNA gene. Suitably, this arrangement is repeated at least 4, 5, 6, 7 or 8 times or more in the constructs of the present disclosure.

Suitably, one of the promoter sequences is a eukaryotic elongation factor promoter such as an EF-1 promoter (for example, EF-1α). Suitably, this promoter is operably linked to a tRNA synthetase gene and/or a nucleic acid sequence of interest. Suitably, this arrangement is repeated at least once in the constructs of the present disclosure.

RNA PIII Promoter

Suitably any promoter capable of directing RNA Pol III transcription in eukaryotic cells—such as mammalian or insect cells—may be used in the construct described herein. RNA Pol III promoters include intragenic and extragenic (internal and external) promoters.

Suitably said promoter is, or is derived from, the eukaryotic U6 promoter, suitably, the *Homo sapien* U6 promoter.

An exemplary U6 promoter is described in *The Journal of Biological Chemistry* (1987) 262(3), 1187-1193.

An exemplary U6 promoter for use in human and/or mouse systems is described in *Journal of the American Chemical Society* (2010) 132(12), 4086-4088.

Another exemplary U6 promoter comprises or consists of the sequence set forth below:

TGGGCAGGAAGAGGGCCTATTTCCCATGATTCCTTCATATTTGCATATAC

GATACAAGGCTGTTAGAGAGATAATTAGAATTAATTTGACTGTAAACACA

AAGATATTAGTACAAAATACGTGACGTAGAAAGTAATAATTTCTTGGGTA

GTTTGCAGTTTTAAAATTATGTTTTAAAATGGACTATCATATGCTTACCG

TAACTTGAAAGTATTTCGATTTCTTGGCTTTATATATCTTGTGGAAAGGA

CGAAACACCG

Suitably, the promoter is, or is derived from, a U6 promoter capable of directing RNA Pol III transcription in mammalian cells—such as mouse or human cells—operably linked to one or more tRNA genes, as described herein.

Elongation Factor Promoter

Suitably any eukaryotic elongation factor promoter capable of directing expression in eukaryotic cells—such as mammalian or insect cells—may be used in the construct described herein.

Suitably said promoter is, or is derived from, the etikaryotic elongation factor 1 (EF-1) promoter.

Suitably said promoter is, or is derived from, the EF-1α promoter.

An exemplary EF-1α promoter is described in *Anticancer Res.* (2002), 22(6A), 3325-30.

Another exemplary EF-1α promoter comprises or consists of the sequence set forth below:

CTAGTAAGGATCTGCGATCGCTCCGGTGCCCGTCAGTGGGCAGAGCGCAC

ATCGCCCACAGTCCCCGAGAAGTTGGGGGGAGGGGTCGGCAATTGAACGG

GTGCCTAGAGAAGGTGGCGCGGGGTAAACTGGGAAAGTGATGTCGTGTAC

TGGCTCCGCCTTTTTCCCGAGGGTGGGGGAGAACCGTATATAAGTGCAGT

AGTCGCCGTGAACGTTCTTTTTCGCAAGGGGTTTGCCGCCAGAACACAGC

TGAAGCTTCGAGGGGCTCGCATCTCTCCTTCACGCGCCCGCCGCCCTACC

TGAGGCCGCCATCCACGCCGCTTGAGTCCCGTTCTCCCGCCTCCCGCCTG

TGGTGCCTCCTGAACTGCGTCCGCCGTCTAGGTAAGTTTAAAGCTCAGGT

CGAGACCGGGCCTTTGTCCGGCGCTCCCTTGGAGCCTACCTAGACTCAGC

CGGCTCTCCACGCTTTGCCTGACCCTGCTTGCTCAACTCTACGTCTTTGT

TTCGTTTTCTGTTCTGCGCCGTTACAGATCCAAGCTGTGACCGGCGCCTA

CTCTAG

Suitably, the promoter is, or is derived from, an EF-1α promoter capable of directing transcription in mammalian cells—such as mouse or human cells—operably linked to tRNA synthetase and/or a nucleic acid sequence of interest as described herein.

Host Cells

Suitable host cells may include bacterial cells (e.g., *E. coli*), but most suitably host cells are eukaryotic cells, for example insect cells (e.g. *Drosophila* such as *Drosophila melanogaster*), yeast cells, nematodes (e.g. *C. elegans*), mice (e.g. *Mus musculus*), or mammalian cells (such as Chinese hamster ovary cells (CHO) or COS cells, human 293T cells, HeLa cells, NIH 3T3 cells, and mouse erythroleukemia (MEL) cells) or human cells or other eukaryotic cells. Other suitable host cells are known to those skilled in the art. Suitably, the host cell is a mammalian cell—such as a human cell or an insect cell.

Other suitable host cells which may be used generally in the embodiments of the invention are those mentioned in the examples section.

Vector DNA can be introduced into host cells via conventional transformation or transfection techniques. As used herein, the terms "transformation" and "transfection" are intended to refer to a variety of well-recognized techniques for introducing a foreign nucleic acid molecule (e.g., DNA) into a host cell, including calcium phosphate or calcium chloride co-precipitation, DEAF-dextran-mediated transfection, lipofection, or electroporation. Suitable methods for transforming or transfecting host cells are well known in the art.

When creating cell lines it is generally preferred that stable cell lines are prepared. For stable transfection of mammalian cells for example, it is known that, depending upon the expression vector and transfection technique used, only a small fraction of cells may integrate the foreign DNA into their genome. In order to identify and select these integrants, a gene that encodes a selectable marker (for example, for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector or can be introduced on a separate vector. Cells stably transfected with the introduced nucleic acid molecule can be identified by drug selection (for example, cells that have incorporated the selectable marker gene will survive, while the other cells die).

In one embodiment, the constructs described herein are integrated into the genome of the host cell. An advantage of stable integration is that the uniformity between individual cells or clones is achieved. Another advantage is that selection of the best producers may be carried out. Accordingly, it is desirable to create stable cell lines.

In another embodiment, the constructs described herein are transfected into a host cell. An advantage of transfecting the constructs into the host cell is that protein yields may be maximised.

In one aspect, there is described a cell comprising the nucleic acid construct or the vector described herein.

eRF1

Unless otherwise apparent from the context, references herein to 'eRF1' refer to eukaryotic eRF1.

When used herein, especially in discussions of eRF1, 'mutant' has its natural meaning of 'other than wild-type'. Clearly, the wild type residue may vary depending on the particular species of eRF1 being used. References to particular residues should be construed with reference to the *H. sapiens* wild type reference sequence for eRF1 of GenBank Accession Number AF095901.1. The database release at the date of filing is relied on. In case of any doubt, this means Genetic Sequence Data Bank NCBI-GenBank Flat File Release 209.0 dated Aug. 15, 2015.

For avoidance of doubt, wild type human eRF1 polypeptide sequence is regarded as:

```
                                                            (SEQ ID NO: 4)
  1    maddpsaadr nveiwkikkl iksleaargn gtsmisliip pkdqisrvak miadefgtas 61    niksrvnrls vlgaitsvqq riklynkvpp nglvvycgti vteegkekkv nidfepfkpi 121    ntslylcdnk fhtealtall sddskfgfiv idgsgalfgt lqgntrevlh kftvdlpkkh 181    grggqsalrf arlrmekrhn yvrkvhetav qlfisgdkvn vaglvlagsa dfktelsqsd 241    mfdqrlqskv lklvdisygg engfnqaiel stevlsnvkf iqekkligry fdeisqdtgk 301    ycfgvedtlk alemgaveil ivyenidimr yvlhcqgtee ekilyltpeq ekdkshftdk 331    etgqehelie smpllewfan nykkfgatle ivtdksqegs qfvkgfggig gliryrvdfq 421    gmevqggdde ffdlddy
```

In particular, amino acid addresses given in the application correspond to the numbering of the eRF1 reference sequence above. Where truncated or extended forms of eRF1 are used (e.g. if a 6his tag is added or where a section of the polypeptide is deleted) then the amino acid numbering should be treated as corresponding to the equivalent section of the full length reference sequence and not as an 'absolute' or rigidly inflexible numeric address. By way of explanation, if the description mentions a substitution of E55, this means amino acid 55 of the eRF1 reference sequence above. If another species position 55 is not E in the wild type, the amino acid corresponding to E55 of the human wild type sequence is identified for example by aligning the sequence of the eRF1 of said other species with the reference sequence above and selecting the corresponding amino acid as is well known in the art. Similarly, if the polypeptide used is truncated by deletion of the first 10 amino acids, the address given will still be E55 (rather than e.g. E45)—this will be easily understood by the skilled reader to refer to the amino acid of the corresponding context with reference to the full length eRF1 sequence above, as is conventional in the art.

The inventors teach that other truncations which remove the N-terminal domain of eRF1 would have a similar effect. The N-terminal domain (roughly amino acid 1-130) of eRF1 interacts with the messenger RNA and the stop codon. If the whole or part of this domain is deleted, in use it should form inactive eRf1-eRF3 complexes (exemplified by the delta 100 variant) and increase stop codon read-through (and toxicity). Suitably the eRF1 used in the invention comprises amino acid sequence corresponding to at least amino acids 131 onwards of SEQ ID NO: 4; suitably comprises amino acid sequence corresponding to at least amino acids 101 onwards of SEQ ID NO: 4.

Suitably the eRF1 used in the invention comprises amino acid sequence corresponding to at least amino acids 101 to the end of SEQ ID NO: 4.

Suitably the eRF1 used in the invention comprises amino acid sequence corresponding to at least amino acids 131 to the end of SEQ ID NO: 4.

Suitably the C-terminal end of eRF1 is not truncated or is truncated only minimally relative to SEQ ID NO: 4. Most suitably the C-terminal end of eRF1 is not truncated relative to SEQ ID NO: 4.

Any alignment required should be carried out by eye, or using any of the widely available sequence alignment programs known in the art, such as the GCG suite of programs (GCG Genetics Computer Group University Research Park 575 Science Drive Madison, Wis. 53711). Most suitably alignments are using ClustalW with the default settings.

Advantageously, certain mutants of eRF1 can be employed in accordance with the present disclosure to provide a substantial increase in unnatural amino acid incorporation in response to one or more stop codons without substantially increasing read-through of other stop codons. Accordingly, it can be advantageous to express the nucleic acid constructs as described herein in a cell together with certain eRF1 mutants.

eRF1 may be expressed using various promoters—such as an EF1 promoter or a CMV promoter.

Most suitably the eRF1 mutants of the invention provide increased efficiency of unnatural amino acid incorporation.

Suitably the eRF1 mutants of the invention increase efficiency of unnatural amino acid incorporation relative to a natural translation control.

Suitably the eRF1 mutants of the invention provide increased efficiency of unnatural amino acid incorporation relative to a wild type eRF1 control.

This may be easily determined as taught herein, for example by reference to the examples section.

In certain embodiments, the mutant eRF1 is integrated into the host cell, suitably stably integrated into the host cell.

In certain embodiments, the mutant eRF1 is expressed from one or more of the nucleic acid constructs described herein in a host cell.

In certain embodiments, the nucleic acid sequence encoding the mutant eRF1 is on a separate construct or a separate vector.

Eukaryotic translation termination factor 1 (eRF1), also known as TB3-1, is a protein that in humans is encoded by the ETF1 gene. In eukaryotes, this is the only release factor which recognizes all three stop codons. Termination of protein biosynthesis and release of the nascent polypeptide chain are signaled by the presence of an in-frame stop codon at the aminoacyl site of the ribosome. The process of translation termination is universal and is mediated by protein release factors (RFs) and GTP.

An exemplary eRF1 gene sequence is the wild type *Homo sapiens* eRF1 gene sequence as described in GenBank Accession Number AF095901.1. Suitably, the eRF1 gene can be codon optimized, for example, for *Drosophila melanogaster*.

Using shRNA to knock down eRF1 expression in mammalian cells can also be deleterious after providing a transient increase in suppression. High levels of stop codon read through can also occur. Clearly these deleterious effects should be avoided and shRNA should suitably not be used in the present disclosure.

eRF1 mutants useful in the invention are disclosed in the table below:

| Column I<br>Mutant Site(s) | Column II<br>Exemplary Mutations | Column III<br>Effect (Fold improvement) |
|---|---|---|
| E55 | E55D | 5.1 |
| N129, K130 | N129P, K130Q | 3.2 |
| T122, S123 | T122Q, S123F | 3.0 |
| E55 | E55A | 2.8 |
| Y125 | Y125F | 2.6 |
| T58, S60, S64, L125, N129 | T58K, S60T, S64D, L125F, N129S | 2.5 |
| S123, L124, Y125 | S123A, L124I, Y125L | 2.5 |
| S123, L124, Y125 | S123R, L124W, Y125R | 1.9 |
| S123, L124, Y125 | S123H, L124A, Y125G | 1.9 |
| M51, K130 | M51A, K130M | 1.8 |
| S123, L124, Y125 | S123A, L124L, Y125V | 1.8 |
| S123, L124, Y125 | S123L, L124C, Y125S | 1.8 |
| S123, L124, Y125 | S123L, L124S, Y125S | 1.8 |
| S123, L124, Y125 | S123V, L124T, Y125P | 1.7 |
| Δ100 (N-term truncation)* | Δ100 (N-term truncation)* | 6.8 |
| S70, G73 ** | S70A, G73S ** | 0.67 |

*In choosing which eRF1 mutants to employ, the skilled person will take account of the interaction between cell viability and increased suppression. For example, the Δ100 eRF1 mutant can result in high levels of stop codon read through and sick cells. The Δ100 eRF1 mutant is therefore suitably not used in the present disclosure.
** Not useful for UAG as an incorporation signal, but may find application for UGA.

Occasionally there is mention of unmutated site(s), such as "L124L". Clearly this is not a mutation since the wild type "L" is not changed. This is to be understood as showing that L124 is NOT mutated in that particular eFR1 i.e. position L124 is left as wild-type (as L) in that particular combination of mutations/that particular exemplary eRF1.

For each mutation at a given position there is believed to be a number of closely related amino acids that will give a similar effect. The 'exemplary mutants' are not intended to be exhaustive. Also contemplated are mutations to 'other than wild-type' to the residues identified in column I above. More suitably conservative substitutions may be made to those residues mentioned in Column II, for example according to the table below. Amino acids in the same block in the second column and preferably in the same line in the third column of the table below may be substituted for each other:

| ALIPHATIC | Non-polar | G A P<br>I L V |
|---|---|---|
| | Polar - uncharged | C S T M<br>N Q |
| | Polar - charged | D E<br>K R |
| AROMATIC | | H F W Y |

For example, E55 in column I may be mutated to 'other than E'. More suitably E55 may be mutated to an amino acid conservative to the specific mutations in Column II—such as E55D or E55A or E55G or E55P. Most suitably E55 may be mutated to an amino acid specifically mentioned in Column II such as E55A or E55D, most suitably E55D. The same applies to the other residues listed in Column I.

All S123, L124, Y125 mutants perform well compared to E55D in DLR assays (1-2× better than E55D), but perform less well than E55D in protein expression tests. They remain useful in the invention but the most preferred mutant is E55D.

(sfGFP(3TAG).

Although some mutations are presented in combinations, those combinations are especially preferred examples of the invention. Disclosed is the use of individual eRF1 mutants; suitably said mutant eRF1 comprises a mutation relative to SEQ ID NO: 4 selected from the group consisting of E55, N129, K130, K122, S123, Y125, T58, S60, S64, L125, S123, L124, M51, and K130. Suitably said mutant eRF1 comprises a mutation relative to SEQ ID NO: 4 selected from the group consisting of E55D, N129P, K130Q, T122Q, S123F, E55A, Y125F, T58K, S60T, S64D, L125F, N129S, S123A, L124I, Y125L, S123R, L124W, Y125R, S123H, L124A, Y125G, M51A, K130M, Y125V, S123L, L124C, Y125S, S123L, L124S, Y125S, S123V, L124T, and Y125P.

eRF1 may be provided in a host cell by transient expression or by genomic integration. For example, using the TRex Flip-In system (human HEK293-derived) to get inducible expression of the eRF1 mutant in a stable genetic background. In one embodiment the relevant nucleic acids are introduced by transient transfection. In one embodiment the relevant nucleic acids are introduced by stable cell line creation.

Various especially suitable mutants and combinations are described herein including M51A/K130M, T122Q/S123F, S70A/G73S, E55D, E55A, N129P/K130Q and Y125F. Suitably, the eRF1 mutant used in the present disclosure comprises a mutation at E55. Suitably, the eRF1 mutant used in the present disclosure is selected from the group consisting of E55D, E55A, N129P/K130Q and Y125F or a combination of two or more thereof. These mutations are made with respect to the wild type *Homo sapiens* eRF1 amino acid sequence which is derived from GenBank Accession Number AF095901.1 or a codon optimised variant thereof.

The eRF1 protein shows very strong homology across most eukaryotic organisms. We used the human eRF1 as the example to introduce our mutations, but eRF1s from other species may also carry the same mutations (e.g. E55D in a human or insect eRF1 protein). We teach that these alternate species mutant eRF1 proteins should have similar technical effects as shown for the exemplary eRFs herein.

We used the preferred eRF1 mutant (engineered human (*H. sapiens*) eRF1 variant) to successfully enhance unnatural amino acid incorporation in diverse eukaryotic host cells including CHO cells (*C. griseus*), HEK cells (*H. sapiens*) and Dmel cells (*D. melanogaster*). The eRF1 proteins in these organisms are highly conserved (table 1).

TABLE 1

Pair-wise similarity of eRF1 in various species. The percentage given indicates conserved amino acid identities across the protein, as determined by ClustalW alignment.

| | H. sapiens | C. griseus | D. melanogaster | S. cerevisiae |
|---|---|---|---|---|
| H. sapiens | — | | | |
| C. griseus | 92% | — | | |
| D. melanogaster | 84% | 78% | — | |
| S. cerevisiae | 67% | 62% | 67% | — |

Given the level of conservation between the various unicellular (yeast) and multicellular (mammal, insects) eukaryotic organisms it is supported that eRF1 variants from various eukaryotic species will be functional in multiple other eukaryotic species host cells. For example, the host cell may be human, mouse, C. elegans, donkey, yeast or other eukaryotic host cell.

Suitably the mutant eRF1 has amino acid sequence having at least 60% sequence identity to the human wild type eRF1 sequence of SEQ ID NO: 4; suitably the mutant eRF1 has amino acid sequence having at least 67% sequence identity to the human wild type eRF1 sequence of SEQ ID NO: 4; suitably the mutant eRF1 has amino acid sequence having at least 84% sequence identity to the human wild type eRF1 sequence of SEQ ID NO: 4; suitably the mutant eRF1 has amino acid sequence having at least 92% sequence identity to the human wild type eRF1 sequence of SEQ ID NO: 4, suitably the mutant eRF1 has amino acid sequence having at least 95% sequence identity to the human wild type eRF1 sequence of SEQ ID NO: 4, suitably the mutant eRF1 has amino acid sequence having at least 98% sequence identity to the human wild type eRF1 sequence of SEQ ID NO: 4, or even more.

In one embodiment, suitably percentage identity levels are calculated before specific mutations recited for the mutant eFR1's are introduced. Preferably the percentage identity levels are calculated including the specific mutations recited for the mutant eFR1's.

Suitably the host cell is in vitro. When the host cell is in an organism, suitably the host is non-human.

We have introduced the exemplary human eRF1 into cell lines from three eukaryotic species (human, hamster, flies), as well as eukaryotic live animals (flies).

The engineered human eRF1 enhances unnatural amino acid incorporation in species where the native eRF1 is only 84% conserved (Dmel insect cells).

We have used constructs to replace the native yeast eRF1 with our exemplary human eRF1 variant (Plasmids derived from Nucleic Acids Res. 2010 September; 38(16):5479-92). This shows that diverse eRF1 proteins can be used with only 67% conservation (sequence identity), and cover a large range of eukaryotic organisms.

Of course the nucleic acid sequence for eRF1 (or a variant) is not important one exemplary human eRF1 variant has been codon optimised to express well in insect cells, but also works in human cell lines. Thus the codon optimisation of the nucleic acid (if desired) is a matter for the skilled operator.

It is an advantage of the invention that amber suppression is increased. Suitably the eRF1 mutants described herein are used in amber suppression.

In a further aspect, there is provided a method for incorporating an unnatural amino acid into a protein of interest in a eukaryotic cell—such as a mammalian cell or an insect cell comprising the steps of: i) providing a eukaryotic cell expressing a tRNA synthetase and tRNA pair, a nucleic acid sequence of interest and a mutant eRF1; ii) incubating the cell in the presence of an unnatural amino acid to be incorporated into a protein encoded by the nucleic acid sequence of interest, wherein said unnatural amino acid is a substrate for the tRNA synthetase; and iii) incubating the cell to allow incorporation of said unnatural amino acid into the protein of interest via the orthogonal tRNA-tRNA synthetase pair.

The use of a mutant eRV1 for incorporating an unnatural amino acid into a protein of interest in a eukaryotic cell is also disclosed.

There is also disclosed a method of identifying a mutant of eRF1 that increases the incorporation of an unnatural amino acid in a protein of interest is also provided. The method comprises the steps of: (i) providing a cell that is capable in incorporating an unnatural amino into a protein of interest, suitably wherein said cell is the eukaryotic cell as described herein; (ii) incubating the cell in the presence of the unnatural amino acid to be incorporated into the protein of interest and in the presence and absence of the mutant of eRF1, wherein said unnatural amino acid is a substrate for the tRNA synthetase; and (iii) determining the level of unnatural amino acid incorporation into the protein of interest in the presence and absence of the mutant of eRF1, wherein an increase in the level of unnatural amino acid incorporation into the protein of interest in the presence the mutant of eRF1 is indicative that said mutant of eRF1 increases the incorporation of an unnatural amino acid in the protein of interest.

Methods for incorporating one or more mutations into a eRF1 include site-directed mutagenesis and the like which are well known in the art. Suitably, the mutations that are selected may be based on mutations in amino acids in eRF1 that have an effect on termination at amber codons, as described in references 25-30. Suitably, the mutations that are selected may be located in the N-terminal domain of eRF1 (see FIG. 2a) that interacts with the stop codon on the mRNA within the ribosome. Desirably, the eRF1 mutants result in efficient unnatural amino acid incorporation in response to a selected codon—such as TAG—without increasing read-through of other stop codons.

In one embodiment, release factor mutants—such as eRF1—are not used in the present disclosure.

In one embodiment, expression of endogenous release factor—such as eRF1—is decreased or deleted from the host cell. This can be achieved by, for example, a disruption one or more of the genomic loci encoding eRF1, or through RNA-mediated gene silencing of eRF1.

Making a Protein Comprising Unnatural Amino Acid(s)

An orthogonal or expanded genetic code can be used in the present disclosure, in which one or more specific codons present in the nucleic acid sequence of interest are allocated to encode the unnatural amino acid so that it can be genetically incorporated into the protein of interest by using an orthogonal tRNA synthetase/tRNA pair. The orthogonal tRNA synthetase/tRNA pair is capable of charging a tRNA with an unnatural amino acid and is capable of incorporating that unnatural amino acid into the polypeptide chain in response to the codon.

The codon may be the codon amber, ochre, opal or a quadruplet codon. The codon simply has to correspond to the orthogonal tRNA which will be used to carry the unnatural amino acid. Suitably, the codon is amber. Suitably, the codon is an orthogonal codon.

Unnatural amino acid incorporation is to a large extent performed on the amber UAG codon. Suitably the codon is UAG or UGA, most suitably UAG (amber). An exemplary mutation that minimises activity of the release factor on the amber (UAG) stop codon (e.g. E55D). Other mutations described may not affect recognition of the amber stop codon, but reduce termination activity on UGA or UAA stop codons (opal/ochre). This is exemplified by S70A, G73S. The skilled operator will select the eRF1 mutants to suit their needs when using codons other than UAG (amber).

It should be noted that the specific examples shown herein have used the amber codon and the corresponding tRNA/tRNA synthetase. As noted above, these may be varied.

Alternatively, in order to use other codons without going to the trouble of using or selecting alternative tRNA/tRNA synthetase pairs capable of working with the unnatural amino acid, the anticodon region of the tRNA may simply be swapped for the desired anticodon region for the codon of choice. The anticodon region is not involved in the charging or incorporation functions of the tRNA nor recognition by the tRNA synthetase so such swaps are entirely within the ambit of the skilled person.

Thus, alternative orthogonal tRNA synthetase/tRNA pairs may be used if desired.

A host cell can be used to produce (for example, express) a protein that comprises one or more unnatural amino acids.

The host cell into which the constructs or vectors disclosed herein are introduced is cultured or maintained in a suitable medium such that the tRNA, the tRNA synthetase and the protein of interest are produced. The medium also comprises the unnatural amino acid(s) such that the protein of interest incorporates the unnatural amino acid(s). Such proteins are encoded by a nucleic acid comprising one or more codons as described herein within the coding sequence. The orthogonal tRNA synthetase/tRNA pair charges a tRNA with an unnatural amino acid and incorporates the unnatural amino acid into the polypeptide chain in response to the codon.

In a further aspect, there is a provided a method for incorporating an unnatural amino acid into a protein of interest in a eukaryotic cell comprising the steps of: i) providing a eukaryotic cell comprising the construct(s) or vector(s) described herein; ii) incubating the cell in the presence of one or more unnatural amino acids to be incorporated into a protein of interest encoded the nucleic acid sequence of interest, wherein said unnatural amino acid is a substrate for the tRNA synthetase; and iii) incubating the cell to allow incorporation of said unnatural amino acid into the protein of interest via the orthogonal tRNA-tRNA synthetase pair.

Proteins comprising an unnatural amino acid(s) are prepared by introducing the nucleic acid constructs described herein comprising the tRNA and tRNA synthetase and comprising a nucleic acid sequence of interest with one or more in-frame orthogonal (stop) codons into a host cell. The host cell is exposed to a physiological solution comprising the unnatural amino acid(s), and the host cells are then maintained under conditions which permit expression of the protein of interest's encoding sequence. The unnatural amino acid(s) is incorporated into the polypeptide chain in response to the codon.

Advantageously, more than one unnatural amino acid is incorporated into the protein of interest. Alternatively two or more unnatural amino acids may be incorporated into the protein of interest at two or more sites in the protein. Suitably at least three unnatural amino acids may be incorporated into the protein of interest at three or more sites in the protein. Suitably at least four unnatural amino acids may be incorporated into the protein of interest at four or more sites in the protein. Suitably at least five unnatural amino acids may be incorporated into the protein of interest at five or more sites in the protein. Suitably at least six unnatural amino acids may be incorporated into the protein of interest at six or more sites in the protein. Suitably at least seven unnatural amino acids may be incorporated into the protein of interest at seven or more sites in the protein. Suitably at least eight unnatural amino acids may be incorporated into the protein of interest at eight or more sites in the protein.

When multiple unnatural amino acids are to be incorporated into a protein of interest, it will be understood that multiple codons will need to be incorporated into the encoding nucleic acid sequence at the desired positions such that the tRNA synthetase/tRNA pairs can direct the incorporation of the unnatural amino acids in response to the codon(s). At least 1, 2, 3, 4, 5, 6, 7 or 8 or more codon encoding nucleic acids may be incorporated into the nucleic acid sequence of interest.

When it is desired to incorporate more than one type of unnatural amino acid into the protein of interest into a single protein, a second or further orthogonal tRNA-tRNA synthetase pair may be used to incorporate the second or further unnatural amino acid; suitably said second or further orthogonal tRNA-tRNA synthetase pair recognises a different codon in the nucleic acid encoding the protein of interest so that the two or more unnatural amino acids can be specifically incorporated into different defined sites in the protein in a single manufacturing step. In certain embodiments, two or more orthogonal tRNA-tRNA synthetase pairs may therefore be used.

Once the protein of interest incorporating the unnatural amino acid(s) has been produced in the host cell it can be extracted therefrom by a variety of techniques known in the art, including enzymatic, chemical and/or osmotic lysis and physical disruption. The protein of interest can be purified by standard techniques known in the art such as preparative chromatography, affinity purification or any other suitable technique.

Unnatural Amino Acids

As used herein, the term "unnatural amino acid" refers to an amino acid other than the 20 amino acids that occur naturally in protein.

Non-limiting examples of unnatural amino acids include: a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthypalanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α, α disubstituted amino acid; a β-amino acid; a cyclic amino acid other than proline or histidine, and an aromatic amino acid other than phenylalanine, tyrosine or tryptophan.

In order to incorporate one or more unnatural amino acid(s) of choice into a protein as described herein, the skilled operator simply selects the correct synthetase capable of charging the orthogonal tRNA recognising the codon.

Specific examples of incorporation of different unnatural amino acids are provided herein.

In Example 2, the incorporation of ($N^\varepsilon$-[(tert-butoxy)carbonyl]-l-lysine) and ($N^\varepsilon$-[((2-methylcycloprop-2-en-1-yl)methoxy)carbonyl]-1-lysine is demonstrated. The structures of these compounds are shown in FIG. 22B. Both of these substrates are known efficient substrates for the PylRS/tRNA$_{CUA}$ pair (*Nat Biotechnol* 2014, 32, 465 and *J Am Chem Soc* 2009, 131, 8720).

In Example 9, the incorporation of Boc-K ($N^\varepsilon$-[(tert-butoxy)carbonyl]-L-lysine, Norbonene-K ($N^c$-norbornene-2-yloxycarbonyl-L-lysine), Cyclopropene-K ($N^\varepsilon$-[((2-methylcycloprop-2-en-1-yl)methoxy)carbonyl]-L-lysine) and Bicyclonyne-K ($N^\varepsilon$-([(1R,8S)-bicyclo[6.1.0]non-4-yn-9-yl-methoxy]carbonyl)-Lysine) is shown.

WO2010/139948 describes the incorporation of aliphatic or straight chain carbon backbone amino acids capable of supporting alkyne-azide bonding into a protein of interest using an orthogonal tRNA-tRNA synthetase pair.

WO2013/10844 describes the incorporation of a norbornene amino acid into a protein of interest using an orthogonal tRNA-tRNA synthetase pair.

Antibodies

Suitably, the nucleic acid sequence of interest encodes an antibody or an antibody fragment. One or more unnatural amino acids—suitably, 2, 3, 4, 5, 6, 7 or 8 or more unnatural amino acids—may be incorporated into an antibody or an antibody fragment.

As used herein, term "antibody" refers to a protein of the immunoglobulin family that is capable of binding a corresponding antigen non-covalently, reversibly, and in a specific manner. The term includes, but is not limited to, monoclonal antibodies, human antibodies, humanized antibodies, camelid antibodies, chimeric antibodies, and anti-idiotypic (anti-Id) antibodies. The antibodies can be of any isotype/class and can therefore include IgG, IgE, IgM, IgD, IgA and IgY, or subclass of antibodies—such as IgG1, IgG2, IgG3, IgG4, IgA1 and IgA2.

As used herein, the term "antibody fragment", refers to one or more portions of an antibody that retains the ability to specifically interact with (for example, by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)$_2$ fragment, a bivalent fragment comprising two Fab fragments linked by a disulphide bridge at the hinge region; a Fd fragment consisting of the VH and CH1 domains; a Fv fragment consisting of the VL and VH domains of a single arm of an antibody; a dAb fragment, which consists of a VH domain; and an isolated complementarity determining region (CDR), or other epitope-binding fragments of an antibody. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFV"). Such single chain antibodies are encompassed within the term "antigen binding fragment." These antigen binding fragments are obtained using conventional techniques known to those of skill in the art, and the fragments can be screened for activity in the same manner as intact antibodies.

The antibody may be monospecific, bi-specific, or multispecific. A multispecific antibody may be specific for different epitopes of one target protein or may contain antigen-binding domains specific for more than one target protein. The antibody can be linked to or co-expressed with another functional molecule—such as another peptide or protein. For example, an antibody or fragment thereof can be functionally linked to one or more other molecular entities—such as another antibody or antibody fragment to produce a bi-specific or a multi-specific antibody with a second binding specificity. Functional linking may be achieved using chemical coupling, genetic fusion, or non-covalent association for example.

Other exemplary bispecific formats include scFv-based or diabody bispecific formats, IgG-scFv fusions, dual variable domain (DVD)-rig, Quadroma, knobs-into-holes, common light chain (e.g., common light chain with knobs-into-holes, etc.), CrossMab, CrossFab, (SEED)body, leucine zipper, Duobody, IgG1/IgG2 and dual acting Fab (DAF)-IgG bispecific formats (see, for example, in *mAbs* (2012) 4:6, 1-11).

Suitably, the antibodies that are used are human antibodies. The term "human antibody" includes antibodies having variable regions in which both the framework and CDR regions are derived from sequences of human origin. Furthermore, if the antibody contains a constant region, the constant region also is derived from such human sequences, for example, human germline sequences, or mutated versions of human germline sequences or antibody containing consensus framework sequences derived from human framework sequences analysis. The human antibodies can include amino acid residues not encoded by human sequences (for example, mutations introduced by random or site-specific mutagenesis in vitro or by somatic mutation in vivo, or a conservative substitution to promote stability or manufacturing).

Antibody Drug Conjugate

The antibody or antibody fragment with one or more unnatural amino acids incorporated therein may be used to prepare an antibody drug conjugate (ADC).

ADCs comprise an antibody(s) or antibody fragment(s) conjugated to a drug moiety. The drug moiety can be any drug moiety that has a desired impact on the cell in which the ADC is present. By way of example, it can be an anti-cancer agent, anti-hematological disorder agent, an autoimmune treatment agent, an anti-inflammatory agent, an antifungal agent, an antibacterial agent, an anti-parasitic agent, an anti-viral agent, or an anesthetic agent, or a radioisotope and the like.

The antibodies or antibody fragments can be conjugated to one or more identical or different drug moieties as required. The antibodies or antibody fragments may be conjugated to a drug moiety that modifies a given biological response. Thus, for example, the drug moiety may be a protein, peptide, or polypeptide possessing a desired biological activity. Such proteins may include, for example, a toxin, a cytotoxin, a protein—such as tumor necrosis factor, a cytokine, an apoptotic agent, an anti-angiogenic agent, or, a biological response modifier—such as a lymphokine.

Various methods for conjugating a drug moiety to antibodies or antibody fragments are well known in the art. For example, reference can be made to *MAbs* (2014) 6(1): 46-53 which reviews current methods for site-specific drug conjugation to antibodies. Various techniques for chemical modification of proteins are also known in the art (see, for example, *Nat Chem Biol.* (2011) 7, 876-84; *Bioconjugate Techniques,* Elsevier (2008) and *Chem Biol.* (2010) 17, 213-27).

A drug moiety can be joined to an antibody or an antibody fragment via a linker. As used herein, a "linker" refers to any chemical moiety that is capable of linking an antibody or antibody fragment to a drug moiety. Linkers can be susceptible to cleavage (cleavable linker), such as, acid-induced cleavage, photo-induced cleavage, peptidase-induced cleavage, esterase-induced cleavage, and disulfide bond cleavage. Alternatively, linkers can be substantially resistant to cleavage (for example, stable linker or noncleavable linker).

The ADCs can be characterized and selected for their physical/chemical properties and/or biological activities by various assays known in the art. For example, an antibody can be tested for its antigen binding activity by known methods—such as ELISA, FACS, Biacore or Western blot. Transgenic animals and cell lines are particularly useful in screening ADCs that have potential as prophylactic or therapeutic treatments. Screening for a useful ADC may involve administering a candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. The candidate ADC may be screened serially and individually, or in parallel under medium or high-throughput screening format.

Thus, in a further aspect, there is provided a method of preparing an antibody-drug conjugate comprising the steps of: i) providing the eukaryotic cell described herein, wherein the nucleic acid sequence of interest encodes an antibody or an antibody fragment; ii) incubating the cell in the presence of the unnatural amino acid to be incorporated into the antibody or antibody fragment, wherein said unnatural amino acid is a substrate for the tRNA synthetase; iii) obtaining an antibody or antibody fragment in which an unnatural amino acid has been incorporated therein; and vi) conjugating the antibody or antibody fragment with a drug moiety via the unnatural amino acid. A linker between the unnatural amino acid and the drug moiety may be used.

In one embodiment, the antibody or an antibody fragment comprising one or more (for example, 2, 3, 4, 5, 6, 7 or 8 or more) unnatural amino acids is conjugated to a drug moiety through a linkage between the unnatural amino acid and the drug moiety. Traditionally, a drug moiety is conjugated non-selectively to cysteine or lysine residues in the antibody or antibody fragment. However, this strategy often leads to heterogeneous products, which make optimisation of the biological, physical, and pharmacological properties of an ADC challenging. The use of unnatural amino acids as conjugation points to synthesize homogeneous ADCs with precise control of conjugation site and stoichiometry offers a number of advantages which can include improved pharmacokinetics and improved potency. Site-specific conjugation methods are therefore highly desirable.

To date, many ADCs have targeted an average of 4 drugs per antibody. This ratio has been chosen as an optimal combination of cytotoxicity and pharmacokinetic stability (see *Acc. Chem. Res* (2008) 41(1) 98-107 and *Clin. Cancer. Res* (2004) 10(20):7063-7070). Accordingly, a particular embodiment relates to an antibody or antibody fragment comprising about 4 unnatural amino acids that can be or are conjugated to a drug moiety through a linkage between the unnatural amino acid and the drug moiety.

In one exemplary embodiment, the antibody is an anti-HER2/neu IgG1 humanized antibody or a variant or derivative thereof—such as Trastuzumab.

Different non-naturally occurring amino acids (for example, $N^\epsilon$-[((2-methylcycloprop-2-en-1-yl)methoxy)carbonyl]-L-lysine) for conjugation of one or more small molecules will be incorporated. The molecules can be conjugated with the unnatural amino acid(s) containing mAbs using tetrazine chemistry. The molecules can include cytotoxic molecules or chemical moieties that induce immune responses.

Advantageously, $N^\epsilon$-[((2-methylcycloprop-2-en-1-yl)ethoxy)carbonyl]-L-lysine) exhibits very high incorporation rates at amber codons (and subsequently higher protein expression). Compared with many of the UAAs which are used for protein conjugation in the public domain, cyclopropene has a longer side chain and a more solvent-exposed conjugation handle. This long side-chain, combined with the high rates of amber-codon incorporation, should allow for incorporation of the UAA at more sites within the mAb scaffold. This flexibility can be important for customising different antibody-drug conjugates.

Kits

Kits for producing a protein of interest comprising one or more unnatural amino acids are also provided.

In one aspect, there is provided a kit for incorporating an unnatural amino acid into a protein in a eukaryotic cell comprising: (i) the nucleic acid constructs described herein; or (ii) the combination of nucleic acid constructs described herein; or (iii) the vector described herein; or (iv) the combination of vectors described herein; or (v) the cell described herein; and (vi) optionally, an unnatural amino acid.

Suitably, the kit further comprises a nucleic acid construct or a vector encoding a mutant eRF1, or a cell comprising same.

The kits may also comprise printed instructional materials describing a method for using the reagents to produce such proteins.

General Recombinant DNA Techniques

The present invention employs, unless otherwise indicated, conventional techniques of chemistry, molecular biology, microbiology and recombinant DNA technology, which are within the capabilities of a person of ordinary skill in the art. Such techniques are explained in the literature. See, for example, M. Green & J. Sambrook, 2012, Molecular Cloning: A Laboratory Manual, Cold Spring Harbor Laboratory Press. This text is herein incorporated by reference.

The invention is now described by way of numbered paragraphs:

paragraph 1. A nucleic acid construct for expressing a tRNA synthetase and tRNA pair in a eukaryotic cell, suitably a mammalian or insect cell, comprising:

(i) a nucleic acid sequence encoding the tRNA synthetase operably linked to a first promoter capable of expressing the tRNA synthetase; and (ii) a nucleic acid sequence encoding the tRNA operably linked to a second promoter capable of expressing the tRNA, wherein the first and second promoters are in opposite directions to each other, or wherein the tRNA is present in multiple copies on the nucleic acid construct.

paragraph 2. The nucleic acid construct according to paragraph 1, wherein the nucleic acid construct further comprises a nucleic acid sequence encoding a nucleic acid sequence of interest operably linked to a further promoter capable of expressing the nucleic acid sequence of interest in a eukaryotic cell.

paragraph 3. The nucleic acid construct according to paragraph 2, wherein the promoter is oriented in the same direction as the first promoter, optionally, wherein the promoter capable of expressing the nucleic acid sequence of interest n a eukaryotic cell is the same as the first promoter or different to the first promoter.

paragraph 4. The nucleic acid construct according to any of paragraphs 1 to 3, further comprising a nucleic acid sequence encoding a mutant eRF1, suitably a mutant *Homo sapiens* eRF1, suitably, wherein the mutant eRF1 is selected from the group consisting of E55D, E55A, N129P/K130Q and Y125F or a combination of two or more thereof.

paragraph 5. The nucleic acid construct according to paragraph 4, wherein the nucleic acid sequence encoding the mutant eRF1 and the nucleic acid sequence encoding the tRNA synthetase are linked via a self-cleaving peptide in the same open reading frame.

paragraph 6. A nucleic acid construct for expressing a tRNA and a nucleic acid sequence of interest in a eukaryotic cell, said nucleic acid sequence of interest comprising a codon recognised by the tRNA at the position for incorporation of an unnatural amino acid comprising:

(i) a nucleic acid sequence comprising the nucleic acid sequence of interest operably linked to a first promoter capable of expressing the nucleic acid sequence of interest in a eukaryotic cell; and (ii) a nucleic acid sequence encoding the tRNA operably linked to a second promoter capable of expressing the tRNA, wherein the first and second promoters are in opposite directions to each other, or wherein the tRNA is present in multiple copies on the nucleic acid construct.

paragraph 7. The nucleic acid construct according to paragraph 6, further comprising a nucleic acid sequence encoding a mutant eRF1, suitably a mutant Homo sapiens eRF1, suitably, wherein the mutant eRF1 is selected from the group consisting of E55D, E55A, N129P/K130Q and Y125F or a combination of two or more thereof.

paragraph 8. The nucleic acid construct according to any of the preceding paragraphs, wherein the first and second promoters are in opposite directions to each other and wherein the tRNA is present in multiple copies on the nucleic acid construct.

paragraph 9. The nucleic acid construct according to any of the preceding paragraphs, wherein the tRNA is linked directly to the promoter or indirectly to the promoter, suitably wherein the nucleic acid construct comprises a terminator sequence connected to the tRNA with a linker.

paragraph 10. The nucleic acid construct according to any of the preceding paragraphs, wherein each copy of the nucleic acid sequence encoding the tRNA is under the control of a separate promoter.

paragraph 11. The nucleic acid construct according to any of the preceding paragraphs, wherein the promoter arrangement comprises an elongation factor promoter oriented in a first direction and a Pol III promoter oriented in a second direction.

paragraph 12. The nucleic acid construct according to any of the preceding paragraphs, wherein the first promoter is or is derived from an EF-1 promoter.

paragraph 13. The nucleic acid construct according to any of the preceding paragraphs, wherein the second promoter is or is derived from a U6 promoter.

paragraph 14. The nucleic acid construct according to any of the preceding paragraphs, wherein the tRNA is present in 4, 5, 6, 7 or 8 or more copies on the nucleic acid construct(s).

paragraph 15. The nucleic acid construct according to any of the preceding paragraphs, wherein the tRNA is a wild-type or a variant tRNA, suitably a U25C variant of PylT.

paragraph 16. The nucleic acid construct according to any of the preceding paragraphs, wherein the nucleic acid sequence of interest comprises at least 1, 2, 3 or 4 stop codons.

paragraph 17. The nucleic acid construct according to any of paragraphs 2 to 16, wherein the nucleic acid sequence of interest encodes an antibody or an antibody fragment.

paragraph 18. The nucleic acid construct according to any of the preceding paragraphs, wherein said tRNA synthetase is orthogonal to the endogenous tRNAs in the eukaryotic cell and/or said tRNA is orthogonal to the endogenous tRNA synthetases in the eukaryotic cell and/or said tRNA synthetase is orthogonal to the endogenous tRNAs in the eukaryotic cell and said tRNA is orthogonal to the endogenous tRNA synthetases.

paragraph 19. A combination of nucleic acid constructs comprising the nucleic acid construct according to any of paragraphs 1 to 5 and 8 to 18 and the nucleic acid construct according to any of paragraphs 6 to 18.

paragraph 20. The combination of nucleic acid constructs according to paragraph 19, wherein the nucleic acid sequence encoding the mutant eRF1 is on a separate construct.

paragraph 21. A vector comprising the nucleic acid construct according to any of paragraphs 1 to 18.

paragraph 22. A combination of vectors comprising a vector comprising the nucleic acid construct according to any of paragraphs 1 to 5 and 8 to 18 and a vector comprising the nucleic acid construct according to any of paragraphs 6 to 18.

paragraph 23. The combination of vectors according to paragraph 22, wherein the nucleic acid sequence encoding the mutant eRF1 is on a separate vector.

paragraph 24. A cell comprising the nucleic acid construct according to any of paragraphs 1 to 18, the combination of nucleic acid constructs according to paragraph 19 or paragraph 20, the vector according to paragraph 21 or the combination of vectors according to paragraph 22 or paragraph 23.

paragraph 25. The cell according to paragraph 24, further comprising a nucleic acid construct encoding a mutant eRF1, suitably a mutant Homo sapiens eRF1.

paragraph 26. The cell according to paragraph 25, wherein the mutant eRF1 is selected from the group consisting of E55D, E55A, N129P/K130Q and Y125F or a combination of two or more thereof, suitably, where in the mutations are made in the *Homo sapiens* eRF1 gene sequence as described in GenBank Accession Number AF095901.1.

paragraph 27. The cell according to any of paragraphs 24-26, wherein the cell is an insect cell or a mammalian cell.

paragraph 28. The cell according to any of paragraphs 24-27, wherein the cell is transiently or stably transfected with the nucleic acid.

paragraph 29. A kit for incorporating an unnatural amino acid into a protein in a eukaryotic cell, suitably a mammalian or insect cell, comprising:

(i) the nucleic acid construct according to any of paragraphs 1 to 5 and 8 to 18 and the nucleic acid construct according to any of paragraphs 6 to 18; or (ii) the combination of nucleic acid constructs according to paragraph 19 or paragraph 20; or (iii) the vector according to paragraph 21; or (iv) the combination of vectors according to paragraph 22 or paragraph 23; or (v) the insect or mammalian cell according to paragraph 27 or paragraph 28; and (vi) optionally, an unnatural amino acid.

paragraph 30. The kit according to paragraph 29, further comprising a nucleic acid construct or a vector encoding a mutant eRF1, or a cell comprising same.

paragraph 31. A method for incorporating an unnatural amino acid into a protein of interest in a eukaryotic cell, suitably a mammalian or insect cell, comprising the steps of:

i) providing the cell according to paragraph 27 or paragraph 28, wherein said cell comprises the combination of nucleic acid constructs according to paragraph 19 or paragraph 20 or the combination of vectors according to paragraph 22 or paragraph 23; and ii) incubating the cell in the presence of the unnatural amino acid to be incorporated into a protein of interest encoded by the nucleic acid sequence of interest, wherein said unnatural amino acid is a substrate for the tRNA synthetase; and iii) incubating the cell to allow incorporation of said unnatural amino acid into the protein of interest via the orthogonal tRNA-tRNA synthetase pair.

paragraph 32. The method according to paragraph 31, wherein at least 3, 4, or 5 unnatural amino acids are incorporated into the protein of interest.

paragraph 33. A method of preparing an antibody-drug conjugate comprising the steps of:

i) providing the cell according to paragraph 27 or paragraph 28, wherein said cell comprises the combination of nucleic acid constructs according to paragraph 19 or paragraph 20 or the combination of vectors according to paragraph 22 or paragraph 23, and wherein the nucleic acid sequence of interest encodes an antibody or an antibody fragment;

ii) incubating the cell in the presence of the unnatural amino acid to be incorporated into the antibody or antibody fragment, wherein said unnatural amino acid is a substrate for the tRNA synthetase;

iii) obtaining an antibody or antibody fragment in which an unnatural amino acid has been incorporated therein; and iv) conjugating the antibody or antibody fragment with a drug moiety via the unnatural amino acid.

paragraph 34. Use of: (i) the nucleic acid construct according to any of paragraphs 1 to 5 and 8 to 18 and the nucleic acid construct according to any of paragraphs 6 to 18; or (ii) the combination of nucleic acid constructs according to paragraph 19 or paragraph 20; or (iii) the vector according to paragraph 21; or (iv) the combination of vectors according to paragraph 22 or paragraph 23; or (v) the insect or mammalian cell according to paragraph 27 or paragraph 28, for incorporating an unnatural amino acid into a protein of interest in a eukaryotic cell, suitably a mammalian or insect cell.

paragraph 35. A method for incorporating an unnatural amino acid into a protein of interest in a eukaryotic cell, suitably a mammalian or insect cell, comprising the steps of:

i) providing a eukaryotic cell expressing an orthogonal tRNA synthetase and tRNA pair, a nucleic acid sequence of interest and a mutant eRF1, said nucleic acid sequence of interest comprising a codon recognised by the tRNA at the position for incorporation of an unnatural amino acid;

ii) incubating the eukaryotic cell in the presence of an unnatural amino acid to be incorporated into a protein encoded by the nucleic acid sequence of interest, wherein said unnatural amino acid is a substrate for the orthogonal tRNA synthetase; and iii) incubating the eukaryotic cell to allow incorporation of said unnatural amino acid into the protein of interest via the orthogonal tRNA-tRNA synthetase pair.

paragraph 36. Use of a mutant eRF7 for incorporating an unnatural amino acid into a protein of interest in a eukaryotic cell, suitably a mammalian or insect cell.

paragraph 37. A method of identifying a mutant of eRF1 that increases the incorporation of an unnatural amino acid in a protein of interest, comprising the steps of:

(i) providing a cell that is capable in incorporating an unnatural amino into a protein of interest, suitably, wherein said cell expresses an orthogonal tRNA synthetase and tRNA pair, a nucleic acid sequence of interest and optionally a mutant eRF1, said nucleic acid sequence of interest comprising a codon recognised by the tRNA at the position for incorporation of an unnatural amino acid;

incubating the cell in the presence of the unnatural amino acid to be incorporated into the protein of interest and in the presence and absence of the mutant of eRF1, wherein said unnatural amino acid is a substrate for the tRNA synthetase; and determining the level of unnatural amino acid incorporation into the protein of interest in the presence and absence of the mutant of eRF1, wherein an increase in the level of unnatural amino acid incorporation into the protein of interest in the presence the mutant of eRF1 is indicative that said mutant of eRF1 increases the incorporation of an unnatural amino acid in the protein of interest.

paragraph 38. A construct, vector, cell, kit, method or use substantially as described herein with reference to the accompanying description and drawings.

DESCRIPTION OF THE EMBODIMENTS

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

EXAMPLES

Example 1—Materials & Methods

DNA Constructs

Reporter constructs were derived from the previously described plasmid pMbPylRS-mCherr-TAG-EGHP-HA1 restriction sites was replaced with sfGFP 150TAG, codon-optimized (Supplementary Information Table S1) for expression in human cell lines (Life Technologies), to create plasmid CMV-PylRS/CMV-sfGFP(TAG). The same region was replaced with a Renilla-TAG-firefly luciferase cassette to create plasmid. CMV-PylRS/CMV-DLR(TAG). Stop or sense codons were introduced by site-directed mutagenesis into sfGFP 150TAG or the Renilla-TAG-firefly luciferase cassette in pJet1.2 (Thermo scientific), using KOD Hot Start polymerase (Novagen). Subcloning the resulting mutants into pMbPylRS-mCherry-TAG-EGFP-HA gave sfGFP 150Leu (CMV-PylRS/CMV-sfGFP), and sfGFP 101, 133, 150TAG (CMV-PylRS/CMV-sfGFP(TAG)3) and the dual luciferase reporter plasmids containing TAA (CMV-PylRS/CMV-DLR(TAA)), TGA (CMV-PylRS/CMV-DLR(TGA)) and SER (CMV-PylRS/CMV-DLR).

For the 4×U6 PylT plasmid series, a PB220PA-1 backbone (System Biosciences) was used. The CMV cassette was replaced with an EF-1α cassette from CD532A-2 (System Biosciences), subcloning the SpeI/SalI fragment into SpeI/SalI of PB220PA-1. The optimized U6 promoter/*Methanosarchia mazei* pyrrolysine tRNA insert (Supplementary Information Table S1) was synthesized (Life technologies) with SpeI/AvrII flanking sites. A 4×U6 PylT tandem cassette was constructed by repeated insertion of the SpeI/AvrII fragment into a unique Spa site 5' of the EF1 promoter. The (U6-PylT*)4/EF-1α-PylRS, (U6-PylT*)4/EF-1α-sfGFP(TAG) and (U6-PylT*)4/EF-1α-sfGFP(TAG)3 plasmids were constructed by subcloning of the relevant genes from AG28, CMV-PylRS/CMV-sfGFP and CMV-PylRS/CMV-S2. The mCherry-TAG-EGFP cassette between the MfeI and NheI sfGFP(TAG)3.

The Homo sapiens eRF1 gene (GenBank: AF095901.1) was codon optimized for *Drosophila melanogaster* (Supplementary Information Table S1), and extended by an N-terminal His6 tag, a C-terminal triple stop (UAAUGAUAG). The codon optimization was performed using the Helixweb toolkit2. Additional mutations were introduced by site-directed mutagenesis (Supplementary Information Table 2), and the resulting constructs cloned into the mammalian expression vectors pcDNATM5/FRT/TO using restriction sites HindIII/NotI to create the peRF1(X) vectors in which X represents the mutation, and eRF1 is expressed from a CMV promoter.

Cell Culture, Antibodies and Assays

Adherent HEK293T cells were maintained on Dulbecco's modified Eagle's medium (DMEM)-Glutamax (Gibco), supplemented with 10% FBS in a 5% CO2 atmosphere at 37° C. Transient transfections were performed using TransIT®-293 (Mires) transfection reagent or polyethylenimin (Max PEI, Polysciences) in a 3:1 PEI:DNA ratio following the manufacturers protocol.

Expression of proteins and eRF1 depletion was confirmed by immunoblotting with antibodies against eRF1 (ab30928, Abcam), Actin (#4967, Cell Signaling Technology), FLAG (A8592, Sigma-Aldrich), HIS (27E8, Cell Signaling Technology), HA (C29F4, Cell Signaling Technology) and corresponding secondary HRP-linked antibodies (#7074, #7076, #7077, Cell Signaling Technology). Depletion of eRF1 was achieved by transfection of commercially available eRF1 shRNAs (sc-37871-SH, Santa Cruz Biotechnology) in equal amounts to other transfected plasmids.

Amino acid 1 was commercially available (E1610.0025, Bachem), amino acid 2 was synthesized as previously described. For protein expression, amino acid solutions were prepared as neutralized stock solutions in culture media, and added to cultured cells either with the preincubated transfection mixture (TransIT-293, 96 well plates) or while changing the culture media four hours post transfection (PEI, 24 well plates, 10 cm culture dishes, T75 flasks).

Northern Blotting

Total RNA was isolated from HEK293T cells using Qiazol lysis reagent (Qiagen) and precipitated with isopropanol. Northern blotting was performed with the NorthernMax-Gly kit (Ambion); the RNA was denatured in glyoxal load dye, separated on a 2% agarose gel, transferred onto BrightStar-Plus positively charged nylon membrane (Ambion) and cross-linked by UV via a Stratalinker 2400 UV crosslinker (Strategene). The membrane was hybridized overnight at 37° C. with a 5'-biotinylated DNA probe (5'-GGAAACCCCGGGAATCTAACCCGGCTGAACG-GATTTAGAG-3'). The hybridized probe was detected using chemiluminescent nucleic acid detection module (Thermo Scientific).

Dual Luciferase Assay

HEK293T cells were transfected in a 96 well plate (Costar #3595, Corning) using twice the suggested amount of DNA (total 0.2 µg) and TransIT®-293 reagent (0.6 µl) per well. Dual Luciferase assays were performed according to a simplified manufacturer's protocol (Promega). After 16 hours of growth the culture media was removed, and cells lysed in 20 µl of passive lysis buffer for 15 minutes at room temperature. 10 µl of lysate were then added to 50 µl of Luciferase Assay Buffer II, in white 96 well plates (Nunc 236105, Thermo Scientific). Subsequently, the firefly luciferase luminescence measurement was taken (Pherastar FS, BMG Labtech), the reaction quenched and the Renilla luminescence measurement taken after addition of 50 µl Stop & Glo buffer. Experiments were performed in quadruplicate, with three replicates used for dual luciferase measurements, and the remaining replicate for immunoblotting after lysis in 50 µl of RIPA buffer (Sigma) with Complete protease inhibitor (Roche).

Transient Expression of sfGFP Variants

Figure 10:
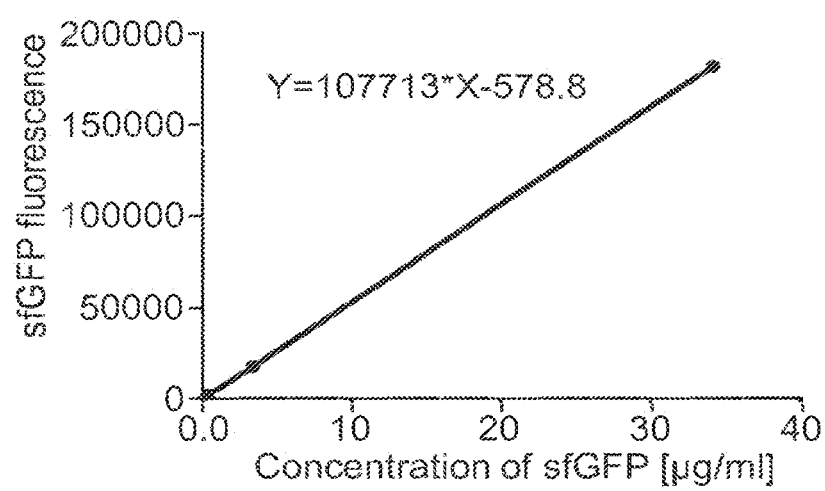
FIG. 10 illustrates the calibration curve for the fluorometric quantification of sfGFP in lysis buffer. The fluorescence intensity of purified and serially diluted sfGFP is plotted against the concentration of sfGFP in the sample. The protein was purified after bacterial expression, quantified by absorbance measurements at 280 nm and diluted in RIPA-buffer with added protease inhibitor.

Expressions of sfGFP(TAG) and sfGFP(TAG)3 for fluorescent assays were performed in 24 well plates. Routinely, 100000 cells were seeded per well, grown over night and transiently transfected using 160 ng DNA per plasmid, 1.5 µl of PEI (1 mg/ml) and 50 µl reduced serum media (Opti-MEM, Gibco). Four hours post transfection, the media was exchanged and amino acid 1 or 2 added to the fresh growth media. Following 48 hours of growth, the supernatant was carefully removed and cells lysed in 100 µl RIPA buffer (Sigma) with added Complete protease inhibitor (Roche) while shaking. 50 µl of the lysate were transferred into 96 well plates (Costar #3595, Corning) and the fluorescence intensity determined at 485/520 nm (Pherastar FS, BMG Labtech). sfGFP was quantified in lysates using a calibration curve (FIG. 10).

For calibration purposes, sfGFP was expressed in *E. coli* DH10b cells from a p15A-based plasmid under pBAD promoter control, and purified by Ni-affinity chromatography as described previously[4]. Protein purity was verified by coomassie staining after SDS-PAGE.

The absolute protein concentration in the reference sample was determined by measuring the absorbance at 280 nm (extinction coefficient 0.6845) serially diluted (1:10 per step) in RIPA buffer (Sigma) supplemented with Complete protease Inhibitor (Roche). The fluorescense intensity (excitation 485 nm, emission 520 nm) for a given concentration of sfGFP was measured in a volume of 50 µl in 96-well plates (Costar, Corning) in triplicate. Measurements outside of the linear range of the microplate reader for a given gain setting (Pherastar FS, BMG Labtech) were discarded and the remaining data points fitted to a linear curve. Subsequent measurements of sfGFP fluorescence in cell lysates were performed under the same conditions, and sfGFP concentrations determined with reference to the standard curve (Prism6, Graphpad).

Protein expression for mass spectrometry was performed in 10 cm culture dishes. HEK293T were transfected in a 10 cm tissue culture dish with 15 μg DNA with PEI. Cell culture media was exchanged 4 hours post transfection, and incubated for 72 hours with amino acid. Cells were washed twice with PBS and lysed in 1 mL RIPA buffer. Cleared lysate was added to 50 μL GFP-Trap® M (ChromoTek) and incubated for 4 hours at 4° C. Beads were magnetically separated and washed with 1 mL RIPA, 1 mL PBS, 1 mL PBS+500 mM NaCl, 1 mL ddH2O and eluted in 1% Acetic Acid/ddH2O.
Mass Spectrometry Electrospray mass spectrometry was carried out using an Agilent 1200 LC-MS system equipped with a 6130 Quadrupole spectrometer. The solvent system consisted of 0.1% formic acid in H2O as buffer A, and 0.1% formic acid in acetonitrile (MeCN) as buffer B. Protein UV absorbance was monitored at 214 and 280 nm. Protein MS acquisition was carried out in positive ion mode and total protein masses were calculated by deconvolution within the MS Chemstation software (Agilent Technologies)[6].

Example 2—Increasing tRNA Levels Increases Unnatural Amino Acid Incorporation Efficiency We optimized the expression levels of $tRNA_{CUA}$ to increase the efficiency of unnatural amino acid incorporation in mammalian cells. Investigators have used different PylRS and tRNA plasmids that vary the copy number of PylRS, $tRNA_{CUA}$ and the choice of promoters[17-20]. However, there are no reports that quantify the yields of proteins bearing unnatural amino acids incorporated with the PylRS/$tRNA_{CUA}$ pair in mammalian cells, nor are there reports that quantify the efficiencies of unnatural amino acid incorporation relative to the expression of a control protein expressed from a gene that does not contain an amber stop codon. These experiments are crucial for understanding how well unnatural amino acid incorporation in mammalian cells compares to natural protein synthesis.

Figure 22A:
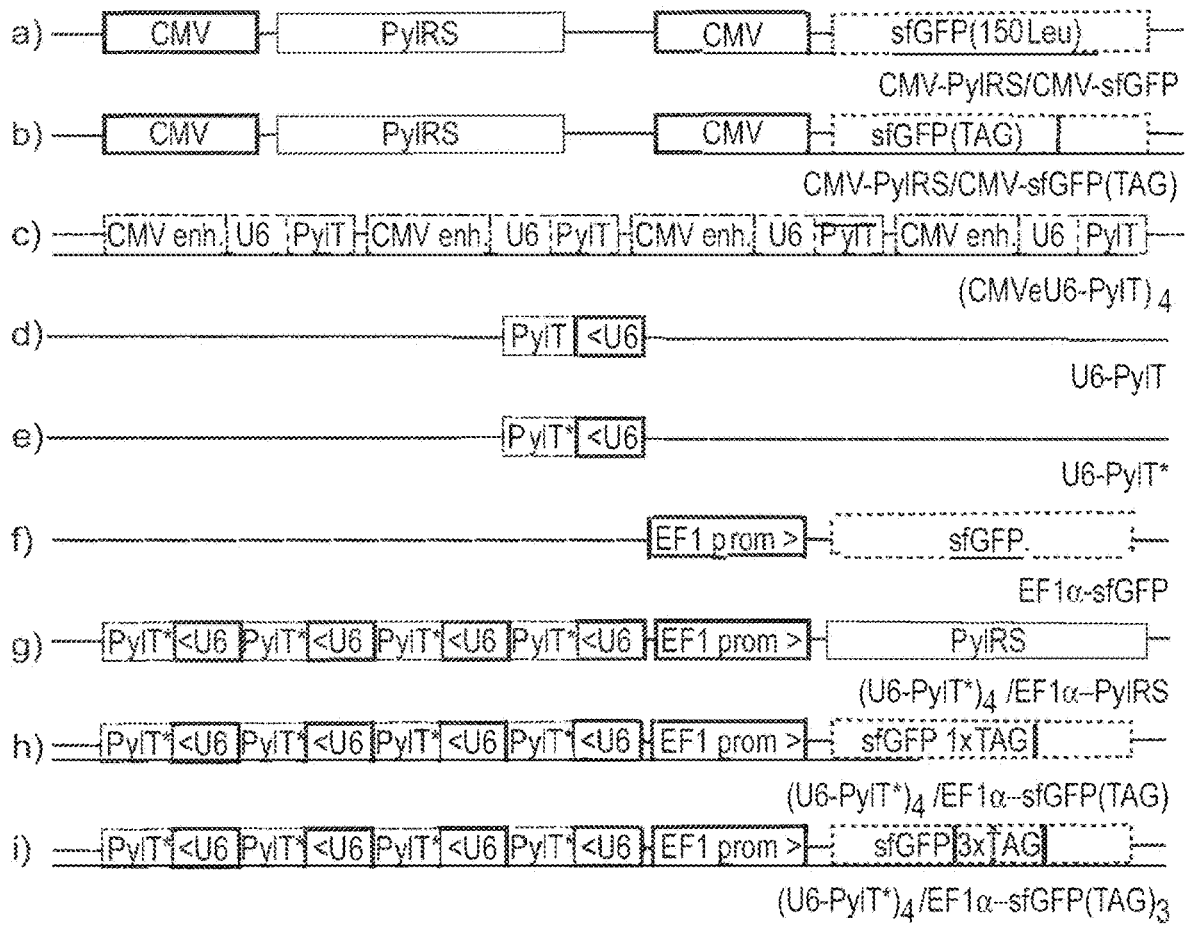
FIGS. 22A-22B show the plasmid constructs and unnatural amino acids used.
Figure 22B:
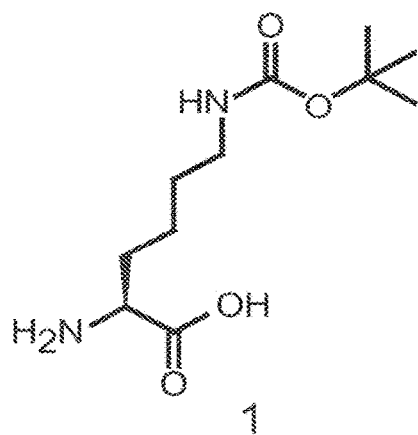
Figure 22B:
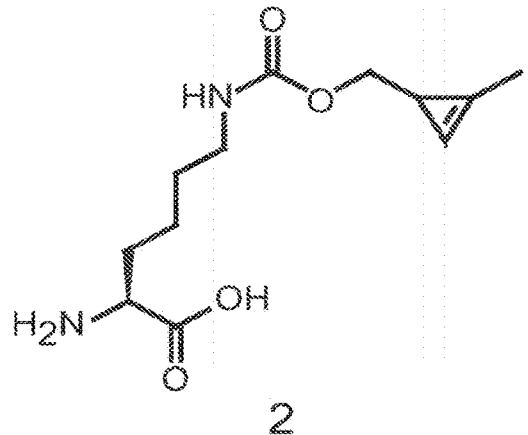

We first tested the efficiency of unnatural amino acid incorporation using plasmids b and c bearing a single copy of PylRS on a CMV promoter and four copies of $tRNA_{CUA}$ each driven by a U6 promoter with a CMV enhancer[17,19] (Construct schematics are shown in FIG. 22A). This system directed the incorporation of 1 (NE-$^\varepsilon$[(tert-butoxy)carbonyl]-L-lysine, or 2 (N$^\varepsilon$-[((2-methylcycloprop-2-en-1-yl)methoxy)carbonyl]-L-lysine (FIG. 22B), both known and efficient substrates for the PylRS/$tRNA_{CUA}$ pair[21,22]) in response to an amber codon at position 150 in sfGFP[23] (CMV-sfGWP(TAG)) with efficiencies of 5% and 7% (FIGS. 1A-1B); all incorporation efficiencies are reported as a percentage of sfGFP levels produced from an otherwise identical control construct bearing a leucine codon in place of the amber codon at position 150 (plasmid a, FIG. 22A). Next we replaced the four copies of $tRNA_{CUA}$ with a single copy of $tRNA_{CUA}$ on an optimized U6 promoter, leading to a small decrease in unnatural amino acid incorporation efficiency (plasmids b and d).

Unlike the original four-copy cassette, (c), the new U6 $tRNA_{CUA}$ cassette, (d), does not contain the CMV enhancer, and produces a precise 5' end for the tRNA, that does not require nuclease processing. Northern blots (FIG. 1C) demonstrate that the levels of Pyl $tRNA_{CUA}$ produced from d, are comparable to the levels produced from c. This indicates that the altered tRNA expression construct provides more copies of the tRNA per copy of the tRNA gene. Replacing $tRNA_{CUA}$ with a U25C variant[24] increased the incorporation efficiency slightly from 2.7%-3.5% to 4.7-5.1% (plasmids b and e, FIG. 22A) and had a small effect on $tRNA_{CUA}$ level.

Creating tandem arrays, each containing four copies of U6 Pyl $tRNA_{CUA}$ (bearing U25C) and switching the promoter for the protein coding genes from CMV to EF-1α (plasmids g and h, FIG. 22A) led to a substantial increase in sfGFP bearing 1 or 2. In this system amino acid 1 was incorporated in response to the amber codon in sfGFP with an efficiency of 62%, while 2 was incorporated with an efficiency of approximately 129%. Western blots demonstrate that changing the promoter of the protein coding genes to EF-1α does not change the levels of PylRS (anti-FLAG b+e vs g+h, FIG. 1B) or wt sfGFP (a vs f FIG. 1B), demonstrating that neither PylRS levels nor maximal levels of sfGFP expression are substantially altered by changing to the EF1 α promoter. However, northern blots demonstrate that tRNA levels are much higher in this system than in all other systems tested, strongly suggesting that the large increases in unnatural amino acid incorporation efficiency we observe are caused by an increase in tRNA level.

Example 3—Ectopic Expression of Selected eRF1 Variants does not Increase Read Through of Stop Codons Next, we asked if we could further enhance unnatural amino acid incorporation efficiency, without increasing read-through of other stop codons, by engineering eRF1. While the efficiency of unnatural amino acid incorporation was already good with the optimized synthetase and tRNA system, we envisioned that eRF1 engineering might further improve this efficiency and allow us to efficiently incorporate unnatural amino acids at multiple sites in a protein.

We first identified amino acid positions in eRF1 that are reported to have an effect on termination at amber codons from genetic or biochemical studies[25-30]. These mutations are in the N-terminal domain of eRF1 (FIG. 2A) that interacts with the stop codon on the mRNA within the ribosome. To assess the effect of the eRF1 mutants on translational termination in mammalian cells we quantified suppressor tRNA independent read-through at the amber, opal and ochre stop codon in HEK 293T cells and in HEK 293T cells bearing added, overexpressed human eRF1 and eRF1 mutants (FIG. 2B). eRF1 forms a complex with eRF3, primarily mediated through the C-terminal domain on eRF1[37], that mediates translational termination. eRF3 is present in cells at levels comparable to endogenous eRF1, and therefore eRF3 limits the number of termination complexes that may form[35]. Overexpression of eRF1 N-terminal domain mutants may bias (by mass action) these complexes towards containing the eRF1 mutants, thereby revealing the phenotype of the eRF1 mutations.

We introduced each eRF1 variant into cells (FIG. 2B), and measured basal read-through of stop codons, using three dual luciferase reporters (FIG. 2C). Each reporter contained an N-terminal Renilla luciferase followed by a stop codon (amber, opal or ochre) and a C-terminal firefly luciferase[31-34]. The read through of the stop codons was between 0.08 and 0.12% (TAG 0.09%, TGA 0.12%, TAA 0.08%), providing a benchmark for further experiments. Ectopic overexpression of eRF1 led to a decrease in read-through of all three stop codons (TAG 0.03%, TGA 0.07%, TAA 0.04%), consistent with the increased level of eRF1 in cells[35]. This decrease in read-through is small, consistent with the levels of eRF3 being comparable to the levels of endogenous eRF1, and eRF3 levels limiting the number of functional termination complexes that can be formed[35].

Introduction of eRF1 variants increased stop codon readthrough with respect to the introduction of wild-type eRF1. However, for all eRF1 mutants tested, except two, read through of all three stop codons was not increased above the levels found in the absence of ectopically expressed eRF1. We conclude that ectopic expression of most of the eRF1 variants tested does not increase read through of stop codons above basal levels.

The two eRF1 mutants which increase read through of stop codons above levels normally found in cells are eRF1 Δ100, a mutant that increases read-through to 1.6% (TAA), 2% (TAG) and 15% (TGA) and the T122Q, S123F mutant[29] that selectively increases read-through at TGA codons 2-fold. Reduction of endogenous eRF1 levels by shRNA increased basal read-through for all three stop codons 2- to 3-fold.

The effect of the eRF1 Δ100 mutant on read through of all stop codons is expected, as the N-terminal domain, from which the residues are deleted, mediates recognition of all three stop codons in mRNA, but does not mediate interactions with eRF3[36-39]. The mutant is therefore predicted to form inactive complexes with eRF3, decreasing the number of functional eRF1/eRF3 complexes that can mediate termination. Similarly, the effects of shRNA against eRFA1 on all stop codons are expected[40] since a decrease in eRF1 should lead to a decrease in termination on all stop codons.

Example 4—eRF1 Mutants Increase Unnatural Amino Acid Incorporation Efficiency

Figure 2D:
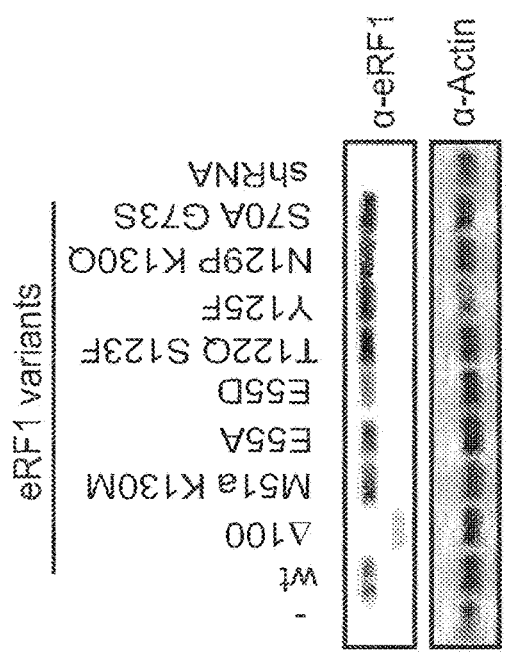

To investigate the effects of eRF1, eRF1 mutants and shRNA on unnatural amino acid incorporation, we transfected cells with the relevant eRF1 mutant (FIG. 2D). Each sample was also provided with the dual luciferase reporter of amber suppression, a single copy of the orthogonal pyrrolysyl tRNA-synthetase (PylRS)/tRNACUA pair (the arrangement shown as b+d in FIG. 22A, but with a dual luciferase reporter replacing sfGFP). We used this system to maximize the dynamic range with which we could measure the enhancement provided by eRF1 variants. The amino acid 1 was added to all cells. In one case, an shRNA construct to endogenous eRF1[40] was added allowing us to compare the effects of ectopically expressed eRF1 mutants to knocking down endogenous eRF1.

The dual luciferase assay was used to determine the effects of eRF1 on unnatural amino acid incorporation efficiency (FIG. 2E). In the absence of ectopically expressed release factor, the efficiency of unnatural amino acid incorporation was approximately 5.3% in this assay. The incorporation efficiency was decreased slightly upon ectopic expression of wild-type release factor, and increased to 13% upon shRNA knockdown of endogenous eRF1. The efficiency of incorporation for 1 increased in the presence of all mutant release factors except the S70A, G73S mutant. This mutant was described previously as a bipotent LAR specific eRF1.[28,41]

Figure 9:
FIG. 9 illustrates human eRF1 variants expressed following transient transfection of HEK 293T cells with peRF1(X) and CMV-PylRS/CMIT-DLR(TAG). The negative control (−) detects endogenous eRF1. The absolute expression levels of protein produced in the dual luciferase assay are shown by α-Renilla western blot. No tfx is untransfected cells.

Two eRF1 mutants led to the most efficient unnatural amino acid incorporation: eRF1 (E55D), 27%; and eRF1 (Δ100), 36%. The incorporation efficiencies with the Δ100 mutant and the E55D mutant are 5- to 7-fold greater than the incorporation efficiency in cells that do not contain ectopically expressed release factor. Interestingly, while strongly enhancing amber readthrough in the presence and absence of the PylRS/tRN$_{CUA}$ pair, the eRF1Δ100 mutant significantly reduced the total amount of luciferase produced in both situations, consistent with a drastic disruption of termination at all three stop codons having global effects on translation efficiency (FIG. 9). In addition, the Δ100 mutant leads to readthrough of all three stop codons in the absence of suppressor tRNAs; therefore, we did not investigate this release factor mutant further. We focused further work on eRF1 (E55D). This release factor mutant has been identified to removes formyl-methionine from the initiator tRNA in response to the ochre and opal codon more efficiently than in response to the amber codon, in an in vitro assay using rabbit reticulocyte ribosomes.[25]

Example 5—An Optimized System for Incorporating Multiple Unnatural Amino Acids

Figure 3A:
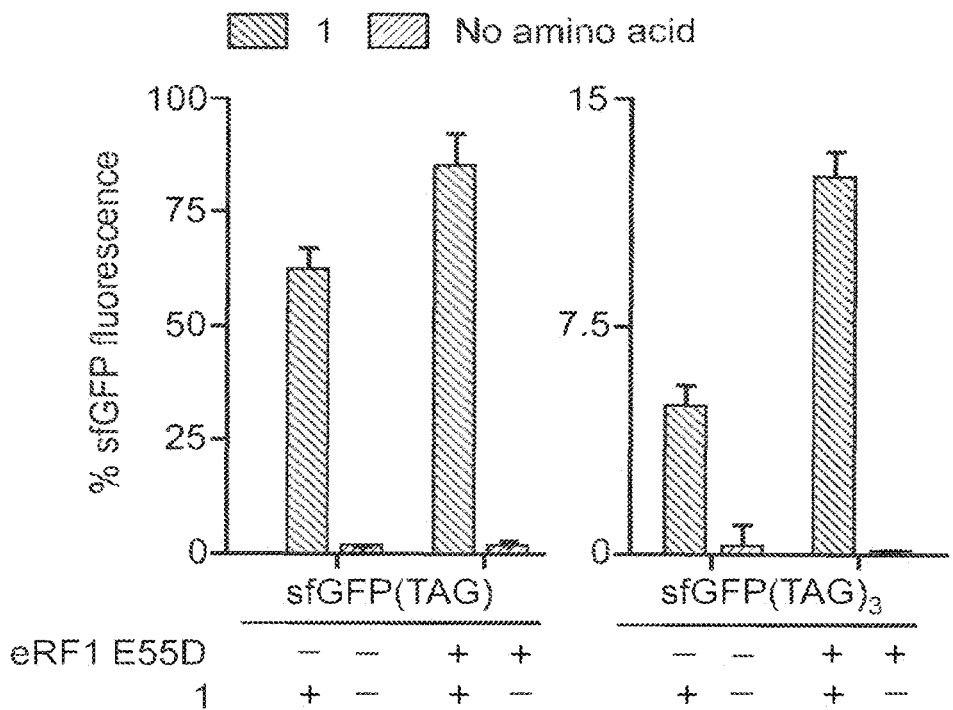
FIGS. 3A-3D illustrates combining eRF1 E55D with an optimized PylRS/tRNA$_{CUA}$ pair expression system enables efficient incorporation of multiple unnatural amino acids into recombinant proteins in mammalian cells.
Figure 3B:
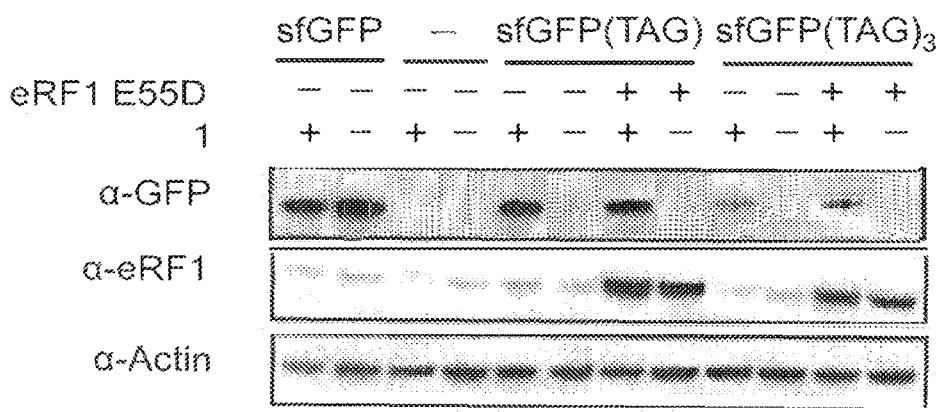

Next, we combined the optimized synthetase and tRNA system and the E55D mutant of eRF1. (FIG. 3A-3D). We find that the addition of eRF1 (E55D) to cells containing the PylRS/tRNA$_{CUA}$ pair, grown in the presence of 1, increases the incorporation of 1 into sfGFP(TAG) from 62% to 85% (FIG. 3A), Similarly, the addition of the eRF1 (E55D) increases the efficiency with which 1 is incorporated into sfGFP(TAG)3, that contains amber stop codons at positions K101, D133 and V15014 of GPF, from 5% to 12% (FIG. 3A-3B). The yield of sfGFP-1 from sfGFP(TAG) was 0.65 μg from $10^5$ cells, while the yield of sfGFP-(1)3 from sfGFP-(TAG)3 was 0.1 μg per $10^5$ cells (FIG. 10; all yields are quoted per number of cells seeded, and were measured 48 h after transfection).

Figure 3C:
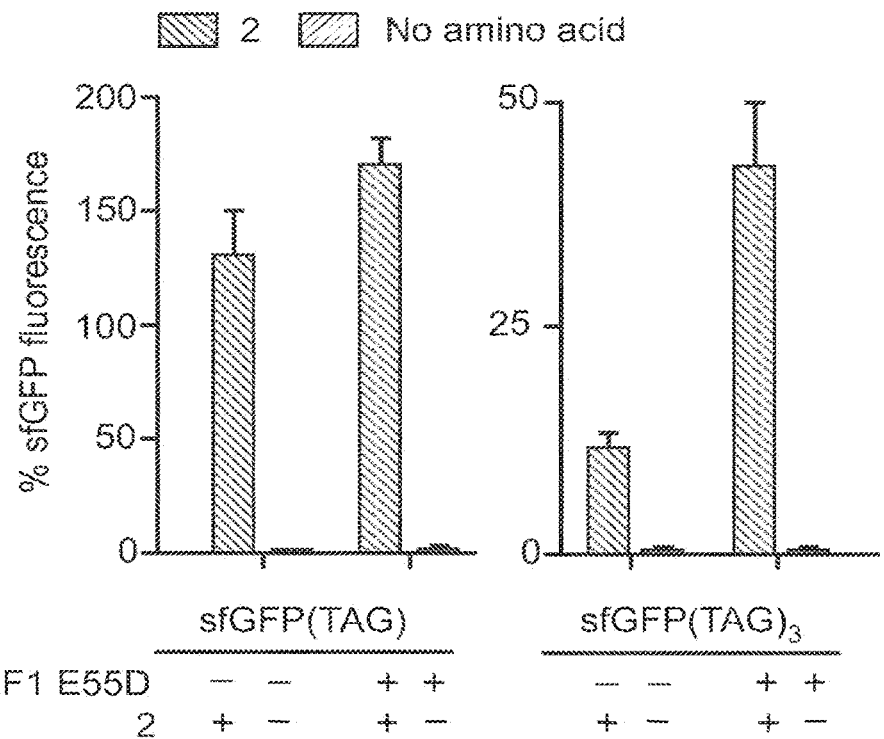
Figure 3D:
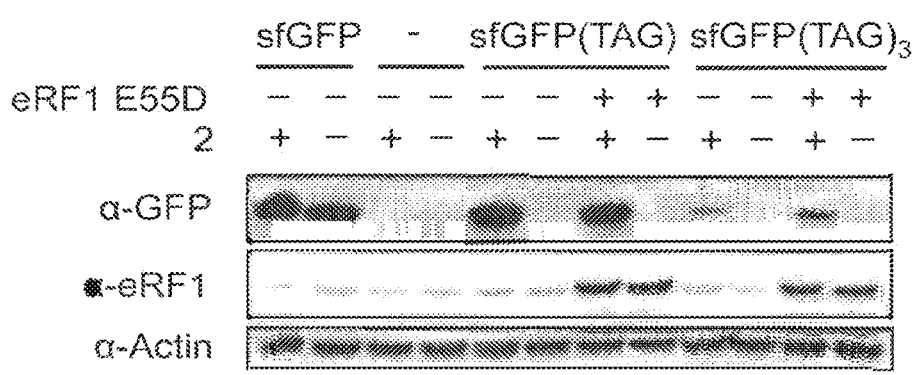
Figure 4A:
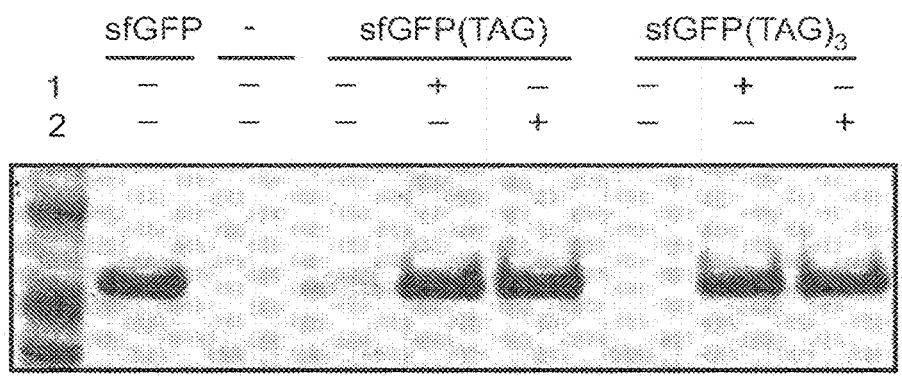
FIGS. 4A-4B illustrates the expression, purification and characterization of recombinant sfGFP incorporating one or three unnatural amino acids (FIG. 4A). Plasmids g, h (or i, FIG. 22A) and eRF1 E55D were transiently transfected into REK293T cells, and grown in the presence or absence of 2 mM amino acid 1 or 0.5 mM amino acid 2 for 48 hours. Full-length sfGFP was purified by Ni-NTA chromatography.
Figure 4B:
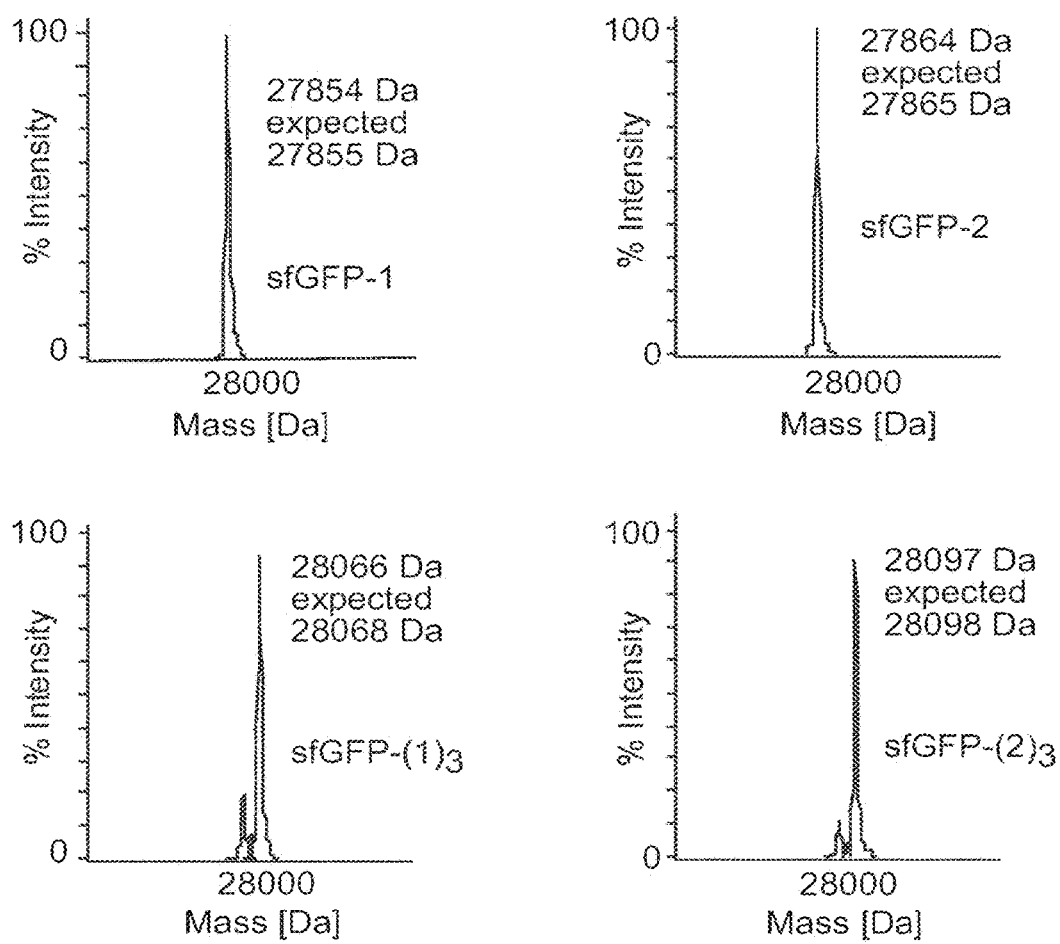
Figure 11A:
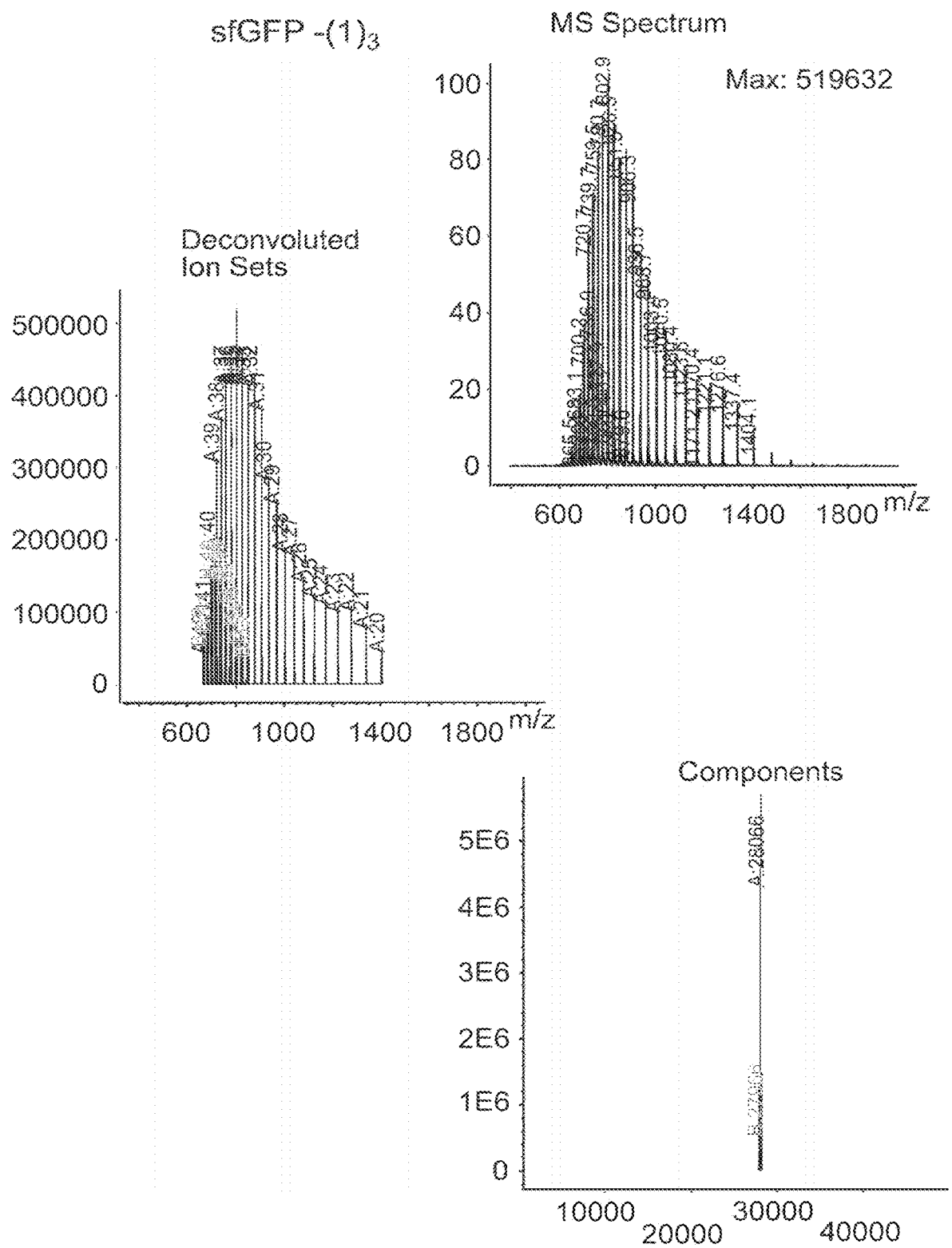
FIGS. 11A-11B illustrates electrospray ionization mass spectrometry which confirms the quantitative incorporation of unnatural amino acids 1 (FIG. 11A) and 2 (FIG. 11B), at three sites in sfGFP. The minor component represents the spontaneous cleavage at the carbamate groups of one 1 or 2 during detection, producing a native lysine. The corresponding mass loss is calculated to be 100 or 110 Da, respectively. We have previously observed that carbamate cleavage of 1 occurs in the electron spray ionization process[7].
Figure 11B:
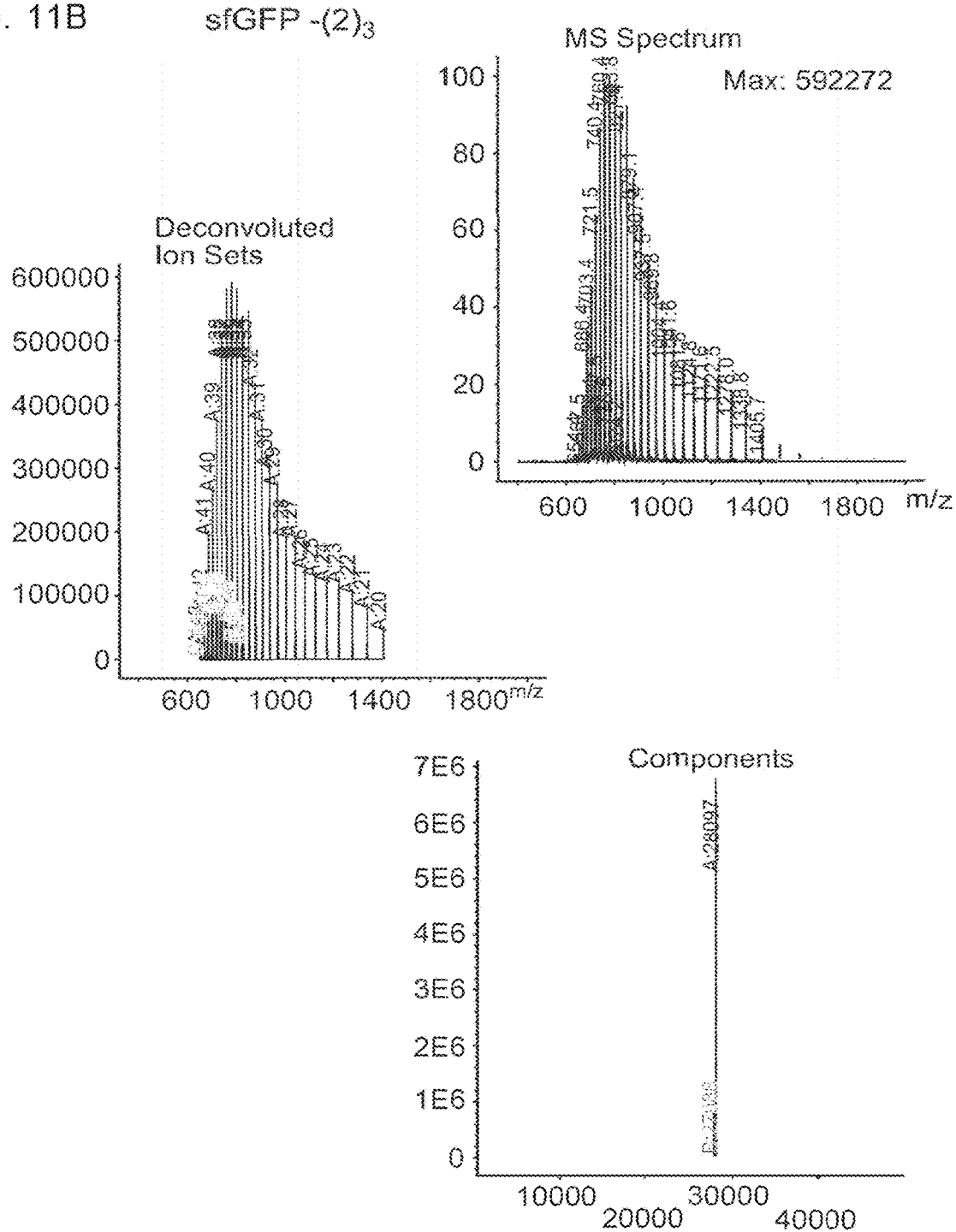

We find that the addition of the eRF1 (E55D) to cells containing the PylRS/tRNA$_{CUA}$ pair, grown in the presence of 2, increases the incorporation of 2 into sfGFP(TAG) from 129% to 157%, and that the addition of the eRF1 (E55D) quadruples the efficiency of producing of sfGFP-(2)$_3$ from sfGFP(TAG)$_3$ from 11% to 43% (FIG. 3C-3D). The yield of sfGFP-2 from sfGFP(TAG) was 1.76 μg per $10^5$ cells, while the yield of sfGFP-(2)$_3$ from sfGFP(TAG)$_3$ was 0.49 μg per 105 cells (FIG. 10). Full-length sfGFP was purified from cell lysates containing the optimized system (FIG. 4A). Electrospray ionization mass spectrometry demonstrated the site-specific incorporation of one and three molecules of 1 and 2 into sfGFP from sfGFP(TAG) and sfGFP(TAG)$_3$ respectively (FIG. 4B, FIGS. 11A-11B). This data, in combination with the no amino acid controls in FIG. 4A demonstrate the high fidelity incorporation of unnatural amino acids in the presence of eRF1 (E55D).

Example 6—Genomic Integration of Inducible eRF1 Mutants Enhances Amber Suppression The eRF1-enhanced expression system described so far relies on the parallel transfection of three plasmids in order to introduce all necessary components for unnatural amino acid incorporation into cells. By genomic integration of the eRF1 E55D mutant, only two plasmids (FIGS. 1A-1C, construct g combined with h or i) have to be transfected, increasing the amount of these plasmids delivered into cells.

By using the tetracycline inducible promoter for eRF1, a cell line was created that can be switched from a standard cell culture maintenance mode into a high efficiency amber suppression mode when required, by addition of tetracycline to the growth media.

The eRF1 variants were introduced into a Flp-In™ T-REx™ 293 cell line (Life Technologies). The cell line contains a single, transcriptionally active genomic FRT target site, and thereby removes variation in expression levels due to the genomic insertion site. It is therefore an ideal tool for comparing the effect of multiple genetic constructs in distinct stable cell lines. We created the necessary FRT donor plasmids, based on pcDNAT™5/FRT/TO (Life Technologies).

Both the *D. melanogaster* recoded human eRF1 wt and the eRF1 E55D variants were successfully integrated into the genome. The resulting Trek 293 wt and E55D cell lines could be maintained both under induced and uninduced conditions for several months, suggesting negligible toxic effects.

Figure 5A:
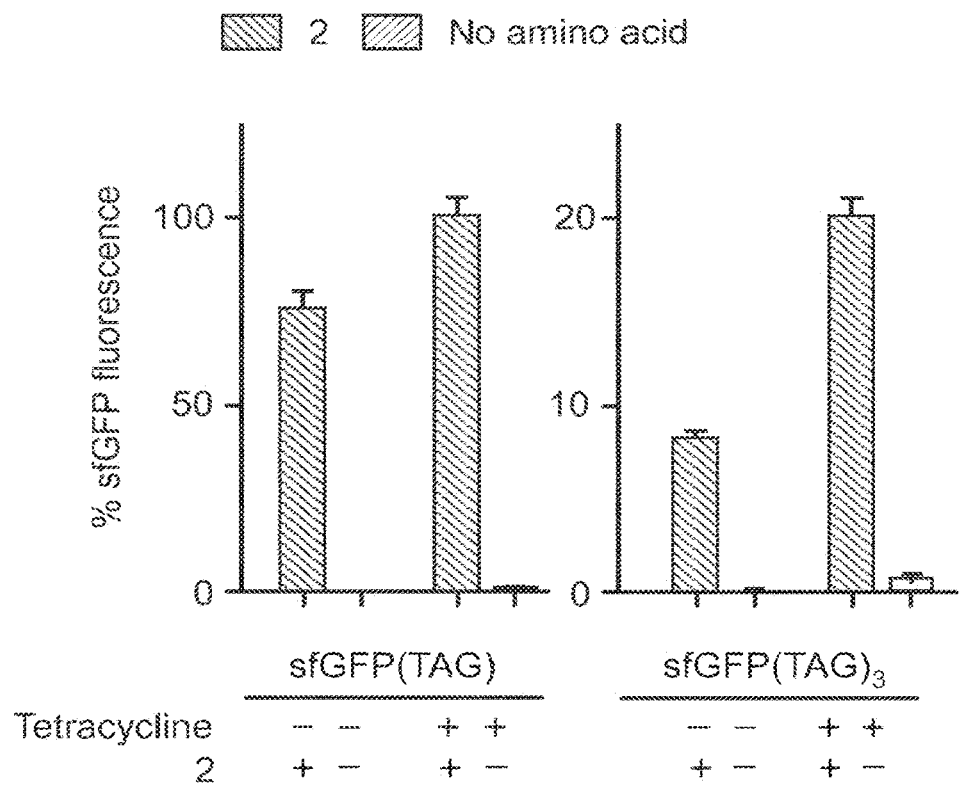
FIGS. 5A-5D illustrates stable expression of eRF1 E55D from genomic integration enhances amber suppression in T-Rex 293 Flp-In cells. Stable eRF1 lines were created by using the T-Rex 293 Ftp-In system (Life Technologies), giving uniform expression of the inserted transgene due to insertion at a defined target locus.
Figure 5B:
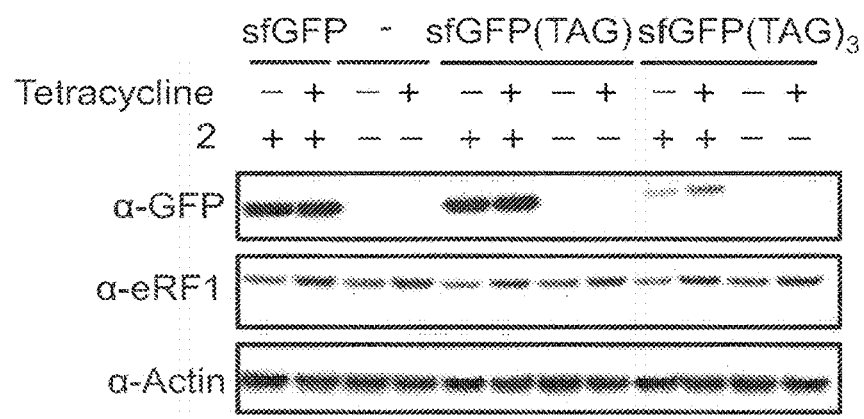

Amber suppression efficiency was determined by transient transfection of the constructs containing the PylRS/tRNA$_{CUA}$ and sfGFP reporter (constructs g+h/i, FIG. 1A-1C), in a 1:1 ratio. In the presence of 0.5 mM amino acid 2, amber suppression increased from 75% to 99% in sfGFP (TAG), and from 8% to 20% in sfGFP(TAG)$_3$ upon induction of eRF1 expression by addition of 1 µg/mL tetracycline (FIG. 5A) compared to sfGFP(wt).

The observed effect is less pronounced compared to the introduction of eRF1 by transient transfection (FIG. 4A-4B). Immunostaining the cell lysates for eRF1 shows that the levels of eRF1 are successfully raised upon induction (FIG. 5D), but less pronounced compared to eRF1 expression following transient transfection (FIG. 4A-4B). This is consistent with the presence of a single genomic integration site, compared to the delivery of multiple copies of the plasmid by transient transfection per cell. In the presence of endogenous, wild type eRF1, amber suppression can only be enhanced if sufficient eRF1 E55D exists to prevent the formation of wild type eRF1/eRF3 complexes with the ability to terminate at UAG codons.

Example 7—Constitutive Expression of shRNA(eRF1) Increases Amber-Read Through in Cell Lines with Stable Integration of eRF1 E55D As strong expression of eRF1 variants enables enhanced amber suppression (FIGS. 3A-3C), so should the reduction of endogenous eRF1 in the presence of transgenic eRF1 (Carnes et al. 2003; Ilegems et al. 2004). A reduction of endogenous eRF1 levels by shRNAs is linked to an unspecific increase in basal stop codon read-through (FIGS. 3B-3C). In line with the concept of a stable cell line with enhanced amber suppression potential, the eRF1 specific set of shRNAs used earlier was now introduced into the cell lines by random lentiviral integration into the genome (Santa Cruz Biotechnology). Cells with successful integration events were selected based on acquired resistance to puromycin. Both cell lines containing eRF1 E55D and eRF1 wild-type were created, and could be maintained in the presence and absence of tetracydine for several weeks.

Amber suppression efficiency was determined after transient transfection of the PylRS/tRNA$_{CUA}$ pair and the sfGFP (TAG) or sfGFP(TAG)$_3$ reporter constructs (plasmid g+h/I, FIG. 1A). Amber suppression efficiency is shown as total sfGFP fluorescence over background, and normalization to sfGFP(wt) in the same cell line.

The integration and induction of eRF1 E55D caused an increase in amber suppression in the presence of 0.5 mM 2 from 87% to 99% compared to the "blank" parent cell line, TRex 293 Flp-In. In contrast, the induction of eRF1 wt reduced amber suppression on average to 81%.

Figure 5C:
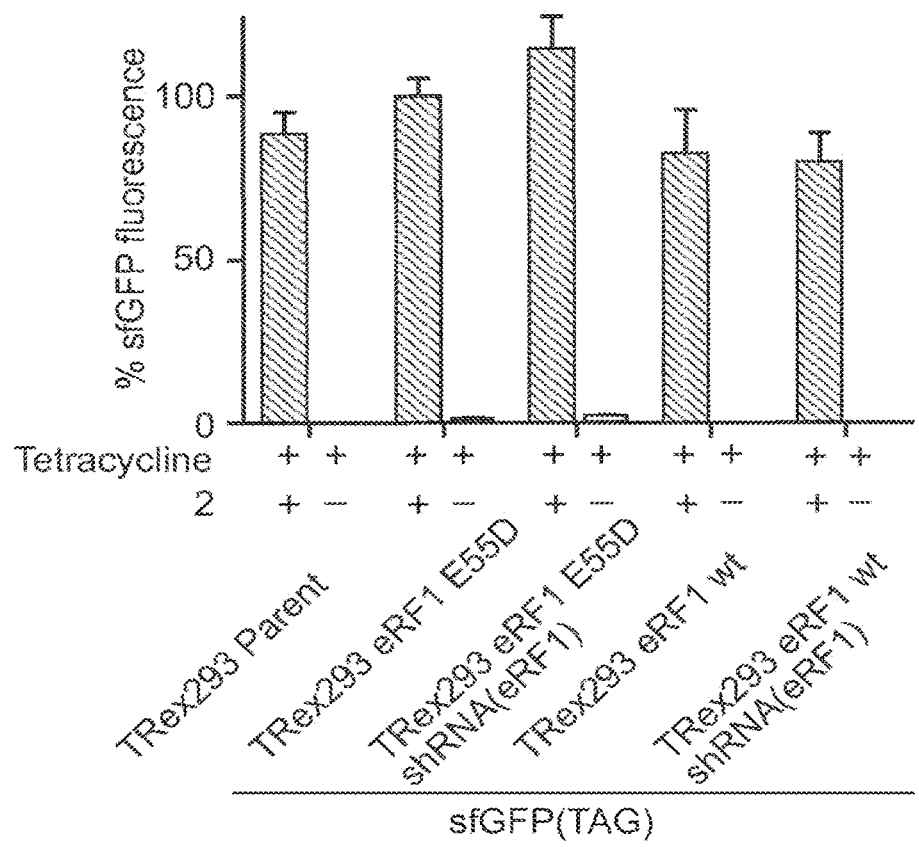
Figure 5D:
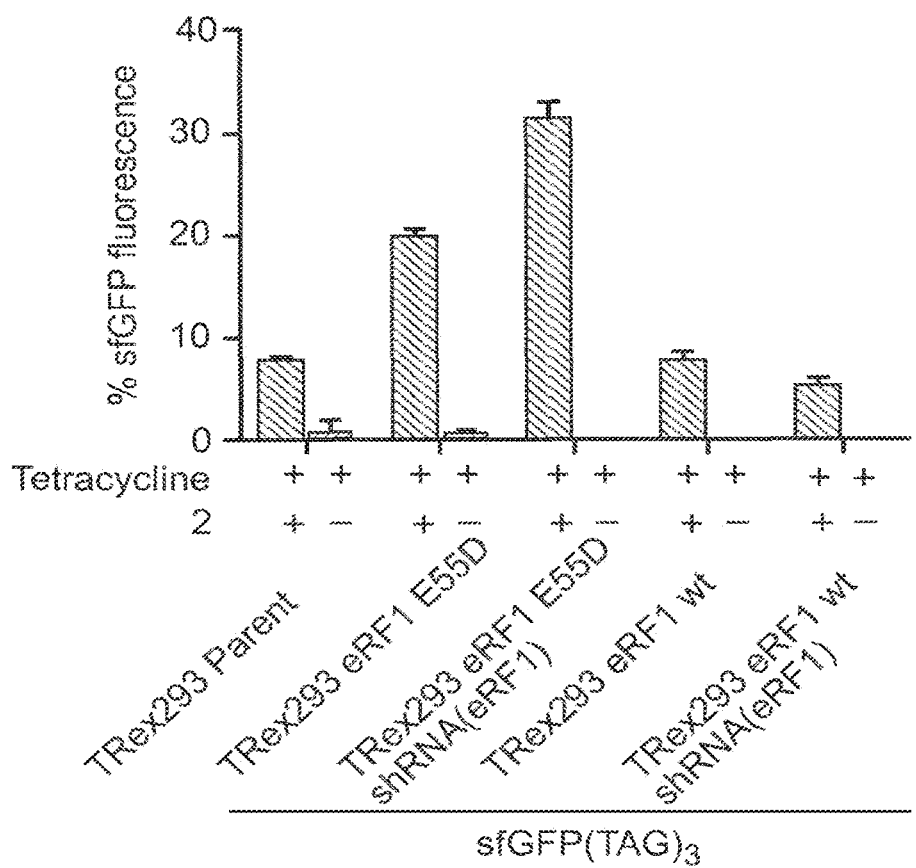

The cell lines with constitutive expression of eRF1-specific shRNAs increased relative fluorescence to 114% in the eRF1 E55D background, but maintained suppression at 79% in the eRF1 wt background (FIG. 5C). Amber suppression efficiency with a sfGFP(TAG)$_3$ reporter was 76% in the Trey 293 Flp-In parent cell line. The stable line expressing eRF1 E55D shows an increase in amber suppression to 19%, further increasing to 31% in the cell line expressing both eRF1 E55D and shRNA(eRF1). In contrast, the cell line expressing eRF1 wt shows no change in amber suppression compared to the parent cell line at 7.6%. The derived cell line expressing both eRF1 wt and shRNA(eRF1) displays a minor reduction in suppression efficiency to 5% (FIG. 5D).

Overall, the relative amber suppression efficiency can be enhanced by stable integration of a single copy of eRF1 E55D, and further enhancements require either a reduction in endogenous eRF1 levels, or an increased expression of eRF1 E55D. In either case, quantitative expression of sfGFP-2 can be achieved, and sfGFP-2, can be produced with an efficiency of 30-40% of sfGFP.

Example 8—eRF1 Mutants Increase Unnatural Amino Acid Incorporation Efficiency in Dmel Cells We also evaluated the effect of selected eRF1 mutants in an insect cell based expression system. Cell lines derived from *Drosophila*, such as Schneider 2 cells, are routinely used for the large scale expression of proteins. The incorporation of unnatural amino acids in proteins in these systems has been demonstrated using the *M. mazei* PylRS/tRNA$_{CUA}$ pair and suitable expression systems (Bianco et al. 2012; Elliott et al. 2014).

Four constructs were used to drive unnatural amino acid incorporation: a PylRS/tRNA$_{CUA}$ expression construct, a reporter construct containing GFP-mCherry or GFP-TAG-mCherry a UAS driver and an expression construct for each eRF1 variant.

Figure 6A:
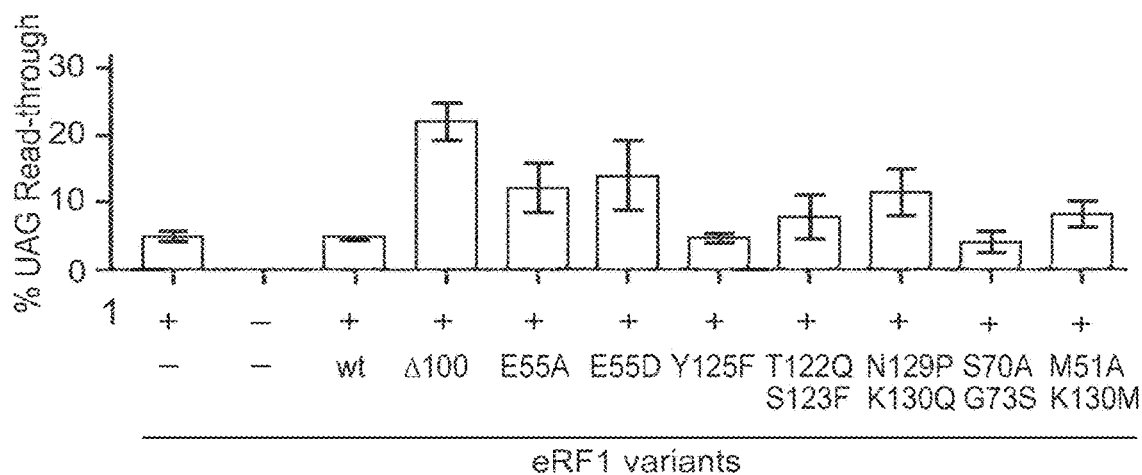
FIGS. 6A-6C illustrates the effect of mutations in eRF1 on stop codon read-through in Dmel cells, and incorporation of 1 (1 mM) using the PylRS/tRNA$_{CUA}$ pair.
Figure 6B:
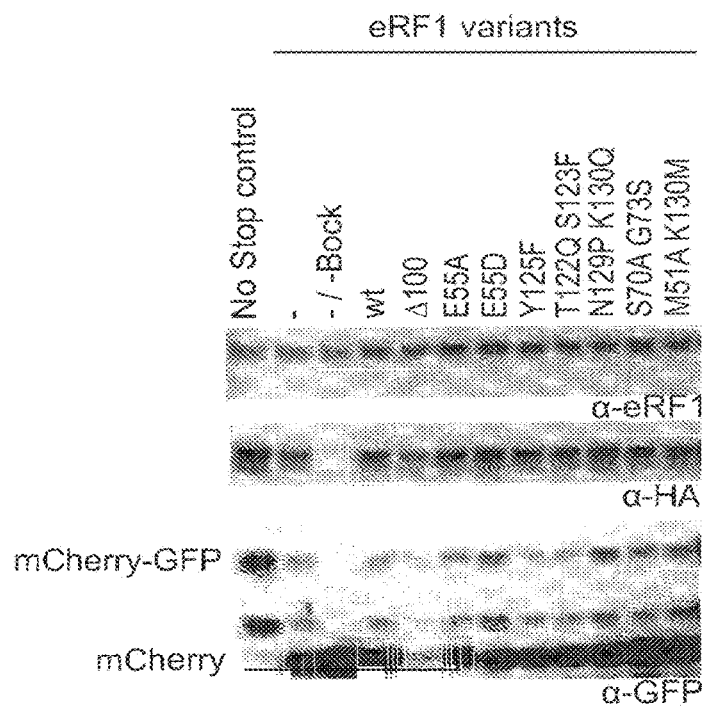
Figure 6C:
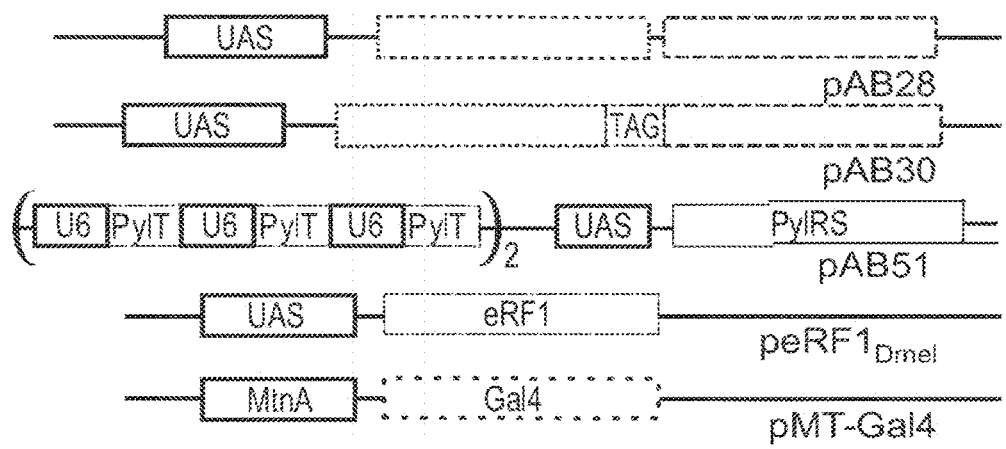

Overall, the transfection efficiency in Dmel cells is lower than in the mammalian system, and the resulting cell lysate and blots represent a mixture of transfected and untransfected cells, reducing the apparent effect (FIG. 6A). A visual indicator is the Δ100 mutant, showing a weak band corresponding to ectopic, truncated eRF1 below the endogenous eRF1 band (FIG. 6B). The quantification of amber suppression shown in FIG. 6A is based on three independent transfection experiments, with the corresponding blots being quantified individually.

The expression of wild-type release factor causes a very minor reduction in read-through, whereas the expression of the eRF1 Moo mutant increases read-through levels five-fold, from 4.8% to 23%. This effect is accompanied by a strong reduction in the total amount of truncated GFP, suggesting a significant disruption of the overall translation process (FIG. 6B).

The E55D mutant shows the second largest increase in read-through levels of the variants tested, a four-fold increase to 15%. Similarly, the mutations E55A and NK129PQ increase read-through roughly three-fold, to 12%. Mutant S70A G73S, reported to enhance UGA read-through, shows no effect on amber suppression.

Despite the differences both in the cellular context and the reporter system used, these results closely mirror the relative effect sizes previously observed in mammalian cells. The only exception is mutation Y125F, which appears to have a negligible effect in Dmel cells, but improved UAG read-through in the mammalian system.

Figure 7:
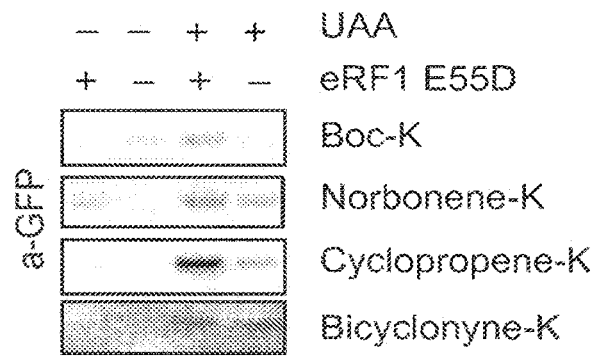
FIG. 7 illustrates the incorporation of four distinct a1 amino acids into sfGFP(TAG) in the presence of an eRF1 E55D mutant.
Figure 8:
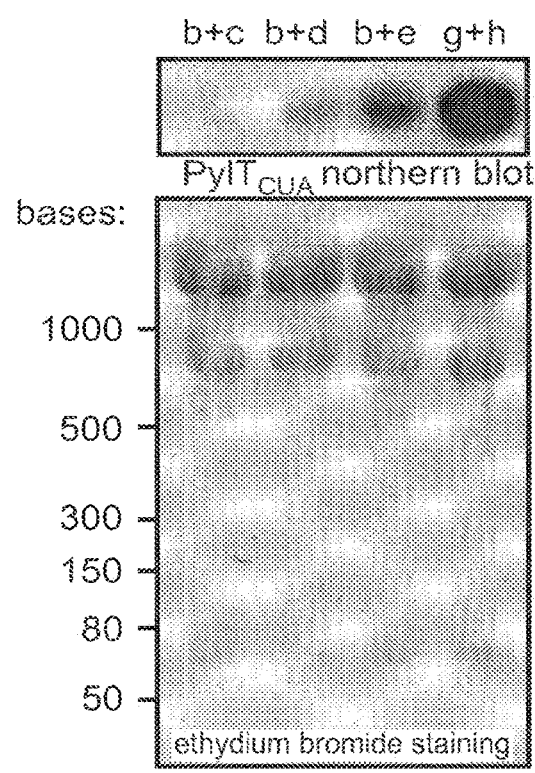
FIG. 8 illustrates Northern blot using a universal PylT/PylTU25C probe. Total RNA was extracted 24 hours after transient transfection with plasmids b+c, b+d, b+e, g+h (FIG. 22A) analogous to FIGS. 1A-1B.

Example 9—eRF1 E55D Mutant Increases Incorporation Efficiency of a Wide Range of Unnatural Amino Acids and tRNA Synthetase Variants Incorporation of four distinct unnatural amino acids—Boc-K (N$^\varepsilon$-[(tert-butoxy)carbonyl]-L-lysine, Norbonene-K (N^ε-norbornene-2-yloxycarbonyl-L-lysine), Cycloprope-ne-K (N^ε-[((2-methylcycloprop-2-en-1-yl)methoxy)carbo-nyl]-L-lysine) and Bicyclonyne-K (N^ε-([(1R,8S)-bicyclo [6.1.0]non-4-yn-9-ylmethoxy]carbonyl)-Lysine) into sfGFP (TAG) was improved in the presence of eRF1 E55D mutant, as shown in FIG. 7. The T-REx 293 eRF1 E55D generated in Example 6 was used to inducibly express eRF1 E55D.

Amber suppression efficiency was determined by transient transfection of the constructs containing the PylRS/tRNA$_{CUA}$ and sfGFP$_{150TAG}$ reporter (constructs g+h/i, FIG. 1), in a 1:1 ratio. Amber suppression efficiency was determined base on the expression of sfGFP by western blotting. In all cases, the presence of eRF1 E55D mutant increased expression of sfGFP.

Example 10—Discussion

We have defined the efficiency of unnatural amino acid incorporation relative to a natural translation control, allowing us to quantitatively benchmark improvements in unnatural amino acid incorporation efficiency. The optimized system we have created provides a 17- to 20-fold improvement in unnatural amino acid incorporation efficiency with amino acids 1 and 2. For amino acid 1 the incorporation efficiency is increased from 5% to 85%, while for amino acid 2 the incorporation efficiency is increased from 7% to 157% of a no stop codon control. Moreover, the optimized system increases the yield of proteins incorporating 1 and 2 at three positions from unmeasurably low levels to 12% and 43% of a no stop control respectively.

Various factors contribute to the dramatic improvement in unnatural amino acid incorporation, which include: the optimization of tRNA$_{CUA}$ levels to optimize PylRS/tRNA$_{CUA}$ expression; and the development and use of engineered eRF1 variants. While the incorporation of unnatural amino acids is quite efficient in response to a single amber codon using the optimized PylRS/tRNA$_{CUA}$ system alone, the efficiency is further improved by the addition of eRF1 (for example, E55D). The effect of the eRF1 mutant on unnatural amino acid incorporation is more dramatic when incorporating unnatural amino acids at multiple sites, increasing the yield of protein containing amino acid 1 at three sites, 2- to 3-fold and the yield of protein containing 2 at three sites, 4-fold.

Example 11—Demonstration of Alternate eRF1 Mutants

We initially screened the eRF1 variants by transient transfection in a HEK 293T cell line. The table below lists the screened mutations ranked by their effect on unnatural amino acid incorporation (BocK). The relevant protocols and supporting material are as in the above examples.

| Mutation | Effect (Fold improvement) | Assay/comment |
|---|---|---|
| E55D | 5.1 | DLR assay, 2 mM BocK |
| N129P, K130Q | 3.2 | DLR assay, 2 mM BocK |
| T122Q, S123F | 3.0 | DLR assay, 2 mM BocK |
| E55A | 2.8 | DLR assay, 2 mM BocK |
| Y125F | 2.6 | DLR assay, 2 mM BocK |
| T58K, S60T, S64D, L125F, N129S | 2.5 | DLR assay, 2 mM BocK |
| S123A, L124I, Y125L | 2.5 | sfGFP(3TAG), 2 mM BocK |
| S123R, L124W, Y125R | 1.9 | sfGFP(3TAG), 2 mM BocK |
| S123H, L124A, Y125G | 1.9 | sfGFP(3TAG), 2 mM BocK |
| M51A, K130M | 1.8 | DLR assay, 2 mM BocK |
| S123A, L124L, Y125V | 1.8 | sfGFP(3TAG), 2 mM BocK |
| S123L, L124C, Y125S | 1.8 | sfGFP(3TAG), 2 mM BocK |
| S123L, L124S, Y125S | 1.8 | sfGFP(3TAG), 2 mM BocK |
| S123V, L124T, Y125P | 1.7 | sfGFP(3TAG), 2 mM BocK |
| Δ100 (N-term truncation) | 6.8 | DLR assay, 2 mM BocK |
| S70A, G73S | 0.67 | Not useful for UAG as a incorporation signal, but may find application for UGA. DLR assay, 2 mM BocK |

Example 12—eRF1 Mutant Functionalities in Diverse Eukaryotic Species

The invention finds application in diverse eukaryotic species. The invention can be applied in insect cells such as fly cells (e.g. *Drosophila*), fungal cells such as yeast cells and other eukaryotes.

We used transient transfection to introduce the mutant eRF1 into insect (Dmel) cell lines.

Methods:

Transient Transfection of D.mel-2 Cells (S2)

*Drosophila* S2 cells (D.Mel: Invitrogen) were maintained on complete Express 5 SFM medium (Life technologies Ltd.), enriched with 2 mM L-glutamine and pen/strep (50 I.U./mL penicillin, 50 µg/mL streptomycin) in T75 flasks following standard cell culture practices. Twenty-four hours prior to transfections, cells were detached from the surface by scraping or shaking, and 5 ml suspended were cells diluted with 8 ml of pre-warmed medium. For 24-well plates 0.5 ml suspended cells were seeded per well and grown over night. Cells were transiently transfected using Fugene HD (Promega). For each well, 1.75 µl Fugene HD were mixed with 15 µl sterile water and incubated at room temperature for five minutes. Similarly, 0.75 µg DNA (0.3 µg each of reporter, PylRS/PylT and eRF1 constructs, 0.15 µg GAL4) were diluted in 15 µl sterile water and added to the diluted Fugene HD reagent, followed by incubation at room temperature for 15 minutes. In each well containing target cells the spent growth media was taken off and the cells were carefully washed with 500 µl sterile PBS. Each well was then filled with 500 µl of Express 5 medium, 0.2 mM CuSo$_4$ (Sigma), 2 mM/ml glutamine and unnatural amino acid, if required. 1 was dissolved in sterile water/NaOH (20 mM 1), and added to the growth media. The pH was subsequently adjusted to 6.5 using 4 M HCl. The final concentration of 2 in the growth media was 2 mM, unless otherwise noted. 25 µl of the 30 µl transfection mix were added drop-wise to each well. The plates were carefully shaken and incubated over night at 25° C. Sixteen hours post transfection each well was washed using PBS, and cells lysed in 100 µl RIPA buffer (Sigma) with added Complete protease inhibitor (Roche) while shaking at room temperature for 15 minutes.

Unnatural amino acid incorporation was determined by the expression of a GFP-TAG-mCherry construct. The ratio of full length protein over truncated protein was determined by quantification on blots immunostained for GFP, as described for HEK293T cells.

*Drosophila melanogaster* Genetic Constructs

A human eRF1 gene, optimized for a *D. melanogaster* codon usage containing a terminal His$_6$ tag and a triple-stop termination signal, was cloned into plasmid SG105 (Bianco et al, 2012) using BamHI/NotI restriction sites (primer eRF1_SG105). SG105 is derived from UASp, and contains a second multiple cloning site downstream of the white locus (Rørth, 1998). AB51 contains six copies of a U6-PylT cassette and UAS-PylRS (Ambra Bianco, unpublished data).
Determining Unnatural Amino Acid Incorporation Efficiency in *D. melanogaster*

Transgenic fly lines containing the eRF1 variants were created by P element injection using a *Drosophila* embryo injection service (Bestgene Inc). eRF1 Δ100 and E55D constructs cloned into plasmid SG105 were successfully microinjected, and returned nine and seven unique lines, respectively.

Fly line stocks were maintained on apple plates at 16° C. For genetic crosses and unnatural amino incorporation experiments, flies were maintained at 25° C. Fly lines containing the eRF1 Δ100 or E55D variants were crossed with virgin females from FT74-S2-nos fly lines. The resulting offspring was screened for the correct combination of genetic markers depending on each eRF1 line, maintained for further experiments.

The FT74-S2-nos line supports unnatural amino acid incorporation using the PylRS/PylT$_{CUA}$ pair and expresses a dual luciferase reporter. The constructs integrates on the genome are a UAS-dual-luciferase(TAG) reporter, UAS-PylRS, four copies of a U6-PylT cassette (Triple-Rep-L) and a nos-Gal4-VP16 cassette (Bloomington 4937) The creation of these constructs and line is discussed in (Bianco et al, 2012).

Compound 2 was fed to flies mixed into yeast paste. 2 was dissolved in water/NaOH to a final concentration of 10 mM, and dried yeast added until a pasty consistency was reached. 1M HCl was added to neutralize the paste. In order to measure unnatural amino acid incorporation in fly lines, 15 female flies of each line expressing the necessary components for unnatural amino incorporation as well as an eRF1 variant were set-up in tubes with 5 males, and supplied with a small amount of 10 mM 2-yeast paste. The flies were transferred into new tubes with fresh 2-yeast paste after 24 and 48 hours. On the third day, the transfer into a fresh tube with 2-yeast paste was performed in the morning, and female flies were dissected in the afternoon. For dissection, flies were collected on a CO$_2$ pad. Female flies were transferred to dissection glasses under a microscope, and the ovaries isolated from the thorax by careful removal of the posterior tip. The ovaries from 10-12 flies were collected in PBS buffer, and transferred into a 1.5 ml microcentrifuge tube. The tube was centrifuged in a table top centrifuge at the lowest setting for 30 seconds, and the supernatant removed. After adding 100 μl 1× passive lysis buffer (Promega), the ovaries were ground up using a plastic pestle, until the solution approached a milky appearance. Debris was removed by centrifugation at full speed for 3 minutes. The supernatant was carefully taken off, and pelleted again at full speed for 1 minute. 10 μl of this lysate were used per dual luciferase assay in a 96-well format, with three replicates per sample. The assay (Promega) was performed as described for mammalian cell lysates.

Figure 12A:
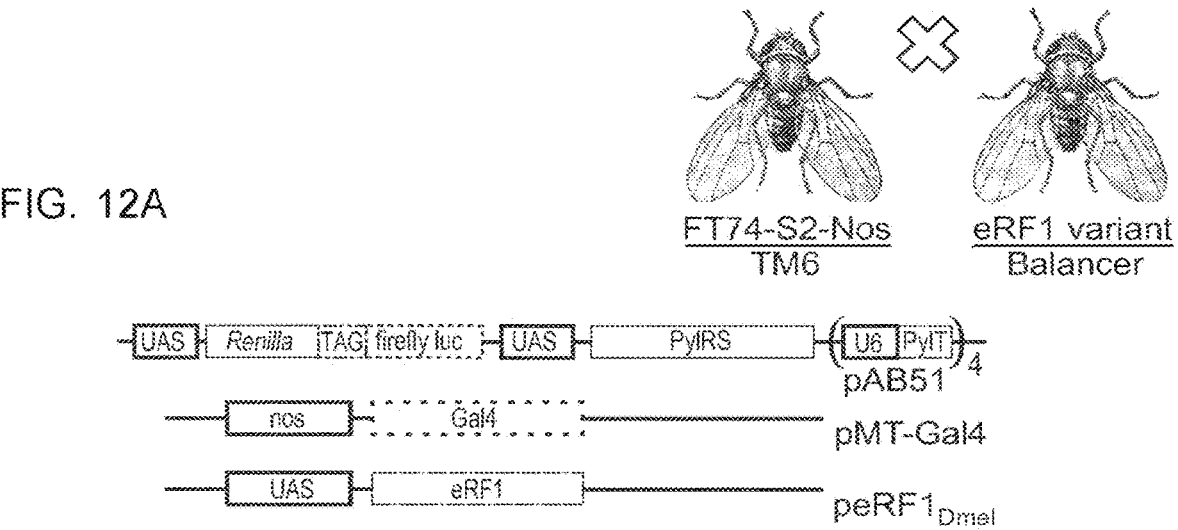
FIGS. 12A, 12B, and 12C Screening transgenic D. melanogaster fly lines for effects of eRF1 E55D or Δ100 expression in ovaries on stop codon readthrough in a dual-luciferase reporter assay.
Figure 12B:
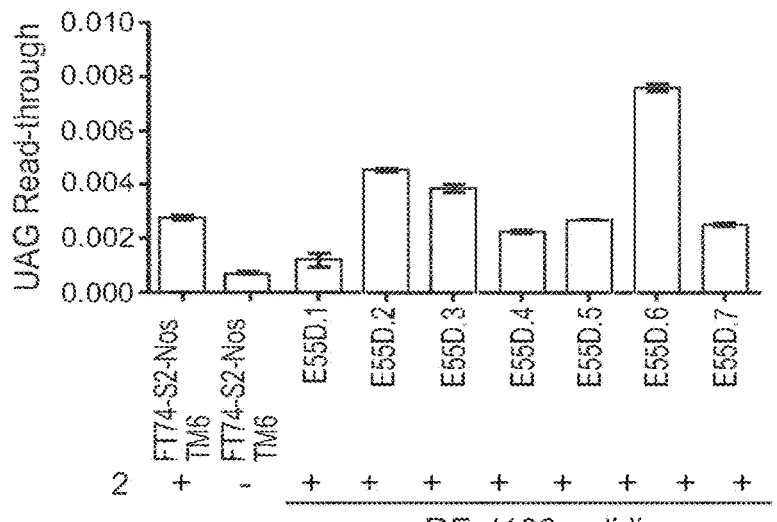
Figure 12C:
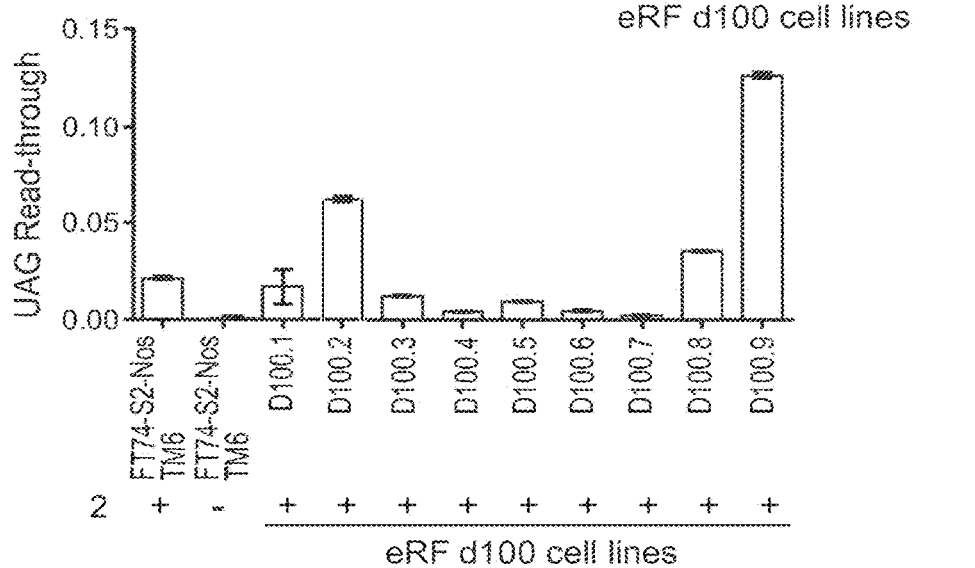

See FIGS. 12A-12C.

A. Illustration of the genetic background. Virgin females from fly line FT74-S2-Nos/TM6, expressing a pyrrolysyl aaRS/tRNA$_{CUA}$ pair, a dual-luciferase reporter and an ovary-specific promoter were crossed to males from balanced fly lines generated by random genomic insertion of eRF1 E55D or Δ100 after microinjection (Bestgene). B, C. Measuring stop codon readthrough in a dual luciferase assay. Twelve female flies with the correct genetic markers from each genetic cross were collected, and fed on 10 mM CyP-yeast paste for 72 hours. The ovaries were collected by dissection, pooled and tested for UAG read-through. Panel B lists the results for all fly lines generated from eRF1 E55D integration events; panel C lists the results for eRF1 Δ100.

Figure 13:
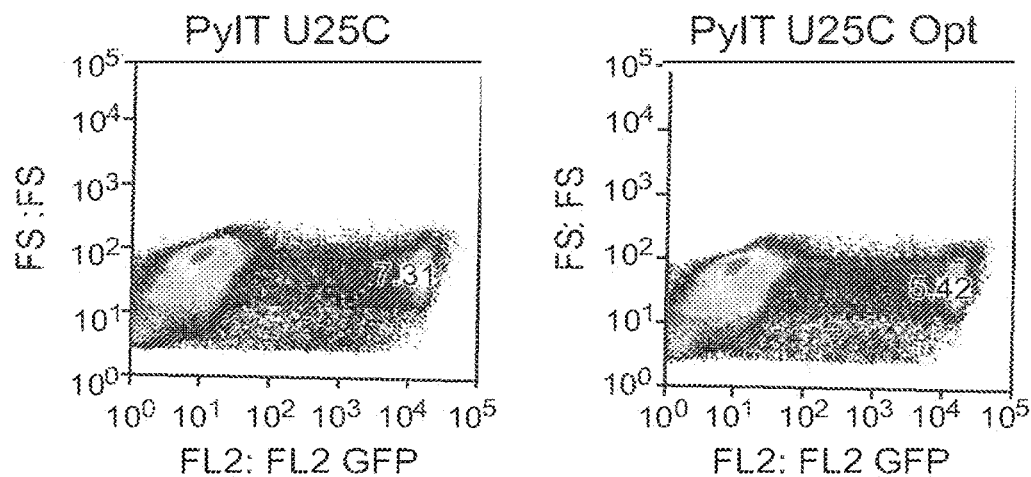
FIG. 13 shows FACs plots

Example 13—Both PylT U25C and PylT U25C Opt Variants Efficiently Amber Suppression in HEK Cells HEK cells transfected with GFP150UAG and 4× PylT U25C or 4× PlyT U25C Opt, analysed for GFP fluorescence via FACS, GFP-positive population circled in pink with percentage labelled, MFI of replicates for graph. Standard transfection and flow cytometry protocols, expressed in 2 mM BocK. See FIG. 13.

Figure 14:
FIG. 14 shows a photograph
Figure 15:
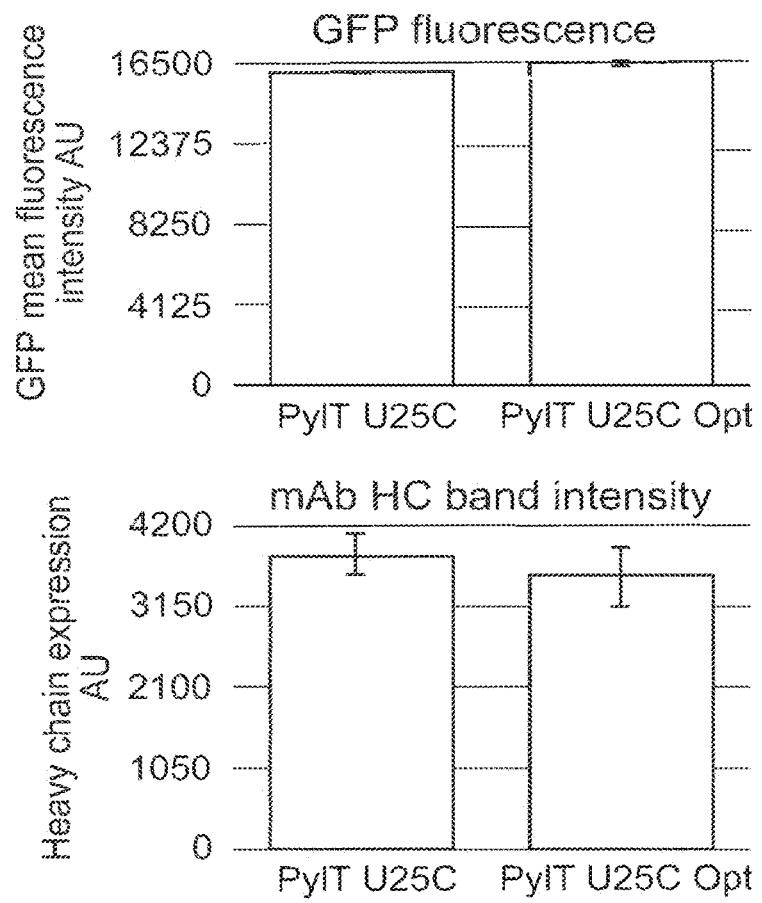
FIG. 15 shows bar charts
Figure 16:
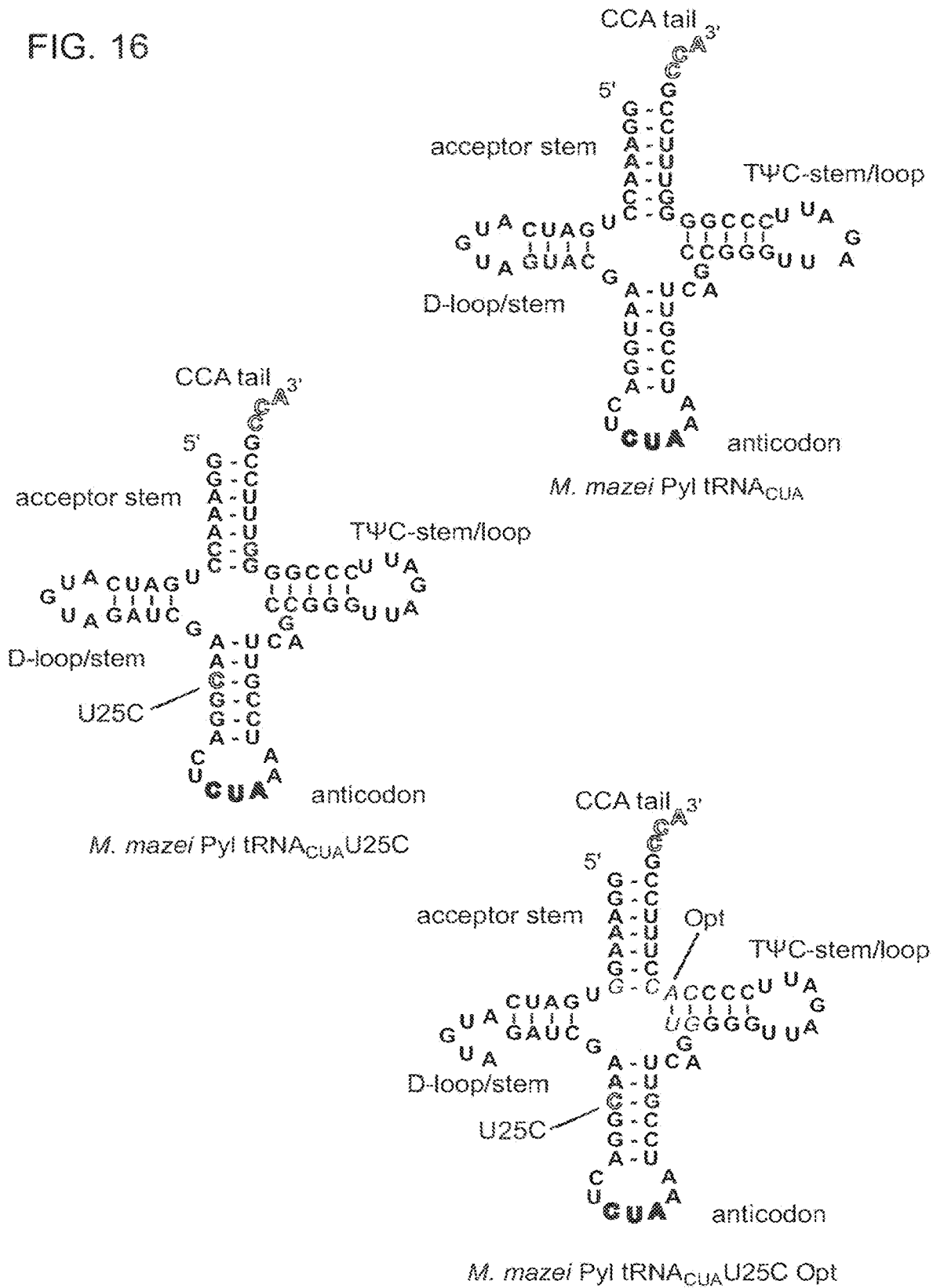
FIG. 16 shows PylT U25C and PylT U25C Opt variants

Western blot of Trasturzumab heavy chain, position A114UAG, LC and HC on separate plasmids, each with either 4× PylT U25C or 4× PlyT U25C Opt. Blot intensities of replicates measured for graph. Standard transfection and western blot protocols, expressed in 2 mM BocK. See FIG. 14 and FIG. 15.

tRNA cloverleaf diagrams for parental M. Mazei Pyl tRNA(cua anticodon) for comparison, U25C derivative, U25C and Opt derivative. U25C mutation in green, six nucleotide Opt mutation set in pink. See FIG. 16.

Sequence alignments of DNA sequence for tRNA variants (differences in black), note that the CCA tail is not explicitly encoded in mammalian plasmids, but is post-transcriptionally added by the cell. See FIG. 17.

```
M. Mazei PylT U25C Opt
GGAAACGTGATCATGTAGATCGAACGGACTCTAAATCCGTTCAGTGGGGT
TAGATTCCCCACGTTTCCG (1x) Human U6 promoter ::M. Mazei PylT U25C Opt::
3' UTR and terminator
CCTAGTTGGGCAGGAAGAGGGCCTATTTCCCATGATTCCTTCATATTTGC

ATATACGATACAAGGCTGTTAGAGATAATTAGAATTAATTTGACTGTAAA

CACAAAGATATTAGTACAAAATACGTGACGTAGAAAGTAATAATTTCTTG

GGTAGTTTGCAGTTTTAAAATTATGTTTTAAAATGGACTATCATATGCTT

ACCGTAACTTGAAAGTATTTCGATTTCTTGGCTTTATATATCTTGTGGAA

AGGACGAAACACCGGAAACGTGATCATGTAGATCGAACGGACTCTAAATC

CGTTCAGTGGGGTTAGATTCCCCACGTTTCCGGACAAGTGCGGTTTTT (4x) Human U6 promoter :: M. Mazei PylT U25C Opt::
3' UTR and terminator as cloned
TGGGCGATGTGCGCTCTGCCCACTGACGGGCACCGGAGCGATCGCAGATC

CCCTAGTTGGGCAGGAAGAGGGCCTATTTCCCATGATTCCTTCATATTTG

CATATACGATACAAGGCTGTTAGAGAGATAATTAGAATTAATTTGACTGT

AAACACAAAGATATTAGTACAAAATACGTGACGTAGAAAGTAATAATTTC

TTGGGTAGTTTGCAGTTTTAAAATTATGTTTTAAAATGGACTATCATATG

CTTACCGTAACTTGAAAGTATTTCGATTTCTTGGCTTTATATATCTTGTG

GAAAGGACGAAACACCGGAAACGTGATCATGTAGATCGAACGGACTCTAA

ATCCGTTCAGTGGGGTTAGATTCCCCACGTTTCCGGACAAGTGCGGTTTT

TAGAATTACAACTTATATCGTATGGGCTAGACTCGAGCCTAGTTGGGCAG

GAAGAGGGCCTATTTCCCATGAATTCCTTCATATTTGCATATACGATACA

AGGCTGTTAGAGAGATAATTAGAATTAATTTGACTGTAAACACAAAGATA
```

-continued

```
TTAGTACAAAATACGTGACGTAGAAAGTAATAATTTCTTGGGTAGTTTGC

AGTTTTAAAATTATGTTTTAAAATGGACTATCATATGCTTACCGTAACTT

GAAAGTATTTCGATTTCTTGGCTTTATATATCTTGTGGAAAGGACGAAAC

ACCGGAAACGTGATCATGTAGATCGAACGGACTCTAAATCCGTTCAGTGG

GGTTAGATTCCCCACGTTTCCGGACAAGTGCGGTTTTTGCGGCCGCGATA

TCTGCAGAATTCACACTGGACTAGGATCCGAGCTCCCTAGTTGGGCAGGA

AGAGGGCCTATTTCCCATGATTCCTTCATATTTGCATATACGATACAAGG

CTGTTAGAGAGATAATTAGAATTAATTTGACTGTAAACACAAAGATATTA

GTACAAAATACGTGACGTAGAAAGTAATAATTTCTTGGGTAGTTTGCAGT

TTTAAAATTATGTTTTAAAATGGACTATCATATGCTTACCGTAACTTGAA

AGTATTTCGATTTCTTGGCTTTATATATCTTGTGGAAAGGACGAAACACC

GGAAACGTGATCATGTAGATCGAACGGACTCTAAATCCGTTCAGTGGGG

TTAGATTCCCCACGTTTCCGGACAAGTGCGGTTTTTGGTACCAAGCTTAA

GCAGACTCGTCGTGACTACATTAGCCTAGTTGGGCAGGAAGAGGGCCTAT

TTCCCATGATTCCTTCATATTTGCATATACGATACAAGGCTGTTAGAGAG

ATAATTAGAATTAATTTGACTGTAAACACAAAGATATTAGTACAAAATAC

GTGACGTAGAAAGTAATAATTTCTTGGGTAGTTTGCAGTTTTAAATTATG

TTTTAAAATGGACTATCATATGCTTACCGTAACTTGAAAGTATTTCGATT

TCTTGGCTTTATATATCTTGTGGAAAGGACGAAACACCGGAAACGTGATC

ATGTAGATCGAACGGACTCTAAATCCGTTCAGTGGGGTTAGATTCCCCAC

GTTTCCGGACAAGTGCGGTTTTTCCTAGTGGCCTTGGAGGCCTTTTCCCC

GTATCCCCAGGTGTCTGCAGGCTCAAAGAGCAGCGAGAAGC
```

This 4× cassette may replace the 4× PylT U25C cassette in various vectors described above, such as pKYM1 with GFP (150 uag), Trastuzumab LC and FTC (114 uag).

Example 14—eRF1 E55D Increases Antibody Expression

All experiments were done with 2 mM bocK unless otherwise stated. Ones listed as "CypK" were done with 0.5 cyclopropene. Both are pyrollysine mimetics. HC and LC were on separate plasmids and were co-transfected at a 1:1 ratio using standard PEI protocols. For the GFP studies, only a single plasmid was transfected. Since the unnatural machinery tRNA/synthetases are on the same plasmid as the GFP/mAb genes, no additional plasmids were necessary for these studies.

Antibody expression was done in a LC-ices-HC format from a single vector containing both the antibody genes as well as the Pyrollysine unnatural amino acid tRNA and synthetase. This 4× PylT(u25c)/PylS construct is as described above.

eRF1 was expressed from pcDNA5, a standard expression vector. eRF1 was transfected at 1:5 ratio to the antibody plasmid. Experiment was done in Expi293 cells, a suspension HEK system, and transfected with PEI using standard protocols. Cultures were 30 mL each, 60 ug of DNA with 180 ug of PET, expression for 7 days.

Figure 18:
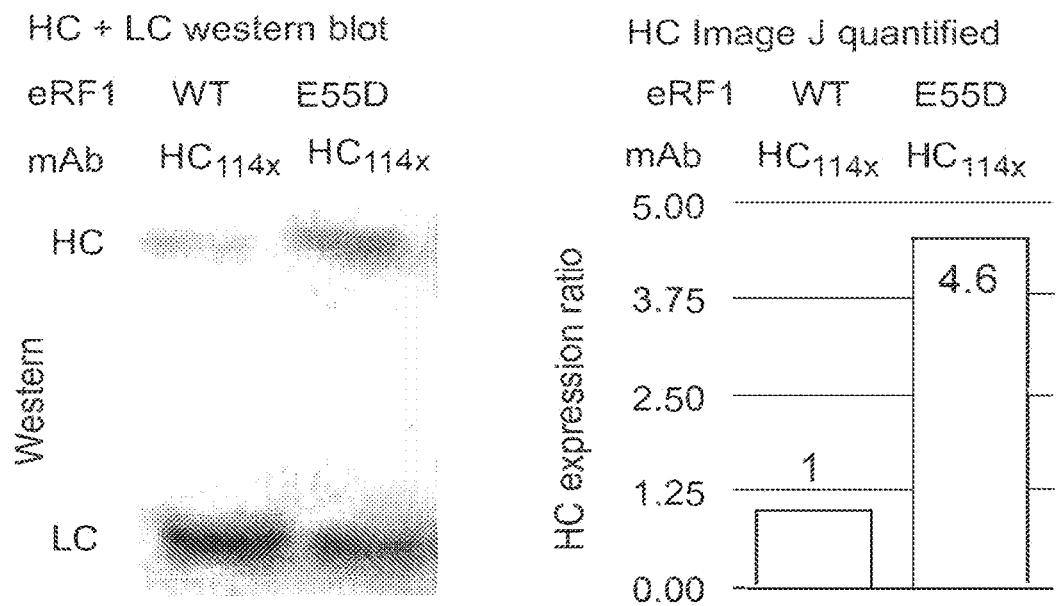
FIG. 18 shows a photograph and a bar chart

Western blot was directly from supernatant of culture, using anti-HC and anti-LC antibodies conjugated to HRP. Trastuzumab with a UAG amber codon at position Ala114 of the heavy chain shows increased expression with eRF1 E55D with our expression system in HEK cells. See FIG. 18.

Figure 19:
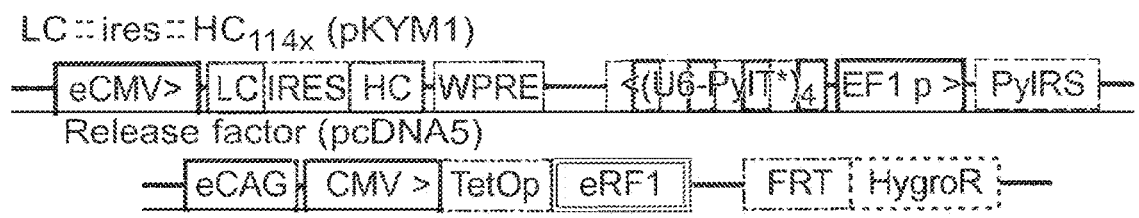
FIG. 19 shows diagrams
Figure 20:
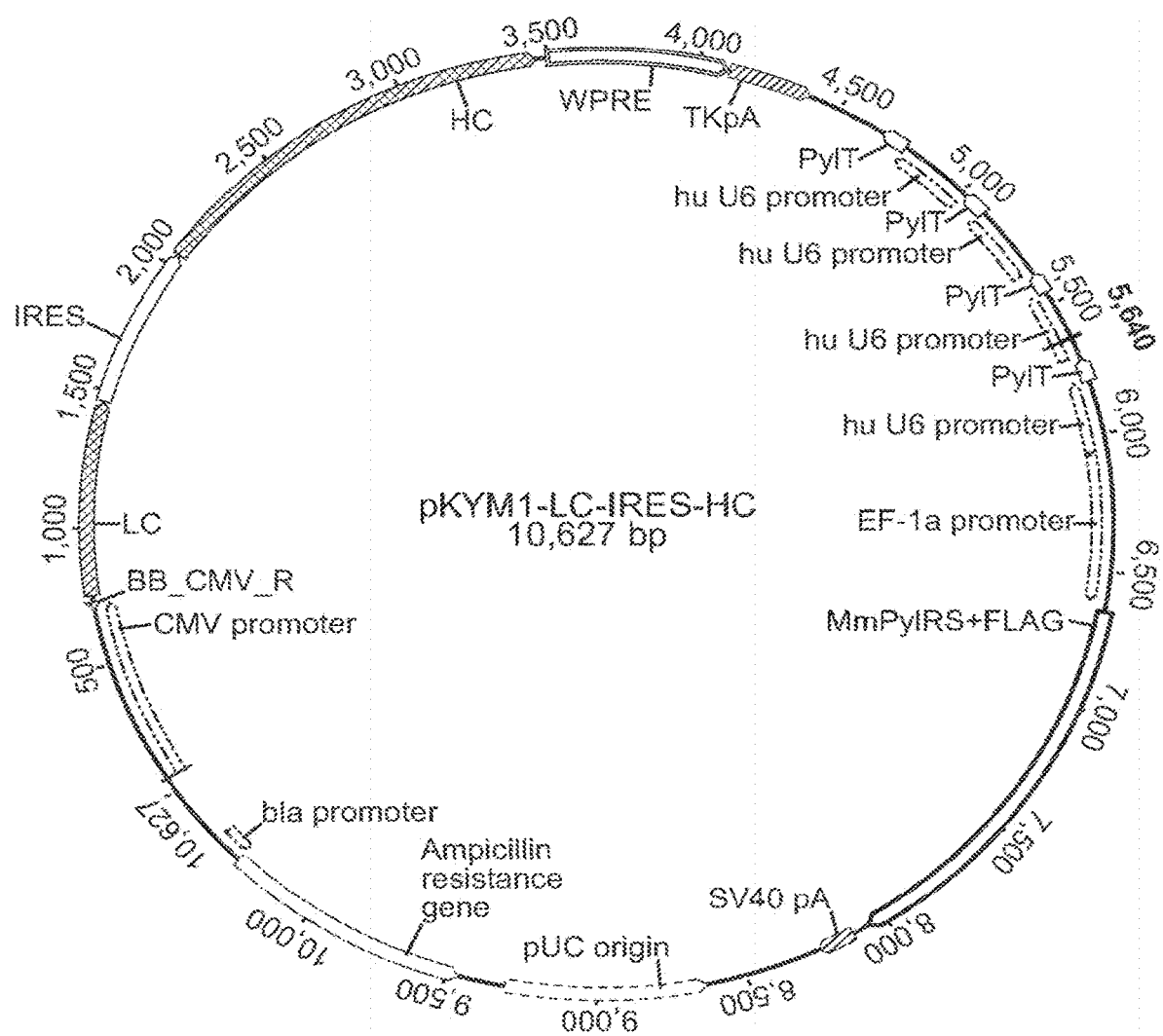
FIG. 20 shows a diagram

Constructs are in FIG. 19. Plasmid diagram is in FIG. 20. Sequences below.

```
pKYm1 LC-ires-HC sequence
GTTAGGCGTTTTGCGCTGCTTCGCGATGTACGGGCCAGATATACGCGTTG

ACATTGATTATTGACTAGTTATTAATAGTAATCAATTACGGGGTCATTAG

TTCATAGCCCATATATGGAGTTCCGCGTTACATAACTTACGGTAAATGGC

CCGCCTGGCTGACCGCCCAACGACCCCCGCCCATTGACGTCAATAATGAC

GTATGTTCCCATAGTAACGCCAATAGGGACTTTCCATTGACGTCAATGGG

TGGAGTATTTACGGTAAACTGCCCACTTGGCAGTACATCAAGTGTATCAT

ATGCCAAGTACGCCCCCTATTGACGTCAATGACGGTAAATGGCCCGCCTG

GCATTATGCCCAGTACATGACCTTATGGGACTTTCCTACTTGGCAGTACA

TCTACGTATTAGTCATCGCTATTACCATGGTGATGCGGTTTTGGCAGTAC

ATCAATGGGCGTGGATAGCGGTTTGACTCACGGGGATTTCCAAGTCTCCA

CCCCATTGACGTCAATGGGAGTTTGTTTTGGCACCAAAATCAACGGGACT

TTCCAAAATGTCGTAACAACTCCGCCCCATTGACGCAAATGGGCGGTAGG

CGTGTACGGTGGGAGGTCTATATAAGCAGAGCTCGTTTAGTGAACCGTAG

ATCGCCTGGAGACGCCATCCACGCTGTTTTGACCTCCATAGAAGACACCG

GGACCGATCCAGCCTCCGGACTCTAGAGGATCGAATTAAGCTTGGTACCG

CCGCCACCATGGGATGGTCATGTATCATCCTTTTTCTAGTAGCAACTGCA

ACCGGTGTACATTCTGACATCCCAGATGACCCAGTCCCCGAGCTCTCTGT

CTGCGTCTGTTGGTGACCGCGTTACCATCACCTGCCGTGCGTCCCAGGAC

GTTAACACCGCCGTGGCGTGGTATCAACAGAAACCGGGTAAAGCGCCAAA

ACTGCTGATCTACTCCGCGTTTTTCCTGTACTCTGGTGTTCCGTCTCGTT

TCAGCGGTTCTCGTTCTGGTACTGACTTCACCCTCACCATCTCTTCTCTG

CAGCCGGAAGACTTCGCGACCTACTACTGCCAGCAGCACTACACCACCCC

ACCGACCTTCGGTCAGGGCACCAAAGTTGAAATCAAACGTACGGTGGGTG

CACCATCTGTCTTCATCTTCCCGCCATCTGATGAGCAGTTGAAATCTGGA

ACTGCCTCTGTTGTGTGCCTGCTGAATAACTTCTACCCCAGAGAAGCCAA

AGTGCAGTGGAAGGTGGACAACGCCCTGCAGAGCGGAAACAGCCAGGAAA

GCGTGACAGAGCAGGATTCCAAGGATTCCACATACAGCCTGAGCAGCACA

CTGACACTGTCCAAGGCCGACTACGAGAAGCACAAGGTGTACGCCTGCGA

AGTGACACACCAGGGACTGTCCTCCCCTGTGACAAAGACCTTCAACAGAG

GAGAATGCTGAGGCCGCGCCCCTCTCCCTCCCCCCCCCCTAACGTTACTG

GCCGAAGCCGCTTGGAATAAGGCCGGTGTGCGTTTGTCTATATGTTATTT

TCCACCATATTGCCGTCTTTTGGCAATGTGAGGGCCCGGAAACCTGGCCC

TGTCTTCTTGACGAGCATTCCTAGGGGTCTTTCCCCTCTCGCCAAAGGAA

TGCAAGGTCTGTTGAATGTCGTGAAGGAAGCAGTTCCTCTGGAAGCTTCT

TGAAGACAAACAACGTCTGTAGCGACCCTTTGCAGGCAGCGGAACCCCCC

ACCTGGCGACAGGTGCCTCTGCGGCCAAAAGCCACGTGTATAAGATACAC

CTGCAAAGGCGGCACAACCCCAGTGCCACGTTGTGAGTTGGATAGTTGTG
```

-continued

```
GAAAGAGTCAAATGGCTCTCCTCAAGCGTATTCAACAAGGGGCTGAAGGA
TGCCCAGAAGGTACCCCATTGTATGGGATCTGATCTGGGGCCTCGCTGCA
CATGCTTTACATGTGTTTAGTCGAGGTTAAAAAAACGTCTAGGCCCCCG
AACCACGGGACGTGGTTTTCCTTTCAAAAACACGATAATACCTCCGGAA
TTGGGATGGTCATGTATCATCCTTTTTCTAGTAGCAACTTTCAACCGGTG
TACATTCTGAAGTTCAGCTGGTTAATGTGGTGGTGGTCTGGTTCAACCG
GGTGGCTCCCTGCGTCTGTCTTGTGCGGCCTCTGGTTTAACATCAAAGAT
ACCTATATCCACTGGGTTCGTCAGGCGCCAGGCAAAGGTCTGGAATGGGT
TGCGCGTATCTACCCGACCAACGGTTACACCCGCTACGCGGACTCTGTTA
AAGGTCGTTTCACCATCTCTGCGGACACCTCTAAAAACACCGCGTACCTG
CAGATGAACTCTCTGCGTGCGGAAGACACCGCCGTTTACTACTGCTTCTC
GTTGGGGTGGTGACGGTTTCTACGCGATGGACTACTGGGGTCAGGGTACG
CTGGTTACCGTTTCTTCTTAGTCGACCAAGGGCCCATCGGTCTTCCCCCT
GGCACCCTCCTCCAAGAGCACCTCTGGGGCACAGCGGCCCTGGGCTGCCT
GGTCAAGGACTACTTCCCCGAACCTGTGACGGTCTCGTGGAACTCAGGCG
CCCTGACCAGCGGCGTGCACACCTTCCCGGCTGTCCTACAGTCCTCAGGA
CTCTACTCCCTCAGCAGCGTGGTGACCGTGCCCTCCAGCAGCTTTGGGCA
CCCAGACCTACATCTGCAACGTGAATCACAAGCCCAGCAACACCAAGGTG
GACAAGAAAGTTGAGCCCAAATCTTGTGACAAAACTCACACATGCCCACC
GTGCCCAGCACCTGAACTCCTGGGGGGACCGTCAGTCTTCCTCTTCCCCC
CAAAACCCAAGGACACCCTCATGATCTCCCGGACCCCTGAGGTCACATGC
GTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGC
AGTACAACAGCACGTACCGTGTGGTCAGCGTCCTCACCGTCCTGCACCAG
GACTGGCTGAATGGCAAGGAGTACAAGTGCAAGGTCTCCAACAAAGCCCT
CCCAGCCCCCATCGAGAAAACCATCTCCAAAGCCAAAGGGCAGCCCCGAG
AACCACAGGTGTACACCCTGCCCCCATCCCGGGAGGAGATGACCAAGAAC
CAGGTCAGCCTGACCTGCCTCGTCAAAGGCTTCTATCCCAGCGACATCGC
CGTGGAGTGGGAGAGCAATGGGCAGCCGGAGAACAACTACAAGACCACGC
CTCCCGTGCTGGACTCCGACGGCTCCTTCTTCCTCTATAGCAAGCTCACCG
TGGACAAGAGCAGGTGGCAGCAGGGGAACGTCTTCTCATGCTCCGTGATG
CATGAGGCTCTGCACAACGACTACACGCAGAAGAGCCTCTCCCTGTCCCC
GGGTTGAGCTCGAGTCTAGAGGGTTCGATCCCTACCGGTTAGTAATGAGT
TTAAACTCGACAATCAACCTCTGGATTACAAAATTTGTGAAAGATTGACT
GGTATTCTTAACTATGTTGCTCCTTTTACGCTATGTGGATACGCTGCTTT
AATGCCTTTGTATCATGCTATTGCTTCCCGTATGGCTTTCATTTTCTCCT
CCTTGTATAAATCCTGGTTGCTGTCTCTTTATGAGGAGTTGTGGCCCGTTG
TCAGGCAACGTGGCGTGGTGTGCACTGTGTTTGCTGACGCAACCCCCACT
GGTTGGGGCATTGCCACCACCTGTCAGCTCCTTTCCGGGACTTTCGCTTT
CCCCCTCCCTATTGCCACGGCGGAACTCATCGCCGCCTGCCTTGCCCGCT
GCTGGACAGGGGCTCGGCTGTTGGGCACTGACAATTCCGTGGTGTTGTCG
```

-continued

```
GGGAAGCTGACGTCCTTTCCATGGCTGCTCGCCTGTGTTGCCACCTGGAT
TCTGCGCGGGACGTCCTTCTGCTACGTCCCTTCGGCCCTCAATCCAGCGG
ACCTTCCTCCCGCGGCCTGCTGCCGGCTCTGCGGCCTCTTCCGCGTCTTC
GCCTTCGCCCTCAGACGAGTCGGATCTCCCTTTGGGCCGCCTCCCCGCCT
GGAAACGGGGGAGGCTAACTGAAACACGGAAGGAGACAATACCGGAAGGA
ACCCGCGCTATGACGGCAATAAAAAGACAGAATAAAACGCACGGGTGTTG
GGTCGTTTGTTCATAAACGCGGGGTTCGGTCCCAGGGCTGGCAGTCTGTC
GATACCCCACCGAGACCCCATTGGGGCCAATACGCCCGCGTTTCTTCCTT
TTCCCCACCCCACCCCCCAAGTTCGGGTGAAGGCCCAGGGCTCGCAGCCA
ACGTCGGGGCGGCAGGCCCTGCCATAGCAGATCTGCGCAGCTCTATAAAG
TAACAAAACTTTTATGAGGGACAGCCCCCCCCCAAAGCCCCCAGGGATGT
AATTACGTCCGTCCCCGCTAGGGGGCAGCAGCGAGCCGCCCGGGGCTCCG
CTCCGGTCCGGCGCTCCCCCCGCATCCCCGAGCCGGCAGCGTGCGGGAC
AGCCCGGGCACGGGGAAGCTTGGCACGGGATCGCTTTCCTCTGAACGCTT
CTCGCTGCTGTTGAGCCTGCAGACACCTCGGGGGATACGGGGAAAAGGCC
TCCAAAGGCCACTAGGAAAAACCGCACTTGTCCGGAAACCCCGGGAATCT
AACCCGGCTGAACGGATTTAGAGTCCATTCGATCTACATGATCAGGTTTC
CGGTGTTTCGTCCTTTCCACAAGATATATAAAGCCAAGAAATCGAAATAC
TTTCAAGTTACGGTAAGCATATGATAGTCCATTTTAAAACATAATTTTAA
AACTGCAAACTACCCAAGAAATTATTACTTTCTACCTTCACGTATTTTG
TACTAATATCTTTGTGTTTACAGTCAAATTAATTCTAATTATCTCTCTAA
CAGCCTTGTATCGTATATGCAAATATGAAGGAATCATGGGAAATAGGCCC
TCTTCCTGCCCAACTAGGAAAAACCGCACTTGTCCGGAAACCCCGGGAAT
CTAACCCGGCTGAACGGATTTAGAGTCCATTCGATCTACATGATCAGGTT
TCCGGTGTTTCGTCCTTTCCACAAGATATATAAAGCCAAGAAATCGAAAT
ACTTTCAAGTTACGGTAAGCATATGATAGTCCATTTAAAACATAATTTT
AAAACTGCAAACTACCCAAGAAATTATTACTTTCTACGTCACGTATTTTG
TACTAATATCTTTGTGTTTACAGTCAAATTAATTCTAATTATCTCTCTAA
CAGCCTTGTATCGTATATGCAAATATGAAGGAATCATGGGAAATAGGCCC
TCTTCCTGCCCAACTAGGAAAAACCGCACTTGTCCGGAAACCCCGGGAAT
CTAACCCGGCTGAACGGATTTAGAGTCCATTCGATCTACATGATCAGGTT
TCCGGTGTTTCGTCCTTTCCACAAGATATATAAAGCCAAGAAATCGAAAT
ACTTTCAAGTTACGGTAAGCATATGATAGTCCATTTAAAACATAATTTT
AAAACTGCAAACTACCCAAGAAATTATTACTTTCTACGTCACGTATTTTG
TACTAATATCTTTGTGTTTACAGTCAAATTAATTCTAATTATCTCTCTAA
CAGCCTTGTATCGTATATGCAAATATGAAGGAATCATGGGAAATAGGCCC
TCTTCCTGCCCAACTAGTAAGGATCTGCGATCGCTCCGGTGCCCGTCAGT
GGGCAGAGCGCACATCGCCCACAGTCCCCGAGAAGTTGGGGGGAGGGGTC
GGCAATTGAACGGGTGCCTAGAGAAGGTGGCGCGGGGTAAACTGGGAAAG
TGATGTCGTGTACTGGCTCCGCCTTTTTCCCGAGGGTGGGGGAGAACCGT
```

-continued

```
ATATAAGTGCAGTAGTCGCCGTGAACGTTCTTTTTCGCAACGGGTTTGCC
GCCAGAACACAGCTGAAGCTTCGAGGGGCTCGCATCTCTCCTTCACGCGC
CCGCCGCCCTACCTGAGGCCGCCATCCACGCGGTTGAGTCGCGTTCTGCC
GCCTCCCGCCTGTGGTGCCTCCTGAACTGCGTCCGCCGTCTAGGTAAGTT
TAAAGCTCAGGTCGAGACCGGGCCTTTGTCCGGCGCTCCCTTGGAGCCTA
CCTAGACTCAGCCGGCTCTCCACGCTTTGCCTGACCCTGCTTGCTCAACT
CTACGTCTTTGTTTCGTTTTCTGTTCTGCGCCGTTACAGATCCAAGCTGT
GACCGGCGCCTACTCTAGAGCTAGCGTTTAAACTTAAGCTTGCCACCATG
GACTACAAGGACGACGACGACATTGGACAAGAAGCCCCTGAACACCCTGA
TCAGCGCCACAGGACTGTGGATGTCCAGAACCGGCACCATCCACAAGATC
AAGCACCACGAGGTGTCCCGGTCCAAAAATCTACATCGAGATGGCCTGCG
GCGATCACCTGGTCGTCAACAACAGCAGAAGCAGCCGGACAGCCAGAGCC
CTGCGGCACCACAAGTACAGAAAGACCTGCAAGCGGTGCAGAGTGTCCGA
CGAGGACCTGAACAAGTTCCTGACCAAGGCCAACGAGGACCAGACCAGCG
TGAAAGTGAAGGTGGTGTCCGCCCCCACCCGGACCAAGAAAGCCATGCCC
AAGAGCGTGGCCAGAGCCCCCAAGCCCCTGGAAAACACCGAAGCCGCTCA
GGCCCAGCCCAGCGGCAGCAAGTTCAGCCCCGCCATCCCCGTGTCTACCC
AGGAAAGCGTCAGCGTCCCCGCCAGCGTGTCCACCAGCATCTCTAGCATC
TCAACCGGCGCCACAGCTTCTCCCCTGGTCAAGGGCAACACCAACCCCAT
CACCAGCATGTCTGCCCCTGTGCAGGCCTCTGCTTCAGCCCTGACCAAGT
CCCAGACCGACCGGCTGGAAGTGCTCCTGAACCCCAAGGACGAGATCAGC
CTGAACAGCGGCAAGCCCTTCCGGGAGCFGGAAAGCGAGCTGCTGAGCCG
GCGGAAGAAGGACCTCCAGCAAATCTACGCCGAGGAACGGGAGAACTACC
TGGGCAAGCTGGAAAGAGAGATCACCCGGTTCTTCGTGGACCGGGGCTTC
CTGGAAATCAAGAGCCCCATCCTGATCCCCCTGGAGTACATCGAGCGGAT
GGGCATCGACAACGACACCGAGCTGAGCAAGCAGATTCCGGGTGGACAAG
AACTTCTGCCTGCGGCCCATGCTGGCCCCCAACCTGTACAACTACCTGCG
GAAACTGGATCGCGCTCTGCCCGACCCCATCAAGATTTTCGAGATCGGCC
CCTGCTACCGGAAAGAGAGCGACGGCAAAGAGCACCTGGAAGAGTTTACA
ATGCTGAACTTTTGCCAGATGGGCAGCGGCTGCACCAGAGAGAACCTGGA
ATCCATCATCACCGACTTCTGAACCACCTGGGGATCGACTrCAAGATCGT
GGGCGACAGCTGCATGGTGTACGGCGACACCCTGGACGTGATGCACGGCG
ACCTGGAACTGTCTAGCGCCGTCGTGGGACCCATCCCTCTGGACCGGGAG
TGGGGCATCGATAAGCCCTGGATCGGAGCCGGCTTCGGCCTGGAACGGCT
GCTGAAAGTCAAGCACGACTTTAAGAACATCAAGCGGGCTGCCAGAAGCG
AGAGCTACTACAACGGCATCAGCACCAACCTGTGATGAGGATCCGCGGCC
GCGCCCCTCTCCCTCCCCCCCCCCTAACGTTACTGGCCGAAGCCGGAGTT
CTTCGCCCACCCCAACTTGTTTATTGCAGCTTATAATGGTTACAAATAAA
GCAATAGCATCACAAATTTCACAAATAAAGCATTTTTTTCACTGCATTCT
AGTTGTGGTTTGTCCAAACTCATCAATGTATCTTATCATGTCTGTATACC
GTCGACCTCTAGCTAGAGCTTGGCGTAATCATGGTCATAGCTGTTTCCTG
```

-continued

```
TGTGAAATTGTTATCCGCTCACAATTCCACACAACATACGAGCCGGAAGC
ATAAAGTGTAAAGCCTGGGGTGCCTAATGAGTGAGCTAACTCACATTAAT
TGCGTTGCGCTCACTGCCCGGTTTCCAGTCGGGAAACCTGTCGTGCCAG
CTGCATTAATGAATCGGCCAACGCGCGGGGAGAGGCGGTTTGCGTATTGG
GCGCTGTTCCGCTTCCTCGCTCACTGACTCGCTGCGCTCGGTGGTTCGGC
TGCGGCGAGCGGTATCAGCTCACTCAAAGGCGGTAATACGGTTATCCACA
GAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCC
GCCCCCTGACGAGCATCACAAAAATCGACGCTCAAGTCAGAGGTGGCGAA
ACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTT
TCTCCCTTCGGGAAGCGTGGCGCTTTCTCAATGCTCACGCTGTAGGTAT
CTCAGTTCGGTGTAGGTCGTTCGCTCCAAGCTGGGCTGTGTGCACGAACC
CCCCGTTCAGCCGGACCGCTCrCGCCTTATCCGGTAACTATCGTCTTGAG
TCCAACCCGGTAAGACACGACTTTTTCGCCACTGGCAGCAGCCACTGGTA
ACAGGATTAGCAGAGCGAGGTATGTAGGCGGTGCTACAGAGTTCTTGAAG
TGGTGGCCTAACTACGCCTACACTAGAAGGACAGTATTTGGTATCTGCGC
TCTGCTGGAGCCAGTTACCTTCGGAAAAAGAGTTGGTAGCTCTTGATCCG
GCAAACAAACCACCGCTGGTAGCGGTGGTTTTTTTGTTTGCAAGCAGCAG
ATTACCTTAGAAAAAAGGATCTCAAGAAGATCCTTCTATCTTTTCTACG
GGGTCTGACGCTCAGTGGAACGAAAACTCACGTTAAGGGATTTTGGTCAT
GAGATTATCAAAAAGGATCTTCACCTAGATCCTTTTAAATTAAAAATGAA
GTTTTAAATCAATCTAAAGTATATATGAGTAAACTTGGTCTGACAGTTAC
CAATGCTTAATCAGTGAGGCACCTATCTCAGCGATCTGTCTATTTCGTTC
ATCCATAGTTGCCTGACTCCCCGTCGTGTAGATAACTACGATACGGGAGG
GCTTACCATCTGGCCCCAGTGCTGCAATGATACCGCGAGACCCACGCTCA
CCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTT
GCCGGGAAGCTAGAGTAAGTAGTTTGCCAGTTAATAGTTTGCGCAACGTT
GTTGCCATTGCTACAGGCATCGTGGTGTCACGCTCGTCGTTGGTATGGCT
TCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAAT
TCTCTTACTGTCATGCCATCCGTAAGATGCTTTTCTGTGACTGGTGAGTA
CTCAACCAAGTCATTCTGAGAATAGTGTATGCGGCGACCGAGTTGCTCTT
GCCCGGCGTCAATACGGGATAATACCGCGCCACATAGCAGAACTTTAAAA
GTTTCTCATCATTTTTAACGTTCTTCGGGGCGAAAACTCTCAAGGATCTA
CCGCTCTGAGATCCAGTTCGATGTAACCCACTCGTGCACCCAACTGATCT
TCAGCATCTTTTACTTTCACCAGCGTTTCTGGGTGAGCAAAAACAGGAAG
GCAAAATGCCGCAAAAAAGGGAATAAGGGCGACACGGAAATGTTGAATAC
```

```
                    -continued
TCATACTCTTCCTTTTTCAATATTATTGAAGCATTTATCAGGGTTATTGT

CTCATGAGCGGATACATATTTGAATCTATTTAGAAAAATAAACAAATAGG

GGTTCCGCGCACATTTCCCCGAAAAGTGCCACCTGACGTCGACGGATCGG

GAGATCTTCCCGATCCCCTATGGTCGACTCTCAGTACAATCTGCTCTGAT

GCCGCATAGTTAAGCCAGTATCTGCTCCCTGCTTGTGTTGGAGGTCGC

TGAGTAGTGCGCGAGCAAAATTTAAGCTACAACAAGGCAAGGCTTGACCG

ACAATTGCATGAAGAATCTGCTTAGG
```

Example 15—eRF1 E55D Enhances BCN Incorporation in HEK Cells

Figure 21A:
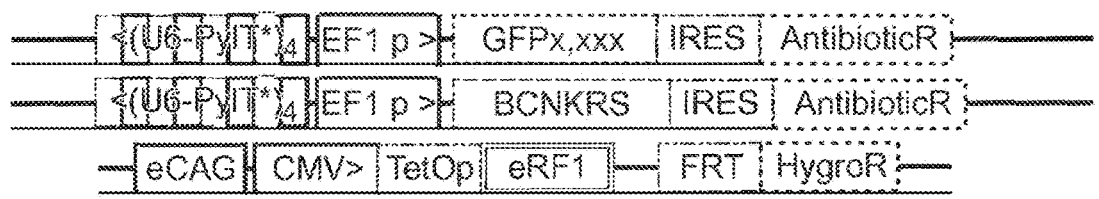
FIG. 21A shows a diagram.
Figure 21B:
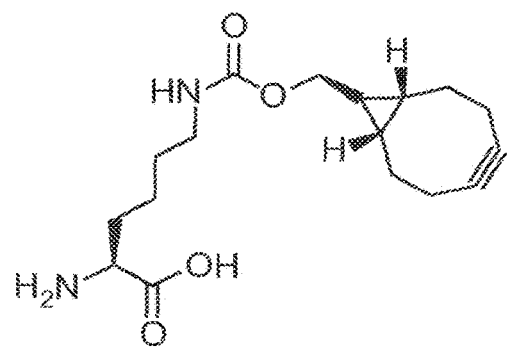
FIG. 21B shows a chemical structure and FIG. 21C two graphs.
Figure 21C:
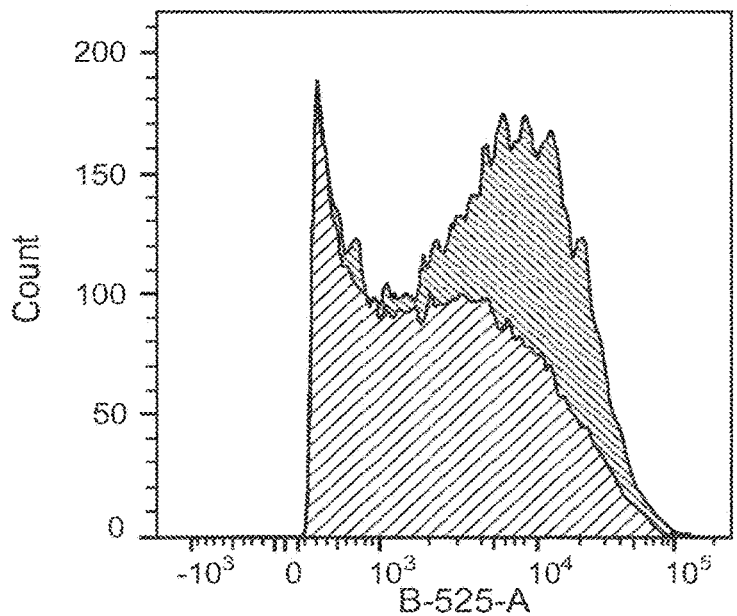
Figure 21C:
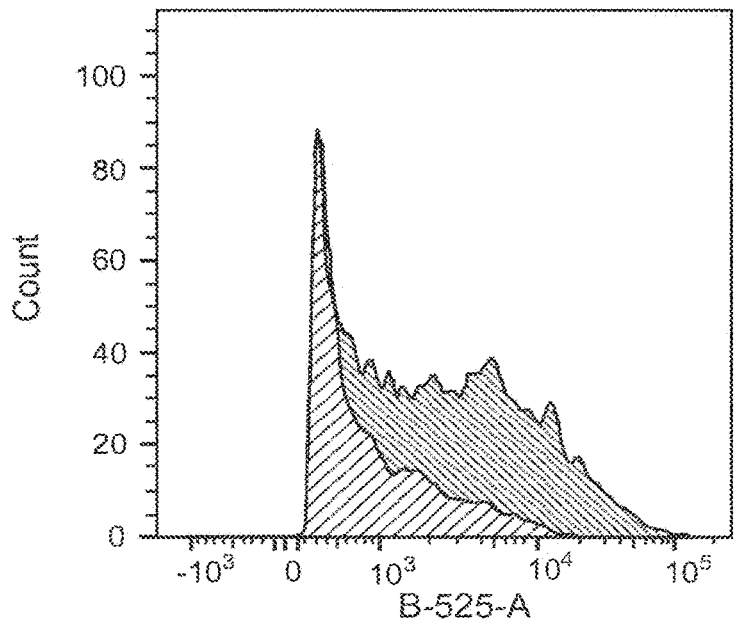

HEK293 3 day expression, 1 mM BCN (Nepsilon-(bicyclo[6.1.0]non-4-yn-9-ylmethoxy)carbonyl-L-lysine)), 1:1:1 ratio plasmids, standard protocols as described above. See FIGS. 21AS-21B.

Genetic Encoding of Bicyclononynes and trans-Cyclooctenes for Rapid Site-Specific Protein Labeling in Vitro and in Live Mammalian Cells via Fluorogenic Diels-Alder Reactions.

*J. Am. Chem. Soc.* 2012 134:10317-10320

K. Lang, L. Davis, S. Wallace, M. Mahash, D. J. Cox, M. L. Blackman, J. M. Fox & Chin.

Abbreviations

PylRS, pyrrolysyl-tRNA synthetase; PylT, pyrrolysyl-tRNA synthetase; eRF1, eukaryotic release factor 1; eRF3, eukaryotic release factor 3; sfGFP, super-folder green fluorescent protein.

REFERENCES (1) Lang, K.; Chin, J. W. *Chem Rev* 2014, 114, 4764.
(2) Kim, C. H.; Axup, J. Y.; Schultz, P. G. *Curr Opin Chem Biol* 2013, 17, 412.
(3) Baker, A. S.; Deiters, A. *ACS Chem Biol* 2014, 9, 7
(4) Davis, L.; Chin, J. W. *Nat Rev Mot Cell Biol.* 2012, 13, 168.
(5) Chin, J. W. *Annu Rev Biochem* 2014, 83: 379
(6) Bertram, G.; limes, S.; Minella, O.; Richardson, J.; Stansfield, I. *Microbiology* 2001, 147, 255.
(7) Jackson, R. J.; Hellen, C. U.; Pestova, T. V. *Adv Protein Chem Struct Biol* 2012, 86, 45.
(8) Dever, T. E.; Green, R. *Cold Spring Harb Perspect Biol.* 2012, 4, a013706.
(9) Scolnick, E.; Tompkins, R.; Caskey, T.; Nirenberg, M. *Proc Natl Acad Sci USA* 1968, 61, 768.
(10) Petry, S.; Brodersen, D. E.; Murphy, F. V. L; Dunham, C. M.; Selmer, M.; Tarry, M. J.; Kelley, A. C.; Ramakrishnan, V. *Cell* 2005, 123, 1255.
(11) Konecki, D. S.; Aune, K. C.; Tate, W.; Caskey, C. T. *J Biol Chem* 1977, 252, 4514.
(12) Wang, K.; Neumann, H.; Peak-Chew, S. Y.; Chin, J. W. *Nat Biotechnol* 2007, 25, 770.
(13) Mukai, T.; Hayashi, A.; Iraha F.; Sato, A.; Ohtake, K.; Yokoyama, S.; Sakamoto, K. *Nucleic Acids Res* 2010, 38, 8188.
(14) Johnson, D. B.; Xu, J.; Shen, Z.; Takimoto, J. K.; Schultz, M. D.; Schmitz, R. J.; Xiang, Z.; Ecker, J. R.; Briggs, S. P.; Wang, L. *Nat Chem Biol* 2011, 7, 779.
(15) Lajoie, M. J.; Rovner, A. J.; Goodman, D. B.; Aerni, H. R.; Haimovich, A. D.; Kuznetsov, G.; Mercer, J. A.; Wang, H. H.; Carr, P. A.; Mosberg, J. A.; Rohland, N.; Schultz, P. G.; Jacobson, J. M.; Rinehart, J.; Church, G. M.; Isaacs, F. J. *Science* 2013, 342, 357.
(16) Wu, I. L.; Patterson, M. A.; Carpenter Desai, H. E.; Mehl, R. A.; Giorgi, G.; Conticello, V. P. *Chem biochem* 2013, 14, 968.
(17) Mukai, T.; Kobayashi, T.; Hino, N.; Yanagisawa, T.; Sakamoto, K.; Yokoyama, S. *Biochemical and Biophysical Research Communications* 2008, 371, 818.
(18) Chen, P. R.; Groff, D.; Guo, J.; Ou, W.; Cellitti, S.; Geierstanger, B. H.; Schultz, P. G. *Angewandte Chemie International Edition* 2009, 48, 4052.
(19) Gautier, A.; Nguyen, D. P.; Lusic, H.; An, W.; Deiters, A.; Chin, J. W. *J Am Chem Soc* 2010, 132, 4086.
(20) Xiao, H.; Chattedee, A.; Choi, S. H.; Bajjuri, K. M.; Sinha, S. C.; Schultz, P. G. *Angew Chem Int Ed Engl* 2013, 52, 14080.
(21) Elliott, T. S.; Townsley, F. M.; Bianco, A.; Ernst, R. J.; Sachdeva, A.; Elsasser, S. J.; Davis, L.; Lang, K.; Pisa, R.; Gneiss, S.; Lilley, K. S.; Chin, J. W. *Nat Biotechnol* 2014, 32, 465.
(22) Nguyen, D. P.; Lusic, H.; Neumann, H.; Kapadnis, P. B.; Deiters, A.; Chin, J. W. *J Am Chem Soc* 2009, 131, 8720.
(23) Miyake-Stoner, S. J.; Refakis, C. A.; Hammill, J. T.; Lusic, H.; Hazen, J. L.; Deiters, A.; Mehl, R. A. *Biochemistry* 2010, 49, 1667.
(24) Chatterjee, A.; Sun, S. B.; Furman, J. L.; Xiao H.; Schultz, P. G. *Biochemistry* 2013, 52, 10
(25) Kolosov, P.; Frolova, L.; Seit-Nebi, A.; Dubovaya, V.; Kononenko, A.; Oparina, N.; Justesen, J.; Efirnov, A.; Kisselev, L. *Nucleic Acids Res* 2005, 33, 6418.
(26) Bulygin, K. N.; Khairulina, Y. S.; Kolosov, P. M.; Ven'yaminova, A. G.; Graifer, D. M.; Vorobjev, Y. N.; Frolova, L. Y.; Kisselev, L. L.; Karpova, G. G. *RNA* 2010, 16, 1902.
(27) Seit-Nebi A.; Frolova, L.; Kisselev, L. *EMBO Rep* 2002, 3, 881.
(28) Eliseev, B.; Kryuchkova, P.; Alkalaeva, E.; Frolova, L. *Nucleic Acids Res* 2011, 39, 599.
(29) Lekomtsev, S.; Kolosov, P.; Bidou, L.; Frolova, L.; Rousset, J. P.; Kisselev, L. *Proc Natl Acad Sci USA* 2007, 104, 10824.
(30) Kryuchkova, P.; Grishin, A.; Eliseev, B.; Karyagina, A.; Frolova, L.; Aikalaeva, E. *Nucleic Acids Res* 2013, 41, 4573.
(31) Grentzmann, G.; Ingram, J. A.; Kelly, P. J.; Gesteland, R. F.; Atkins, J. F. *RNA* 1998, 4, 479.
(32) Keeling, K. M.; Lanier, J.; Du, M.; Salas-Marco, J.; Gao, L.; Kaenjak-Angeletti, A.; Bedwell, D. M. *RNA* 2004, 10, 691.
(33) Salas-Marco, J.; Fan-Minogue, H.; Kallmeyer, A. K.; Klobutcher, L. A.; Farabaug P. J.; Bedwell, D. M. *Mol Cell Biol* 2006, 26, 438.
(34) Conard, S. E.; Buckley, J.; Dang, M.; Bedwell, G. J.; Carter, R. L.; Khass M.; Bedwell, D. M. *RNA* 2012, 18, 1210.
(35) Le Goff, X.; Philippe, M.; Jean-Jean, O. *Mol Cell Biol* 1997, 17, 3164.
(36) Merkulova, T. I.; Frolova, L. Y.; Lazar, M.; Camonis, J.; Kisselev, L. L. *FEBS Lett* 1999, 443, 41.

(37) Cheng, Z.; Saito, K.; Pisarev, A. V.; Wada, M.; Pisareva, V. P.; Pestova, T. V.; Gajda, M.; Round, A.; Kong, C.; Lim, M.; Nakamura, Y.; Svergun, D. I.; Ito, K.; Song, H. *Genes Dev* 2009, 23, 1106.

(38) Kononenko, A. V.; Mitkevich, V. A.; Dubovaya, V. I.; Kolosov, P. M.; Makarov, A. A.; Kisselev, L. L. *Proteins* 2008, 70, 388.

(39) des Georges, A.; Hashem, Y.; Unbehaun, A.; Grassucci, R. A.; Taylor, D.; Hellen, C. U.; Pestova, T. V.; Frank, J. *Nucleic Acids Res* 2014, 42, 3409.

(40) Janzen, D. M.; Geballe, A. P. *Nucleic Acids Res* 2004, 32, 4491.

(41) Liang, H.; Wong, J. Y.; Bao, Q.; Cavalcanti, A. R.; Landweber, L. F. *J Mol Evol* 2005, 60, 337.

SUPPLEMENTARY REFERENCES (1) Gautier, A.; Nguyen, D. P.; Lusic, H.; An, T.; Deiters, A.; Chin, J. W. *J Am Chem Soc* 2010, 132, 4086.

(2) Hoover, D. M.; Lubkowski, J. *Nucleic Acids Res* 2002, 30, e43. S12

(3) Elliott, T. S.; Townsley, F. M.; Bianco, A.; Ernst, R. J.; Sachdeva, A.; Elsasser, S. J.; Davis, L.; Lang, K.; Pisa, R.; Greiss, S.; Lilley, K. S.; Chin, J. W. *Nat Biotechnol* 2014, 32, 465.

(4) Arbely, E.; Torres-Kolbus, J.; Deiters, A.; Chin, J. W. *J Am Chem Soc* 2012, 134, 11912.

(5) Wilkins, M. R.; Gasteiger, E.; Bairoch, A.; Sanchez, J. C.; Williams, K. L.; Appel, R. D.; Hochstrasser, D. F. *Methods Mol Biol* 1999, 112, 531.

(6) Nguyen, D. P.; Garcia M. M.; Kapadnis P. B.; Neumann, N.; Chin, J. W. *J Am Chem Soc* 2009, 131, 40.

(7) Nguyen, D. P.; Mahesh, M.; Elsasser, S. J.; Hancock, S. M.; Uttamapinant, C.; Chin, J. W. *J Am Chem Soc* 2014, 136, 2240.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology and chemistry or related fields are intended to be within the scope of the following claims.

Supplementary Table S1

Nucelotide sequences of synthetic genes used in this study A. Sequence of the modified U6-PylT* expression cassette. PylT is underlined, and the anticodon marked in red. B. Sequence of sfGFP(TAG), with H. sapiens codon optimization and a C-terminal polyhisidine tag. The amber codon in position 150 is marked in red. C shows the human eRF1 sequence after codon optimisation for D. melanogaster, with an N-terminal polyhistidine tag.

A. U6-PylT* U25C
agtcagtcactagtTGGGCAGGAAGAGGGCCTATTTCCCATGATTCCTTC
ATATTTGCATATACGATACAAGGCTGTTAGAGAGATAATTAGAATTAATT
TGACTGTAAACACAAAGATATTAGTACAAAATACGTGACGTAGAAAGTAA
TAATTTCTTGGGTAGTTTGCAGTTTTAAAATTATGTTTTAAAATGGACTA
TCATATGCTTACCGTAACTTGAAAGTATTTCGATTTCTTGGCTTTATATA
TCTTGTGGAAAGGACGAAACACCggaaacctgatcatgtagatcgaaCgg
actctaaatccgttcagccgggttagattcccggggtttccgGACAAGTG
CGGTTTTTcctaggagtcagtc B. sfGFP(TAG) H. sapiens optimized, C-terminal HisTag
ATGGTGTCCAAGGGCGAGGAACTGTTCACCGGCGTGGTGCCCATCCTG
GTGGAACTGGATGGCGACGTGAACGGCCACAAGTTCTCTGTGCGGGGA
GAGGGCGAAGGCGACGCCACAAATGGCAAGCTGACCCTGAAGTTCATC
TGCACCACCGGCAAGCTGCCCGTGCCTTGGCCTACCCTCGTGACCACA
CTGACCTACGGCGTGCAGTGCTTCAGCAGATACCCCGACCATATGAAG
CGGCACGACTTCTTCAAGAGCGCCATGCCCGAGGGCTACGTGCAGGAA
CGGACCATCAGCTTCAAGGACGACGGCACCTACAAGACCAGAGCCGAA
GTGAAGTTCGAGGGCGACACCCTCGTGAACCGGATCGAGCTGAAGGGC
ATCGATTTCAAAGAGGACGGCAACATCCTGGGCCACAAGCTGGAGTAC
AACTTCAACAGCCACTAGGTGTACATCACCGCCGACAAGCAGAAGAAC
GGCATCAAGGCCAACTTCAAGATCCGGCACAACGTGGAAGATGGCAGC
GTGCAGCTGGCCGACCACTACCAGCAGAACACCCCCCATCGGAGATGG
CCCCGTGCTGCTGCCCGACAACCACTACCTGAGCACCCAGAGCGTGCT
GAGCAAGGACCCCAACGAGAAGCGGGACCACATGGTGCTGCTGGAATT
CGTGACCGCCGCTGGCATCACCCACGGCATGGACGAGCTGTACAAGGG
CAGCCACCATCACCATCACCATTAATAATAA C. H. sapiens eRF1 D. melanogaster optimized, N-terminal HisTag
ATGCATCATCACCATCACCACGCCGATGATCCAAGCGCCGCAGACCGC
AATGTTGAGATCTGGAAGATAAAAAAGCTGATAAAGAGCTTGGAGGCC
GCACGGGGCAACGGCACGTCCATGATATCCCTCATTATCCCACCAAAG
GATCAGATCAGCCGTGTGGCGAAGATGTTGGCGGATGAGTTCGGAACG
GCCAGTAACATTAAAAGTCGCGTGAACCGGCTGTCGGTCTTGGGCGCC
ATCACTTCCGTGCAGCAACGTCTGAAACTGTACAACAAAGTCCCACCC
AACGGTTTGGTCGTCTACTGCGGTACGATAGTTACCGAGGAAGGAAAG
GAGAAGAAAGTGAATATTGATTTCGAACCATTTAAACCGATAAACACT
AGCTTGTACTTGTGCGACAATAAGTTTCATACAGAGGCACTCACGGCC
CTGCTGAGCGACGACTCGAAATTCGGATTCATTGTCATTGATGGAAGT
GGAGCGCTGTTCGGCACGCTGCAGGGTAACACGCGCAGGTCTTGCACA
AATTCACCGTGGACTTGCCCAAAAAGCATGGCCGTGGTGGCCAGAGCG
CCCTCAGGTTTGCGCGGCTGCGCATGGAAGCGCCATAACTACGTGC
GCAAGGTCGCAGAGACGGCTGTGCAGCTGTTCATCTCGGGTGATAAGG
TAAATGTCGCGGGACTGGTGCTCGCCGGCAGCGCGACTTCAAAACCGA
GCTGAGTCAGTCCGACATGTTCGATCAGGTCTGCAGCGAAGGTACTGA
AGCTCGTAAGAAGGTAGCTACGGCGGCGAGAACGGCTTCAATCAGGCC
ATCGAACTGAGTACCGAAGTCCTCAGTAACCTAAAGTTTATTCAGGAA
AAAAGTTGATTGGACGCTACTTTGATGAAATAAGCCAAGATACGGGCA
AATACTGTTTTGGCGTCGAGGATACTCTGAAAGA=CGCTCGAGATGGG
AGCAGTGGAAATACTCATCGTATATGAAAATCTCGATATAATGCGCTA
TGTACTGCATTGCCAAGGAACAGAGAGGAGAAAAATTCTCTACCTCAC
CCCCGGAGCAAGAGAAGGACAAGAGCCATTTTACAGACAAGGAGACGG
GCCAAGAGCACGAGCTCATTGAGTCGATGCCCTTGCTCGAATGGTTTG
CAACAACTACAAGAAGTTCGGGCCATCGGCGGCATCCTCCGCTACCGG
GTGGATTTCCAAGGCATGGAATATCAAGGTGGAGATGATGAATTCTTC
GATTTGGATGATTACTAATGATAG Supplementary Table S2

| eRF1_E55Af | 5'-GAAGATGTTGGCGGATGCCTTCGGAACGGCCAGTAAC-3' |
|---|---|
| eRF1_e55Ar | 5'-GTTACTGGCCGTTCCGAAGGCATCCGCCAACATCTTC-3' |

Supplementary Table S2

| | |
|---|---|
| eRF1_e55Df | 5'-GATGTTGGCGGATGATTTCGGAACGGCCAG-3' |
| eRF1_e55Dr | 5'-CTGGCCGTTCCGAAATCATCCGCCAACATC-3' |
| eRF1_Y125Ff | 5'-CCGATAAACACTAGCTTGTTCTTGTGCGACAATAAGTTTC-5'-3' |
| eRF1_Y125Fr | 5'-GAAACTTATTGTCGCACAAGAACAAGCTAGTGTTTATCGG-5'-3' |
| eRF1_TS122QFf | 5'-CATTTAAACCGATAAACCAATTCTTGTACTTGTGCGAC-3' |
| eRF1_TS122QFr | 5'-GTCGCACAAGTACAAGAATTGGTTTATCGGTTTAAATG-3' |
| eRF1_NK129PQf | 5'-GCTTGTACTTGTGCGACCCACAGTTTCATACAGAGGCAC-3' |
| eRF1_NK129PQr | 5'-GTGCCTCTGTATGAAAG=CTGTGGGTCGCACAAGTACAAGC-3' |
| eRF1_SVLG70AVLSf | 5'-GCGTGAACCGGCTGGCCGTGCTGAGCGCCATCACTTCC-3' |
| eRF1_SVLG70AVLSr | 5'-GGAAGTGATGGCGCTCAGCACGGCCAGCCGGTTCACGC-3' |
| eRF1_K130Mf | 5'-GTACTTGTGCGACAATATGTTTCATACAGAGGCAC-3' |
| eRF1_K130Mr | 5'-GTGCCTCTGTATGAAACATATTGTCGCACAAGTAC-3' |
| eRF1_M51Mf | 5'-GTGTGGCGAAGGCCTTGGCGGATGAG-3' |
| eRF1_M51Mr | 5'-CTCATCCGCCAAGGCCTTCGCCACAC-3' |
| DLR_Ser_f | 5'-CTGAAGAACGAGCAAATCTCCACGGGGGCCCTAGGAGATC-3' |
| DLR_Ser_r | 5'-GATCTCCTAGGGGCCCCGTGGAGATTTGCTCGTTCTTCAG-3' |
| DLR_TAA_f | 5'-GAAGAACGAGCAAATCTAAACGGGGGCCCCTAGGAG-3' |
| DLR_TAA_r | 5'-CTCCTAGGGGCCCCCGTTTAGATTTGCTCGTTCTTC-3' |
| DLR_TAG_f | 5'-GAAGAACGAGCAAATCTAGACGGGGGCCCCTAGG-3' |
| DLR_TAG_r | 5'-CCTAGGGGCCCCCGTCTAGATTTGCTCGTTCTTC-3' |
| DLR_TGA_f | 5'-CTGAAGAACGAGCAAATCTGAACGGGGGCCCCTAGGAGATC-3' |
| DLR_TGA_r | 5'-GATCTCCTAGGGGCCCCCGTTCAGATTTGCTCGTTCTTCAG-3' |
| sfGFP_TAG150Lf | 5'-CTTCAACAGCCACCTGGTGTACATCACC-3' |
| sfGFP_TAG150Lr | 5'-GGTGATGTACACCAGGTGGCTGTTGAAG-3' |
| sfGFP_D133TAGf | 5'-GGCATCGATTTCAAAGAGTAGGGCAACATCCTGGG-3' |
| sfGFP_D133TAGr | 5'-CCCAGGATGTTGCCCTACTCTTTGAAATCGATGCC-3' |
| sfGFP_K101TAGf | 5'-GGACCATCAGCTTCTAGGACGACGGCACCTACAAGACC-3' |
| sfGFP_K101TAGr | 5'-GGTCTTGTAGGTGCCGTCGTCCTAGAAGCTGATGGTCC-3' |

SEQUENCES

SEQ ID NO: 1
ACTCTTCCTTTTTCAATATTATTGAAGCATTTATCAGGGTTATTGTCTCA
TGAGCGGATACATATTTGAATGTATTTAGAAAAATAAACAAATAGGGGTT
CCGCGCACATTTCCCCGAAAAGTGCCACCTAAATTGTAAGCGTTAATATT
TTGTTAAAATTCGCGTTAAATTTTTGTTAAATCAGCTCATTTTTTAACCA
ATAGGCCGAAATCGGCAAAATCCCTTATAAATCAAAAGAATAGACCGAGA
TAGGGTTGAGTGTTGTTCCAGTTTGGAACAAGAGTCCACTATTAAAGAAC
GTGGACTCCAACGTCAAGGGCGAAAACCGTCTATCAGGGCGATGCCC
ACTACGTGAACCATCACCCTAATCAAGTTTTTGGGGTCGAGGTGCCGTA
AAGCACTAAATCGGAACCCTAAAGGGAGCCCCCGATTTAGAGCTTGACGG
GGAAAGCCGGCGAACGTGGCGAGAAAGGAAGGGAAGAAAGCGAAAGGAGC
GGGCGCTAGGGCGCTGGCAAGTGTAGCGGTCACGCTGCGCGTAACCACCA
CACCCGCCGCGCTTAATGCGCCGCTACAGGGCGCGTCCCATTCGCCATTC
AGGCTGCGCAACTGTTGGGAAGGGCGATCGGTGCGGGCCTCTTCGCTATT
ACGCCAGCTGGCGAAAGGGGGATGTGCTGCAAGGCGATTAAGTTGGGTAA
CGCCAGGGTTTTCCCAGTCACGACGTTGTAAAACGACGGCCAGTGAGCGC
GCCTCGTTCATTCACGTTTTTGAACCCGTGGAGGACGGGCAGACTCGCGG
TGCAAATGTGTTTTACAGCGTGATGGAGCAGATGAAGATGCTCGACACGC
TGCAGAACACGCAGCTAGATTAACCCTAGAAAGATAATCATATTGTGACG
TACGTTAAAGATAATCATGCGTAAAATTGACGCATGTGTTTTATCGGTCT
GTATATCGAGGTTTATTTATTAATTTGAATAGATATTAAGTTTTATTATA
TTTACACTTACATACTAATAATAAATTCAACAAACAATTTATTTATGTTT
ATTTATTTATTAAAAAAAAACAAAAACTCAAAATTTCTTCTATAAAGTAA
CAAAACTTTTATGAGGGACAGCCCCCCCCCAAAGCCCCCAGGGATGTAAT
TACGTCCCTCCCCCGCTAGGGGGCAGCAGCGAGCCGCTCCGGGGCTCCGCT
CCGGTCCGGCGCTCCCCCGCATCCCCGAGCCGGCAGCGTGCGGGGACAG
CCCGGGCACGGGAAGGTGGCACGGGATCGCTTTCCTCTGAACGCTTCTC
GCTGCTCTTTGAGCCTGCAGACACCTGGGGGATACGGGGAAAGGCCTC
CAAGGCCACTAGGAAAAACCGCACTTGTCCGGAACCCCGGGAATCTAAC
CCGGCTGAACGGATTTAGAGTCCATTCGATCTACATGATCAGGTTTCCGG
TGTTTCGTCCTTTTCCACAAGATATATAAAGCCAAGAAATCGAAATACTTT

| SEQUENCES |
|---|
| CAAGTTACGGTAAGCATATGATAGTCCATTTTAAAACATAATTTTAAAAC |
| TGCAAACTACCCAAGAAATTATTACTTTCTACGTCACGTATTTTGTACTA |
| ATATCTTTGTGTTTACAGTCAAATTAATTCTAATTATCTCTCTAACAGCC |
| TTGTATCGTATATGCAAATATGAAGGAATCATGGGAAATAGGCCCTCTTC |
| CTGCCCAACTAGGAAAAACCGCACTTGTCCGGAAACCCCGGGAATCTAAC |
| CCGGCTGAACGGATTTAGAGTCCATTCGATCTACATGATCAGGTTTCCGG |
| TGTTTCGTCCTTTCCACAAGATATATAAAGCCAAGAAATCGAAATACTTT |
| CAAGTTACGGTAAGCATATGATAGTCCATTTTAAAACATAATTTTAAAAC |
| TGCAAACTACCCAAGAAATTATTACTTTCTACGTCACGTATTTTGTACTA |
| ATATCTTTGTGTTTACAGTCAAATTAATTCTAATTATCTCTCTAACAGCC |
| TTGTATCGTATATGCAAATATGAAGGAATCATGGGAAATAGGCCCTCTTC |
| CTGCCCAACTAGGAAAAACCGCACTTGTCCGGAAACCCCGGGAATCTAAC |
| CCGGCTGAACGGATTTAGAGTCCATTCGATCTACATGATCAGGTTTCCGG |
| TGTTTCGTCCTTTCGACAAGATATATAAAGCCAAGAAATCGAAATACTTT |
| CAAGTTACGGTAAGCATATGATAGTCCATTTTAAAACATAATTTTAAAAC |
| TGCAAACTACCCAAGAAATTATTACTTTCTACGTCACGTATAITTTGTACTA |
| ATATCTTTGTGTTTACAGTCAAATTAATTCTAATTATCTCTCTAACAGCC |
| TTGTATCGTATATGCAAATATGAAGGAATCATGGGAAATAGGCCCTCTTC |
| CTGCCCAACTAGGAAAAACCGCACTTGTCCGGAAACCCCGGGAATCTAAC |
| CCGGCTGAACGGATTTAGAGTCCATTCGATCTACATGATCAGGTTTCCGG |
| TGTTTCGTCCTTTCCACAAGATATATAAAGCCAAGAAATCGAAATACTTT |
| CAAGTTACGGTAAGCATATGATAGTCCATTTTAAAACATAATTTTAAAAC |
| TGCAAACTACCCAAGAAATTATTACTTTCTACGTCACGTATTTTGTACTA |
| ATATCTTTGTGTTTACAGTCAAATTAATTCTAATTATCTCTCTAACAGCC |
| TTGTATCGTATATGCAAATATGAAGGAATCATGGGAAATAGGCCCTCTTC |
| CTGCCCAACTAGGAAAAACCGCACTTGTCCGGAAACCCCGGGAATCTAAC |
| CCGGCTGAACGGATTTAGAGTCCATTCGATCTACATGATCAGGTTTCCGG |
| TGTTTCGTCCTTTCCAGAAGATATATAAAGCCAAGAAATCGAAATACTTT |
| CAAGTTACGGTAAGCATATGATAGTCCATTTTAAAACATAATTTTAAAAC |
| TGCAAACTACCCAAGAAATTATTACTTTCTACGTCACGTATTTTGTACTA |
| ATATCTTTGTGTTTACAGTCAAATTAATTCTAATTATCTCTCTAACAGCC |
| TTGTATCGTATATGCAAATATGAAGGAATCATGGGAAATAGGCCCTCTTC |
| CTGCCCAACTAGTAAGGATCTGCGATCGCTCCGGTGCCCGTCAGTGGGCA |
| GAGCGCACATCGCCCACAGTCCCCGGAAGTTGGGGGGAGGGTCGGCAA |
| TTGAACGGGTGCCTAGAGAAGGTGGCGCGGGGTAAACGGGGAAAGTGATG |
| TCGTGTACTGGCTCCGCCTTTTTCCCGAGGGTGGGGGAGAACCGTATATA |
| AGTGCAGTAGTCGCCGTGAACGTTCTTTTTCGCAACGGGTTTGCCGCCAG |
| AACACAGCTGAAGCTTCGAGGGGCTCGCATCTCTCCTTCACGCGCCCGCT |
| GCCCTACCTGAGGCCGCCATCCACGCCGGTTGAGTCGCGTTCTGCCGCCT |
| CCCGCCTGTGGTGCCTCCTGAACTGCGTCCGCCGTCTAGGTAAGTTTAAA |
| GCTCAGGTCGAGACCGGGCCTTTGTCCGGCGCTCCCTTGGAGCCTACCTA |
| GACTCAGCCGGCTCTCCACGCTTTGCCTGACCCTGCCTTGCTCAACTCTAC |
| GTCTTTGTTTCGTTTTCTGTTCTGCGCCGTTACAGATCCAAGCTGTGACC |
| GGCGCCTACTCTAGAGCTAGCGTTTAAACTTAAGCTTGCCACCATGGACT |
| ACAAGGACGACGACGACAAGGACAAGAAGCCCCTGAACACCCTGATCAGC |
| GCCACAGGACTGTGGATGTCCAGAACCGGCACCATCCACAAGATCAAGCA |
| CCACGAGGTGTCCCGGTCCAAAATCTACATCGAGATGGCCTGCGGCGATC |
| ACCTGGTCGTCAACAACAGCAGAAGCAGCCGGACAGCCAGAGCCCTGCGG |
| CACCACAAGTACAGAAAGACCTGCAAGCGGTGCAGAGTGTCCGACGAGGA |
| CCTGAACAAGTTCCTGACCAAGGCCAACGAGGACAGACCAGCGTGAAAG |
| TGAAGGTGGTGTCCGCCCCCACCCGGACCAAGAAAGCCATGCCCAAGAGC |
| GTGGCCAGAGCCCCAAGCCCTGGAAAACACCGAAGCCGCTCAGGCCCA |
| GCCCAGCGGCAGCAAGTTCAGCCCCGCCATCCCCGTGTCTACCCAGGAAA |
| GCGTCAGCGTCCCGCCAGCGTGCTCCACCAGCATCTCTAGCATCTCAAG |
| GGCGCCCACAGCTTCTGCCCTGGTCAAGGCAACACCAACCCCATCACCAG |
| CATGTCTGCCCCTGTGCAGGCCTCTGCCCCAGCCCTGACCAAGTCCCAGA |
| CCGACCGGCTGGAAGTGCTCCTGAACCCCAAGGACGAGATCAGCCTGAAC |
| AGCGGCAAGCCCTTCCGGGAGCTGGAAAGCGAGCTGCTGAGCCGGCGGAA |
| GAAGGACCTCCAGCAAATCTACGCGGAACGGGAACAGGACTACCTGGGCA |
| AGCTGGAAAGAGATCACCCGGTTCTTCGTGGACCGGGGCTTCCTGGAA |
| ATCAAGAGCCCCATCCTGATCCCCCTGGAGTACATCGAGCGGATGGGCAT |
| CGACAACGACACCGAGCTGAGCAAGCAGATTTTCCGGGTGGACAAGAACT |
| TCTGCCGGCGGCCCATGGTGGCCCCCAACCTGTACAACTACCTGCGGAAA |
| CTGGATCGCGCTCTGCCCGACCCCATCAAGATTTTCGAGATCGGCCCCTG |
| CTACCGGAAAGAGAGCGACGGCAAAGAGCACCTGGAGAGTTTACAATGC |
| TGAACTTTTGCCAGATGGGCAGCGCTGCACCAGAGAGAACCTGGAATCC |
| ATCATCACCGACTTTCTGAACCACCTGGGGATCGACTTCAAGATCGTGGG |
| CGACAGCTGCATGGTGTACGGCGACACCCTGGACGTGATGCACGGCGACC |
| TGGAACTGTCTAGCGCCGTCGTGGGACCCATCCCTCTGGACCGGGAGTGG |
| GGCATCGATAAGCCCTGGATCGGAGCCGGCTTCGGCCTGGAACGGCTGCT |

| SEQUENCES |
|---|
| GAAAGTCAAGCACGACTTTAAGAACATCAAGCGGGCTGCCAGAAGCGAGA |
| GCTACTACAACGGCATCAGCACCAACCTGTGATGATAAGGATCCAAAATG |
| TACAGCGGCCGCGCCCCTCTCCCTCCCCCCCCCCTAACGTTACTGGCCGA |
| AGCCGCTTGGAATAAGGCCGGTGTGCGTTTGTCTATATGTTATTTTCCAC |
| CATATTGCCGTCTTTTGGCAATGTGAGGGCCCGGAAACCTGGCCCTGTCT |
| TCTTGACGAGCATTCCTAGGGGTCTTTCCCCTCTCGCCAAAGGAATGCAA |
| GGTCTGTTGAATGTCGTGAAGGAAGCAGTTCCTCTGGAAGCTTCTTGAAG |
| ACAAACAACGTCTGTAGCGACCCTTTGCAGGCAGCGGAACCCCCCACCTG |
| GCGACAGGTGCCTCTGCGGCAAAAGCCACGTGTATAAGATACACCTGCA |
| AAGGCGGCACAACCCCAGTGCCACGTTGTGAGTTGGATAGTTGTGGAAAG |
| AGTCAAATGGCTCTCCTCAAGCGTATTCAACAAGGGCTGAAGGATGCCC |
| AGAAGGTACCCCATTGTATGGGATCTGATCTGGGGCCTCGGTGCACATGC |
| TTTACATGTGTTTAGTCGAGGTTAAAAAAACGTCTAGGCCCCCCGAACCA |
| CGGGGACGTGGTTTTCCTTTGAAAAACACGATAATACCTCCGGAATGATT |
| GAACAAGATGGATTGCACGCAGGTTCTCCGGCCGCTTGGGTGGAGAGGCT |
| ATTCGGCTATGACTGGGCACAACAGACAATCGGCTGCTCTGATGCCGCCG |
| TGTTCCGGCTGTCAGCGCAGGGGCGCCCGGTTCTTTTTGTCAAGACCGAC |
| CTGTCCGGTGCCCTGAATGAACTGCAGGACGAGGCAGCGCGGCTATCGTG |
| GCTGGCCACGACGGGCGTTCCTTGCGCAGCTGTGCTCGACGTTGTCACTG |
| AAGCGGGAAGGGACTGGCTGCTATTGGGCGAAGTGCCGGGGCAGGATCTC |
| CTGTCATCTCACCTTGCTCCTGCCGAGAAAGTATCCATCATGGCTGATGC |
| AATGCGGCGGCTGCATACGCTTGATCCGGCTACCTGCCCATTCGACCACC |
| AAGCGAAACATCGCATCGAGCGAGCACGTACTCGGATGGAAGCCGGTCTT |
| GTCGATCAGGATGATCTGGACGAAGAGCATCAGGGGCTCGCGCCAGCCGA |
| ACTGTTCGCCAGGCTCAAGGCGCGCATGCCCGACGGCGAGGATCTCGTCG |
| TGACCCATGGCGATGCCTGCTTGCCGAATATCATGGTGGAAAATGGCCGC |
| TTTTCTGGATTCATCGACTGTGGCCGGCTGGGTGTGGCGGACCGCTATCA |
| GGACATAGCGTTGGCTACCCGTGATATTGCTGAAGAGCTTGGCGGCGAAT |
| GGGCTGACCGCTTCCTCGTGCTTTACGGTATCGCCGCTCCCGATTCGCAG |
| CGCATCGCCTTCTATCGCCTTCTTGACGAGTTCTTCTGAGTCGACAATCA |
| ACCTCTGGATTACAAAATTTGTGAAAGATTGACTGGTATTCTTAACTATG |
| TTGCTCCTTTTACGCTATGTGGATACGCTGCTTTAATGCCTTTGTATCAT |
| GTTAACTTGTTTATTGCAGCTTATAATGGTTACAAATAAAGCAATAGCAT |
| CACAAATTTCACAAATAAAGCATTTTTTTCACTGCATTCTAGTTGTGGTT |
| TGTCCAAACTCATCAATGTATCTTATCATGTCTGGAATTGACTCAAATGA |
| TGTCAATTAGTCTATCAGAAGCTATCTGGTCTCCCTTCCGGGGGACAAGA |
| CATCCCTGTTTAATATTTAAACAGCAGTGTTCCCAAACTGGGTTCTTATA |
| TCCCTTGCTCTGGTCAACCAGGTTGCAGGGTTTCCTGTCCTCACAGGAAC |
| GAAGTCCCTAAAGAAACAGTGGCAGCCAGGTTTAGCCCCGGAATTGACTG |
| GATTCCTTTTTAGGGCCCATTGGTATGGCTTTTTCCCCGTATCCCCCCA |
| GGTGTCTGCAGGCTCAAAGAGCAGCGAGAAGCGTTCAGAGGAAAGCGATC |
| CCGTGCCACCTTCCCCGTGCCCGGGCTGTCCCCGCACGCTGCCGGCTCGG |
| GGATGCGGGGGGAGCGCCGGACCGGAGCGGAGCCCCGGGCGGCTCGCTGC |
| TGCCCCCTAGCGGGGGAGGGACGTAATTACATCCCTGGGGGCTTTGGGGG |
| GGGGCTGTCCCTGATATCTATAACAAGAAAATATATATATATAAGTTAT |
| CACGTAAGTAGAACATGAAATAACAATATAATTATCGTATGAGTTAAATC |
| TTAAAAGTCACGTAAAAGATAATCATGCGTCATTTTGACTCACGCGGTCG |
| TTATAGTTCAAAATCAGTGAGACTTACCGCATTGACAAGCACGCCTCACG |
| GGAGCTCCAAGCGGCGACTGAGATGTCCTAAATGCACAGCGACGGATTCG |
| CGCTATTTAGAAAGAGAGAGCAATATTTCAAGAATGCATGCGTCAATTTT |
| ACGCAGACTATCTTTCTAGGGTTAATCTAGCTGCATCAGGATCATATCGT |
| CGGGTCTTTTTTCCGGCTCAGTGATCGCCCAAGCTGGCGCTATCTGGGCA |
| TCGGGGAGGAAGAAGCCCGTGCCTTTTCCCGCGAGGTTGAAGCGGCATGG |
| AAAGAGTTTGCCGAGGATGACTGCTGCTGCATTGACGTTGAGCGAAAACG |
| CACGTTTACCATGATGATTCGGGAAGGTGTGGCCATGCACGCCTTTAACG |
| GTGAACTGTTCGTTGAGGCCACCTGGGATACCAGTTCGTCGCGGCTTTTC |
| CGGACACAGTTCCGGATGGTCAGCCCGAAGCGCATCAGCAACCCGAACAA |
| TACCGGCGACAGCCGGAACTGCCGTGCCGGTGTGCAGATTAATGACAGCG |
| GTGCGGCGCTGGGATATTACGTCAGCGAGGACGGGTATCCTGGCTGGATG |
| CCGCAGAAATGGACATGGATACCCCGTGAGTTACCCGGCGGGCGCGCTTG |
| GCGTAATCATGGTCATAGCTGTTTCCTGTGTGAAATTGTTATCCGCTCAC |
| AATTCCACACAACATACGAGCCGGAAGCATAAAGTGTAAAGCCTGGGGTG |
| CCTAATGAGTGAGCTAACTCACATTAATTGCGTTGCGCTCACTGCCCGCT |
| TTCCAGTCGGGAAACCTGTCGTGCCAGCTGCATTAATGAATCGGCCAACG |
| CGCGGGGAGAGGCGGTTTGCGTATTGGGCGCTCTTCCGCTTCCTCGCTCA |
| CTGACTCGCTGCGCTCGGTCGTTCGGCTGCGGCGAGCGGTATCAGCTCAC |
| TCAAAGGCGGTAATACGGTTATCCACAGAATCAGGGGATAACGCAGGAAA |
| GAACATGTGAGCAAAAGGCCAGCAAAAGGCCAGGAACCGTAAAAAGGCCG |
| CGTTGCTGGCGTTTTTCCATAGGCTCCGCCCCCCTGACGAGCATCACAAA |
| AATCGACGCTCAAGTCAGAGGTGGCGAAACCCGACAGGACTATAAAGATA |
| CCAGGCGTTTCCCCCTGGAAGCTCCCTCGTGCGCTCTCCTGTTCCGACCC |
| TGCCGCTTACCGGATACCTGTCCGCCTTTCTCCCTTCGGGAAGCGTGGCG |
| CTTTCTCATAGCTCACGCTGTAGGTATCTCAGTTCGGTGTAGGTCGTTCG |
| CTCCAAGCTGGGCTGTGTGCACGAACCCCCCGTTCAGCCCGACCGCTGCG |
| CCTTATCCGGTAACTATCGTCTTGAGTCCAACCCGGTAAGACACGACTTA |
| TCGCCACTGGCAGCAGCCACTGGTAACAGGATTAGGAGAGCGAGGTATGT |
| AGGCGGTGCTACAGAGTTCTTGAAGTGGTGGCCTAACTACGGCTACACTA |

-continued

SEQUENCES

GAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAA
AACTCACGTTAAGGGATTTTGGTCATGAGATTATCAAAAAGGATCTTCAC
CTAGATCCTTTTAAATTAAAAATGAAGTTTTAAATCAATCTAAAGTATAT
ATGAGTAAACTTGGTCTGACAGTTACCAATGCTTAATCAGTGAGGCACCT
ATCTCAGCGATCTGTCTATTTCGTTCATCCATAGTTGCCTGACTCCCCGT
CGTGTAGATAACTACGATACGGGAGGGCTTACCATCTGGCCCCAGTGCTG
CAATGATACCGCGAGACCCACGCTCACCGGCTCCAGATTTATCAGCAATA
AACCAGCCAGCCGGAAGGGCCGAGCGCAGAAGTGGTCCGCAACTTTATCC
GCCTCCATCCAGTCTATTAATTGTTGCCGGGAAGCTAGAGTAAGTAGTTC
GCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTC
CTTCGGTCCTCCGATCGTTGTCAGAAGTAAGTTGGCCGCAGTGTTATCAC
TCATGGTTATGGCAGCACTGCATAATTCTCTTACTGTCATGCCATCCGTA
AGATGCTTTTCTGTGACTGGTGAGTACTCAACCAAGTCATTCTGAGAATA
GTGTATGCGGCGACCGAGTTGCTCTTGCCCGGCGTCAATACGGGATAATA
CCGCGCCACATAGCAGAACTTTAAAAGTGCTCATCATTGGAAAACGTTCT
TCGGGGCGAAAACTCTCAAGGATCTTACTGCTGTTGAGATCCAGTTCGAT
GTAACCCACTCGTGCACCCAACTGATCTTCAGCATCTTTTACTTTCACCA
GCGTTTCTGGGTGAGCAAAAACAGGAAGGCAAAATGCCGCAAAAAAGGGA
ATAAGGGCGACACGGAAATGTTGAATACTCAT

SEQ ID NO: 2
ACTCTTCCTTTTTCAATATTATTGAAGCATTTATCAGGGTTATTGTCTCA
TGAGCGGATACATATTTGAATGTATTTAGAAAAATAAACAAATAGGGGTT
CCGCGCACATTTCCCCGAAAAGTGCCACCTAAATTGTAAGCGTTAATATT
TTGTTAAAATTCGCGTTAAATTTTTGTTAAATCAGCTCATTTTTTAACCA
ATAGGCCGAAATCGGCAAAATCCCTTATAAATCAAAAGAATAGACCGAGA
TAGGGTTGAGTGTTGTTCCAGTTTGGAACAAGAGTCCACTATTAAAGAAC
GTGGACTCCAACGTCAAAGGGCGAAAAACCGTCTATCAGGGCGATGGCC
ACTACGTGACCATCACCCTAATCAAGTTTTTTGGGGTCGAGGTGCCGTAA
AGCACTAAATCGGAACCCTAAAGGGAGCCCCCGATTTAGAGCTTGACGGG
GAAAGCCGGCGAACGTGGCGAGAAAGGAAGGGAAGAAAGCGAAAGGAGCG
GGCGCTAGGGCGCTGGCAAGTGTAGCGGTCACGCTGCCGTAACCACCAC
ACCCGCCGCGCTTAATGCGCCGCTACAGGGCGCGTCCCATTCGCCATTCA
GGCTGCGCAACTGTTGGGAAGGGCGATCGGTGCGGGCCTCTTCGCTATTA
CGCCAGCTGGCGAAAGGGGGATGTGCTGCAAGGCGATTAAGTTGGGTAAC
GCCAGGGTTTTCCCAGTCACGACGTTGTAAAACGACGGCCAGTGAGCGCG
CCTCGTTCATTCACGTTTTTGAACCCGTGGAGGACGGGCAGACTCGCGGT
GCAAATGTGTTTTACAGCGTGATGGAGCAGATGAAGATGCTCGACACGCT
GCAGAACACGCAGCTAGATTAACCCTAGAAAGATAATCATATTGTGACGT
ACGTTAAAGATAATCATGCGTAAAATTGACGCATGTGTTTTATCGGTCTG
TATATCGAGGTTTATTTATTAATTTGAATAGATATTAAGTTTTATTATAT
TTACACTTACATACTAATAATAAATTCAACAAACAATTTATTTATGTTTA
TTTATTTATTAAAAAAAACAAAAACTCAAAATTTCTTCTATAAAGTAAC
AAAACTTTTATGAGGGACAGCCCCCCCCCAAAGCCCCCAGGGATGTAATT
ACGTCCCTCCCCCGCTACGGGGCACCAGCGAGCCGCCCGGGGCTCCGCTC
CGGTCCGGCGCTCCCCCCGCATCCCCGAGCCGGCAGCGTGCGGGGACAGC
CCGGGCACGGGGAAGGTGGCACGGGATCGCTTTCCTCTGAACGCTTCTCG
CTGCTCTTTGAGCCTGCAGACACCTGGGGGGATACGGGGAAAAGGCCTCC
AAGGCCACTAGGAAAAACCGCACTTGTCCGGAAACCCCGGGAATCTAACC
CGGCTGAACGGATTTAGAGTCCATTCGATCTACATGATCAGGTTTCCGGT
GTTTCGTCCTTTCCACAAGATATATAAAGCCAAGAAATCGAAATACTTTC
AAGTTACGGTAAGCATATGATAGTCCATTTTAAAACATAATTTTAAAACT
GCAAACTACCCAAGAAATTATTACTTTCTACGTCACGTATTTTGTACTAA
TATCTTTGTGTTTACAGTCAAATTAATTCTAATTATCTCTCAACAGCCT
TGTATCGTATATGCAAATATGAAGGAATCATGGGAAATAGGCCCTCTTCC
TGCCCAACTAGGAAAAACCGCACTTGTCCGGAAACCCCGGGAATCTAACC
CGGCTGAACGGATTTAGAGTCCATTCGATCTACATGATCAGGTTTCCGGT
GTTTCGTCCTTTCCACAAGATATATAAAGCCAAGAAATCGAAATACTTTC
AAGTTACGGTAAGCATATGATAGTCCATTTTAAAACATAATTTTAAAACT
GCAAACTACCCAAGAAATTATTACTTTCTACGTCACGTATTTTGTACTAA
TATCTTTGTGTTTACAGTCAAATTAATTCTAATTATCTCTCAACAGCCT
TGTATCGTATATGCAAATATGAAGGAATCATGGGAAATAGGCCCTCTTCC
TGCCCAACTAGGAAAAACCGCACTTGTCCGGAAACCCCGGGAATCTAACC
CGGCTGAACGGATTTAGAGTCCATTCGATCTACATGATCAGGTTTCCGGT
GTTTCGTCCTTTCCACAAGCCGGCTGAACGGATTTAGAGTCCATTCGATC

TACATGATCAGGTTTCCGGTGTTTCGTCCTTTCCACAAGATTTTAAAACT
GCAAACTACCCAAGAAATTATTACTTTCTACGTCACGTATTTTGTACTAA
TATCTTTGTGTTTACAGTCAAATTAATTCTAATTATCTCTCTAACAGCCT
TGTATCGTATATGCAAATATGAAGGAATCATGGGAAATAGGCCCTCTTCC
TGCCCAACTAGGAAAAACCGCACTTGTCCGGAAACCGCGGGAATCTAAGC
CGGCTGAACGGATTTAGAGTCCATTCGATCTACATGATCAGGITTCCGGT
GTTTCGTCCTTTCCACAAGATATATAAAGCCAAGAAATCGAAATACTTTC
AAGTTACGGTAAGGATATGATAGTCCATTTTAAAACATAATTTTAAAACT
GCAAACTACCCAAGAAATTATTACTTTCTACGTCACGTATTTTGTACTAA
TATCTTTGTGTTTACAGTCAAATTAATTCTAATTATCTCTCTAACAGCCT
TGTATCGTATATGCAAATATGAAGGAATCATGGGAAATAGGCCCTCTTCC
TGCCCAACTAGGAAAAACCGCACTTGTCCGGAAACCCCGGGAATCTAACC
CGGCTGAACGGATTTAGAGTCCATTCGATCTACATGATCAGGITTCCGGT
GTTTCGTCCTTTCCACAAGATATATAAAGCCAAGAAATCGAAATACTTTC
AAGTTACGGTAAGCATATGATAGTCCATTTTAAAACATAATTTTAAAACT
GCAAACTACCCAAGAAATTATTACTTTCTACGTCACGTATTTTGTACTAA
TATCTTTGTGTTTACAGTCAAATTAATTCTAATTATCTCTCTAACAGCCT
TGTATCGTATATGCAAATATGAAGGAATCATGGGAAATAGGCCCTCTTCC
TGCCCAACTAGTAAGGATCTGCGATCGCTCCGGTGCCCGTCAGTGGGCAG
AGCGCACATCGCCCACAGTCCCCAGAAGTTGGGGGGAGGGGTCGGCAAT
TGAACGGGTGCCTAGAGAAGGTGGCGCGGGGTAAACTGGGAAAGTGATGT
CGTGTACTGGCTCCGCCTTTTTCCCGAGGGTGGGGGAGAAAGCTTCGAGG
GGCTCGCATCTCTCCTTCACGCGCCCGCCGCCCTACCTGAGGCCGCCATC
CACGCCGGTTGAGTCGCGTTCTGCCGCCTCCCGCCTGTGGTGCCTCCTGA
ACTGCGTCCGCCGTCTAGGTAAGTTTAAAGCTCAGGTCGAGACCGGGCCT
TTGTCCGGCGCTCCCTTGGAGCCTACCTAGACTCAGCCGGCTCTCCACGC
TTTGCCTGACCCTGCTTGCTCAACTCTACGTCTTTGTTTCGTTTTCTGTT
CTGCGCCGTTACAGATCCAAGCTGTGACCGGCGCCTACTCTAGAGCTAGC
GAATTCGAATTTAAATTCGGATCACCACCATGGTGTCCAAGGGCGAGGAAC
TGTTCACCGGCGTGGTGCCCATCCTGGTGGAACTGGATGGCGACGGGAAC
GGCCACAAGTTCTCTGTGCGGGGAGAGGGCGAAGGCGACGCCACAAATGG
CAAGCTGACCCTGAAGTTCATCTGCACCACCGGCAAGCTGCCCGTGCCTT
GGCCTACCCTCGTGACCACACTGACCTACGGCGTGCAGTGCTTCAGCAGA
TACCCCGACCATATGAAGCGGCACGACTTCTTCAAGAGCGCCATGCCCGA
GGGCTACGTGCAGGAACGGACCATCAGCTTCAAGGACGACGGCACCTACA
AGACCAGGGCCGAAGTGAAGTTCGAGGGCGACACCCTCGTGAACCGGATC
GAGCTGAAGGGCATTGATTTCAAAGAGGACGGCAACATCCTGGGCCACAA
GCTGGAGTACAACTTCAACAGCCACTAGGTGTACATCACCGCCGACAAGC
AGAAGAACGGCATCAAGGCCAACTTCAAGATCCGGCACAACGTGGAAGAT
GGCAGCGTGCAGCTGGCCGACCACTACCAGCAGAACACCCCCATCGGAGA
TGGCCCCGTGCTGCTGCCCGACAACCACTACCTGAGCACCCAGAGCGTGC
TGAGCAAGGACCCCAACGAGAAGCGGGACCACATGGTGCTGCTGGAATTC
GTGACCGCCGCTGGCATCACCCACGGCATGGACGAGCTGTACAAGGGCAG
CCACCATCACCATCACCATTGATAAGGATCCCAGTTACCATCGATGATCC
GCGGCCGCGCCCCTCTCCCTCCCCCCCCCTAACGTTACTGGCCGAAGCC
GCTTGGAATAAGGCCGGTGTGCGTTTGTCTATATGTTATTTTCCACCATA
TTGCCGTCTTTTGGCAATGTGAGGGCCCGGAAACCTGGCCCTGTCTTCTT
GACGAGCATTCCTAGGGGTCTTTCCCCTCTCGCCAAAGGAATGCAAGGTC
TGTTGAATGTCGTGAAGGAAGCAGTTCCTCTGGAAGCTTCTTGAAGACAA
ACAACGTCTGTAGCGACCCTTTGCAGGCAGCGGAACCCCCCACCTGGCGA
CAGGTGCCTCTGCGGCCAAAAGCCACGTGTATAAGATACACCTGCAAAGG
CGGCACAACCCCAGTGCCACGTTGTGAGTTGGATAGTTGTGGAAAGAGTC
AAATGGCTCTCCTCAAGCGTATTCAACAAGGGGCTGAAGGATGCCCAGAA
GGTACCCCATTGTATGGGATCTGATCTGGGGCCTCGGTGCACATGCTTTA
CATGTGTTTAGTCGAGGTTAAAAAAACGTCTAGGCCCCCCGAACCACGGG
GACGTGGTTTTCCTTTGAAAAACACGATAATACCTCCGGAATGATTGAAC
AAGATGGATTGCACGCAGGTTCTCCGGCCGCTTGGGTGGAGAGGCTATTC
GGCTATGACTGGGCACAACAGACAATCGGCTGCTCTGATGCCGCCGTGTT
CCGGCTGTCAGCGCAGGGGCGCCCGGTTCTTTTTGTCAAGACCGACCTGT
CCGGTGCCCTGAATGAACTGCAGGACGAGGCAGCGCGGCTATCGTGGCTG
GCCACGACGGGCGTTCCTTGCGCAGCTGTGCTCGACGTTGTCACTGAAGC
GGGAAGGGACTGGCTGCTATTGGGCGAAGTGCCGGGGCAGGATCTCCTGT
CATCTCACCTTGCTCCTGCCGAGAAAGTATCCATCATGGCTGATGCAATG
CGGCGGCTGCATACGCTTGATCCGGCTACCTGCCCATTCGACCACCAAGC
GAAACATCGCATCGAGCGAGCACGTACTCGGATGGAAGCCGGTCTTGTCG
ATCAGGATGATCTGGACGAAGAGCATCAGGGGCTCGCGCCAGCCGAACTG
TTCGCCAGGCTCAAGGCGCGCATGCCCGACGGCGAGGATCTCGTCGTGAC
CCATGGCGATGCCTGCTTGCCGAATATCATGGTGGAAAATGGCCGCTTTT
CTGGATTCATCGACTGTGGCCGGCTGGGTGTGGCGGACCGCTATCAGGAC
ATAGCGTTGGCTACCCGTGATATTGCTGAAGAGCTTGGCGGCGAATGGGC
TGACCGCTTCCTCGTGCTTTACGGTATCGCCGCTCCCGATTCGCAGCGCA
TCGCCTTCTATCGCCTTCTTGACGAGTTCTTCTGAGTCGACAATCAACCT
CTGGATTACAAAATTTGTGAAAGATTGACTGGTATTCTTAACTATGTTGC
TCCTTTTACGCTATGTGGATACGCTGCTTTAATGCCTTTGTATCATGTTA
ACTTGTTTATTGCAGCTTATAATGGTTACAAATAAAGCAATAGCATCACA
AATTTCACAAATAAAGCATTTTTTCACTGCATTCTAGTTGTGGTTTGTC
CAAACTCATCAATGTATCTTATCATGTCTGGAATTGACTCAAATGATGTC

SEQUENCES

```
AATTAGTCTATCAGAAGCTATCTGGTCTCCCTTCCGGGGACAAGACATC
CCTGTTTAATATTTAAACAGCAGTGTTCCCAAACTGGGTTCTTATATCCC
TTGCTCTGGTCAACCAGGTTGCAGGGTTTCCTGTCCTCACAGGAACGAAG
TCCCTAAAGAAACAGTGGCAGCCAGGTTTAGCCCCGGAATTGACTGGATT
CCTTTTTTAGGGCCCATTGGTATGGCTTTTTCCCCGTATCCCCCCAGGTG
TCTGCAGGCTCAAAGAGCAGCGAGAAGCGTTCAGAGGAAAGCGATCCCGT
GCCACCTTCCCCGTGCCCGGGCGTGTCCCCGCACGCTGCCGGCTCGGGGAT
GCGGGGGAGCGCCGGACCGGAGCGGAGCCCCGGGCGGCTCGCTGCTGCC
CCCTAGCGGGGAGGGACGTAATTACATCCCTGGGGGCTTTGGGGGGGGG
CTGTCCCTGATATCTATAACAAGAAAATATATATATAATAAGTTATCACG
TAAGTAGAACATGAAATAACAATATAATTATCGTATGAGTTAAATCTTAA
AAGTCACGTAAAAGATAATCATGCGTCATTTTGACTCACGCGGTCGTTAT
AGTTCAAAATCAGTGACACTTACCGCATTGACAAGCACGCCTCACGGGAG
CTCCAAGCGGCGACTGAGATGTCCTAAATGCACAGCGACGGATTCGCGCT
ATTTTAGAAAGAGAGAGCAATATTTCAAGAATGCATGCGTCAATTTTACGC
AGACTATCTTTCTAGGGTTAATCTAGCTGCATCAGGATCATATCGTCGGG
TCTTTTTTCCGGCTCAGTCATCGCCCAAGCTGGCGCTATCTGGGCATCGG
GGAGGAAGAAGCCCGTGCCTTTTCCCGCGAGGTTGAAGCGGCATGCAAAG
AGTTTGCCGAGGATGACTGCTGCTGCATTGACGTTGAGCGAAAACGCACG
TTTACCATGATGATTCGGGAAGGTGTGGCCATGCACGCCTTTAACGGTGA
ACTGTTCGTTCAGGCCACCTGGGATACCAGTTCGTCGCGGCTTTTCCGGA
CACAGTTCCGGATGGTCAGCCCGAAGCGCATCAGCAACCCGAACAATACC
GGCGACAGCCGGAACTGCCGTGCCGGTGTGCAGATTAATGACAGCGGTGC
GGCGCTGGGATATTACGTCAGCGAGGACGGGTATCCTGGCTGGATGCCGC
AGAAATGGACATGGATACCCCGGGAGTTACCCGGCGGGCGCGCTTGGCGT
AATCATGGTCATAGCTGTTTCCTGTGTGAAATTGTTATCCGCTCACAATT
CCACACAACATACGAGCCGGAAGCATAAAGTGTAAAGCCTGGGGTGCCTA
ATGAGTGAGCTAACTCACATTAATTGCGTTGCGCTCACTGCCCGCTTTCC
AGTCGGGAAACCTGTCGTGCCAGCTGCATTAATGAATCGGCCAACGCGCG
GGGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCAA
AGGCGGTAATACGGTTATCCACAGAATCAGGGGATAACGCAGGAAAGAAC
ATGTGAGCAAAAGGCCAGCAAAAGGCCAGGAACCGTAAAAAGGCCGCGTT
GCTGGCGTTTTTCCATAGGCTCCGCCCCCTGACGAGCATCACAAAAATC
GACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTT
CTCATAGCTCACGCTGTGGTATCTCAGTTCGGTGTAGGTCGTTCGCTCCA
AGCTGGGCTGTGTGCACGAACCCCCCGTTCAGCCCGACCGCTGCGCCTTA
TCCGGTAACTATCGTCTTGAGTCCAACCCGGTAAGACACGACTTATCGCC
ACTGGCAGCAGCCACTGGTAACAGGATTAGCAGAGCGAGGTATGTAGGCG
GTGCTACAGAGTTCTTGAAGTGGTGGCCTAACTACGGCTACACTAGAAGG
ACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTT
TTTTTGTTTGCAAGCAGCAGATTACGCGCAGAAAAAAAGGATCTCAAGAA
GATCCTTTGATCTTTTCTACGGGTCTGACGCTCAGTGGAACGAAAACTC
ACGTTAAGGGATTTTGGTCATGAGATTATCAAAAAGGATCTTCACCTAGA
TCCTTTTAAATTAAAAATGAAGTTTTAAATCAATCTAAAGTATATATGAG
```

SEQUENCES

```
TAAACTTGGTCTGACAGTTACCAATGCTTAATCAGTGAGGCACCTATCTC
AGCGATCTGTCTATTTCGTTCATCCATAGTTGCCTGACTCCCCGTCGTGT
AGATAACTACGATACGGGAGGGCTTACCATCTGGCCCCAGTGCTGCAATG
ATACCGCGAGACCCACGCTCACCGGCTCCAGATTTATCAGCAATAAACCA
GCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCA
GTTAATAGTTTGCGCAACGTTGTTGCCATTGCTACAGGCATCGTGGTGTC
ACGCTCGTCGTTTGGTATGGCTTCATTCAGCTCCGGTTCCCAACGATCAA
GGCGAGTTACATGATCCCCCATGTTGTGCAAAAAAGCGGTTAGCTCCTTC
GGTCCTCCGATCGTTGTCAGAAGTAAGTTGGCCGCAGTGTTATCACTCAT
GGTTATGGCAGCACTGCATAATTCTCTTACTGTCATGCCATCCGTAAGAT
GCTTTTCTGTGACTGGTGAGTACTCAACCAAGTCATTCTGAGAATAGTGT
ATGCGGCGACCGAGTTGCTCTTGCCCGGCGTCAATACGGGATAATACCGC
GCCACATAGCAGAACTTTAAAAGTGCTCATGATTGGAAAACGTTCTTCGG
GGCGAAAACTCTGAAGGATCTTACCGCTGTTGAGATCCAGTTCGATGTAA
CCCACTCGTGCACCCAACTGATCTTCAGCATCTTTTACTTTCACCAGCGT
TTCTGGGTGAGCAAAAACAGGAAGGCAAAATGCCGCAAAAAAGGGAATAA
GGGCGACACGGAAATGTTGAATACTCAT
```

SEQ ID NO: 3
```
ATGGCCGATGATCCAAGCGCCGCAGACCGCAATGTTGAGATCTGGAAGAT
AAAAAAGCTGATAAAGAGCTTGGAGGCCGGACGGGGCAACGGCACGTTCCA
TGATATCCCTCATTATCCCACCAAAGGATCAGATCAGCCGTGTGGCGAAG
ATGTTGGCGGATGAGTTCGGAACGGCCAGTAACATTAAAAGTCGCGTGAA
CCGGCTGTCGGTCTTGGGCGCCATCACTTCCGTGCAGCAACGTCTGAAAC
TGTACAACAAAGTCCCACCCAACGGTTTGGTCGTCTACTGCGGTACGATA
GTTACCGAGGAAGGAAAGGAGAAGAAAGTGAATATTGATTTCGAACCATT
TAAACCGATAAACACTAGCTTGTTCTTGTGCGACAATAAGTTTCATACAG
AGGCACTCACGGCCTGCTGAGCGACGACTCGAAATTCGGATTGATTGTC
ATTGATGGAAGTGGAGCGCTGTTCGGACACGCTGCAGGGTAACACGCGCGA
GGTCTTGCACAAATTCACCGTGGACTTGCCCAAAAAGCATGGCCGTGGTG
GCCAGAGCGCCCTCAGGTTTGCGCGGCTGCGCATGGAGAAGCGCCATAAC
TACGTGCGCAAGGTCGCAGAGACGGCTGTGCAGCTGTTCATCTCGGGTGA
TAAGGTAAATGTCGCGGGACTGGTGCTCGCCGGCAGCGCGGACTTCAAAA
CCGAGCTGAGTCAGTCCGACATGTTCGATCAGCGTCTGCAGTCGAAGGTA
CTGAAGCTCGTCGACATTAGCTACGGCGGCGAGAACGGCTTCAATCAGGC
CATCGAACTGAGTACCGAAGTCCTCAGTAACGTAAAGTTTATTGAGGAAA
AAAAGTTGATTGGACGCTACTTTGATGAAATAAGCCAAGATACGGGCAAA
TACTGTTTTGGCGTCGAGGATACTCTGAAAGCGCTCGAGATGGGAGCAGT
GGAAATACTCATCGTATATGAAAATCTCGATATAATGCGCTATGTACTGC
ATTGCCAAGGAACAGAAGAGGAGAAAATTCTCTACCTCACCCCGGAGCAA
GAGAAGGACAAGAGCCATTTTACAGACAAGGAGCGGGCCAAGAGCACGA
GCTCATTGAGTCGATGCCCTTGCTCGAATGGTTTGCCAACAACTACAAGA
AGTTCGGCGCGACCCTGGAAATTGTCACGGATAAATCGCAGGAGGGCAGC
CAGTTTGTGAAGGGCTTCGGTGGCATCGGCGGCATCCTCCGCTACCGGGT
GGATTTCCAAGGCATGGAATATCAAGGTGGAGATGATGAATTCTTCGATT
TGGATGATTACTAATGATAG
```

The invention claimed is:

1. A method for incorporating an unnatural amino acid into a protein of interest in a eukaryotic cell, said method comprising the steps of:
   providing a eukaryotic cell expressing an orthogonal tRNA synthetase-tRNA pair, a nucleic acid sequence of interest encoding said protein of interest, and a mutant eRF1, wherein said mutant eRF1 increases unnatural amino acid incorporation in response to one or more TAG (amber) stop codons without substantially increasing read-through of other stop codons, said mutant eRF1 having an amino acid sequence having at least 84.5% sequence identity to SEQ ID NO: 4, wherein said mutant eRF1 comprises an E55D mutation relative to SEQ ID NO: 4
   said nucleic acid sequence of interest comprising a codon recognised by the tRNA at the position for incorporation of said unnatural amino acid;
   b. incubating the eukaryotic cell in the presence of said unnatural amino acid to be incorporated into the protein of interest, wherein said unnatural amino acid is a substrate for the orthogonal tRNA synthetase; and
   c. incubating the eukaryotic cell to allow incorporation of said unnatural amino acid into the protein of interest via the orthogonal tRNA synthetase-tRNA pair.

2. A method according to claim 1, wherein said mutant eRF1 provides increased efficiency of unnatural amino acid incorporation relative to a wild type eRF1 control.

3. A method according to claim 1, wherein said mutant eRF1 further comprises a mutation or combination of mutations relative to SEQ ID NO: 4 selected from the group consisting of
   b. N129P, K130Q
   c. T122Q, S123F
   e. Y125F
   f. T58K, S60T, S64D, Y125F, N129S
   g. S123A, L124I, Y125L
   h. S123R, L124W, Y125R
   i. S123H, L124A, Y125G
   j. M51A, K130M
   k. S123A, L124L, Y125V
   l. S123L, L124C, Y125S
   m. S123L, L124S, Y125S, and
   n. S123V, L124T, Y125P.

4. A method according to claim 1, wherein said mutant eRF1 further comprises a mutation or combination of mutations relative to SEQ ID NO: 4 selected from the group consisting of
   a.
   b. N129, K130
   d. Y125
   e. T58, S60, S64, Y125, N129
   f. S123, L124, Y125
   g. S123, L124, Y125
   h. S123, L124, Y125
   i. M51, K130
   j. S123, L124, Y125
   k. S123, L124, Y125
   l. S123, L124, Y125 and
   m. 5123, L124, Y125.

5. A method according to claim 1, wherein said eukaryotic cell is a mammalian or insect cell.

6. A method according to claim 1, wherein said codon is a stop codon, and said stop codon is optionally UAG.

7. A method according to claim 1, wherein the orthogonal tRNA synthetase-tRNA pair comprises a pyrrolysyl-tRNA synthetase (PylRS)/PylT tRNA$_{CUA}$ pair.

8. A method according to claim 1, wherein the tRNA is:
   a. a U25C variant of PylT, or
   b. an Opt variant of PylT, or
   c. a U25C-Opt variant of PylT.

9. A method according to claim 1, wherein the unnatural amino acid is BocK, CypK or BCNK.

10. A method for incorporating an unnatural amino acid into a protein of interest in a eukaryotic cell, said method comprising the steps of:
   a. providing a eukaryotic cell expressing an orthogonal tRNA synthetase-tRNA pair, a nucleic acid sequence of interest encoding said protein of interest, and a mutant eRF1, wherein said mutant eRF1 increases unnatural amino acid incorporation in response to one stop codon without substantially increasing read-through of other stop codons, said mutant eRF1 having an amino acid sequence having at least 84.5% sequence identity to SEQ ID NO: 4, wherein said mutant eRF1 comprises a mutation or combination of mutations relative to SEQ ID NO: 4 selected from the group consisting of:
      i. N129P, K130Q
      ii. T122Q, S123F
      iii. E55A
      iv. Y125F
      v. T58K, S60T, S64D, Y125F, N129S
      vi. S123A, L124I, Y125L
      vii. S123R, L124W, Y125R
      viii. S123H, L124A, Y125G
      ix. M51A, K130M
      x. S123A, L124L, Y125V
      xi. S123L, L124C, Y125S
      xii. S123L, L124S, Y125S
      xiii. S123V, L124T, Y125P said nucleic acid sequence of interest comprising a codon recognised by the tRNA at the position for incorporation of said unnatural amino acid;
   b. incubating the eukaryotic cell in the presence of said unnatural amino acid to be incorporated into the protein of interest, wherein said unnatural amino acid is a substrate for the orthogonal tRNA synthetase; and
   c. incubating the eukaryotic cell to allow incorporation of said unnatural amino acid into the protein of interest via the orthogonal tRNA synthetase-tRNA pair.

11. A method according to claim 10, wherein said mutant eRF1 provides increased efficiency of unnatural amino acid incorporation relative to a wild type eRF1 control.

12. A method according to claim 10, wherein said stop codon is TAG (amber).

13. A method according to claim 10, wherein said eukaryotic cell is a mammalian or insect cell.

14. A method according to claim 10, wherein said codon is a stop codon, and said stop codon is optionally UAG.

15. A method according to claim 10, wherein the orthogonal tRNA synthetase-tRNA pair comprises a pyrrolysyl-tRNA synthetase (PylRS)/PylT tRNA$_{CUA}$ pair.

16. A method according to claim 10, wherein the tRNA is:
   a. a U25C variant of PylT, or
   b. an Opt variant of PylT, or
   c. a U25C-Opt variant of PylT.

17. A method according to claim 10, wherein the unnatural amino acid is BocK, CypK or BCNK.

* * * * *

UNITED STATES PATENT AND TRADEMARK OFFICE
CERTIFICATE OF CORRECTION

PATENT NO. : 10,738,339 B2
APPLICATION NO. : 15/521103
DATED : August 11, 2020
INVENTOR(S) : Jason W Chin et al.

It is certified that error appears in the above-identified patent and that said Letters Patent is hereby corrected as shown below:

In the Claims

At Column 155, Claim number 1, Line number 37, please replace:
"providing a eukaryotic cell expressing an orthogonal"
With:
--a. providing a eukaryotic cell expressing an orthogonal--.

At Column 155, Claim number 1, Line number 45, please replace:
"least 84.5% sequence identity to SEQ ID NO: 4,"
With:
--least 84% sequence identity to SEQ ID NO: 4,--.

At Claim number 3, from Column number 155, Line number 65 to Column number 156, Line number 40, please replace:
"b. N129P, K130Q
c. T122Q, S123F
e. Y125F
f. T58K, S60T, S64D, Y125F, N129S
g. S123A, L124I, Y125L
h. S123R, L124W, Y125R
i. S123H, L124A, Y125G
j. M51A, K130M
k. S123A, L124L, Y125V
l. S123L, L124C, Y125S
m. S123L, L124S, Y125S, and
n. S123V, L124T, Y125P."
With:
--a. N129P, K130Q
b. T122Q, S123F
c. Y125F Signed and Sealed this
Third Day of November, 2020

Andrei Iancu
*Director of the United States Patent and Trademark Office*

CERTIFICATE OF CORRECTION (continued)
U.S. Pat. No. 10,738,339 B2 d. T58K, S60T, S64D, Y125F, N129S
e. S123A, L124I, Y125L
f. S123R, L124W, Y125R
g. S123H, L124A, Y125G
h. M51A, K130M
i. S123A, L124L, Y125V
j. S123L, L124C, Y125S
k. S123L, L124S, Y125S, and
l. S123V, L124T, Y125P.--.

At Column 156, Claim number 4, Line number 45-56, please replace:
"a.
b. N129, K130
d. Y125
e. T58, S60, S64, Y125, N129
f. S123, L124, Y125
g. S123, L124, Y125
h. S123, L124, Y125
i. M51, K130
j. S123, L124, Y125
k. S123, L124, Y125
l. S123, L124, Y125 and
m. 5123, L124, Y125."
With:
--a. N129, K130
b. Y125
c. T58, S60, S64, Y125, N129
d. S123, L124, Y125
e. S123, L124, Y125
f. S123, L124, Y125
g. M51, K130
h. S123, L124, Y125
i. S123, L124, Y125
j. S123, L124, Y125 and
k. S123, L124, Y125.--.

At Column 157, Claim number 10, Line number 13, please replace:
"sequence having at least 84.5% sequence identity to"
With:
--sequence having at least 84% sequence identity to--.

SEQUENCE LISTING

<160> NUMBER OF SEQ ID NOS: 67

<210> SEQ ID NO 1
<211> LENGTH: 9683
<212> TYPE: DNA
<213> ORGANISM: Artificial Sequence
<220> FEATURE:
<223> OTHER INFORMATION: nucleic acid expression construct

<400> SEQUENCE: 1

```
actcttcctt tttcaatatt attgaagcat ttatcagggt tattgtctca tgagcggata      60
catatttgaa tgtatttaga aaataaaca ataggggtt ccgcgcacat ttccccgaaa      120
agtgccacct aaattgtaag cgttaatatt tgttaaaat tcgcgttaaa ttttttgttaa     180 atcagctcat tttttaacca ataggccgaa atcggcaaaa tcccttataa atcaaaagaa     240
tagaccgaga tagggttgag tgttgttcca gtttggaaca agagtccact attaaagaac     300
gtggactcca acgtcaaagg gcgaaaaacc gtctatcagg gcgatggccc actacgtgaa     360
```

```
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660 gcgaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaacttttt atgagggaca gccccccccc aaagccccca   1140
gggatgtaat tacgtccctc ccccgctagg gggcagcagc gagccgcccg gggctccgct   1200
ccggtccggc gctccccccg catccccgag ccggcagcgt gcggggacag cccgggcacg   1260
gggaaggtgg cacgggatcg cttttcctctg aacgcttctc gctgctcttt gagcctgcag   1320
acacctgggg ggatacggggg aaaaggcctc caaggccact aggaaaaacc gcacttgtcc   1380
ggaaaccccg ggaatctaac ccggctgaac ggatttagag tccattcgat ctacatgatc   1440
aggtttccgg tgtttcgtcc tttccacaag atatataaag ccaagaaatc gaaatacttt   1500
caagttacgg taagcatatg atagtccatt ttaaaacata attttaaaac tgcaaactac   1560
ccaagaaatt attactttct acgtcacgta ttttgtacta atatctttgt gtttacagtc   1620
aaattaattc taattatctc tctaacagcc ttgtatcgta tatgcaaata tgaaggaatc   1680
atgggaaata ggccctcttc ctgcccaact aggaaaaacc gcacttgtcc ggaaaccccg   1740
ggaatctaac ccggctgaac ggatttagag tccattcgat ctacatgatc aggtttccgg   1800
tgtttcgtcc tttccacaag atatataaag ccaagaaatc gaaatacttt caagttacgg   1860
taagcatatg atagtccatt ttaaaacata attttaaaac tgcaaactac ccaagaaatt   1920
attactttct acgtcacgta ttttgtacta atatctttgt gtttacagtc aaattaattc   1980
taattatctc tctaacagcc ttgtatcgta tatgcaaata tgaaggaatc atgggaaata   2040
ggccctcttc ctgcccaact aggaaaaacc gcacttgtcc ggaaaccccg ggaatctaac   2100
ccggctgaac ggatttagag tccattcgat ctacatgatc aggtttccgg tgtttcgtcc   2160
tttccacaag atatataaag ccaagaaatc gaaatacttt caagttacgg taagcatatg   2220
atagtccatt ttaaaacata attttaaaac tgcaaactac ccaagaaatt attactttct   2280
acgtcacgta ttttgtacta atatctttgt gtttacagtc aaattaattc taattatctc   2340
tctaacagcc ttgtatcgta tatgcaaata tgaaggaatc atgggaaata ggccctcttc   2400
ctgcccaact aggaaaaacc gcacttgtcc ggaaaccccg ggaatctaac ccggctgaac   2460
ggatttagag tccattcgat ctacatgatc aggtttccgg tgtttcgtcc tttccacaag   2520
atatataaag ccaagaaatc gaaatacttt caagttacgg taagcatatg atagtccatt   2580
ttaaaacata attttaaaac tgcaaactac ccaagaaatt attactttct acgtcacgta   2640
ttttgtacta atatctttgt gtttacagtc aaattaattc taattatctc tctaacagcc   2700
ttgtatcgta tatgcaaata tgaaggaatc atgggaaata ggccctcttc ctgcccaact   2760
```

```
agtaaggatc tgcgatcgct ccggtgcccg tcagtgggca gagcgcacat cgcccacagt    2820
ccccgagaag ttgggggag gggtcggcaa ttgaacgggt gcctagagaa ggtggcgcgg     2880
ggtaaactgg gaaagtgatg tcgtgtactg gctccgcctt tttcccgagg gtgggggaga   2940
accgtatata agtgcagtag tcgccgtgaa cgttctttt cgcaacgggt ttgccgccag    3000
aacacagctg aagcttcgag gggctcgcat ctctccttca cgcgcccgcc gccctacctg   3060
aggccgccat ccacgccggt tgagtcgcgt tctgccgcct cccgcctgtg gtgcctcctg   3120
aactgcgtcc gccgtctagg taagtttaaa gctcaggtcg agaccgggcc tttgtccggc   3180
gctcccttgg agcctaccta gactcagccg gctctccacg ctttgcctga ccctgcttgc   3240
tcaactctac gtctttgttt cgttttctgt tctgcgccgt tacagatcca agctgtgacc   3300
ggcgcctact ctagagctag cgtttaaact taagcttgcc accatggact acaaggacga   3360
cgacgacaag gacaagaagc ccctgaacac cctgatcagc gccacaggac tgtggatgtc   3420
cagaaccggc accatccaca agatcaagca ccacgaggtg tcccggtcca aaatctacat   3480
cgagatggcc tgcggcgatc acctggtcgt caacaacagc agaagcagcc ggacagccag   3540
agccctgcgg caccacaagt acagaaagac ctgcaagcgg tgcagagtgt ccgacgagga   3600
cctgaacaag ttcctgacca aggccaacga ggaccagacc agcgtgaaag tgaaggtggt   3660
gtccgccccc acccggacca agaaagccat gcccaagagc gtggcagag ccccaagcc    3720
cctggaaaac accgaagccg ctcaggccca gcccagcggc agcaagttca gccccgccat   3780
ccccgtgtct acccaggaaa gcgtcagcgt ccccgccagc gtgtccacca gcatctctag   3840
catctcaacc ggcgccacag cttctgccct ggtcaagggc aacaccaacc ccatcaccag   3900
catgtctgcc cctgtgcagg cctctgcccc agccctgacc aagtcccaga ccgaccggct   3960
ggaagtgctc ctgaacccca aggacgagat cagcctgaac agcggcaagc ccttccggga   4020
gctgaaagc gagctgctga ccggcggaa gaaggacctc cagcaaatct acgccgagga   4080
acgggagaac tacctgggca agctggaaag agagatcacc cggttcttcg tggaccgggg   4140
cttcctggaa atcaagagcc ccatcctgat cccctggag tacatcgagc ggatgggcat   4200
cgacaacgac accgagctga gcaagcagat tttccgggtg gacaagaact tctgcctgcg   4260
gcccatgctg gcccccaacc tgtacaacta cctgcggaaa ctggatcgcg ctctgcccga   4320
ccccatcaag attttcgaga tcggcccctg ctaccgaaa gagagcgacg gcaaagagca   4380
cctggaagag tttacaatgc tgaacttttg ccagatgggc agcggctgca ccagagagaa   4440
cctggaatcc atcatcaccg actttctgaa ccacctgggg atcgacttca agatcgtggg   4500
cgacagctgc atggtgtacg gcgacaccct ggacgtgatg cacggcgacc tggaactgtc   4560
tagcgccgtc gtgggaccca tccctctgga ccggagtgg ggcatcgata agccctggat   4620
cggagccggc ttcggcctgg aacggctgct gaaagtcaag cacgacttta gaacatcaa   4680
gcgggctgcc agaagcgaga gctactacaa cggcatcagc accaacctgt gatgataagg   4740
atccaaaatg tacagcggcc gcgcccctct ccctccccc ccctaacgt tactggccga    4800
agccgcttgg aataaggccg gtgtgcgttt gtctatatgt tattttccac catattgccg   4860
tcttttggca atgtgagggc ccggaaacct ggccctgtct tcttgacgag cattcctagg   4920
ggtcttttcc ctctcgccaa aggaatgcaa ggtctgttga atgtcgtgaa ggaagcagtt   4980
cctctggaag cttcttgaag acaaacaacg tctgtagcga ccctttgcag gcagcggaac   5040
cccccacctg gcgacaggtg cctctgcggc caaaagccac gtgtataaga tacacctgca   5100
```

```
aaggcggcac aaccccagtg ccacgttgtg agttggatag ttgtggaaag agtcaaatgg      5160
ctctcctcaa gcgtattcaa caaggggctg aaggatgccc agaaggtacc ccattgtatg      5220
ggatctgatc tggggcctcg gtgcacatgc tttacatgtg tttagtcgag gttaaaaaaa      5280
cgtctaggcc ccccgaacca cggggacgtg gttttccttt gaaaaacacg ataatacctc      5340
cggaatgatt gaacaagatg gattgcacgc aggttctccg gccgcttggg tggagaggct      5400
attcggctat gactgggcac aacagacaat cggctgctct gatgccgccg tgttccggct      5460
gtcagcgcag gggcgcccgg ttcttttgt caagaccgac ctgtccggtg ccctgaatga       5520
actgcaggac gaggcagcgc ggctatcgtg gctggccacg acgggcgttc cttgcgcagc      5580
tgtgctcgac gttgtcactg aagcgggaag ggactggctg ctattgggcg aagtgccggg      5640
gcaggatctc ctgtcatctc accttgctcc tgccgagaaa gtatccatca tggctgatgc      5700
aatgcggcgg ctgcatacgc ttgatccggc tacctgccca ttcgaccacc aagcgaaaca      5760
tcgcatcgag cgagcacgta ctcggatgga agccggtctt gtcgatcagg atgatctgga      5820
cgaagagcat caggggctcg cgccagccga actgttcgcc aggctcaagg cgcgcatgcc      5880
cgacggcgag gatctcgtcg tgacccatgg cgatgcctgc ttgccgaata tcatggtgga      5940
aaatggccgc ttttctggat tcatcgactg tggccggctg ggtgtggcgg accgctatca      6000
ggacatagcg ttggctaccc gtgatattgc tgaagagctt ggcggcgaat gggctgaccg      6060
cttcctcgtg ctttacggta tcgccgctcc cgattcgcag cgcatcgcct tctatcgcct      6120
tcttgacgag ttcttctgag tcgacaatca acctctggat tacaaaattt gtgaaagatt      6180
gactggtatt cttaactatg ttgctccttt tacgctatgt ggatacgctg ctttaatgcc      6240
tttgtatcat gttaacttgt ttattgcagc ttataatggt tacaaataaa gcaatagcat      6300
cacaaatttc acaaataaag catttttttc actgcattct agttgtggtt tgtccaaact      6360
catcaatgta tcttatcatg tctggaattg actcaaatga tgtcaattag tctatcagaa      6420
gctatctggt ctcccttccg ggggacaaga catccctgtt taatatttaa acagcagtgt      6480
tcccaaactg ggttcttata tcccttgctc tggtcaacca ggttgcaggg tttcctgtcc      6540
tcacaggaac gaagtcccta agaaacagt ggcagccagg tttagccccg gaattgactg       6600
gattcctttt ttagggccca ttggtatggc ttttttcccg tatccccca ggtgtctgca       6660 ggctcaaaga gcagcgagaa gcgttcagag gaaagcgatc ccgtgccacc ttccccgtgc      6720
ccgggctgtc cccgcacgct gccggctcgg ggatgcgggg ggagcgccgg accggagcgg      6780
agccccgggc ggctcgctgc tgcccccctag cggggaggg acgtaattac atccctgggg       6840
gctttggggg ggggctgtcc ctgatatcta taacaagaaa atatatat aataagttat        6900 cacgtaagta gaacatgaaa taacaatata attatcgtat gagttaaatc ttaaaagtca      6960
cgtaaaagat aatcatgcgt cattttgact cacgcggtcg ttatagttca aaatcagtga      7020
cacttaccgc attgacaagc acgcctcacg ggagctccaa gcggcgactg agatgtccta      7080
aatgcacagc gacggattcg cgctatttag aaagagagag caatatttca agaatgcatg      7140
cgtcaatttt acgcagacta tctttctagg gttaatctag ctgcatcagg atcatatcgt      7200
cgggtctttt ttccggctca gtcatcgccc aagctggcgc tatctgggca tcggggagga      7260
agaagcccgt gccttttccc gcgaggttga agcggcatgg aaagagtttg ccgaggatga      7320
ctgctgctgc attgacgttg agcgaaaacg cacgtttacc atgatgattc gggaaggtgt      7380
ggccatgcac gcctttaacg gtgaactgtt cgttcaggcc acctgggata ccagttcgtc      7440
gcggcttttc cggacacagt tccggatggt cagcccgaag cgcatcagca acccgaacaa      7500
```

```
taccggcgac agccggaact gccgtgccgg tgtgcagatt aatgacagcg gtgcggcgct    7560
gggatattac gtcagcgagg acgggtatcc tggctggatg ccgcagaaat ggacatggat    7620
accccgtgag ttaccggcg ggcgcgcttg gcgtaatcat ggtcatagct gtttcctgtg     7680
tgaaattgtt atccgctcac aattccacac aacatacgag ccggaagcat aaagtgtaaa    7740
gcctggggtg cctaatgagt gagctaactc acattaattg cgttgcgctc actgcccgct    7800
ttccagtcgg gaaacctgtc gtgccagctg cattaatgaa tcggccaacg cgcggggaga    7860
ggcggtttgc gtattgggcg ctcttccgct tcctcgctca ctgactcgct gcgctcggtc    7920
gttcggctgc ggcgagcggt atcagctcac tcaaaggcgg taatacggtt atccacagaa    7980
tcaggggata acgcaggaaa gaacatgtga gcaaaaggcc agcaaaaggc caggaaccgt    8040
aaaaaggccg cgttgctggc gttttccat aggctccgcc cccctgacga gcatcacaaa     8100
aatcgacgct caagtcagag gtggcgaaac ccgacaggac tataaagata ccaggcgttt    8160
ccccctggaa gctccctcgt gcgctctcct gttccgaccc tgccgcttac cggatacctg    8220
tccgcctttc tcccttcggg aagcgtggcg ctttctcata gctcacgctg taggtatctc    8280
agttcggtgt aggtcgttcg ctccaagctg ggctgtgtgc acgaaccccc cgttcagccc    8340
gaccgctgcg ccttatccgg taactatcgt cttgagtcca acccggtaag acacgactta    8400
tcgccactgg cagcagccac tggtaacagg attagcagag cgaggtatgt aggcggtgct    8460
acagagttct tgaagtggtg gcctaactac ggctacacta aaggacagt atttggtatc      8520
tgcgctctgc tgaagccagt taccttcgga aaaagagttg gtagctcttg atccggcaaa    8580
caaaccaccg ctggtagcgg tggttttttt gtttgcaagc agcagattac gcgcagaaaa    8640
aaaggatctc aagaagatcc tttgatcttt tctacggggt ctgacgctca gtggaacgaa    8700
aactcacgtt aagggatttt ggtcatgaga ttatcaaaaa ggatcttcac ctagatcctt    8760
ttaaattaaa aatgaagttt taaatcaatc taaagtatat atgagtaaac ttggtctgac    8820
agttaccaat gcttaatcag tgaggcacct atctcagcga tctgtctatt tcgttcatcc    8880
atagttgcct gactccccgt cgtgtagata actacgatac ggagggcttt accatctggc    8940
cccagtgctg caatgatacc gcgagaccca cgctcaccgg ctccagattt atcagcaata    9000
aaccagccag ccggaagggc cgagcgcaga agtggtcctg caactttatc cgcctccatc    9060
cagtctatta attgttgccg ggaagctaga gtaagtagtt cgccagttaa tagtttgcgc    9120
aacgttgttg ccattgctac aggcatcgtg gtgtcacgct cgtcgtttgg tatggcttca    9180
ttcagctccg gttcccaacg atcaaggcga gttacatgat cccccatgtt gtgcaaaaaa    9240
gcggttagct ccttcggtcc tccgatcgtt gtcagaagta agttggccgc agtgttatca    9300
ctcatggtta tggcagcact gcataattct cttactgtca tgccatccgt aagatgcttt    9360
tctgtgactg gtgagtactc aaccaagtca ttctgagaat agtgtatgcg gcgaccgagt    9420
tgctcttgcc cggcgtcaat acgggataat accgcgccac atagcagaac tttaaaagtg    9480
ctcatcattg gaaaacgttc ttcggggcga aaactctcaa ggatcttacc gctgttgaga    9540
tccagttcga tgtaacccac tcgtgcaccc aactgatctt cagcatcttt tactttcacc    9600
agcgtttctg ggtgagcaaa aacaggaagg caaaatgccg caaaaaaggg aataagggcg    9660
acacggaaat gttgaatact cat                                            9683

<210> SEQ ID NO 2
<211> LENGTH: 9400
<212> TYPE: DNA
```

<213> ORGANISM: Artificial Sequence
<220> FEATURE:
<223> OTHER INFORMATION: nucleic acid expression construct

<400> SEQUENCE: 2

```
actcttcctt tttcaatatt attgaagcat ttatcagggt tattgtctca tgagcggata      60
catatttgaa tgtatttaga aaataaaca aatagggtt ccgcgcacat ttccccgaaa       120
agtgccacct aaattgtaag cgttaatatt ttgttaaaat tcgcgttaaa ttttttgttaa    180
atcagctcat ttttaacca ataggccgaa atcggcaaaa tcccttataa atcaaaagaa     240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt ttggggtcg aggtgccgta aagcactaaa tcggaaccct     420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgc gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaaa caaaaactca   1080
aaatttcttc tataaagtaa caaaacttttt atgagggaca gccccccccc aaagccccca   1140
gggatgtaat tacgtccctc ccccgctagg gggcagcagc gagccgcccg gggctccgct   1200
ccggtccggc gctcccccg catccccgag ccggcagcgt gcgggacag cccgggcacg    1260
gggaaggtgg cacgggatcg ctttcctctg aacgcttctc gctgctcttt gagcctgcag   1320
acacctgggg ggatacgggg aaaaggcctc caaggccact aggaaaaacc gcacttgtcc   1380
ggaaacccg ggaatctaac ccggctgaac ggatttagag tccattcgat ctacatgatc   1440
aggtttccgg tgtttcgtcc tttccacaag atatataaag ccaagaaatc gaaatacttt   1500
caagttacgg taagcatatg atagtccatt ttaaaacata attttaaaac tgcaaactac   1560
ccaagaaatt attactttct acgtcacgta ttttgtacta atatctttgt gtttacagtc   1620
aaattaattc taattatctc tctaacagcc ttgtatcgta tatgcaaata tgaaggaatc   1680
atgggaaata ggccctcttc ctgcccaact aggaaaaacc gcacttgtcc ggaaacccg    1740
ggaatctaac ccggctgaac ggatttagag tccattcgat ctacatgatc aggtttccgg   1800
tgtttcgtcc tttccacaag atatataaag ccaagaaatc gaaatacttt caagttacgg   1860
taagcatatg atagtccatt ttaaaacata attttaaaac tgcaaactac ccaagaaatt   1920
attactttct acgtcacgta ttttgtacta atatctttgt gtttacagtc aaattaattc   1980
taattatctc tctaacagcc ttgtatcgta tatgcaaata tgaaggaatc atgggaaata   2040
ggccctcttc ctgcccaact aggaaaaacc gcacttgtcc ggaaacccgg ggaatctaac   2100
ccggctgaac ggatttagag tccattcgat ctacatgatc aggtttccgg tgtttcgtcc   2160
tttccacaag atatataaag ccaagaaatc gaaatacttt caagttacgg taagcatatg   2220
```

```
atagtccatt ttaaaacata attttaaaac tgcaaactac ccaagaaatt attactttct    2280
acgtcacgta ttttgtacta atatctttgt gtttacagtc aaattaattc taattatctc    2340
tctaacagcc ttgtatcgta tatgcaaata tgaaggaatc atgggaaata ggccctcttc    2400
ctgcccaact aggaaaaacc gcacttgtcc ggaaaccccg gaatctaac ccggctgaac     2460 ggatttagag tccattcgat ctacatgatc aggtttccgg tgtttcgtcc tttccacaag    2520
atatataaag ccaagaaatc gaaatacttt caagttacgg taagcatatg atagtccatt    2580
ttaaaacata attttaaaac tgcaaactac ccaagaaatt attactttct acgtcacgta    2640
ttttgtacta atatctttgt gtttacagtc aaattaattc taattatctc tctaacagcc    2700
ttgtatcgta tatgcaaata tgaaggaatc atgggaaata ggccctcttc ctgcccaact    2760
aggaaaaacc gcacttgtcc ggaaaccccg gaatctaac ccggctgaac ggatttagag     2820
tccattcgat ctacatgatc aggtttccgg tgtttcgtcc tttccacaag atatataaag    2880
ccaagaaatc gaaatacttt caagttacgg taagcatatg atagtccatt ttaaaacata    2940
attttaaaac tgcaaactac ccaagaaatt attactttct acgtcacgta ttttgtacta    3000
atatctttgt gtttacagtc aaattaattc taattatctc tctaacagcc ttgtatcgta    3060
tatgcaaata tgaaggaatc atgggaaata ggccctcttc ctgcccaact agtaaggatc    3120
tgcgatcgct ccggtgcccg tcagtgggca gagcgcacat cgcccacagt ccccgagaag    3180 ttgggggggag gggtcggcaa ttgaacgggt gcctagagaa ggtggcgcgg ggtaaactgg    3240
gaaagtgatg tcgtgtactg gctccgcctt ttcccgagg gtgggggaga accgtatata      3300
agtgcagtag tcgccgtgaa cgttcttttt cgcaacgggt ttgccgccag aacacagctg    3360
aagcttcgag gggctcgcat ctctccttca cgcgcccgcc gccctacctg aggccgccat    3420
ccacgccggt tgagtcgcgt tctgccgcct cccgcctgtg gtgcctcctg aactgcgtcc    3480
gccgtctagg taagtttaaa gctcaggtcg agaccgggcc tttgtccggc gctcccttgg    3540
agcctaccta gactcagccg gctctccacg ctttgcctga ccctgcttgc tcaactctac    3600
gtctttgttt cgttttctgt tctgcgccgt tacagatcca agctgtgacc ggcgcctact    3660
ctagagctag cgaattcgaa tttaaatcgg atcaccacca tggtgtccaa gggcgaggaa    3720
ctgttcaccg gcgtggtgcc catcctggtg gaactggatg gcgacgtgaa cggccacaag    3780
ttctctgtgc ggggagaggg cgaaggcgac gccacaaatg gcaagctgac cctgaagttc    3840
atctgcacca ccggcaagct gcccgtgcct tggcctaccc tcgtgaccac actgacctac    3900
ggcgtgcagt gcttcagcag ataccccgac catatgaagc ggcacgactt cttcaagagc    3960
gccatgcccg agggctacgt gcaggaacgg accatcagct tcaaggacga cggcacctac    4020
aagaccagag ccgaagtgaa gttcgagggc gacaccctcg tgaaccggat cgagctgaag    4080
ggcattgatt tcaaagagga cggcaacatc ctgggccaca gctggagta caacttcaac     4140 agccactagg tgtacatcac cgccgacaag cagaagaacg gcatcaaggc caacttcaag    4200
atccggcaca acgtggaaga tggcagcgtg cagctggccg accactacca gcagaacacc    4260
cccatcggag atggccccgt gctgctgccc gacaaccact acctgagcac ccagagcgtg    4320
ctgagcaagg accccaacga gaagcgggac cacatggtgc tgctggaatt cgtgaccgcc    4380
gctggcatca cccacggcat ggacgagctg tacaagggca gccaccatca ccatcaccat    4440
tgataaggat cccagttacc atcgatgatc cgcggccgcg ccctctccc tccccccccc     4500 ctaacgttac tggccgaagc cgcttggaat aaggccggtg tgcgtttgtc tatatgttat    4560
```

```
tttccaccat attgccgtct tttggcaatg tgagggcccg gaaacctggc cctgtcttct    4620
tgacgagcat tcctaggggt cttcccctc tcgccaaagg aatgcaaggt ctgttgaatg    4680
tcgtgaagga agcagttcct ctggaagctt cttgaagaca acaacgtct gtagcgaccc    4740
tttgcaggca gcggaacccc ccacctggcg acaggtgcct ctgcggccaa agccacgtg    4800
tataagatac acctgcaaag gcggcacaac cccagtgcca cgttgtgagt tggatagttg    4860
tggaaagagt caaatggctc tcctcaagcg tattcaacaa ggggctgaag gatgcccaga    4920
aggtaccccca ttgtatggga tctgatctgg ggcctcggtg cacatgcttt acatgtgttt    4980
agtcgaggtt aaaaaaacgt ctaggccccc cgaaccacgg gacgtggtt ttcctttgaa    5040
aaacacgata atacctccgg aatgattgaa caagatggat tgcacgcagg ttctccggcc    5100
gcttgggtgg agaggctatt cggctatgac tgggcacaac agacaatcgg ctgtctgat    5160
gccgccgtgt tccggctgtc agcgcagggg cgcccggttc tttttgtcaa gaccgacctg    5220
tccggtgccc tgaatgaact gcaggacgag gcagcgcggc tatcgtggct ggccacgacg    5280
ggcgttcctt gcgcagctgt gctcgacgtt gtcactgaag cgggaaggga ctggctgcta    5340
ttgggcgaag tgccggggca ggatctcctg tcatctcacc ttgctcctgc cgagaaagta    5400
tccatcatgg ctgatgcaat gcggcggctg catacgcttg atccggctac ctgcccattc    5460
gaccaccaag cgaaacatcg catcgagcga gcacgtactc ggatggaagc cggtcttgtc    5520
gatcaggatg atctggacga agagcatcag gggctcgcgc cagccgaact gttcgccagg    5580
ctcaaggcgc gcatgcccga cggcgaggat ctcgtcgtga cccatggcga tgcctgcttg    5640
ccgaatatca tggtggaaaa tggccgcttt tctggattca tcgactgtgg ccggctgggt    5700
gtggcggacc gctatcagga catagcgttg gctacccgtg atattgctga agagcttggc    5760
ggcgaatggg ctgaccgctt cctcgtgctt tacggtatcg ccgctcccga ttcgcagcgc    5820
atcgccttct atcgccttct tgacgagttc ttctgagtcg acaatcaacc tctggattac    5880
aaaatttgtg aaagattgac tggtattctt aactatgttg ctcctttac gctatgtgga    5940
tacgctgctt taatgccttt gtatcatgtt aacttgttta ttgcagctta taatggttac    6000
aaataaagca atagcatcac aaatttcaca aataaagcat ttttttcact gcattctagt    6060
tgtggtttgt ccaaactcat caatgtatct tatcatgtct ggaattgact caaatgatgt    6120
caattagtct atcagaagct atctggtctc ccttccgggg acaagacat ccctgtttaa    6180
tatttaaaca gcagtgttcc caaactgggt tcttatatcc cttgctctgg tcaaccaggt    6240
tgcagggttt cctgtcctca caggaacgaa gtccctaaag aaacagtggc agccaggttt    6300
agccccggaa ttgactggat tcctttttta gggcccattg gtatggcttt ttccccgtat    6360
ccccccaggt gtctgcaggc tcaaagagca gcgagaagcg ttcagaggaa agcgatcccg    6420
tgccaccttc cccgtgcccg gctgtcccc gcacgctgcc ggctcgggga tgcggggga    6480
gcgccggacc ggagcggagc cccgggcggc tcgctgctgc cccctagcgg gggagggacg    6540
taattacatc cctgggggct ttgggggggg gctgtccctg atatctataa caagaaaata    6600
tatatataat aagttatcac gtaagtagaa catgaaataa caatataatt atcgtatgag    6660
ttaaatctta aaagtcacgt aaaagataat catgcgtcat tttgactcac gcggtcgtta    6720
tagttcaaaa tcagtgacac ttaccgcatt gacaagcacg cctcacggga gctccaagcg    6780
gcgactgaga tgtcctaaat gcacagcgac ggattcgcgc tatttagaaa gagagagcaa    6840
tatttcaaga atgcatgcgt caattttacg cagactatct ttctagggtt aatctagctg    6900
catcaggatc atatcgtcgg gtcttttttc cggctcagtc atcgcccaag ctggcgctat    6960
```

```
ctgggcatcg gggaggaaga agcccgtgcc ttttcccgcg aggttgaagc ggcatggaaa    7020
gagtttgccg aggatgactg ctgctgcatt gacgttgagc gaaaacgcac gtttaccatg    7080
atgattcggg aaggtgtggc catgcacgcc tttaacggtg aactgttcgt tcaggccacc    7140
tgggatacca gttcgtcgcg gcttttccgg acacagttcc ggatggtcag cccgaagcgc    7200
atcagcaacc cgaacaatac cggcgacagc cggaactgcc gtgccggtgt gcagattaat    7260
gacagcggtg cggcgctggg atattacgtc agcgaggacg ggtatcctgg ctggatgccg    7320
cagaaatgga catggatacc ccgtgagtta cccggcgggc gcgcttggcg taatcatggt    7380
catagctgtt tcctgtgtga aattgttatc cgctcacaat tccacacaac atacgagccg    7440
gaagcataaa gtgtaaagcc tggggtgcct aatgagtgag ctaactcaca ttaattgcgt    7500
tgcgctcact gcccgctttc cagtcgggaa acctgtcgtg ccagctgcat taatgaatcg    7560
gccaacgcgc ggggagaggc ggtttgcgta ttgggcgctc ttccgcttcc tcgctcactg    7620
actcgctgcg ctcggtcgtt cggctgcggc gagcggtatc agctcactca aaggcggtaa    7680
tacggttatc cacagaatca ggggataacg caggaaagaa catgtgagca aaaggccagc    7740
aaaaggccag gaaccgtaaa aaggccgcgt tgctggcgtt tttccatagg ctccgccccc    7800
ctgacgagca tcacaaaaat cgacgctcaa gtcagaggtg gcgaaacccg acaggactat    7860
aaagatacca ggcgtttccc cctggaagct ccctcgtgcg ctctcctgtt ccgaccctgc    7920
cgcttaccgg atacctgtcc gcctttctcc cttcgggaag cgtggcgctt tctcatagct    7980
cacgctgtag gtatctcagt tcggtgtagg tcgttcgctc caagctgggc tgtgtgcacg    8040
aaccccccgt tcagcccgac cgctgcgcct tatccggtaa ctatcgtctt gagtccaacc    8100
cggtaagaca cgacttatcg ccactggcag cagccactgg taacaggatt agcagagcga    8160
ggtatgtagg cggtgctaca gagttcttga agtggtggcc taactacggc tacactagaa    8220
ggacagtatt tggtatctgc gctctgctga agccagttac cttcggaaaa agagttggta    8280
gctcttgatc cggcaaacaa accaccgctg gtagcggtgg tttttttgtt tgcaagcagc    8340
agattacgcg cagaaaaaaa ggatctcaag aagatccttt gatcttttct acggggtctg    8400
acgctcagtg gaacgaaaac tcacgttaag ggattttggt catgagatta tcaaaaagga    8460
tcttcaccta gatcctttta aattaaaaat gaagttttaa atcaatctaa agtatatatg    8520
agtaaacttg gtctgacagt taccaatgct taatcagtga ggcacctatc tcagcgatct    8580
gtctatttcg ttcatccata gttgcctgac tccccgtcgt gtagataact acgatacggg    8640
agggcttacc atctggcccc agtgctgcaa tgataccgcg agacccacgc tcaccggctc    8700
cagatttatc agcaataaac cagccagccg gaagggccga gcgcagaagt ggtcctgcaa    8760
ctttatccgc ctccatccag tctattaatt gttgccggga agctagagta agtagttcgc    8820
cagttaatag tttgcgcaac gttgttgcca ttgctacagg catcgtggtg tcacgctcgt    8880
cgtttggtat ggcttcattc agctccggtt cccaacgatc aaggcgagtt acatgatccc    8940
ccatgttgtg caaaaaagcg gttagctcct tcggtcctcc gatcgttgtc agaagtaagt    9000
tggccgcagt gttatcactc atggttatgg cagcactgca taattctctt actgtcatgc    9060
catccgtaag atgcttttct gtgactggtg agtactcaac caagtcattc tgagaatagt    9120
gtatgcggcg accgagttgc tcttgcccgg cgtcaatacg ggataatacc gcgccacata    9180
gcagaacttt aaaagtgctc atcattggaa aacgttcttc ggggcgaaaa ctctcaagga    9240
tcttaccgct gttgagatcc agttcgatgt aacccactcg tgcacccaac tgatcttcag    9300
```

| catcttttac tttcaccagc gtttctgggt gagcaaaaac aggaaggcaa aatgccgcaa | 9360 |
| aaaagggaat aagggcgaca cggaaatgtt gaatactcat | 9400 |

<210> SEQ ID NO 3
<211> LENGTH: 1320
<212> TYPE: DNA
<213> ORGANISM: Artificial Sequence
<220> FEATURE:
<223> OTHER INFORMATION: codon optimised human eRF1

<400> SEQUENCE: 3

| atggccgatg atccaagcgc cgcagaccgc aatgttgaga tctggaagat aaaaaagctg | 60 |
| ataaagagct tggaggccgc acgggcaacg gcacgtcca tgatatccct cattatccca | 120 |
| ccaaggatc agatcagccg tgtggcgaag atgttggcgg atgagttcgg aacggccagt | 180 |
| aacattaaaa gtcgcgtgaa ccggctgtcg gtcttgggcg ccatcacttc cgtgcagcaa | 240 |
| cgtctgaaac tgtacaacaa gtcccaccc aacggtttgg tcgtcactg cggtacgata | 300 |
| gttaccgagg aaggaaagga aagaaagtg aatattgatt cgaaccatt taaaccgata | 360 |
| aacactagct tgtacttgtg cgacaataag tttcatacag aggcactcac ggccctgctg | 420 |
| agcgacgact cgaaattcgg attcattgtc attgatggaa gtggagcgct gttcggcacg | 480 |
| ctgcaggta cacgcgcga ggtcttgcac aaattcaccg tggacttgcc caaaaagcat | 540 |
| ggccgtggtg gccagagcgc cctcaggttt gcgcggctgc gcatggagaa gcgccataac | 600 |
| tacgtgcgca aggtcgcaga acggctgtg cagctgttca tctcgggtga aggtaaat | 660 |
| gtcgcgggac tggtgctcgc cggcagcgcg gacttcaaaa ccgagctgag tcagtccgac | 720 |
| atgttcgatc agcgtctgca gtcgaaggta ctgaagctcg tcgacattag ctacggcggc | 780 |
| gagaacggct tcaatcaggc catcgaactg agtaccgaag tcctcagtaa cgtaaagttt | 840 |
| attcaggaaa aaagttgat tggacgctac tttgatgaaa taagccaaga tacgggcaaa | 900 |
| tactgttttg cgtcgagga tactctgaaa gcgctcgaga tgggagcagt ggaaatactc | 960 |
| atcgtatatg aaaatctcga tataatgcgc tatgtactgc attgccaagg aacagaagag | 1020 |
| gagaaaattc tctacctcac cccggagcaa gagaaggaca agagccattt tacagacaag | 1080 |
| gagacgggcc aagagcacga gctcattgag tcgatgccct gctcgaatg gtttgccaac | 1140 |
| aactacaaga gttcggcgc gaccctggaa attgtcacgg ataatcgca ggagggcagc | 1200 |
| cagtttgtga agggcttcgg tggcatcggc ggcatcctcc gctaccgggt ggatttccaa | 1260 |
| ggcatggaat atcaaggtgg agatgatgaa ttcttcgatt tggatgatta ctaatgatag | 1320 |

<210> SEQ ID NO 4
<211> LENGTH: 437
<212> TYPE: PRT
<213> ORGANISM: Homo sapiens

<400> SEQUENCE: 4

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30

Ser Met Ile Ser Leu Ile Ile Pro Pro Lys Asp Gln Ile Ser Arg Val
        35                  40                  45

Ala Lys Met Leu Ala Asp Glu Phe Gly Thr Ala Ser Asn Ile Lys Ser
    50                  55                  60

Arg Val Asn Arg Leu Ser Val Leu Gly Ala Ile Thr Ser Val Gln Gln

```
            65                  70                  75                  80
        Arg Leu Lys Leu Tyr Asn Lys Val Pro Pro Asn Gly Leu Val Val Tyr
                        85                  90                  95

Cys Gly Thr Ile Val Thr Glu Glu Gly Lys Glu Lys Lys Val Asn Ile
                        100                 105                 110

Asp Phe Glu Pro Phe Lys Pro Ile Asn Thr Ser Leu Tyr Leu Cys Asp
                        115                 120                 125

Asn Lys Phe His Thr Glu Ala Leu Thr Ala Leu Leu Ser Asp Asp Ser
                    130                 135                 140

Lys Phe Gly Phe Ile Val Ile Asp Gly Ser Gly Ala Leu Phe Gly Thr
        145                 150                 155                 160

Leu Gln Gly Asn Thr Arg Glu Val Leu His Lys Phe Thr Val Asp Leu
                        165                 170                 175

Pro Lys Lys His Gly Arg Gly Gln Ser Ala Leu Arg Phe Ala Arg
                        180                 185                 190

Leu Arg Met Glu Lys Arg His Asn Tyr Val Arg Lys Val Ala Glu Thr
                    195                 200                 205

Ala Val Gln Leu Phe Ile Ser Gly Asp Lys Val Asn Val Ala Gly Leu
                    210                 215                 220

Val Leu Ala Gly Ser Ala Asp Phe Lys Thr Glu Leu Ser Gln Ser Asp
        225                 230                 235                 240

Met Phe Asp Gln Arg Leu Gln Ser Lys Val Leu Lys Leu Val Asp Ile
                        245                 250                 255

Ser Tyr Gly Gly Glu Asn Gly Phe Asn Gln Ala Ile Glu Leu Ser Thr
                        260                 265                 270

Glu Val Leu Ser Asn Val Lys Phe Ile Gln Glu Lys Lys Leu Ile Gly
                    275                 280                 285

Arg Tyr Phe Asp Glu Ile Ser Gln Asp Thr Gly Lys Tyr Cys Phe Gly
                    290                 295                 300

Val Glu Asp Thr Leu Lys Ala Leu Glu Met Gly Ala Val Glu Ile Leu
        305                 310                 315                 320

Ile Val Tyr Glu Asn Leu Asp Ile Met Arg Tyr Val Leu His Cys Gln
                        325                 330                 335

Gly Thr Glu Glu Glu Lys Ile Leu Tyr Leu Thr Pro Glu Gln Glu Lys
                        340                 345                 350

Asp Lys Ser His Phe Thr Asp Lys Glu Thr Gly Gln Glu His Glu Leu
                    355                 360                 365

Ile Glu Ser Met Pro Leu Leu Glu Trp Phe Ala Asn Asn Tyr Lys Lys
                370                 375                 380

Phe Gly Ala Thr Leu Glu Ile Val Thr Asp Lys Ser Gln Glu Gly Ser
        385                 390                 395                 400

Gln Phe Val Lys Gly Phe Gly Ile Gly Ile Leu Arg Tyr Arg
                        405                 410                 415

Val Asp Phe Gln Gly Met Glu Tyr Gln Gly Gly Asp Asp Glu Phe Phe
                        420                 425                 430

Asp Leu Asp Asp Tyr
                    435

<210> SEQ ID NO 5
<211> LENGTH: 437
<212> TYPE: PRT
<213> ORGANISM: Artificial Sequence
<220> FEATURE:
<223> OTHER INFORMATION: mutant eRF1 E55D
```

<400> SEQUENCE: 5

```
Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30

Ser Met Ile Ser Leu Ile Ile Pro Pro Lys Asp Gln Ile Ser Arg Val
        35                  40                  45

Ala Lys Met Leu Ala Asp Asp Phe Gly Thr Ala Ser Asn Ile Lys Ser
50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Lys Val Asn Ile
            100                 105                 110

Asp Phe Glu Pro Phe Lys Pro Ile Asn Thr Ser Leu Tyr Leu Cys Asp
        115                 120                 125

Asn Lys Phe His Thr Glu Ala Leu Thr Ala Leu Leu Ser Asp Asp Ser
130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175

Pro Lys Lys His Gly Arg Gly Gly Gln Ser Ala Leu Arg Phe Ala Arg
            180                 185                 190

Leu Arg Met Glu Lys Arg His Asn Tyr Val Arg Lys Val Ala Glu Thr
        195                 200                 205

Ala Val Gln Leu Phe Ile Ser Gly Asp Lys Val Asn Val Ala Gly Leu
210                 215                 220

Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255

Ser Tyr Gly Gly Glu Asn Gly Phe Asn Gln Ala Ile Glu Leu Ser Thr
            260                 265                 270

Glu Val Leu Ser Asn Val Lys Phe Ile Gln Glu Lys Leu Ile Gly
        275                 280                 285

Arg Tyr Phe Asp Glu Ile Ser Gln Asp Thr Gly Lys Tyr Cys Phe Gly
290                 295                 300

Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

Gly Thr Glu Glu Lys Ile Leu Tyr Leu Thr Pro Glu Gln Glu Lys
            340                 345                 350

Asp Lys Ser His Phe Thr Asp Lys Glu Thr Gly Gln Glu His Glu Leu
        355                 360                 365

Ile Glu Ser Met Pro Leu Leu Glu Trp Phe Ala Asn Asn Tyr Lys Lys
370                 375                 380

Phe Gly Ala Thr Leu Glu Ile Val Thr Asp Lys Ser Gln Glu Gly Ser
385                 390                 395                 400

Gln Phe Val Lys Gly Phe Gly Gly Ile Gly Gly Ile Leu Arg Tyr Arg
                405                 410                 415
```

Val Asp Phe Gln Gly Met Glu Tyr Gln Gly Gly Asp Asp Glu Phe Phe
            420                 425                 430

Asp Leu Asp Asp Tyr
            435

<210> SEQ ID NO 6
<211> LENGTH: 437
<212> TYPE: PRT
<213> ORGANISM: Artificial Sequence
<220> FEATURE:
<223> OTHER INFORMATION: mutant eRF1 N129P K130Q

<400> SEQUENCE: 6

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30

Ser Met Ile Ser Leu Ile Ile Pro Pro Lys Asp Gln Ile Ser Arg Val
        35                  40                  45

Ala Lys Met Leu Ala Asp Glu Phe Gly Thr Ala Ser Asn Ile Lys Ser
    50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Lys Val Asn Ile
            100                 105                 110

Asp Phe Glu Pro Phe Lys Pro Ile Asn Thr Ser Leu Tyr Leu Cys Asp
        115                 120                 125

Pro Gln Phe His Thr Glu Ala Leu Thr Ala Leu Leu Ser Asp Asp Ser
    130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175

Pro Lys Lys His Gly Arg Gly Gly Gln Ser Ala Leu Arg Phe Ala Arg
            180                 185                 190

Leu Arg Met Glu Lys Arg His Asn Tyr Val Arg Lys Val Ala Glu Thr
        195                 200                 205

Ala Val Gln Leu Phe Ile Ser Gly Asp Lys Val Asn Val Ala Gly Leu
    210                 215                 220

Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255

Ser Tyr Gly Gly Glu Asn Gly Phe Asn Gln Ala Ile Glu Leu Ser Thr
            260                 265                 270

Glu Val Leu Ser Asn Val Lys Phe Ile Gln Glu Lys Lys Leu Ile Gly
        275                 280                 285

Arg Tyr Phe Asp Glu Ile Ser Gln Asp Thr Gly Lys Tyr Cys Phe Gly
    290                 295                 300

Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

```
Gly Thr Glu Glu Lys Ile Leu Tyr Leu Thr Pro Glu Gln Glu Lys
            340                 345                 350

Asp Lys Ser His Phe Thr Asp Lys Glu Thr Gly Gln Glu His Glu Leu
            355                 360                 365

Ile Glu Ser Met Pro Leu Leu Glu Trp Phe Ala Asn Asn Tyr Lys Lys
370                 375                 380

Phe Gly Ala Thr Leu Glu Ile Val Thr Asp Lys Ser Gln Glu Gly Ser
385                 390                 395                 400

Gln Phe Val Lys Gly Phe Gly Ile Gly Ile Leu Arg Tyr Arg
                405                 410                 415

Val Asp Phe Gln Gly Met Glu Tyr Gln Gly Gly Asp Glu Phe Phe
                420                 425                 430

Asp Leu Asp Asp Tyr
            435

<210> SEQ ID NO 7
<211> LENGTH: 437
<212> TYPE: PRT
<213> ORGANISM: Artificial Sequence
<220> FEATURE:
<223> OTHER INFORMATION: mutant eFR1 T122Q S123F

<400> SEQUENCE: 7

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30

Ser Met Ile Ser Leu Ile Ile Pro Pro Lys Asp Gln Ile Ser Arg Val
        35                  40                  45

Ala Lys Met Leu Ala Asp Glu Phe Gly Thr Ala Ser Asn Ile Lys Ser
    50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Lys Val Asn Ile
            100                 105                 110

Asp Phe Glu Pro Phe Lys Pro Ile Asn Gln Phe Leu Tyr Leu Cys Asp
        115                 120                 125

Asn Lys Phe His Thr Glu Ala Leu Thr Ala Leu Leu Ser Asp Asp Ser
    130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175

Pro Lys Lys His Gly Arg Gly Gly Gln Ser Ala Leu Arg Phe Ala Arg
            180                 185                 190

Leu Arg Met Glu Lys Arg His Asn Tyr Val Arg Lys Val Ala Glu Thr
        195                 200                 205

Ala Val Gln Leu Phe Ile Ser Gly Asp Lys Val Asn Val Ala Gly Leu
    210                 215                 220

Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255
```

```
Ser Tyr Gly Gly Glu Asn Gly Phe Asn Gln Ala Ile Glu Leu Ser Thr
            260                 265                 270

Glu Val Leu Ser Asn Val Lys Phe Ile Gln Glu Lys Lys Leu Ile Gly
        275                 280                 285

Arg Tyr Phe Asp Glu Ile Ser Gln Asp Thr Gly Lys Tyr Cys Phe Gly
    290                 295                 300

Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

Gly Thr Glu Glu Lys Ile Leu Tyr Leu Thr Pro Glu Gln Glu Lys
            340                 345                 350

Asp Lys Ser His Phe Thr Asp Lys Glu Thr Gly Gln Glu His Glu Leu
        355                 360                 365

Ile Glu Ser Met Pro Leu Leu Glu Trp Phe Ala Asn Asn Tyr Lys Lys
    370                 375                 380

Phe Gly Ala Thr Leu Glu Ile Val Thr Asp Lys Ser Gln Glu Gly Ser
385                 390                 395                 400

Gln Phe Val Lys Gly Phe Gly Gly Ile Gly Gly Ile Leu Arg Tyr Arg
                405                 410                 415

Val Asp Phe Gln Gly Met Glu Tyr Gln Gly Gly Asp Asp Glu Phe Phe
            420                 425                 430

Asp Leu Asp Asp Tyr
            435

<210> SEQ ID NO 8
<211> LENGTH: 437
<212> TYPE: PRT
<213> ORGANISM: Artificial Sequence
<220> FEATURE:
<223> OTHER INFORMATION: mutant eRF1 E55A

<400> SEQUENCE: 8

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30

Ser Met Ile Ser Leu Ile Ile Pro Pro Lys Asp Gln Ile Ser Arg Val
        35                  40                  45

Ala Lys Met Leu Ala Asp Ala Phe Gly Thr Ala Ser Asn Ile Lys Ser
    50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Lys Val Asn Ile
            100                 105                 110

Asp Phe Glu Pro Phe Lys Pro Ile Asn Thr Ser Leu Tyr Leu Cys Asp
        115                 120                 125

Asn Lys Phe His Thr Glu Ala Leu Thr Ala Leu Leu Ser Asp Asp Ser
    130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175
```

```
Pro Lys Lys His Gly Arg Gly Gly Gln Ser Ala Leu Arg Phe Ala Arg
            180                 185                 190

Leu Arg Met Glu Lys Arg His Asn Tyr Val Arg Lys Val Ala Glu Thr
        195                 200                 205

Ala Val Gln Leu Phe Ile Ser Gly Asp Lys Val Asn Val Ala Gly Leu
    210                 215                 220

Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255

Ser Tyr Gly Gly Glu Asn Gly Phe Asn Gln Ala Ile Glu Leu Ser Thr
            260                 265                 270

Glu Val Leu Ser Asn Val Lys Phe Ile Gln Glu Lys Lys Leu Ile Gly
        275                 280                 285

Arg Tyr Phe Asp Glu Ile Ser Gln Asp Thr Gly Lys Tyr Cys Phe Gly
    290                 295                 300

Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

Gly Thr Glu Glu Lys Ile Leu Tyr Leu Thr Pro Glu Gln Glu Lys
            340                 345                 350

Asp Lys Ser His Phe Thr Asp Lys Glu Thr Gly Gln Glu His Glu Leu
        355                 360                 365

Ile Glu Ser Met Pro Leu Leu Glu Trp Phe Ala Asn Asn Tyr Lys Lys
    370                 375                 380

Phe Gly Ala Thr Leu Glu Ile Val Thr Asp Lys Ser Gln Glu Gly Ser
385                 390                 395                 400

Gln Phe Val Lys Gly Phe Gly Gly Ile Gly Gly Ile Leu Arg Tyr Arg
                405                 410                 415

Val Asp Phe Gln Gly Met Glu Tyr Gln Gly Gly Asp Asp Glu Phe Phe
            420                 425                 430

Asp Leu Asp Asp Tyr
        435

<210> SEQ ID NO 9
<211> LENGTH: 437
<212> TYPE: PRT
<213> ORGANISM: Artificial Sequence
<220> FEATURE:
<223> OTHER INFORMATION: mutant eRF1 Y125F

<400> SEQUENCE: 9

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30

Ser Met Ile Ser Leu Ile Ile Pro Pro Lys Asp Gln Ile Ser Arg Val
        35                  40                  45

Ala Lys Met Leu Ala Asp Glu Phe Gly Thr Ala Ser Asn Ile Lys Ser
    50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95
```

```
Cys Gly Thr Ile Val Thr Glu Glu Gly Lys Glu Lys Val Asn Ile
            100                 105                 110
Asp Phe Glu Pro Phe Lys Pro Ile Asn Thr Ser Leu Phe Leu Cys Asp
        115                 120                 125
Asn Lys Phe His Thr Glu Ala Leu Thr Ala Leu Leu Ser Asp Asp Ser
    130                 135                 140
Lys Phe Gly Phe Ile Val Ile Asp Gly Ser Gly Ala Leu Phe Gly Thr
145                 150                 155                 160
Leu Gln Gly Asn Thr Arg Glu Val Leu His Lys Phe Thr Val Asp Leu
                165                 170                 175
Pro Lys Lys His Gly Arg Gly Gln Ser Ala Leu Arg Phe Ala Arg
            180                 185                 190
Leu Arg Met Glu Lys Arg His Asn Tyr Val Arg Lys Val Ala Glu Thr
        195                 200                 205
Ala Val Gln Leu Phe Ile Ser Gly Asp Lys Val Asn Val Ala Gly Leu
    210                 215                 220
Val Leu Ala Gly Ser Ala Asp Phe Lys Thr Glu Leu Ser Gln Ser Asp
225                 230                 235                 240
Met Phe Asp Gln Arg Leu Gln Ser Lys Val Leu Lys Leu Val Asp Ile
                245                 250                 255
Ser Tyr Gly Gly Glu Asn Gly Phe Asn Gln Ala Ile Glu Leu Ser Thr
            260                 265                 270
Glu Val Leu Ser Asn Val Lys Phe Ile Gln Glu Lys Lys Leu Ile Gly
        275                 280                 285
Arg Tyr Phe Asp Glu Ile Ser Gln Asp Thr Gly Lys Tyr Cys Phe Gly
    290                 295                 300
Val Glu Asp Thr Leu Lys Ala Leu Glu Met Gly Ala Val Glu Ile Leu
305                 310                 315                 320
Ile Val Tyr Glu Asn Leu Asp Ile Met Arg Tyr Val Leu His Cys Gln
                325                 330                 335
Gly Thr Glu Glu Glu Lys Ile Leu Tyr Leu Thr Pro Glu Gln Glu Lys
            340                 345                 350
Asp Lys Ser His Phe Thr Asp Lys Glu Thr Gly Gln Glu His Glu Leu
        355                 360                 365
Ile Glu Ser Met Pro Leu Leu Glu Trp Phe Ala Asn Asn Tyr Lys Lys
    370                 375                 380
Phe Gly Ala Thr Leu Glu Ile Val Thr Asp Lys Ser Gln Glu Gly Ser
385                 390                 395                 400
Gln Phe Val Lys Gly Phe Gly Ile Gly Gly Ile Leu Arg Tyr Arg
                405                 410                 415
Val Asp Phe Gln Gly Met Glu Tyr Gln Gly Gly Asp Asp Glu Phe Phe
            420                 425                 430
Asp Leu Asp Asp Tyr
        435

<210> SEQ ID NO 10
<211> LENGTH: 437
<212> TYPE: PRT
<213> ORGANISM: Artificial Sequence
<220> FEATURE:
<223> OTHER INFORMATION: mutant eRF1 T58K S60T S64D Y125F N129S

<400> SEQUENCE: 10

Met Ala Asp Asp Pro Ser Ala Ala Asp Arg Asn Val Glu Ile Trp Lys
1               5                   10                  15
```

```
Ile Lys Lys Leu Ile Lys Ser Leu Glu Ala Ala Arg Gly Asn Gly Thr
            20                  25                  30

Ser Met Ile Ser Leu Ile Ile Pro Lys Asp Gln Ile Ser Arg Val
        35                  40                  45

Ala Lys Met Leu Ala Asp Glu Phe Gly Lys Ala Thr Asn Ile Lys Asp
50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Val Asn Ile
            100                 105                 110

Asp Phe Glu Pro Phe Lys Pro Ile Asn Thr Ser Leu Phe Leu Cys Asp
        115                 120                 125

Ser Lys Phe His Thr Glu Ala Leu Thr Ala Leu Leu Ser Asp Asp Ser
    130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175

Pro Lys Lys His Gly Arg Gly Gly Gln Ser Ala Leu Arg Phe Ala Arg
            180                 185                 190

Leu Arg Met Glu Lys Arg His Asn Tyr Val Arg Lys Val Ala Glu Thr
        195                 200                 205

Ala Val Gln Leu Phe Ile Ser Gly Asp Lys Val Asn Val Ala Gly Leu
    210                 215                 220

Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255

Ser Tyr Gly Gly Glu Asn Gly Phe Asn Gln Ala Ile Glu Leu Ser Thr
            260                 265                 270

Glu Val Leu Ser Asn Val Lys Phe Ile Gln Glu Lys Leu Ile Gly
        275                 280                 285

Arg Tyr Phe Asp Glu Ile Ser Gln Asp Thr Gly Lys Tyr Cys Phe Gly
    290                 295                 300

Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

Gly Thr Glu Glu Glu Lys Ile Leu Tyr Leu Thr Pro Glu Gln Glu Lys
            340                 345                 350

Asp Lys Ser His Phe Thr Asp Lys Glu Thr Gly Gln Glu His Glu Leu
        355                 360                 365

Ile Glu Ser Met Pro Leu Leu Glu Trp Phe Ala Asn Asn Tyr Lys Lys
    370                 375                 380

Phe Gly Ala Thr Leu Glu Ile Val Thr Asp Lys Ser Gln Glu Gly Ser
385                 390                 395                 400

Gln Phe Val Lys Gly Phe Gly Gly Ile Gly Gly Ile Leu Arg Tyr Arg
                405                 410                 415

Val Asp Phe Gln Gly Met Glu Tyr Gln Gly Gly Asp Asp Glu Phe Phe
            420                 425                 430
```

```
Asp Leu Asp Asp Tyr
        435
```

<210> SEQ ID NO 11
<211> LENGTH: 437
<212> TYPE: PRT
<213> ORGANISM: Artificial Sequence
<220> FEATURE:
<223> OTHER INFORMATION: mutant eRF1 S123A L124I Y125L

<400> SEQUENCE: 11

```
Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30

Ser Met Ile Ser Leu Ile Ile Pro Pro Lys Asp Gln Ile Ser Arg Val
        35                  40                  45

Ala Lys Met Leu Ala Asp Glu Phe Gly Thr Ala Ser Asn Ile Lys Ser
    50                  55                  60

Arg Val Asn Arg Leu Ser Val Leu Gly Ala Ile Thr Ser Val Gln Gln
65              70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Val Asn Ile
            100                 105                 110

Asp Phe Glu Pro Phe Lys Pro Ile Asn Thr Ala Ile Leu Leu Cys Asp
        115                 120                 125

Asn Lys Phe His Thr Glu Ala Leu Thr Ala Leu Leu Ser Asp Asp Ser
    130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175

Pro Lys Lys His Gly Arg Gly Gly Gln Ser Ala Leu Arg Phe Ala Arg
            180                 185                 190

Leu Arg Met Glu Lys Arg His Asn Tyr Val Arg Lys Val Ala Glu Thr
        195                 200                 205

Ala Val Gln Leu Phe Ile Ser Gly Asp Lys Val Asn Val Ala Gly Leu
    210                 215                 220

Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255

Ser Tyr Gly Gly Glu Asn Gly Phe Asn Gln Ala Ile Glu Leu Ser Thr
            260                 265                 270

Glu Val Leu Ser Asn Val Lys Phe Ile Gln Glu Lys Lys Leu Ile Gly
        275                 280                 285

Arg Tyr Phe Asp Glu Ile Ser Gln Asp Thr Gly Lys Tyr Cys Phe Gly
    290                 295                 300

Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

Gly Thr Glu Glu Glu Lys Ile Leu Tyr Leu Thr Pro Gly Gln Glu Lys
            340                 345                 350
```

```
Asp Lys Ser His Phe Thr Asp Lys Glu Thr Gly Gln Glu His Glu Leu
            355                 360                 365

Ile Glu Ser Met Pro Leu Leu Glu Trp Phe Ala Asn Asn Tyr Lys Lys
    370                 375                 380

Phe Gly Ala Thr Leu Glu Ile Val Thr Asp Lys Ser Gln Glu Gly Ser
385                 390                 395                 400

Gln Phe Val Lys Gly Phe Gly Ile Gly Gly Ile Leu Arg Tyr Arg
                405                 410                 415

Val Asp Phe Gln Gly Met Glu Tyr Gln Gly Gly Asp Glu Phe Phe
                420                 425                 430

Asp Leu Asp Asp Tyr
            435

<210> SEQ ID NO 12
<211> LENGTH: 437
<212> TYPE: PRT
<213> ORGANISM: Artificial Sequence
<220> FEATURE:
<223> OTHER INFORMATION: mutant eRF1 S123R L124W Y125R

<400> SEQUENCE: 12

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30

Ser Met Ile Ser Leu Ile Ile Pro Pro Lys Asp Gln Ile Ser Arg Val
        35                  40                  45

Ala Lys Met Leu Ala Asp Glu Phe Gly Thr Ala Ser Asn Ile Lys Ser
    50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Lys Val Asn Ile
            100                 105                 110

Asp Phe Glu Pro Phe Lys Pro Ile Asn Thr Arg Trp Arg Leu Cys Asp
        115                 120                 125

Asn Lys Phe His Thr Glu Ala Leu Thr Ala Leu Leu Ser Asp Asp Ser
    130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175

Pro Lys Lys His Gly Arg Gly Gly Gln Ser Ala Leu Arg Phe Ala Arg
            180                 185                 190

Leu Arg Met Glu Lys Arg His Asn Tyr Val Arg Lys Val Ala Glu Thr
        195                 200                 205

Ala Val Gln Leu Phe Ile Ser Gly Asp Lys Val Asn Val Ala Gly Leu
    210                 215                 220

Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255

Ser Tyr Gly Gly Glu Asn Gly Phe Asn Gln Ala Ile Glu Leu Ser Thr
            260                 265                 270
```

-continued

```
Glu Val Leu Ser Asn Val Lys Phe Ile Gln Glu Lys Lys Leu Ile Gly
            275                 280                 285

Arg Tyr Phe Asp Glu Ile Ser Gln Asp Thr Gly Lys Tyr Cys Phe Gly
        290                 295                 300

Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

Gly Thr Glu Glu Lys Ile Leu Tyr Leu Thr Pro Glu Gln Glu Lys
            340                 345                 350

Asp Lys Ser His Phe Thr Asp Lys Glu Thr Gly Gln Glu His Glu Leu
            355                 360                 365

Ile Glu Ser Met Pro Leu Leu Glu Trp Phe Ala Asn Asn Tyr Lys Lys
        370                 375                 380

Phe Gly Ala Thr Leu Glu Ile Val Thr Asp Lys Ser Gln Glu Gly Ser
385                 390                 395                 400

Gln Phe Val Lys Gly Phe Gly Ile Gly Ile Leu Arg Tyr Arg
                405                 410                 415

Val Asp Phe Gln Gly Met Glu Tyr Gln Gly Gly Asp Glu Phe Phe
                420                 425                 430

Asp Leu Asp Asp Tyr
            435

<210> SEQ ID NO 13
<211> LENGTH: 437
<212> TYPE: PRT
<213> ORGANISM: Artificial Sequence
<220> FEATURE:
<223> OTHER INFORMATION: mutant eRF1 S123H, L124A, Y125G

<400> SEQUENCE: 13

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30

Ser Met Ile Ser Leu Ile Ile Pro Pro Lys Asp Gln Ile Ser Arg Val
        35                  40                  45

Ala Lys Met Leu Ala Asp Glu Phe Gly Thr Ala Ser Asn Ile Lys Ser
    50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Lys Val Asn Ile
            100                 105                 110

Asp Phe Glu Pro Phe Lys Pro Ile Asn Thr His Ala Gly Leu Cys Asp
        115                 120                 125

Asn Lys Phe His Thr Glu Ala Leu Thr Ala Leu Leu Ser Asp Asp Ser
    130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175

Pro Lys Lys His Gly Arg Gly Gly Gln Ser Ala Leu Arg Phe Ala Arg
            180                 185                 190
```

```
Leu Arg Met Glu Lys Arg His Asn Tyr Val Arg Lys Val Ala Glu Thr
            195                 200                 205

Ala Val Gln Leu Phe Ile Ser Gly Asp Lys Val Asn Val Ala Gly Leu
        210                 215                 220

Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255

Ser Tyr Gly Gly Glu Asn Gly Phe Asn Gln Ala Ile Glu Leu Ser Thr
            260                 265                 270

Glu Val Leu Ser Asn Val Lys Phe Ile Gln Glu Lys Lys Leu Ile Gly
        275                 280                 285

Arg Tyr Phe Asp Glu Ile Ser Gln Asp Thr Gly Lys Tyr Cys Phe Gly
    290                 295                 300

Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

Gly Thr Glu Glu Lys Ile Leu Tyr Leu Thr Pro Glu Gln Glu Lys
            340                 345                 350

Asp Lys Ser His Phe Thr Asp Lys Glu Thr Gly Gln Glu His Glu Leu
        355                 360                 365

Ile Glu Ser Met Pro Leu Leu Glu Trp Phe Ala Asn Asn Tyr Lys Lys
    370                 375                 380

Phe Gly Ala Thr Leu Glu Ile Val Thr Asp Lys Ser Gln Glu Gly Ser
385                 390                 395                 400

Gln Phe Val Lys Gly Phe Gly Gly Ile Gly Gly Ile Leu Arg Tyr Arg
                405                 410                 415

Val Asp Phe Gln Gly Met Glu Tyr Gln Gly Gly Asp Asp Glu Phe Phe
            420                 425                 430

Asp Leu Asp Asp Tyr
            435

<210> SEQ ID NO 14
<211> LENGTH: 437
<212> TYPE: PRT
<213> ORGANISM: Artificial Sequence
<220> FEATURE:
<223> OTHER INFORMATION: mutant eRF1 M51A K130M

<400> SEQUENCE: 14

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30

Ser Met Ile Ser Leu Ile Ile Pro Pro Lys Asp Gln Ile Ser Arg Val
        35                  40                  45

Ala Lys Ala Leu Ala Asp Glu Phe Gly Thr Ala Ser Asn Ile Lys Ser
    50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Lys Val Asn Ile
            100                 105                 110
```

```
Asp Phe Glu Pro Phe Lys Pro Ile Asn Thr Ser Leu Tyr Leu Cys Asp
            115                 120                 125

Asn Met Phe His Thr Glu Ala Leu Thr Ala Leu Leu Ser Asp Asp Ser
130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175

Pro Lys Lys His Gly Arg Gly Gly Gln Ser Ala Leu Arg Phe Ala Arg
            180                 185                 190

Leu Arg Met Glu Lys Arg His Asn Tyr Val Arg Lys Val Ala Glu Thr
    195                 200                 205

Ala Val Gln Leu Phe Ile Ser Gly Asp Lys Val Asn Val Ala Gly Leu
        210                 215                 220

Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255

Ser Tyr Gly Gly Glu Asn Gly Phe Asn Gln Ala Ile Glu Leu Ser Thr
            260                 265                 270

Glu Val Leu Ser Asn Val Lys Phe Ile Gln Glu Lys Lys Leu Ile Gly
    275                 280                 285

Arg Tyr Phe Asp Glu Ile Ser Gln Asp Thr Gly Lys Tyr Cys Phe Gly
        290                 295                 300

Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

Gly Thr Glu Glu Glu Lys Ile Leu Tyr Leu Thr Pro Glu Gln Glu Lys
            340                 345                 350

Asp Lys Ser His Phe Thr Asp Lys Glu Thr Gly Gln Glu His Glu Leu
    355                 360                 365

Ile Glu Ser Met Pro Leu Leu Glu Trp Phe Ala Asn Asn Tyr Lys Lys
        370                 375                 380

Phe Gly Ala Thr Leu Glu Ile Val Thr Asp Lys Ser Gln Glu Gly Ser
385                 390                 395                 400

Gln Phe Val Lys Gly Phe Gly Ile Gly Gly Ile Leu Arg Tyr Arg
                405                 410                 415

Val Asp Phe Gln Gly Met Glu Tyr Gln Gly Gly Asp Ala Glu Phe Phe
                420                 425                 430

Asp Leu Asp Asp Tyr
            435

<210> SEQ ID NO 15
<211> LENGTH: 438
<212> TYPE: PRT
<213> ORGANISM: Artificial Sequence
<220> FEATURE:
<223> OTHER INFORMATION: mutant eRF1 S123A Y125V

<400> SEQUENCE: 15

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
            20                  25                  30
```

-continued

```
Ser Met Ile Ser Leu Ile Ile Pro Pro Lys Asp Gln Ile Ser Arg Val
         35                  40                  45
Ala Lys Met Leu Ala Asp Glu Phe Gly Thr Ala Ser Asn Ile Lys Ser
 50                  55                  60
Arg Val Asn Arg Leu Ser Val Leu Gly Ala Ile Thr Ser Val Gln Gln
 65                  70                  75                  80
Arg Leu Lys Leu Tyr Asn Lys Val Pro Pro Asn Gly Leu Val Val Tyr
                 85                  90                  95
Cys Gly Thr Ile Val Thr Glu Glu Gly Lys Glu Lys Lys Val Asn Ile
                100                 105                 110
Asp Phe Glu Pro Phe Lys Pro Ile Asn Thr Ala Ala Leu Val Leu Cys
            115                 120                 125
Asp Asn Lys Phe His Thr Glu Ala Leu Thr Ala Leu Leu Ser Asp Asp
            130                 135                 140
Ser Lys Phe Gly Phe Ile Val Ile Asp Gly Ser Gly Ala Leu Phe Gly
145                 150                 155                 160
Thr Leu Gln Gly Asn Thr Arg Glu Val Leu His Lys Phe Thr Val Asp
                165                 170                 175
Leu Pro Lys Lys His Gly Arg Gly Gln Ser Ala Leu Arg Phe Ala
            180                 185                 190
Arg Leu Arg Met Glu Lys Arg His Asn Tyr Val Arg Lys Val Ala Glu
            195                 200                 205
Thr Ala Val Gln Leu Phe Ile Ser Gly Asp Lys Val Asn Val Ala Gly
            210                 215                 220
Leu Val Leu Ala Gly Ser Ala Asp Phe Lys Thr Glu Leu Ser Gln Ser
225                 230                 235                 240
Asp Met Phe Asp Gln Arg Leu Gln Ser Lys Val Leu Lys Leu Val Asp
                245                 250                 255
Ile Ser Tyr Gly Gly Glu Asn Gly Phe Asn Gln Ala Ile Glu Leu Ser
            260                 265                 270
Thr Glu Val Leu Ser Asn Val Lys Phe Ile Gln Glu Lys Lys Leu Ile
            275                 280                 285
Gly Arg Tyr Phe Asp Glu Ile Ser Gln Asp Thr Gly Lys Tyr Cys Phe
290                 295                 300
Gly Val Glu Asp Thr Leu Lys Ala Leu Glu Met Gly Ala Val Glu Ile
305                 310                 315                 320
Leu Ile Val Tyr Glu Asn Leu Asp Ile Met Arg Tyr Val Leu His Cys
                325                 330                 335
Gln Gly Thr Glu Glu Lys Ile Leu Tyr Leu Thr Pro Glu Gln Glu
            340                 345                 350
Lys Asp Lys Ser His Phe Thr Asp Lys Glu Thr Gly Gln Glu His Glu
            355                 360                 365
Leu Ile Glu Ser Met Pro Leu Leu Glu Trp Phe Ala Asn Asn Tyr Lys
370                 375                 380
Lys Phe Gly Ala Thr Leu Glu Ile Val Thr Asp Lys Ser Gln Glu Gly
385                 390                 395                 400
Ser Gln Phe Val Lys Gly Phe Gly Ile Gly Ile Leu Arg Tyr
                405                 410                 415
Arg Val Asp Phe Gln Gly Met Glu Tyr Gln Gly Gly Asp Glu Phe
            420                 425                 430
Phe Asp Leu Asp Asp Tyr
            435
```

<210> SEQ ID NO 16
<211> LENGTH: 437
<212> TYPE: PRT
<213> ORGANISM: Artificial Sequence
<220> FEATURE:
<223> OTHER INFORMATION: mutant eRF1 S123L L124C Y125S

<400> SEQUENCE: 16

| | | | | | | | | | | | | | | | |
|---|---|---|---|---|---|---|---|---|---|---|---|---|---|---|---|
| Met | Ala | Asp | Asp | Pro | Ser | Ala | Ala | Asp | Arg | Asn | Val | Glu | Ile | Trp | Lys |
| 1 | | | | 5 | | | | | 10 | | | | | 15 | |
| Ile | Lys | Lys | Leu | Ile | Lys | Ser | Leu | Glu | Ala | Ala | Arg | Gly | Asn | Gly | Thr |
| | | | 20 | | | | | 25 | | | | | 30 | | |
| Ser | Met | Ile | Ser | Leu | Ile | Ile | Pro | Pro | Lys | Asp | Gln | Ile | Ser | Arg | Val |
| | | 35 | | | | | 40 | | | | | 45 | | | |
| Ala | Lys | Met | Leu | Ala | Asp | Glu | Phe | Gly | Thr | Ala | Ser | Asn | Ile | Lys | Ser |
| | 50 | | | | | 55 | | | | | 60 | | | | |
| Arg | Val | Asn | Arg | Leu | Ser | Val | Leu | Gly | Ala | Ile | Thr | Ser | Val | Gln | Gln |
| 65 | | | | | 70 | | | | | 75 | | | | | 80 |
| Arg | Leu | Lys | Leu | Tyr | Asn | Lys | Val | Pro | Pro | Asn | Gly | Leu | Val | Val | Tyr |
| | | | | 85 | | | | | 90 | | | | | 95 | |
| Cys | Gly | Thr | Ile | Val | Thr | Glu | Glu | Gly | Lys | Glu | Lys | Lys | Val | Asn | Ile |
| | | | 100 | | | | | 105 | | | | | 110 | | |
| Asp | Phe | Glu | Pro | Phe | Lys | Pro | Ile | Asn | Thr | Leu | Cys | Ser | Leu | Cys | Asp |
| | | 115 | | | | | 120 | | | | | 125 | | | |
| Asn | Lys | Phe | His | Thr | Glu | Ala | Leu | Thr | Ala | Leu | Leu | Ser | Asp | Asp | Ser |
| | 130 | | | | | 135 | | | | | 140 | | | | |
| Lys | Phe | Gly | Phe | Ile | Val | Ile | Asp | Gly | Ser | Gly | Ala | Leu | Phe | Gly | Thr |
| 145 | | | | | 150 | | | | | 155 | | | | | 160 |
| Leu | Gln | Gly | Asn | Thr | Arg | Glu | Val | Leu | His | Lys | Phe | Thr | Val | Asp | Leu |
| | | | | 165 | | | | | 170 | | | | | 175 | |
| Pro | Lys | Lys | His | Gly | Arg | Gly | Gly | Gln | Ser | Ala | Leu | Arg | Phe | Ala | Arg |
| | | | 180 | | | | | 185 | | | | | 190 | | |
| Leu | Arg | Met | Glu | Lys | Arg | His | Asn | Tyr | Val | Arg | Lys | Val | Ala | Glu | Thr |
| | | 195 | | | | | 200 | | | | | 205 | | | |
| Ala | Val | Gln | Leu | Phe | Ile | Ser | Gly | Asp | Lys | Val | Asn | Val | Ala | Gly | Leu |
| | 210 | | | | | 215 | | | | | 220 | | | | |
| Val | Leu | Ala | Gly | Ser | Ala | Asp | Phe | Lys | Thr | Glu | Leu | Ser | Gln | Ser | Asp |
| 225 | | | | | 230 | | | | | 235 | | | | | 240 |
| Met | Phe | Asp | Gln | Arg | Leu | Gln | Ser | Lys | Val | Leu | Lys | Leu | Val | Asp | Ile |
| | | | | 245 | | | | | 250 | | | | | 255 | |
| Ser | Tyr | Gly | Gly | Glu | Asn | Gly | Phe | Asn | Gln | Ala | Ile | Glu | Leu | Ser | Thr |
| | | | 260 | | | | | 265 | | | | | 270 | | |
| Glu | Val | Leu | Ser | Asn | Val | Lys | Phe | Ile | Gln | Glu | Lys | Lys | Leu | Ile | Gly |
| | | 275 | | | | | 280 | | | | | 285 | | | |
| Arg | Tyr | Phe | Asp | Glu | Ile | Ser | Gln | Asp | Thr | Gly | Lys | Tyr | Cys | Phe | Gly |
| | 290 | | | | | 295 | | | | | 300 | | | | |
| Val | Glu | Asp | Thr | Leu | Lys | Ala | Leu | Glu | Met | Gly | Ala | Val | Glu | Ile | Leu |
| 305 | | | | | 310 | | | | | 315 | | | | | 320 |
| Ile | Val | Tyr | Glu | Asn | Leu | Asp | Ile | Met | Arg | Tyr | Val | Leu | His | Cys | Gln |
| | | | | 325 | | | | | 330 | | | | | 335 | |
| Gly | Thr | Glu | Glu | Glu | Lys | Ile | Leu | Tyr | Leu | Thr | Pro | Glu | Gln | Glu | Lys |
| | | | 340 | | | | | 345 | | | | | 350 | | |
| Asp | Lys | Ser | His | Phe | Thr | Asp | Lys | Glu | Thr | Gly | Gln | Glu | His | Glu | Leu |
| | | 355 | | | | | 360 | | | | | 365 | | | |
| Ile | Glu | Ser | Met | Pro | Leu | Leu | Glu | Trp | Phe | Ala | Asn | Asn | Tyr | Lys | Lys |

```
              370                 375                 380
Phe Gly Ala Thr Leu Glu Ile Val Thr Asp Lys Ser Gln Glu Gly Ser
385                 390                 395                 400

Gln Phe Val Lys Gly Phe Gly Ile Gly Gly Ile Leu Arg Tyr Arg
                405                 410                 415

Val Asp Phe Gln Gly Met Glu Tyr Gln Gly Gly Asp Asp Glu Phe Phe
                420                 425                 430

Asp Leu Asp Asp Tyr
            435

<210> SEQ ID NO 17
<211> LENGTH: 437
<212> TYPE: PRT
<213> ORGANISM: Artificial Sequence
<220> FEATURE:
<223> OTHER INFORMATION: mutant eRF1 S123L L124S Y125S

<400> SEQUENCE: 17

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
                20                  25                  30

Ser Met Ile Ser Leu Ile Ile Pro Pro Lys Asp Gln Ile Ser Arg Val
            35                  40                  45

Ala Lys Met Leu Ala Asp Glu Phe Gly Thr Ala Ser Asn Ile Lys Ser
        50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Lys Val Asn Ile
                100                 105                 110

Asp Phe Glu Pro Phe Lys Pro Ile Asn Thr Leu Ser Ser Leu Cys Asp
            115                 120                 125

Asn Lys Phe His Thr Glu Ala Leu Thr Ala Leu Leu Ser Asp Asp Ser
130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175

Pro Lys Lys His Gly Arg Gly Gly Gln Ser Ala Leu Arg Phe Ala Arg
            180                 185                 190

Leu Arg Met Glu Lys Arg His Asn Tyr Val Arg Lys Val Ala Glu Thr
        195                 200                 205

Ala Val Gln Leu Phe Ile Ser Gly Asp Lys Val Asn Val Ala Gly Leu
    210                 215                 220

Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255

Ser Tyr Gly Gly Glu Asn Gly Phe Asn Gln Ala Ile Glu Leu Ser Thr
            260                 265                 270

Glu Val Leu Ser Asn Val Lys Phe Ile Gln Glu Lys Lys Leu Ile Gly
        275                 280                 285

Arg Tyr Phe Asp Glu Ile Ser Gln Asp Thr Gly Lys Tyr Cys Phe Gly
```

```
                290                 295                 300
Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

Gly Thr Glu Glu Lys Ile Leu Tyr Leu Thr Pro Glu Gln Glu Lys
                340                 345                 350

Asp Lys Ser His Phe Thr Asp Lys Glu Thr Gly Gln Glu His Glu Leu
                355                 360                 365

Ile Glu Ser Met Pro Leu Leu Glu Trp Phe Ala Asn Asn Tyr Lys Lys
370                 375                 380

Phe Gly Ala Thr Leu Glu Ile Val Thr Asp Lys Ser Gln Glu Gly Ser
385                 390                 395                 400

Gln Phe Val Lys Gly Phe Gly Gly Ile Gly Gly Ile Leu Arg Tyr Arg
                405                 410                 415

Val Asp Phe Gln Gly Met Glu Tyr Gln Gly Gly Asp Asp Glu Phe Phe
                420                 425                 430

Asp Leu Asp Asp Tyr
                435

<210> SEQ ID NO 18
<211> LENGTH: 437
<212> TYPE: PRT
<213> ORGANISM: Artificial Sequence
<220> FEATURE:
<223> OTHER INFORMATION: mutant eRF1 S123V L124T Y125P

<400> SEQUENCE: 18

Met Ala Asp Asp Pro Ser Ala Ala Asp Arg Asn Val Glu Ile Trp Lys
1               5                   10                  15

Ile Lys Lys Leu Ile Lys Ser Leu Glu Ala Ala Arg Gly Asn Gly Thr
                20                  25                  30

Ser Met Ile Ser Leu Ile Ile Pro Pro Lys Asp Gln Ile Ser Arg Val
            35                  40                  45

Ala Lys Met Leu Ala Asp Glu Phe Gly Thr Ala Ser Asn Ile Lys Ser
50                  55                  60

Arg Val Asn Arg Leu Ser Val Leu Gly Ala Ile Thr Ser Val Gln Gln
65                  70                  75                  80

Arg Leu Lys Leu Tyr Asn Lys Val Pro Pro Asn Gly Leu Val Val Tyr
                85                  90                  95

Cys Gly Thr Ile Val Thr Glu Glu Gly Lys Glu Lys Lys Val Asn Ile
            100                 105                 110

Asp Phe Glu Pro Phe Lys Pro Ile Asn Thr Val Thr Pro Leu Cys Asp
            115                 120                 125

Asn Lys Phe His Thr Glu Ala Leu Thr Ala Leu Leu Ser Asp Asp Ser
            130                 135                 140

Lys Phe Gly Phe Ile Val Ile Asp Gly Ser Gly Ala Leu Phe Gly Thr
145                 150                 155                 160

Leu Gln Gly Asn Thr Arg Glu Val Leu His Lys Phe Thr Val Asp Leu
                165                 170                 175

Pro Lys Lys His Gly Arg Gly Gly Gln Ser Ala Leu Arg Phe Ala Arg
            180                 185                 190

Leu Arg Met Glu Lys Arg His Asn Tyr Val Arg Lys Val Ala Glu Thr
            195                 200                 205

Ala Val Gln Leu Phe Ile Ser Gly Asp Lys Val Asn Val Ala Gly Leu
```

```
                210              215              220
Val Leu Ala Gly Ser Ala Asp Phe Lys Thr Glu Leu Ser Gln Ser Asp
225                 230                 235                 240

Met Phe Asp Gln Arg Leu Gln Ser Lys Val Leu Lys Leu Val Asp Ile
                245                 250                 255

Ser Tyr Gly Gly Glu Asn Gly Phe Asn Gln Ala Ile Glu Leu Ser Thr
            260                 265                 270

Glu Val Leu Ser Asn Val Lys Phe Ile Gln Lys Lys Leu Ile Gly
        275                 280                 285

Arg Tyr Phe Asp Glu Ile Ser Gln Asp Thr Gly Lys Tyr Cys Phe Gly
            290                 295                 300

Val Glu Asp Thr Leu Lys Ala Leu Glu Met Gly Ala Val Glu Ile Leu
305                 310                 315                 320

Ile Val Tyr Glu Asn Leu Asp Ile Met Arg Tyr Val Leu His Cys Gln
                325                 330                 335

Gly Thr Glu Glu Lys Ile Leu Tyr Leu Thr Pro Glu Gln Glu Lys
            340                 345                 350

Asp Lys Ser His Phe Thr Asp Lys Glu Thr Gly Gln Glu His Glu Leu
            355                 360                 365

Ile Glu Ser Met Pro Leu Leu Glu Trp Phe Ala Asn Asn Tyr Lys Lys
370                 375                 380

Phe Gly Ala Thr Leu Glu Ile Val Thr Asp Lys Ser Gln Glu Gly Ser
385                 390                 395                 400

Gln Phe Val Lys Gly Phe Gly Ile Gly Gly Ile Leu Arg Tyr Arg
                405                 410                 415

Val Asp Phe Gln Gly Met Glu Tyr Gln Gly Gly Asp Asp Glu Phe Phe
            420                 425                 430

Asp Leu Asp Asp Tyr
            435

<210> SEQ ID NO 19
<211> LENGTH: 11
<212> TYPE: DNA
<213> ORGANISM: Artificial Sequence
<220> FEATURE:
<223> OTHER INFORMATION: linker

<400> SEQUENCE: 19
gacaagtgcg g                                                          11

<210> SEQ ID NO 20
<211> LENGTH: 1290
<212> TYPE: DNA
<213> ORGANISM: Artificial Sequence
<220> FEATURE:
<223> OTHER INFORMATION: codon optimised MbPylRS

<400> SEQUENCE: 20
atggactaca aggacgacga cgacaaggac aagaaacccc tggacgtgct gatcagcgcc        60
accggcctgt ggatgagccg gaccggcacc ctgcacaaga tcaagcacca cgaggtgtca       120
agaagcaaaa tctacatcga gatggcctgc ggcgaccacc tggtggtgaa caacagcaga       180
agctgccgga ccgccagagc cttccggcac acaagtacag aaagacctg caagcggtgc       240 cgggtgtccg acgaggacat caacaacttt ctgaccagaa gcaccgagag caagaacagc       300
gtgaaagtgc gggtggtgtc cgccccaaaa gtgaagaaag ccatgccaa gagcgtgtcc       360 agagccccca gcccctggaa aacagcgtg tccgccaagg ccagcaccaa caccagccgc       420
```

| | |
|---|---|
| agcgtgccca gccccgccaa gagcacccccc aacagctccg tgcccgcctc tgctcctgct | 480 |
| cccagcctga cacggtccca gctggacaga gtggaggccc tgctgtcccc cgaggacaag | 540 |
| atcagcctga acatggccaa gcccttccgg gagctggaac ccgagctggt gacccggcgg | 600 |
| aagaacgact tccagcggct gtacaccaac gaccgggagg actacctggg caagctggaa | 660 |
| cgggacatca ccaagttctt cgtggaccgg ggcttcctgg aaatcaagag ccccatcctg | 720 |
| atccccgccg agtacgtgga gcggatgggc atcaacaacg acaccgagct gtccaagcag | 780 |
| attttccggg tggacaagaa cctgtgcctg cggcctatgc tggcccccac cctgtacaac | 840 |
| tacctgcgga aactggacag aatcctgcct ggccccatca agattttcga agtgggaccc | 900 |
| tgctaccgga agagagcga cggcaaagag cacctggaag agtttacaat ggtgaatttt | 960 |
| tgccagatgg gcagcggctg cacccgggag aacctggaag ccctgatcaa agagttcctg | 1020 |
| gattacctgg aaatcgactt cgagatcgtg ggcgacagct gcatggtgta cggcgacacc | 1080 |
| ctggacatca tgcacggcga cctggaactg agcagcgccg tggtgggacc cgtgtccctg | 1140 |
| gaccgggagt ggggcatcga caagccctgg atcgagccg gcttcggcct ggaacggctg | 1200 |
| ctgaaagtga tgcacggctt caagaacatc aagcgggcca gcagaagcga gagctactac | 1260 |
| aacggcatca gcaccaacct gtgatgataa | 1290 |

<210> SEQ ID NO 21
<211> LENGTH: 1396
<212> TYPE: DNA
<213> ORGANISM: Artificial Sequence
<220> FEATURE:
<223> OTHER INFORMATION: codon optimised MmPylRS

<400> SEQUENCE: 21

| | |
|---|---|
| atggactaca aggacgacga cgacaaggga caagaagccc tgaacaccc tgatcagcgc | 60 |
| cacaggactg tggatgtcca gaaccggcac catccacaag atcaagcacc acgaggtgtc | 120 |
| ccggtccaaa atctacatcg agatggcctg cggcgatcac ctggtcgtca acaacagcag | 180 |
| aagcagccgg acagccagag ccctgcggca ccacaagtac agaaagacct gcaagcggtg | 240 |
| cagagtgtcc gacgaggacc tgaacaagtt cctgaccaag gccaacgagg accagaccag | 300 |
| cgtgaaagtg aaggtggtgt ccgcccccac ccggaccaag aaagccatgc caagagcgt | 360 |
| ggccagagcc cccaagcccc tgaaaaacac cgaagccgct caggcccagc cagcggcag | 420 |
| caagttcagc cccgccatcc ccgtgtctac ccaggaaagc gtcagcgtcc ccgccagcgt | 480 |
| gtccaccagc atctctagca tctcaaccgg cgccacagct tctgccctgg tcaagggcaa | 540 |
| caccaacccc atcaccagca tgtctgcccc tgtgcaggcc tctgccccag cctgaccaa | 600 |
| gtcccagacc gaccggctgg aagtgctcct gaaccccaag gacgagatca gcctgaacag | 660 |
| cggcaagccc ttccgggagc tggaaagcga gctgctgagc cggcggaaga aggacctcca | 720 |
| gcaaatctac gccgaggaac gggagaacta cctgggcaag ctggaaagag atcaccccg | 780 |
| gttcttcgtg gaccggggct tcctggaaat caagagcccc atcctgatcc cctggagta | 840 |
| catcgagcgg atgggcatcg acaacgacac cgagctgagc aagcagattt ccgggtgga | 900 |
| caagaacttc tgcctgcggc ccatgctggc ccccaacctg tacaactacc tgcggaaact | 960 |
| ggatcgcgct ctgcccgacc ccatcaagat tttcgagatc ggcccctgct accggaaaga | 1020 |
| gagcgacggc aaagagcacc tggaagagtt tacaatgctg aacttttgcc agatgggcag | 1080 |
| cggctgcacc agagagaacc tggaatccat catcaccgac tttctgaacc acctggggat | 1140 |

```
cgacttcaag atcgtgggcg acagctgcat ggtgtacggc gacaccctgg acgtgatgca    1200
cggcgacctg gaactgtcta gcgccgtcgt gggacccatc cctctggacc gggagtgggg    1260
catcgataag ccctggatcg agccggctt cggcctggaa cggctgctga aagtcaagca    1320
cgactttaag aacatcaagc gggctgccag aagcgagagc tactacaacg gcatcagcac    1380
caacctgtga tgataa                                                    1396

<210> SEQ ID NO 22
<211> LENGTH: 61
<212> TYPE: DNA
<213> ORGANISM: Methanosarcina mazeii

<400> SEQUENCE: 22
ggaaacctga tcatgtagat cgaatggact ctaaatccgt tcagccgggt tagattcccg    60
g                                                                    61

<210> SEQ ID NO 23
<211> LENGTH: 344
<212> TYPE: DNA
<213> ORGANISM: Artificial Sequence
<220> FEATURE:
<223> OTHER INFORMATION: U6 promoter - linker - terminator

<400> SEQUENCE: 23
tgggcaggaa gagggcctat ttcccatgat tccttcatat ttgcatatac gatacaaggc    60
tgttagagag ataattagaa ttaatttgac tgtaaacaca agatattag tacaaaatac    120 gtgacgtaga aagtaataat ttcttgggta gtttgcagtt ttaaaattat gttttaaaat    180
ggactatcat atgcttaccg taacttgaaa gtatttcgat ttcttggctt tatatatctt    240
gtggaaagga cgaaacaccg gaaacctgat catgtagatc gaatggactc taaatccgtt    300
cagccgggtt agattcccgg ggtttccgga caagtgcggt tttt                     344

<210> SEQ ID NO 24
<211> LENGTH: 260
<212> TYPE: DNA
<213> ORGANISM: Artificial Sequence
<220> FEATURE:
<223> OTHER INFORMATION: exemplary U6 promoter

<400> SEQUENCE: 24
tgggcaggaa gagggcctat ttcccatgat tccttcatat ttgcatatac gatacaaggc    60
tgttagagag ataattagaa ttaatttgac tgtaaacaca agatattag tacaaaatac    120 gtgacgtaga aagtaataat ttcttgggta gtttgcagtt ttaaaattat gttttaaaat    180
ggactatcat atgcttaccg taacttgaaa gtatttcgat ttcttggctt tatatatctt    240
gtggaaagga cgaaacaccg                                                260

<210> SEQ ID NO 25
<211> LENGTH: 556
<212> TYPE: DNA
<213> ORGANISM: Artificial Sequence
<220> FEATURE:
<223> OTHER INFORMATION: exemplary EF-1 alpha promoter

<400> SEQUENCE: 25
ctagtaagga tctgcgatcg ctccggtgcc cgtcagtggg cagagcgcac atcgcccaca    60
gtccccgaga agttgggggg aggggtcggc aattgaacgg gtgcctagag aaggtggcgc    120
ggggtaaact gggaaagtga tgtcgtgtac tggctccgcc ttttccccga gggtggggga    180
```

```
gaaccgtata taagtgcagt agtcgccgtg aacgttcttt ttcgcaacgg gtttgccgcc    240
agaacacagc tgaagcttcg aggggctcgc atctctcctt cacgcgcccg ccgccctacc    300
tgaggccgcc atccacgccg gttgagtcgc gttctgccgc ctcccgcctg tggtgcctcc    360
tgaactgcgt ccgccgtcta ggtaagttta agctcaggt cgagaccggg cctttgtccg     420
gcgctccctt ggagcctacc tagactcagc cggctctcca cgctttgcct gaccctgctt    480
gctcaactct acgtctttgt ttcgtttcct gttctgcgcc gttacagatc caagctgtga    540
ccggcgccta ctctag                                                    556

<210> SEQ ID NO 26
<211> LENGTH: 40
<212> TYPE: DNA
<213> ORGANISM: Artificial Sequence
<220> FEATURE:
<223> OTHER INFORMATION: DNA probe

<400> SEQUENCE: 26 ggaaacccg ggaatctaac ccggctgaac ggatttagag                            40

<210> SEQ ID NO 27
<211> LENGTH: 69
<212> TYPE: DNA
<213> ORGANISM: Artificial Sequence
<220> FEATURE:
<223> OTHER INFORMATION: M. Mazei PylT U25C Opt

<400> SEQUENCE: 27
ggaaacgtga tcatgtagat cgaacggact ctaaatccgt tcagtggggt tagattcccc     60
acgtttccg                                                             69

<210> SEQ ID NO 28
<211> LENGTH: 350
<212> TYPE: DNA
<213> ORGANISM: Artificial Sequence
<220> FEATURE:
<223> OTHER INFORMATION: (1x) Human U6 promoter :: M. Mazei PylT U25C
      Opt :: 3' UTR and terminator

<400> SEQUENCE: 28
cctagttggg caggaagagg gcctatttcc catgattcct tcatatttgc atatacgata     60
caaggctgtt agagagataa ttagaattaa tttgactgta aacacaaaga tattagtaca    120
aaatacgtga cgtagaaagt aataatttct ggggtagttt gcagttttaa aattatgttt    180
taaaatggac tatcatatgc ttaccgtaac ttgaaagtat ttcgatttct tggctttata    240
tatcttgtgg aaaggacgaa acaccggaaa cgtgatcatg tagatcgaac ggactctaaa    300
tccgttcagt ggggttagat tccccacgtt tccggacaag tgcggttttt               350

<210> SEQ ID NO 29
<211> LENGTH: 1642
<212> TYPE: DNA
<213> ORGANISM: Artificial Sequence
<220> FEATURE:
<223> OTHER INFORMATION: (4x) Human U6 promoter :: M. Mazei PylT U25C
      Opt :: 3' UTR and terminator as cloned

<400> SEQUENCE: 29
tgggcgatgt gcgctctgcc cactgacggg caccggagcg atcgcagatc cctagttgg      60 gcaggaagag ggcctatttc ccatgattcc ttcatatttg catatacgat acaaggctgt    120
```

| | |
|---|---|
| tagagagata attagaatta atttgactgt aaacacaaag atattagtac aaaatacgtg | 180 |
| acgtagaaag taataatttc ttgggtagtt tgcagtttta aaattatgtt ttaaaatgga | 240 |
| ctatcatatg cttaccgtaa cttgaaagta tttcgatttc ttggctttat atatcttgtg | 300 |
| gaaaggacga acaccggaa acgtgatcat gtagatcgaa cggactctaa atccgttcag | 360 |
| tggggttaga ttccccacgt ttccggacaa gtgcggtttt tagaattaca acttatatcg | 420 |
| tatgggctag actcgagcct agttgggcag gaagagggcc tatttcccat gattccttca | 480 |
| tatttgcata tacgatacaa ggctgttaga gagataatta gaattaattt gactgtaaac | 540 |
| acaaagatat tagtacaaaa tacgtgacgt agaaagtaat aatttcttgg gtagtttgca | 600 |
| gttttaaaat tatgttttaa aatggactat catatgctta ccgtaacttg aaagtatttc | 660 |
| gatttcttgg ctttatatat cttgtggaaa ggacgaaaca ccggaaacgt gatcatgtag | 720 |
| atcgaacgga ctctaaatcc gttcagtggg gttagattcc ccacgtttcc ggacaagtgc | 780 |
| ggttttgcg gccgcgatat ctgcagaatt cacactggac taggatccga gctccctagt | 840 |
| tgggcaggaa gagggcctat ttcccatgat tccttcatat ttgcatatac gatacaaggc | 900 |
| tgttagagag ataattagaa ttaatttgac tgtaaacaca agatattag tacaaaatac | 960 |
| gtgacgtaga aagtaataat ttcttgggta gtttgcagtt ttaaaattat gttttaaaat | 1020 |
| ggactatcat atgcttaccg taacttgaaa gtatttcgat tcttggctt tatatatctt | 1080 |
| gtggaaagga cgaaacaccg gaaacgtgat catgtagatc gaacggactc taaatccgtt | 1140 |
| cagtggggtt agattcccca cgtttccgga caagtgcggt ttttggtacc aagcttaagc | 1200 |
| agactcgtcg tgactacatt agcctagttg gcaggaaga gggcctattt cccatgattc | 1260 |
| cttcatatt gcatatacga tacaaggctg ttagagagat aattagaatt aatttgactg | 1320 |
| taaacacaaa gatattagta caaaatacgt gacgtagaaa gtaataattt ctgggtagt | 1380 |
| ttgcagtttt aaaattatgt tttaaaatgg actatcatat gcttaccgta acttgaaagt | 1440 |
| atttcgattt cttggcttta tatatcttgt ggaaaggacg aaacaccgga acgtgatca | 1500 |
| tgtagatcga acggactcta aatccgttca gtggggttag attccccacg tttccggaca | 1560 |
| agtgcggttt ttcctagtgg ccttggaggc ttttcccg tatcccccca ggtgtctgca | 1620 |
| ggctcaaaga gcagcgagaa gc | 1642 |

<210> SEQ ID NO 30
<211> LENGTH: 10627
<212> TYPE: DNA
<213> ORGANISM: Artificial Sequence
<220> FEATURE:
<223> OTHER INFORMATION: pKYM1 LC-ires-HC sequence

<400> SEQUENCE: 30

| | |
|---|---|
| gttaggcgtt ttgcgctgct tcgcgatgta cgggccagat atacgcgttg acattgatta | 60 |
| ttgactagtt attaatagta atcaattacg gggtcattag ttcatagccc atatatggag | 120 |
| ttccgcgtta cataacttac ggtaaatggc ccgcctggc gaccgcccaa cgaccccgc | 180 |
| ccattgacgt caataatgac gtatgttccc atagtaacgc caatagggac tttccattga | 240 |
| cgtcaatggg tggagtattt acggtaaact gcccacttgg cagtacatca agtgtatcat | 300 |
| atgccaagta cgccccctat tgacgtcaat gacggtaaat ggcccgcctg gcattatgcc | 360 |
| cagtacatga ccttatggga ctttcctact tggcagtaca tctacgtatt agtcatcgct | 420 |
| attaccatgg tgatgcggtt ttggcagtac atcaatgggc gtggatagcg gtttgactca | 480 |
| cggggatttc caagtctcca ccccattgac gtcaatggga gtttgttttg gcaccaaaat | 540 |

```
caacgggact tccaaaatg tcgtaacaac tccgccccat tgacgcaaat gggcggtagg    600
cgtgtacggt gggaggtcta tataagcaga gctcgtttag tgaaccgtca gatcgcctgg    660
agacgccatc cacgctgttt tgacctccat agaagacacc gggaccgatc cagcctccgg    720
actctagagg atcgaattaa gcttggtacc gccgccacca tgggatggtc atgtatcatc    780
cttttctag tagcaactgc aaccggtgta cattctgaca tccagatgac ccagtccccg    840
agctctctgt ctgcgtctgt tggtgaccgc gttaccatca cctgccgtgc gtcccaggac    900
gttaacaccg ccgtggcgtg gtatcaacag aaaccgggta agcgccaaa actgctgatc    960
tactcccgcg ctttcctgta ctctggtgtt ccgtctcgtt tcagcggttc tcgttctggt   1020
actgacttca ccctcaccat ctcttctctg cagccggaag acttcgcgac ctactactgc   1080
cagcagcact acaccacccc accgaccttc ggtcagggca ccaaagttga aatcaaacgt   1140
acggtggctg caccatctgt cttcatcttc ccgccatctg atgagcagtt gaaatctgga   1200
actgcctctg ttgtgtgcct gctgaataac ttctacccca gagaagccaa agtgcagtgg   1260
aaggtggaca acgccctgca gagcggaaac agccaggaaa gcgtgacaga gcaggattcc   1320
aaggattcca catacagcct gagcagcaca ctgacactgt ccaaggccga ctacgagaag   1380
cacaaggtgt acgcctgcga agtgacacac cagggactgt cctcccctgt gacaaagagc   1440
ttcaacagag gagaatgctg aggccgcgcc cctctccctc ccccccccct aacgttactg   1500
gccgaagccg cttggaataa ggccggtgtg cgtttgtcta tatgttattt tccaccatat   1560
tgccgtcttt tggcaatgtg agggcccgga aacctggccc tgtcttcttg acgagcattc   1620
ctagggtct ttcccctctc gccaaaggaa tgcaaggtct gttgaatgtc gtgaaggaag   1680
cagttcctct ggaagcttct tgaagacaaa caacgtctgt agcgaccctt gcaggcagc   1740
ggaacccccc acctggcgac aggtgcctct gcggccaaaa gccacgtgta taagatacac   1800
ctgcaaaggc ggcacaaccc cagtgccacg ttgtgagttg atagttgtg gaaagagtca   1860
aatggctctc ctcaagcgta ttcaacaagg ggctgaagga tgcccagaag gtaccccatt   1920
gtatgggatc tgatctgggg cctcggtgca catgctttac atgtgtttag tcgaggttaa   1980
aaaaacgtct aggcccccg aaccacgggg acgtggtttt cctttgaaaa acacgataat   2040
acctccggaa tgggatggtc atgtatcatc cttttctag tagcaactgc aaccggtgta   2100
cattctgaag ttcagctggt tgaatctggt ggtggtctgg ttcaaccggg tggctccctg   2160
cgtctgtctt gtgcggcctc tggttttaac atcaaagata cctatatcca ctgggttcgt   2220
caggcgccag gcaaaggtct ggaatgggtt gcgcgtatct acccgaccaa cggttacacc   2280
cgctacgcgg actctgttaa aggtcgtttc accatctctg cggacacctc taaaaacacc   2340
gcgtacctgc agatgaactc tctgcgtgcg gaagacaccg ccgttactat ctgctctcgt   2400
tggggtggtg acggtttcta cgcgatggac tactggggtc agggtacgct ggttaccgtt   2460
tcttcttagt cgaccaaggg cccatcggtc ttccccctgg cacctcctc caagagcacc   2520
tctgggggca cagcggccct gggctgcctg gtcaaggact acttccccga acctgtgacg   2580
gtctcgtgga actcaggcgc cctgaccagc ggcgtgcaca ccttcccggc tgtcctacag   2640
tcctcaggac tctactccct cagcagcgtg gtgaccgtgc cctccagcag cttgggcacc   2700
cagacctaca tctgcaacgt gaatcacaag cccagcaaca ccaaggtgga caagaaagtt   2760
gagcccaaat cttgtgacaa aactcacaca tgcccaccgt gcccagcacc tgaactcctg   2820
ggggaccgt cagtcttcct cttccccca aacccaagg acaccctcat gatctcccgg   2880
```

```
accccctgagg tcacatgcgt ggtggtggac gtgagccacg aagaccctga ggtcaagttc    2940
aactggtacg tggacggcgt ggaggtgcat aatgccaaga caaagccgcg ggaggagcag    3000
tacaacagca cgtaccgtgt ggtcagcgtc ctcaccgtcc tgcaccagga ctggctgaat    3060
ggcaaggagt acaagtgcaa ggtctccaac aaagccctcc cagcccccat cgagaaaacc    3120
atctccaaag ccaaagggca gccccgagaa ccacaggtgt acaccctgcc cccatcccgg    3180
gaggagatga ccaagaacca ggtcagcctg acctgcctgg tcaaaggctt ctatcccagc    3240
gacatcgccg tggagtggga gagcaatggg cagccggaga caactacaa gaccacgcct    3300 cccgtgctgg actccgacgg ctccttcttc ctctatagca agctcaccgt ggacaagagc    3360
aggtggcagc aggggaacgt cttctcatgc tccgtgatgc atgaggctct gcacaaccac    3420
tacacgcaga agagcctctc cctgtccccg ggttgagctc gagtctagag ggttcgatcc    3480
ctaccggtta gtaatgagtt taaactcgac aatcaacctc tggattacaa aatttgtgaa    3540
agattgactg gtattcttaa ctatgttgct ccttttacgc tatgtggata cgctgcttta    3600
atgcctttgt atcatgctat tgcttcccgt atggctttca ttttctcctc cttgtataaa    3660
tcctggttgc tgtctcttta tgaggagttg tggcccgttg tcaggcaacg tggcgtggtg    3720
tgcactgtgt ttgctgacgc aaccccccact ggttgggca ttgccaccac ctgtcagctc    3780
ctttccggga ctttcgcttt ccccctccct attgccacgg cggaactcat cgccgcctgc    3840
cttgcccgct gctggacagg ggctcggctg ttgggcactg acaattccgt ggtgttgtcg    3900
gggaagctga cgtcctttcc atggctgctc gcctgtgttg ccacctggat tctgcgcggg    3960
acgtccttct gctacgtccc ttcggccctc aatccagcgg accttccttc ccgcggcctg    4020
ctgccggctc tgcggcctct tccgcgtctt cgccttcgcc ctcagacgag tcggatctcc    4080
ctttgggccg cctccccgcc tggaaacggg ggaggctaac tgaaacacgg aaggagacaa    4140
taccggaagg aacccgcgct atgacggcaa taaaaagaca gaataaaacg cacgggtgtt    4200
gggtcgtttg ttcataaacg cggggttcgg tcccagggct ggcactctgt cgataccccca   4260 ccgagacccc attggggcca atacgcccgc gtttcttcct tttccccacc cacccccca    4320 agttcgggtg aaggcccagg gctcgcagcc aacgtcgggg cggcaggccc tgccatagca    4380
gatctgcgca gctctataaa gtaacaaaac ttttatgagg gacagccccc ccccaaagcc    4440
cccagggatg taattacgtc cctcccccgc taggggcag cagcgagccg cccgggctc    4500 cgctccggtc cggcgctccc cccgcatccc cgagccggca gcgtgcgggg acagcccggg    4560
cacggggaag gtggcacggg atcgctttcc tctgaacgct tctcgctgct ctttgagcct    4620
gcagacacct gggggatac ggggaaaagg cctccaaggc cactaggaaa accgcactt    4680 gtccggaaac cccgggaatc taacccggct gaacggattt agagtccatt cgatctacat    4740
gatcaggttt ccggtgtttc gtcctttcca caagatatat aaagccaaga atcgaaata    4800 ctttcaagtt acggtaagca tatgatagtc cattttaaaa cataatttta aaactgcaaa    4860
ctacccaaga aattattact ttctacgtca cgtatttgt actaatatct tgtgtttac    4920 agtcaaatta attctaatta tctctctaac agccttgtat cgtatatgca aatatgaagg    4980
aatcatggga aataggccct cttcctgccc aactaggaaa accgcactt gtccggaaac    5040 cccgggaatc taacccggct gaacggattt agagtccatt cgatctacat gatcaggttt    5100
ccggtgtttc gtcctttcca caagatatat aaagccaaga atcgaaata ctttcaagtt    5160 acggtaagca tatgatagtc cattttaaaa cataatttta aaactgcaaa ctacccaaga    5220
aattattact ttctacgtca cgtatttgt actaatatct tgtgtttac agtcaaatta    5280
```

```
attctaatta tctctctaac agccttgtat cgtatatgca aatatgaagg aatcatggga    5340
aataggccct cttcctgccc aactaggaaa aaccgcactt gtccggaaac cccgggaatc    5400
taacccggct gaacggattt agagtccatt cgatctacat gatcaggttt ccggtgtttc    5460
gtcctttcca caagatatat aaagccaaga aatcgaaata ctttcaagtt acggtaagca    5520
tatgatagtc cattttaaaa cataatttta aaactgcaaa ctacccaaga aattattact    5580
ttctacgtca cgtattttgt actaatatct ttgtgtttac agtcaaatta attctaatta    5640
tctctctaac agccttgtat cgtatatgca aatatgaagg aatcatggga aataggccct    5700
cttcctgccc aactaggaaa aaccgcactt gtccggaaac cccgggaatc taacccggct    5760
gaacggattt agagtccatt cgatctacat gatcaggttt ccggtgtttc gtcctttcca    5820
caagatatat aaagccaaga aatcgaaata ctttcaagtt acggtaagca tatgatagtc    5880
cattttaaaa cataatttta aaactgcaaa ctacccaaga aattattact ttctacgtca    5940
cgtattttgt actaatatct ttgtgtttac agtcaaatta attctaatta tctctctaac    6000
agccttgtat cgtatatgca aatatgaagg aatcatggga aataggccct cttcctgccc    6060
aactagtaag gatctgcgat cgctccggtg cccgtcagtg ggcagagcgc acatcgccca    6120
cagtccccga aagttgggg ggaggggtcg gcaattgaac gggtgcctag agaaggtggc    6180
gcggggtaaa ctgggaaagt gatgtcgtgt actggctccg ccttttcccc gagggtgggg    6240
gagaaccgta tataagtgca gtagtcgccg tgaacgttct ttttcgcaac gggtttgccg    6300
ccagaacaca gctgaagctt cgaggggctc gcatctctcc ttcacgcgcc cgccgcccta    6360
cctgaggccg ccatccacgc cggttgagtc gcgttctgcc gcctccgcc tgtggtgcct    6420
cctgaactgc gtccgccgtc taggtaagtt taaagctcag gtcgagaccg gcctttgtc     6480
cggcgctccc ttggagccta cctagactca gccggctctc cacgctttgc ctgaccctgc    6540
ttgctcaact ctacgtcttt gtttcgtttt ctgttctgcg ccgttacaga tccaagctgt    6600
gaccggcgcc tactctagag ctagcgttta aacttaagct tgccaccatg gactacaagg    6660
acgacgacga caaggacaag aagccccctga acacctgat cagcgccaca ggactgtgga    6720
tgtccagaac cggcaccatc cacaagatca agcaccacga ggtgtccgg tccaaaatct    6780
acatcgagat ggcctgcggc gatcacctgg tcgtcaacaa cagcagaagc agccggacag    6840
ccagagccct gcggcaccac aagtacgaaa agacctgcaa cgcgtgcaga gtgtccgacg    6900
aggacctgaa caagttcctg accaaggcca acgaggacca gaccagcgtg aaagtgaagg    6960
tggtgtccgc ccccacccgg accaagaaag ccatgcccaa gagcgtggcc agagccccca    7020
agccccctgg aaacaccgaa gccgctcagg cccagcccag cggcagcaag ttcagccccg    7080
ccatccccgt gtctacccag gaaagcgtca gcgtccccgc cagcgtgtcc accagcatct    7140
ctagcatctc aaccggcgcc acagcttctg ccctggtcaa gggcaacacc aaccccatca    7200
ccagcatgtc tgccctgtg caggcctctg ccccagccct gaccaagtcc cagaccgacc    7260
ggctggaagt gctcctgaac cccaaggacg agatcagcct gaacagcggc aagcccttcc    7320
gggagctgga aagcgagctg ctgagccggc ggaagaagga cctccagcaa atctacgccg    7380
aggaacggga gaactacctg gcaagctgg aaagagagat cacccggttc ttcgtggacc    7440
ggggcttcct ggaaatcaag agccccatcc tgatccccct ggagtacatc gagcggatgg    7500
gcatcgacaa cgacaccgag ctgagcaagc agatttccg ggtggacaag aacttctgcc    7560
tgcggccccat gctggcccccc aacctgtaca actacctgcg gaaactggat cgcgctctgc    7620
```

```
ccgaccccat caagattttc gagatcggcc cctgctaccg gaaagagagc gacggcaaag    7680
agcacctgga agagtttaca atgctgaact tttgccagat gggcagcggc tgcaccagag    7740
agaacctgga atccatcatc accgactttc tgaaccacct ggggatcgac ttcaagatcg    7800
tgggcgacag ctgcatggtg tacgcgaca ccctggacgt gatgcacggc gacctggaac    7860
tgtctagcgc cgtcgtggga cccatccctc tggaccggga gtggggcatc gataagccct    7920
ggatcggagc cggcttcggc ctggaacggc tgctgaaagt caagcacgac tttaagaaca    7980
tcaagcgggc tgccagaagc gagagctact acaacggcat cagcaccaac ctgtgatgag    8040
gatccgcggc cgcgcccctc tccctccccc ccccctaacg ttactggccg aagccggagt    8100
tcttcgccca ccccaacttg tttattgcag cttataatgg ttacaaataa agcaatagca    8160
tcacaaattt cacaaataaa gcattttttt cactgcattc tagttgtggt ttgtccaaac    8220
tcatcaatgt atcttatcat gtctgtatac cgtcgacctc tagctagagc ttggcgtaat    8280
catggtcata gctgtttcct gtgtgaaatt gttatccgct cacaattcca cacaacatac    8340
gagccggaag cataaagtgt aaagcctggg gtgcctaatg agtgagctaa ctcacattaa    8400
ttgcgttgcg ctcactgccc gctttccagt cgggaaacct gtcgtgccag ctgcattaat    8460
gaatcggcca acgcgcgggg agaggcggtt tgcgtattgg gcgctcttcc gcttcctcgc    8520
tcactgactc gctgcgctcg tcgttcggc tgcggcgagc ggtatcagct cactcaaagg    8580
cggtaatacg gttatccaca gaatcagggg ataacgcagg aaagaacatg tgagcaaaag    8640
gccagcaaaa ggccaggaac cgtaaaaagg ccgcgttgct ggcgtttttc cataggctcc    8700
gcccccctga cgagcatcac aaaaatcgac gctcaagtca gaggtggcga acccgacag    8760 gactataaag ataccaggcg tttccccctg gaagctccct cgtgcgctct cctgttccga    8820
ccctgccgct taccggatac ctgtccgcct ttctcccttc gggaagcgtg gcgctttctc    8880
aatgctcacg ctgtaggtat ctcagttcgg tgtaggtcgt tcgctccaag ctgggctgtg    8940
tgcacgaacc cccgttcag cccgaccgct gcgccttatc cggtaactat cgtcttgagt    9000
ccaacccggt aagacacgac ttatcgccac tggcagcagc cactggtaac aggattagca    9060
gagcgaggta tgtaggcggt gctacagagt tcttgaagtg gtggcctaac tacggctaca    9120
ctagaaggac agtatttggt atctgcgctc tgctgaagcc agttaccttc ggaaaaagag    9180
ttggtagctc ttgatccggc aaacaaacca ccgctggtag cggtggtttt tttgtttgca    9240
agcagcagat tacgcgcaga aaaaaggat ctcaagaaga tcctttgatc ttttctacgg    9300
ggtctgacgc tcagtggaac gaaaactcac gttaagggat tttggtcatg agattatcaa    9360
aaaggatctt cacctagatc cttttaaatt aaaaatgaag ttttaaatca atctaaagta    9420
tatatgagta aacttggtct gacagttacc aatgcttaat cagtgaggca cctatctcag    9480
cgatctgtct atttcgttca tccatagttg cctgactccc cgtcgtgtag ataactacga    9540
tacgggaggg cttaccatct ggccccagtg ctgcaatgat accgcgagac ccacgctcac    9600
cggctccaga tttatcagca ataaaccagc cagccggaag ggccgagcgc agaagtggtc    9660
ctgcaacttt atccgcctcc atccagtcta ttaattgttg ccgggaagct agagtaagta    9720
gttcgccagt taatagtttg cgcaacgttg ttgccattgc tacaggcatc gtggtgtcac    9780
gctcgtcgtt tggtatggct tcattcagct ccggttccca acgatcaagg cgagttacat    9840 gatccccat gttgtgcaaa aaagcggtta gctccttcgg tcctccgatc gttgtcagaa    9900
gtaagttggc cgcagtgtta tcactcatgg ttatggcagc actgcataat tctcttactg    9960
tcatgccatc cgtaagatgc ttttctgtga ctggtgagta ctcaaccaag tcattctgag    10020
```

```
aatagtgtat gcggcgaccg agttgctctt gcccggcgtc aatacgggat aataccgcgc    10080
cacatagcag aactttaaaa gtgctcatca ttggaaaacg ttcttcgggg cgaaaactct    10140
caaggatctt accgctgttg agatccagtt cgatgtaacc cactcgtgca cccaactgat    10200
cttcagcatc ttttactttc accagcgttt ctgggtgagc aaaaacagga aggcaaaatg    10260
ccgcaaaaaa gggaataagg gcgacacgga aatgttgaat actcatactc ttccttttc    10320 aatattattg aagcatttat cagggttatt gtctcatgag cggatacata tttgaatgta    10380
tttagaaaaa taaacaaata ggggttccgc gcacatttcc ccgaaaagtg ccacctgacg    10440
tcgacggatc gggagatctc ccgatcccct atggtcgact ctcagtacaa tctgctctga    10500
tgccgcatag ttaagccagt atctgctccc tgcttgtgtg ttggaggtcg ctgagtagtg    10560
cgcgagcaaa atttaagcta caacaaggca aggcttgacc gacaattgca tgaagaatct    10620
gcttagg                                                             10627

<210> SEQ ID NO 31
<211> LENGTH: 1404
<212> TYPE: DNA
<213> ORGANISM: Artificial Sequence
<220> FEATURE:
<223> OTHER INFORMATION: HC A114X DNA sequence with leader peptide

<400> SEQUENCE: 31
atgggatggt catgtatcat cctttttcta gtagcaactg caaccggtgt acattctgaa      60
gttcagctgg ttgaatctgg tggtggtctg gttcaaccgg gtggctccct gcgtctgtct     120
tgtgcggcct ctggttttaa catcaaagat acctatatcc actgggttcg tcaggcgcca     180
ggcaaaggtc tggaatgggt tgcgcgtatc tacccgacca cggttacac ccgctacgcg     240 gactctgtta aaggtcgttt caccatctct gcggacacct ctaaaaacac cgcgtacctg     300
cagatgaact ctctgcgtgc ggaagacacc gccgtttact actgctctcg ttggggtggt     360
gacggtttct acgcgatgga ctactggggt cagggtacgc tggttaccgt tcttcttag     420 tcgaccaagg gcccatcggt cttccccctg gcaccctcct ccaagagcac ctctggggc     480 acagcggccc tgggctgcct ggtcaaggac tacttccccg aacctgtgac ggtctcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctatagc aagctcaccg tggacaagag caggtggcag    1320
caggggaacg tcttctcatg ctccgtgatg catgaggctc tgcacaacca ctacacgcag    1380
```

```
aagagcctct ccctgtcccc gggt                                        1404
```

<210> SEQ ID NO 32
<211> LENGTH: 702
<212> TYPE: DNA
<213> ORGANISM: Artificial Sequence
<220> FEATURE:
<223> OTHER INFORMATION: LC DNA sequence with leader peptide

<400> SEQUENCE: 32

```
atgggatggt catgtatcat cctttttcta gtagcaactg caaccggtgt acattctgac    60
atccagatga cccagtcccc gagctctctg tctgcgtctg ttggtgaccg cgttaccatc   120
acctgccgtg cgtcccagga cgttaacacc gccgtggcgt ggtatcaaca gaaaccgggt   180
aaagcgccaa aactgctgat ctactccgcg tctttcctgt actctggtgt tccgtctcgt   240
ttcagcggtt ctcgttctgg tactgacttc accctcacca tctcttctct gcagccggaa   300
gacttcgcga cctactactg ccagcagcac tacaccaccc caccgacctt cggtcagggc   360
accaaagttg aaatcaaacg tacggtggct gcaccatctg tcttcatctt cccgccatct   420
gatgagcagt tgaaatctgg aactgcctct gttgtgtgcc tgctgaataa cttctacccc   480
agagaagcca aagtgcagtg gaaggtggac aacgccctgc agagcggaaa cagccaggaa   540
agcgtgacag agcaggattc caaggattcc acatacagcc tgagcagcac actgacactg   600
tccaaggccg actacgagaa gcacaaggtg tacgcctgcg aagtgacaca ccagggactg   660
tcctcccctg tgacaaagag cttcaacaga ggagaatgct ga                       702
```

<210> SEQ ID NO 33
<211> LENGTH: 449
<212> TYPE: PRT
<213> ORGANISM: Artificial Sequence
<220> FEATURE:
<223> OTHER INFORMATION: HC with A114X mutation protein sequence, X121
      represents the UAG unnatural site
<220> FEATURE:
<221> NAME/KEY: misc_feature
<222> LOCATION: (121)..(121)
<223> OTHER INFORMATION: Xaa can be any naturally occurring amino acid

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Xaa Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
            145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly

<210> SEQ ID NO 34
<211> LENGTH: 214
<212> TYPE: PRT
<213> ORGANISM: Artificial Sequence
<220> FEATURE:
<223> OTHER INFORMATION: LC protein sequence

<400> SEQUENCE: 34

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
                20                  25                  30
Val Ala Trp Tyr Gln Gln Lys Pro Gly Lys Ala Pro Lys Leu Leu Ile
            35                  40                  45
Tyr Ser Ala Ser Phe Leu Tyr Ser Gly Val Pro Ser Arg Phe Ser Gly
        50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 372
<212> TYPE: DNA
<213> ORGANISM: Artificial Sequence
<220> FEATURE:
<223> OTHER INFORMATION: U6-PylT U25C supp table S1

<400> SEQUENCE: 35
agtcagtcac tagttgggca ggaagagggc ctatttccca tgattccttc atatttgcat      60
atacgataca aggctgttag agagataatt agaattaatt tgactgtaaa cacaaagata     120
ttagtacaaa atacgtgacg tagaaagtaa taatttcttg ggtagtttgc agttttaaaa     180
ttatgtttta aaatggacta tcatatgctt accgtaactt gaaagtattt cgatttcttg     240
gctttatata tcttgtggaa aggacgaaac accggaaacc tgatcatgta gatcgaacgg     300
actctaaatc cgttcagccg ggttagattc ccggggtttc cggacaagtg cggttttcc      360 taggagtcag tc                                                         372

<210> SEQ ID NO 36
<211> LENGTH: 750
<212> TYPE: DNA
<213> ORGANISM: Artificial Sequence
<220> FEATURE:
<223> OTHER INFORMATION: sfGFP(TAG) H. sapiens optimized, C-terminal
      HisTag Supp Table S1

<400> SEQUENCE: 36
atggtgtcca agggcgagga actgttcacc ggcgtggtgc ccatcctggt ggaactggat      60
ggcgacgtga acggccacaa gttctctgtg cggggagagg gcgaaggcga cgccacaaat     120
ggcaagctga ccctgaagtt catctgcacc accggcaagc tgcccgtgcc ttggcctacc     180
ctcgtgacca cactgaccta cggcgtgcag tgcttcagca gataccccga ccatatgaag     240
cggcacgact tcttcaagag cgccatgccc gagggctacg tgcaggaacg gaccatcagc     300
ttcaaggacg acggcaccta caagaccaga gccgaagtga agttcgaggg cgacaccctc     360
gtgaaccgga tcgagctgaa gggcatcgat ttcaaagagg acggcaacat cctgggccac     420
```

```
aagctggagt acaacttcaa cagccactag gtgtacatca ccgccgacaa gcagaagaac    480
ggcatcaagg ccaacttcaa gatccggcac aacgtggaag atggcagcgt gcagctggcc    540
gaccactacc agcagaacac ccccatcgga gatggccccg tgctgctgcc cgacaaccac    600
tacctgagca cccagagcgt gctgagcaag accccaacg agaagcggga ccacatggtg    660
ctgctggaat tcgtgaccgc cgctggcatc acccacggca tggacgagct gtacaagggc    720
agccaccatc accatcacca ttaataataa                                     750

<210> SEQ ID NO 37
<211> LENGTH: 1338
<212> TYPE: DNA
<213> ORGANISM: Artificial Sequence
<220> FEATURE:
<223> OTHER INFORMATION: H. sapiens eRF1 D. melanogaster optimized,
      N-terminal HisTag Supp Table S1

<400> SEQUENCE: 37
atgcatcatc accatcacca cgccgatgat ccaagcgccg cagaccgcaa tgttgagatc     60
tggaagataa aaaagctgat aaagagcttg gaggccgcac ggggcaacgg cacgtccatg    120
atatccctca ttatcccacc aaaggatcag atcagccgtg tggcgaagat gttggcggat    180
gagttcggaa cggccagtaa cattaaaagt cgcgtgaacc ggctgtcggt cttgggcgcc    240
atcacttccg tgcagcaacg tctgaaactg tacaacaaag tcccacccaa cggtttggtc    300
gtctactgcg gtacgatagt taccgaggaa ggaaaggaga agaaagtgaa tattgatttc    360
gaaccattta aaccgataaa cactagcttg tacttgtgcg acaataagtt tcatacagag    420
gcactcacgg ccctgctgag cgacgactcg aaattcggat tcattgtcat tgatggaagt    480
ggagcgctgt tcggcacgct gcagggtaac acgcgcgagg tcttgcacaa attcaccgtg    540
gacttgccca aaaagcatgg ccgtggtggc cagagcgccc tcaggtttgc gcggctgcgc    600
atggagaagc gccataacta cgtgcgcaag gtcgcagaga cggctgtgca gctgttcatc    660
tcgggtgata aggtaaatgt cgcgggactg gtgctcgccg gcagcgcgga cttcaaaacc    720
gagctgagtc agtccgacat gttcgatcag cgtctgcagt cgaaggtact gaagctcgtc    780
gacattagct acggcggcga gaacggcttc aatcaggcca tcgaactgag taccgaagtc    840
ctcagtaacg taaagtttat tcaggaaaaa aagttgattg gacgctactt tgatgaaata    900
agccaagata cgggcaaata ctgttttggc gtcgaggata ctctgaaagc gctcgagatg    960
ggagcagtgg aaatactcat cgtatatgaa aatctcgata taatgcgcta tgtactgcat   1020
tgccaaggaa cagaagagga gaaaattctc tacctcaccc cggagcaaga gaaggacaag   1080
agccatttta cagacaagga gacgggccaa gagcacgagc tcattgagtc gatgcccttg   1140
ctcgaatggt ttgccaacaa ctacaagaag ttcggcgcga ccctggaaat tgtcacggat   1200
aaatcgcagg agggcagcca gtttgtgaag ggcttcggtg gcatcggcgg catcctccgc   1260
taccgggtgg atttccaagg catggaatat caaggtggag atgatgaatt cttcgatttg   1320
gatgattact aatgatag                                                 1338

<210> SEQ ID NO 38
<211> LENGTH: 37
<212> TYPE: DNA
<213> ORGANISM: Artificial Sequence
<220> FEATURE:
<223> OTHER INFORMATION: eRF1_E55Af

<400> SEQUENCE: 38
```
gaagatgttg gcggatgcct tcggaacggc cagtaac                          37

<210> SEQ ID NO 39
<211> LENGTH: 37
<212> TYPE: DNA
<213> ORGANISM: Artificial Sequence
<220> FEATURE:
<223> OTHER INFORMATION: eRF1_E55Ar

<400> SEQUENCE: 39
gttactggcc gttccgaagg catccgccaa catcttc                          37

<210> SEQ ID NO 40
<211> LENGTH: 30
<212> TYPE: DNA
<213> ORGANISM: Artificial Sequence
<220> FEATURE:
<223> OTHER INFORMATION: eRF1_E55Df

<400> SEQUENCE: 40
gatgttggcg gatgatttcg gaacggccag                                  30

<210> SEQ ID NO 41
<211> LENGTH: 30
<212> TYPE: DNA
<213> ORGANISM: Artificial Sequence
<220> FEATURE:
<223> OTHER INFORMATION: eRF1_E55Dr

<400> SEQUENCE: 41
ctggccgttc cgaaatcatc cgccaacatc                                  30

<210> SEQ ID NO 42
<211> LENGTH: 40
<212> TYPE: DNA
<213> ORGANISM: Artificial Sequence
<220> FEATURE:
<223> OTHER INFORMATION: eRF1_Y125Ff

<400> SEQUENCE: 42
ccgataaaca ctagcttgtt cttgtgcgac aataagtttc                       40

<210> SEQ ID NO 43
<211> LENGTH: 40
<212> TYPE: DNA
<213> ORGANISM: Artificial Sequence
<220> FEATURE:
<223> OTHER INFORMATION: eRF1_Y125Fr

<400> SEQUENCE: 43
gaaacttatt gtcgcacaag aacaagctag tgtttatcgg                       40

<210> SEQ ID NO 44
<211> LENGTH: 38
<212> TYPE: DNA
<213> ORGANISM: Artificial Sequence
<220> FEATURE:
<223> OTHER INFORMATION: eRF1_TS122QFf

<400> SEQUENCE: 44
catttaaacc gataaaccaa ttcttgtact tgtgcgac                         38

<210> SEQ ID NO 45
<211> LENGTH: 38
<212> TYPE: DNA

<213> ORGANISM: Artificial Sequence
<220> FEATURE:
<223> OTHER INFORMATION: eRF1_TS122QFr

<400> SEQUENCE: 45
gtcgcacaag tacaagaatt ggtttatcgg tttaaatg         38

<210> SEQ ID NO 46
<211> LENGTH: 39
<212> TYPE: DNA
<213> ORGANISM: Artificial Sequence
<220> FEATURE:
<223> OTHER INFORMATION: eRF1_NK129PQf

<400> SEQUENCE: 46
gcttgtactt gtgcgaccca cagtttcata cagaggcac         39

<210> SEQ ID NO 47
<211> LENGTH: 39
<212> TYPE: DNA
<213> ORGANISM: Artificial Sequence
<220> FEATURE:
<223> OTHER INFORMATION: eRF1_NK129PQr

<400> SEQUENCE: 47
gtgcctctgt atgaaactgt gggtcgcaca agtacaagc         39

<210> SEQ ID NO 48
<211> LENGTH: 38
<212> TYPE: DNA
<213> ORGANISM: Artificial Sequence
<220> FEATURE:
<223> OTHER INFORMATION: eRF1_SVLG70AVLSf

<400> SEQUENCE: 48
gcgtgaaccg gctggccgtg ctgagcgcca tcacttcc         38

<210> SEQ ID NO 49
<211> LENGTH: 38
<212> TYPE: DNA
<213> ORGANISM: Artificial Sequence
<220> FEATURE:
<223> OTHER INFORMATION: eRF1_SVLG70AVLSr

<400> SEQUENCE: 49
ggaagtgatg gcgctcagca cggccagccg gttcacgc         38

<210> SEQ ID NO 50
<211> LENGTH: 35
<212> TYPE: DNA
<213> ORGANISM: Artificial Sequence
<220> FEATURE:
<223> OTHER INFORMATION: eRF1_K130Mf

<400> SEQUENCE: 50
gtacttgtgc gacaatatgt tcatacaga ggcac         35

<210> SEQ ID NO 51
<211> LENGTH: 35
<212> TYPE: DNA
<213> ORGANISM: Artificial Sequence
<220> FEATURE:
<223> OTHER INFORMATION: eRF1_K130Mr

<400> SEQUENCE: 51
gtgcctctgt atgaaacata ttgtcgcaca agtac         35

<210> SEQ ID NO 52
<211> LENGTH: 26
<212> TYPE: DNA
<213> ORGANISM: Artificial Sequence
<220> FEATURE:
<223> OTHER INFORMATION: eRF1_M51Af

<400> SEQUENCE: 52
gtgtggcgaa ggccttggcg gatgag                                          26

<210> SEQ ID NO 53
<211> LENGTH: 26
<212> TYPE: DNA
<213> ORGANISM: Artificial Sequence
<220> FEATURE:
<223> OTHER INFORMATION: eRF1_M51Ar

<400> SEQUENCE: 53
ctcatccgcc aaggccttcg ccacac                                          26

<210> SEQ ID NO 54
<211> LENGTH: 41
<212> TYPE: DNA
<213> ORGANISM: Artificial Sequence
<220> FEATURE:
<223> OTHER INFORMATION: DLR_Ser_f

<400> SEQUENCE: 54
ctgaagaacg agcaaatctc cacgggggcc cctaggagat c                         41

<210> SEQ ID NO 55
<211> LENGTH: 41
<212> TYPE: DNA
<213> ORGANISM: Artificial Sequence
<220> FEATURE:
<223> OTHER INFORMATION: DLR_Ser_r

<400> SEQUENCE: 55
gatctcctag gggcccccgt ggagatttgc tcgttcttca g                         41

<210> SEQ ID NO 56
<211> LENGTH: 36
<212> TYPE: DNA
<213> ORGANISM: Artificial Sequence
<220> FEATURE:
<223> OTHER INFORMATION: DLR_TAA_f

<400> SEQUENCE: 56
gaagaacgag caaatctaaa cggggggccc taggag                               36

<210> SEQ ID NO 57
<211> LENGTH: 36
<212> TYPE: DNA
<213> ORGANISM: Artificial Sequence
<220> FEATURE:
<223> OTHER INFORMATION: DLR_TAA_r

<400> SEQUENCE: 57
ctcctagggg ccccgttta gatttgctcg ttcttc                                36

<210> SEQ ID NO 58
<211> LENGTH: 34
<212> TYPE: DNA
<213> ORGANISM: Artificial Sequence
<220> FEATURE:

<223> OTHER INFORMATION: DLR_TAG_f

<400> SEQUENCE: 58
gaagaacgag caaatctaga cgggggcccc tagg                          34

<210> SEQ ID NO 59
<211> LENGTH: 34
<212> TYPE: DNA
<213> ORGANISM: Artificial Sequence
<220> FEATURE:
<223> OTHER INFORMATION: DLR_TAG_r

<400> SEQUENCE: 59
cctaggggcc cccgtctaga tttgctcgtt cttc                          34

<210> SEQ ID NO 60
<211> LENGTH: 41
<212> TYPE: DNA
<213> ORGANISM: Artificial Sequence
<220> FEATURE:
<223> OTHER INFORMATION: DLR_TGA_f

<400> SEQUENCE: 60
ctgaagaacg agcaaatctg aacgggggcc cctaggagat c                  41

<210> SEQ ID NO 61
<211> LENGTH: 41
<212> TYPE: DNA
<213> ORGANISM: Artificial Sequence
<220> FEATURE:
<223> OTHER INFORMATION: DLR_TGA_r

<400> SEQUENCE: 61
gatctcctag gggcccccgt tcagatttgc tcgttcttca g                  41

<210> SEQ ID NO 62
<211> LENGTH: 28
<212> TYPE: DNA
<213> ORGANISM: Artificial Sequence
<220> FEATURE:
<223> OTHER INFORMATION: sfGFP_TAG150Lf

<400> SEQUENCE: 62
cttcaacagc cacctggtgt acatcacc                                 28

<210> SEQ ID NO 63
<211> LENGTH: 28
<212> TYPE: DNA
<213> ORGANISM: Artificial Sequence
<220> FEATURE:
<223> OTHER INFORMATION: sfGFP_TAG150Lr

<400> SEQUENCE: 63
ggtgatgtac accaggtggc tgttgaag                                 28

<210> SEQ ID NO 64
<211> LENGTH: 35
<212> TYPE: DNA
<213> ORGANISM: Artificial Sequence
<220> FEATURE:
<223> OTHER INFORMATION: sfGFP_D133TAGf

<400> SEQUENCE: 64
ggcatcgatt tcaaagagta gggcaacatc ctggg                         35

```
<210> SEQ ID NO 65
<211> LENGTH: 35
<212> TYPE: DNA
<213> ORGANISM: Artificial Sequence
<220> FEATURE:
<223> OTHER INFORMATION: sfGFP_D133TAGr

<400> SEQUENCE: 65
cccaggatgt tgccctactc tttgaaatcg atgcc                              35

<210> SEQ ID NO 66
<211> LENGTH: 38
<212> TYPE: DNA
<213> ORGANISM: Artificial Sequence
<220> FEATURE:
<223> OTHER INFORMATION: sfGFP_K101TAGf

<400> SEQUENCE: 66
ggaccatcag cttctaggac gacggcacct acaagacc                           38

<210> SEQ ID NO 67
<211> LENGTH: 38
<212> TYPE: DNA
<213> ORGANISM: Artificial Sequence
<220> FEATURE:
<223> OTHER INFORMATION: sfGFP_K101TAGr

<400> SEQUENCE: 67
ggtcttgtag gtgccgtcgt cctagaagct gatggtcc                           38
```